(12) United States Patent
Lee et al.

(10) Patent No.: US 11,998,295 B2
(45) Date of Patent: *Jun. 4, 2024

(54) INSTRUMENT FOR SURGERY

(71) Applicant: LIVSMED INC., Seongnam-si (KR)

(72) Inventors: Jung Joo Lee, Yongin-si (KR); Hee Jin Kim, Seongnam-si (KR)

(73) Assignee: LIVSMED INC., Seongnam-si (KR)

( * ) Notice: Subject to any disclaimer, the term of this patent is extended or adjusted under 35 U.S.C. 154(b) by 0 days.

This patent is subject to a terminal disclaimer.

(21) Appl. No.: 17/959,140

(22) Filed: Oct. 3, 2022

(65) Prior Publication Data

US 2023/0028452 A1     Jan. 26, 2023

Related U.S. Application Data

(63) Continuation of application No. 16/898,917, filed on Jun. 11, 2020, now Pat. No. 11,510,746, which is a
(Continued)

(30) Foreign Application Priority Data

Feb. 17, 2015     (KR) .................. 10-2015-0024304

(51) Int. Cl.
    *A61B 34/00*       (2016.01)
    *A61B 17/00*       (2006.01)
    *A61B 17/29*       (2006.01)

(52) U.S. Cl.
CPC ........ *A61B 34/71* (2016.02); *A61B 17/00234* (2013.01); *A61B 17/2909* (2013.01); *A61B 2017/00323* (2013.01); *A61B 2017/00424* (2013.01); *A61B 2017/00438* (2013.01); *A61B 2017/00477* (2013.01); *A61B 2017/00738* (2013.01); *A61B 2017/2904* (2013.01); *A61B 2017/2908* (2013.01); *A61B 2017/291* (2013.01); *A61B 2017/2911* (2013.01);
(Continued)

(58) Field of Classification Search
CPC .............. A61B 34/71; A61B 17/00234; A61B 17/2909; A61B 2017/00323; A61B 2017/00424; A61B 2017/00477; A61B 2017/00738; A61B 2017/2904; A61B 2017/2908; A61B 2017/2911; A61B 2017/2923; A61B 2017/2944
See application file for complete search history.

(56) References Cited

U.S. PATENT DOCUMENTS

| 3,273,408 A | 9/1966 | Nagel et al. |
| 3,529,481 A | 9/1970 | Budzyn |

(Continued)

FOREIGN PATENT DOCUMENTS

| CN | 102131469 A | 7/2011 |
| JP | S59102587 A | 6/1984 |

(Continued)

OTHER PUBLICATIONS

Japan Patent Office (JPO), "Notice of Reasons for Refusal", Office Action for corresponding Japanese Patent Application No. 2023-069364, issued on Jan. 16, 2024.

*Primary Examiner* — Ryan J. Severson
(74) *Attorney, Agent, or Firm* — Bridgeway IP Law Group, PLLC; Sang Ho Lee; Hyun Woo Shin

(57) ABSTRACT

Provided is an instrument for surgery and, more specifically, to an instrument for surgery which can be manually operated in order to be used for laparoscopic surgery or various types of surgery.

20 Claims, 94 Drawing Sheets

Related U.S. Application Data continuation of application No. 15/551,651, filed as application No. PCT/KR2016/001582 on Feb. 17, 2016, now Pat. No. 10,722,315.

(52) U.S. Cl.
CPC . *A61B 2017/2923* (2013.01); *A61B 2017/294* (2013.01); *A61B 2017/2944* (2013.01)

(56) References Cited

U.S. PATENT DOCUMENTS

| | | |
|---|---|---|
| 5,478,347 A | 12/1995 | Aranyi |
| 5,539,987 A | 7/1996 | Zennyoji |
| 5,792,165 A | 8/1998 | Klieman et al. |
| 5,797,900 A | 8/1998 | Madhani et al. |
| 5,908,436 A | 6/1999 | Cuschieri et al. |
| 5,954,731 A | 9/1999 | Yoon |
| 6,191,017 B1 | 2/2001 | Chittipeddi et al. |
| 6,394,998 B1 | 5/2002 | Wallace et al. |
| 6,432,112 B2 | 8/2002 | Brock et al. |
| 6,554,844 B2 | 4/2003 | Lee et al. |
| 6,676,684 B1 | 1/2004 | Morley et al. |
| 6,692,485 B1 | 2/2004 | Brock et al. |
| 6,889,116 B2 | 5/2005 | Jinno |
| 6,936,042 B2 | 8/2005 | Wallace et al. |
| 6,969,385 B2 | 11/2005 | Moreyra |
| 6,994,716 B2 | 2/2006 | Jinno et al. |
| 7,101,363 B2 | 9/2006 | Nishizawa et al. |
| 7,338,513 B2 | 3/2008 | Lee et al. |
| 7,364,582 B2 | 4/2008 | Lee |
| 7,540,867 B2 | 6/2009 | Jinno et al. |
| 7,648,519 B2 | 1/2010 | Lee et al. |
| 7,686,826 B2 | 3/2010 | Lee et al. |
| 7,914,522 B2 | 3/2011 | Morley et al. |
| 7,942,895 B2 | 5/2011 | Jinno et al. |
| 8,100,824 B2 | 1/2012 | Hegeman et al. |
| 8,465,475 B2 | 6/2013 | Isbell, Jr. |
| 8,668,702 B2 | 3/2014 | Awtar et al. |
| 8,801,731 B2 | 8/2014 | Jeong |
| 8,821,480 B2 | 9/2014 | Burbank |
| 9,033,998 B1 | 5/2015 | Schaible et al. |
| 9,179,927 B2 | 11/2015 | Stefanchik et al. |
| 9,211,159 B2 | 12/2015 | Stefanchik et al. |
| 9,695,916 B2 | 7/2017 | Lee |
| 9,737,302 B2 | 8/2017 | Shelton, IV et al. |
| 9,814,451 B2 | 11/2017 | Sharma et al. |
| 9,869,339 B2 | 1/2018 | Zimmerman et al. |
| 10,105,128 B2 | 10/2018 | Cooper et al. |
| 10,166,082 B1 | 1/2019 | Hariri et al. |
| 10,405,936 B2 | 9/2019 | Awtar et al. |
| 10,631,886 B2 | 4/2020 | Lee et al. |
| 10,695,141 B2 | 6/2020 | Lee |
| 10,709,467 B2 | 7/2020 | Lee et al. |
| 10,722,315 B2 | 7/2020 | Lee et al. |
| D908,873 S | 1/2021 | Kwon et al. |
| D910,172 S | 2/2021 | Kwon et al. |
| 11,129,637 B2 | 9/2021 | Lee et al. |
| 11,154,316 B2 | 10/2021 | Lee et al. |
| 11,246,615 B2 | 2/2022 | Lee et al. |
| 2003/0036748 A1 | 2/2003 | Cooper et al. |
| 2004/0199147 A1 | 10/2004 | Nishizawa et al. |
| 2005/0096694 A1 | 5/2005 | Lee |
| 2006/0020287 A1 | 1/2006 | Lee |
| 2006/0025811 A1 | 2/2006 | Shelton, IV |
| 2006/0190034 A1 | 8/2006 | Nishizawa et al. |
| 2006/0219065 A1 | 10/2006 | Jinno et al. |
| 2007/0208375 A1 | 9/2007 | Nishizawa et al. |
| 2007/0265502 A1 | 11/2007 | Minosawa et al. |
| 2008/0000317 A1 | 1/2008 | Patton et al. |
| 2008/0039255 A1 | 2/2008 | Jinno et al. |
| 2008/0065116 A1 | 3/2008 | Lee et al. |
| 2008/0245175 A1 | 10/2008 | Jinno et al. |
| 2009/0112230 A1 | 4/2009 | Jinno |
| 2010/0198253 A1 | 8/2010 | Jinno et al. |
| 2010/0249818 A1 | 9/2010 | Jinno et al. |
| 2010/0286480 A1 | 11/2010 | Peine et al. |
| 2011/0106145 A1 | 5/2011 | Jeong |
| 2011/0112517 A1 | 5/2011 | Peine |
| 2012/0004648 A1 | 1/2012 | Choi et al. |
| 2012/0330287 A1 | 12/2012 | Yim |
| 2013/0012958 A1 | 1/2013 | Marczyk et al. |
| 2013/0012959 A1 | 1/2013 | Jinno |
| 2013/0144274 A1 | 6/2013 | Stefanchik et al. |
| 2014/0114293 A1 | 4/2014 | Jeong et al. |
| 2014/0194893 A1 | 7/2014 | Jeong et al. |
| 2014/0222019 A1 | 8/2014 | Brudniok |
| 2014/0318288 A1 | 10/2014 | Lee |
| 2014/0350570 A1 | 11/2014 | Lee |
| 2015/0032125 A1 | 1/2015 | Jeong et al. |
| 2015/0150635 A1 | 6/2015 | Kilroy et al. |
| 2016/0008068 A1 | 1/2016 | Hyodo et al. |
| 2016/0256232 A1 | 9/2016 | Awtar et al. |
| 2017/0042560 A1 | 2/2017 | Lee et al. |
| 2018/0110577 A1 | 4/2018 | Lee et al. |
| 2018/0228506 A1 | 8/2018 | Lee et al. |
| 2019/0336230 A1 | 11/2019 | Awtar |
| 2020/0121345 A1 | 4/2020 | Lee et al. |
| 2020/0121406 A1 | 4/2020 | Lee |
| 2020/0146766 A1 | 5/2020 | Lee |
| 2020/0222137 A1 | 7/2020 | Lee et al. |
| 2020/0229835 A1 | 7/2020 | Lee et al. |
| 2020/0237466 A1 | 7/2020 | Lee et al. |
| 2020/0297445 A1 | 9/2020 | Lee et al. |
| 2020/0323601 A1 | 10/2020 | Lee |
| 2020/0375679 A1 | 12/2020 | Lee |
| 2021/0045825 A1 | 2/2021 | Lee et al. |
| 2021/0244427 A1 | 8/2021 | Lee et al. |
| 2021/0244429 A1 | 8/2021 | Lee et al. |
| 2021/0244430 A1 | 8/2021 | Lee et al. |

FOREIGN PATENT DOCUMENTS

| | | |
|---|---|---|
| JP | 64-49739 A | 2/1989 |
| JP | 06-311984 A | 11/1994 |
| JP | H08173442 A | 7/1996 |
| JP | 2004-122286 A | 4/2004 |
| JP | 2006-34978 A | 2/2006 |
| JP | 2006-061364 A | 3/2006 |
| JP | 2006-062019 A | 3/2006 |
| JP | 2006-116194 A | 5/2006 |
| JP | 2008-521485 A | 6/2008 |
| JP | 2010-220786 A | 10/2010 |
| JP | 4701433 B2 | 6/2011 |
| JP | 2011-521703 A | 7/2011 |
| JP | 2011-200666 A | 10/2011 |
| JP | 2015-501697 A | 1/2015 |
| KR | 10-2006-0093060 A | 8/2006 |
| KR | 10-0695471 B1 | 3/2007 |
| KR | 10-2009-0119366 A | 11/2009 |
| KR | 10-2009-0124828 A | 12/2009 |
| KR | 10-0956760 B1 | 5/2010 |
| KR | 10-2010-0099818 A | 9/2010 |
| KR | 10-2010-0118573 A | 11/2010 |
| KR | 10-2011-0005671 A | 1/2011 |
| KR | 10-2011-0014534 A | 2/2011 |
| KR | 10-2011-0028613 A | 3/2011 |
| KR | 101064825 B1 | 9/2011 |
| KR | 10-1075294 B1 | 10/2011 |
| KR | 10-2012-0003091 A | 1/2012 |
| KR | 10-2013-0023311 A | 3/2013 |
| KR | 10-2013-0023755 A | 3/2013 |
| KR | 10-2013-0057250 A | 5/2013 |
| KR | 10-1301783 B1 | 8/2013 |
| KR | 10-1364970 B1 | 2/2014 |
| KR | 10-2014-0113893 A | 9/2014 |
| WO | 2009/100366 A2 | 8/2009 |
| WO | 2009/158115 A1 | 12/2009 |
| WO | 2010/030114 A2 | 3/2010 |
| WO | 2011/115311 A1 | 9/2011 |
| WO | 2012074564 A1 | 6/2012 |
| WO | 2013/077571 A1 | 5/2013 |
| WO | 2013082220 A2 | 6/2013 |

(56) References Cited

FOREIGN PATENT DOCUMENTS

| WO | 2014/012780 A1 | 1/2014 |
| WO | 2014/123390 A1 | 8/2014 |
| WO | 2014/156219 A1 | 10/2014 |

FIG. 11
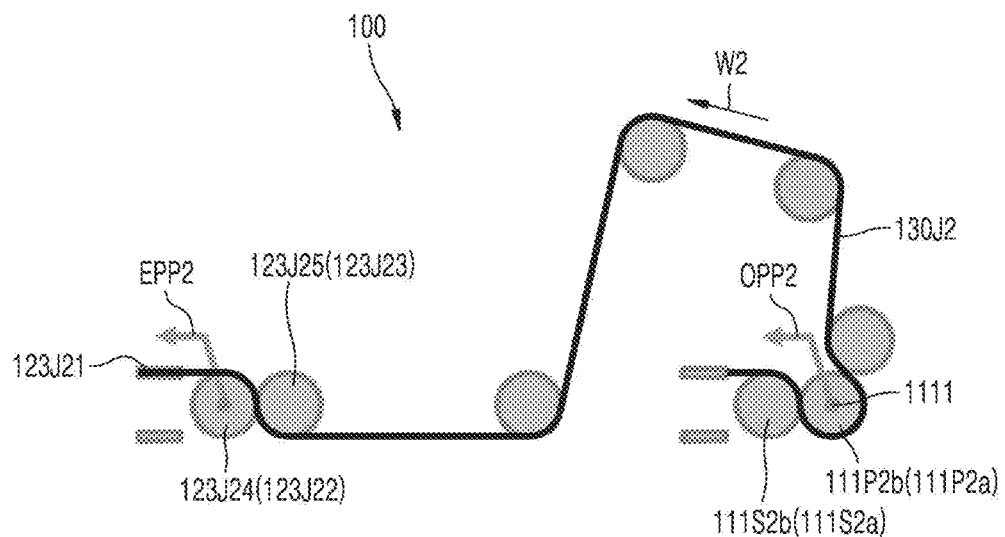
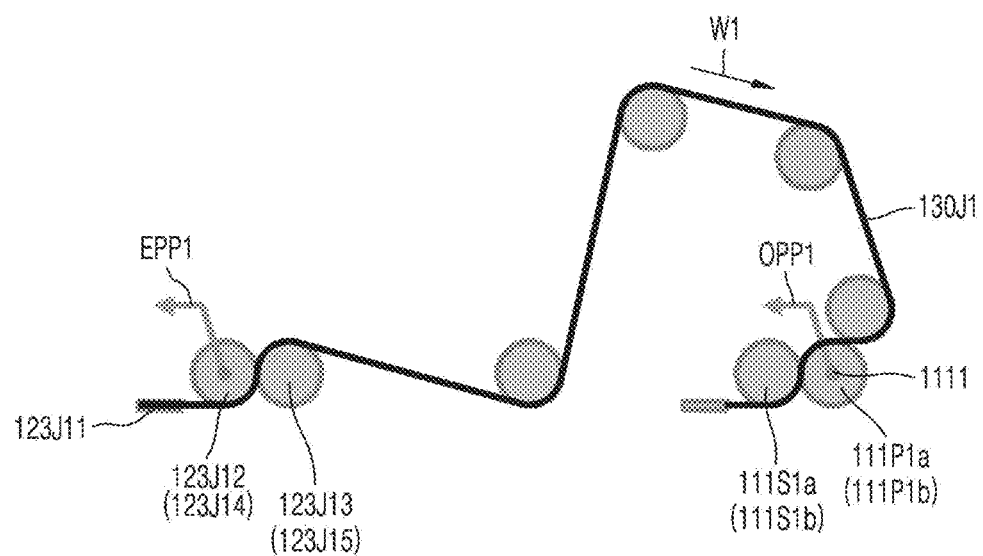

FIG. 13
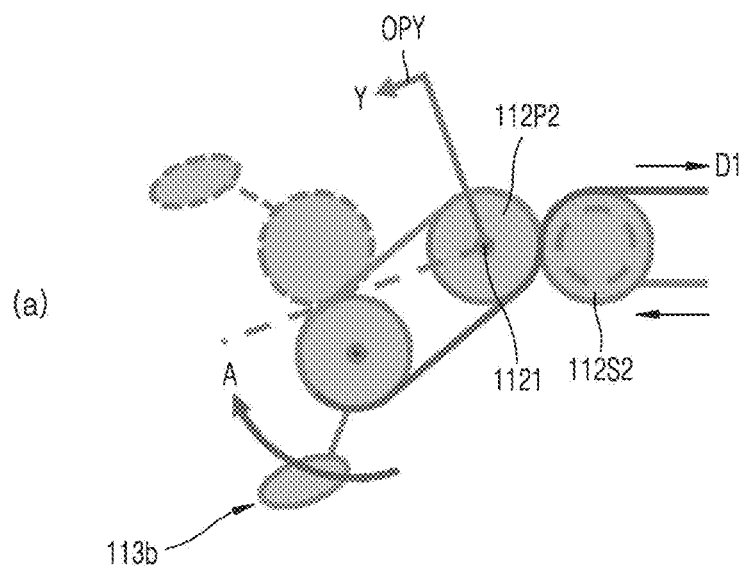
(a)
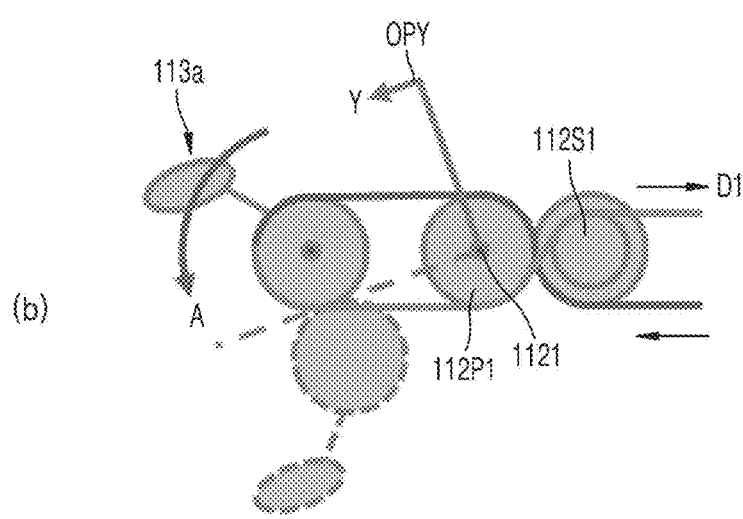
(b)

FIG. 14
(a) 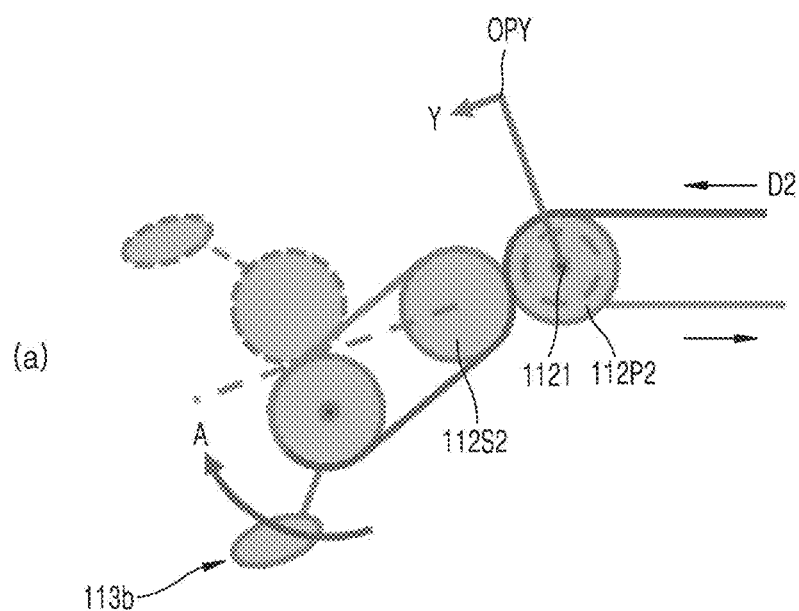
(b) 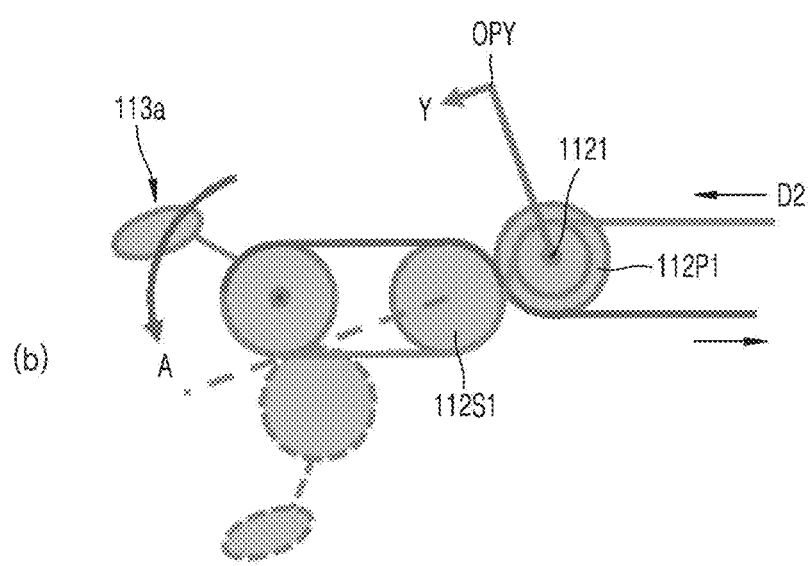

INSTRUMENT FOR SURGERY

CROSS-REFERENCE TO RELATED APPLICATIONS

The present application is a continuation application of U.S. application Ser. No. 16/898,917 filed on Jun. 11, 2020, which is a continuation application of U.S. application Ser. No. 15/551,651 filed on Aug. 17, 2017, which is a national stage application under 35 USC 371 of international application No. PCT/KR2016/001582 filed on Feb. 17, 2016, and claims priority to Korean patent application No. 10-2015-0024304 filed on Feb. 17, 2015, and the entire contents of these prior-filed applications are hereby incorporated by reference.

TECHNICAL FIELD

The present invention relates to an instrument for surgery and, more specifically, to an instrument for surgery which may be manually operated for laparoscopic surgery or various other types of surgery.

BACKGROUND ART

Surgical operations refer to medical operations for curing disease by cutting, incising, or processing the skin, mucous membranes, or other tissue using medical instruments. In particular, open surgery, in which the skin of a surgical site is cut open to cure, shape, or remove an inside organ, causes problems such as bleeding, side effects, pain in patients, or scars. Therefore, as alternatives, a surgical operation, which is performed by forming a hole through the skin and inserting into the hole only a medical instrument such as a laparoscope, a surgical instrument, or a microscope for microsurgery, or a robotic surgical operation, have recently been favored.

Instruments for surgery are tools for performing an operation on a surgical site by handling an end tool provided on an end of a shaft inserted into a hole formed through the skin, and a surgeon may handle the end tool using a robotic arm or manually using a driving unit. Such an end tool of an instrument for surgery is configured to perform motions such as rotation, gripping, or cutting using a certain structure.

However, since instruments for surgery of the related art have unbendable end tools, it is difficult to access a surgical site and perform various surgical actions. In order to solve this problem, an instrument for surgery having a bendable end tool has been developed. However, the operation of a manipulation part for bending the end tool or performing a surgical action does not intuitively match the actual bending of the end tool or the actual surgical action, and thus for surgeons, it is difficult to intuitively handle the instrument for surgery and takes a long time to be able to skillfully use the instrument for surgery.

The above-described background art is technical information that the inventors obtained or learned when or while inventing the present invention, and may not be publicly disclosed before the filing of the present patent application.

DETAILED DESCRIPTION OF THE INVENTION

Technical Problem

To solve the above-described problems, an object of the present invention is to provide an instrument for surgery configured to intuitively match motions of an end tool for bending or surgery with manipulations of a manipulation part. More particularly, to this end, the present invention provides an end tool having a plurality of degrees of freedom, a manipulation part configured to intuitively control the operation of the end tool, and a power transmission part configured to transmit driving force of the manipulation part to the end tool for operating the end tool according to manipulations of the manipulation part.

Technical Solution

An embodiment of the present invention provides an instrument for surgery including: an end tool including a first jaw and a second jaw that are independently rotatable, the end tool being rotatable in at least two directions; a manipulation part configured to control rotation of the end tool in the at least two directions, the manipulation part including a first handle, a yaw manipulation part connected to the first handle and configured to control yaw motion of the end tool, an actuation manipulation part provided at a side of the yaw manipulation part and configured to control actuation motion of the end tool, and a pitch manipulation part provided at a side of the yaw manipulation part and configured to control pitch motion of the end tool, wherein at least one of the yaw manipulation part, the actuation manipulation part, and the pitch manipulation part is directly connected to the first handle; a power transmission part connected to the manipulation part, the power transmission part including a first jaw wire, the first jaw wire transmitting rotation of the manipulation part to the first jaw, and a second jaw wire, the second jaw wire transmitting rotation of the manipulation part to the second jaw; and a connecting part extending in a first direction (X axis), the connecting part being coupled to the end tool at an end portion thereof and coupled to the manipulation part at the other end portion thereof so as to connect the manipulation part to the end tool, the connecting part including a bent part connecting the end tool and the manipulation part to each other and being bent at least once, wherein at least a portion of the manipulation part extends toward the end tool.

Other aspects, features, and advantages will become apparent and more readily appreciated from the accompanying drawings, claims, and detailed description.

Advantageous Effects of the Invention

According to the present invention, a direction in which a surgeon handles the manipulation part is intuitively identical to a direction in which the end tool is operated. Therefore, surgeons may conveniently perform surgery, and the accuracy, reliability, and speed of surgery may be improved.

DESCRIPTION OF THE DRAWINGS

FIG. 11 is a view illustrating configurations of pulleys and wires relating to pitch motion of the instrument shown in FIG. 7 separately with respect to the first jaw and the second jaw, according to the embodiment of the present invention.

FIG. 13 is a view illustrating an example of a direct-type yaw joint.

FIG. 14 is a view illustrating an example of an indirect-type yaw joint.

BEST MODE

Figure 1A:
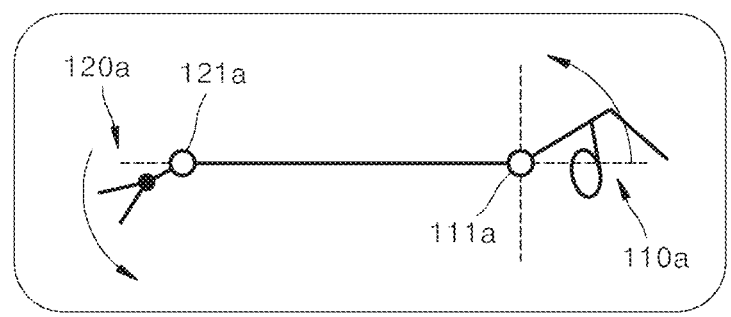
FIG. 1A is a schematic view illustrating a pitch motion of an instrument for surgery of the related art.

The present invention may include various embodiments and modifications, and particular embodiments thereof are illustrated in the drawings and will be described herein in detail. However, it will be understood that the present invention is not limited to the embodiments and includes all modifications, equivalents, and replacements within the idea and technical scope of the present invention. Moreover, detailed descriptions related to well-known functions or configurations will be omitted in order not to unnecessarily obscure subject matters of the present invention.

Although terms such as "first" and "second" may be used herein to describe various elements or components, these elements or components should not be limited by these terms. These terms are only used to distinguish one element or component from other elements or components.

The terminology used herein is for explaining specific embodiments only and is not intended to limit the present invention. As used herein, the singular forms "a," "an", and "the" are intended to include the plural forms as well, unless the context clearly indicates otherwise. It will be understood that terms such as "comprise," "include," and "have," when used herein, specify the presence of state features, integers, steps, operations, elements, components, or combinations thereof, but do not preclude the presence or addition of one or more other features, integers, steps, operations, elements, components, or combinations thereof.

Hereinafter, embodiments of the present invention will be described in detail with reference to the accompanying drawings. In the following description, like reference numerals denote like elements, and redundant descriptions thereof will be omitted.

In addition, it will be understood that various embodiments of the present invention may be interpreted or implemented in combination, and technical features of each embodiment may be interpreted or implemented in combination with technical features of other embodiments.

<First Embodiment of Instrument for Surgery>

An instrument for surgery of the present invention is characterized in that if a manipulation part is rotated in one direction for at least any one of pitch, yaw, and actuation motions, an end tool is rotated in intuitively the same direction as the direction in which the manipulation part is manipulated.

Figure 1B:
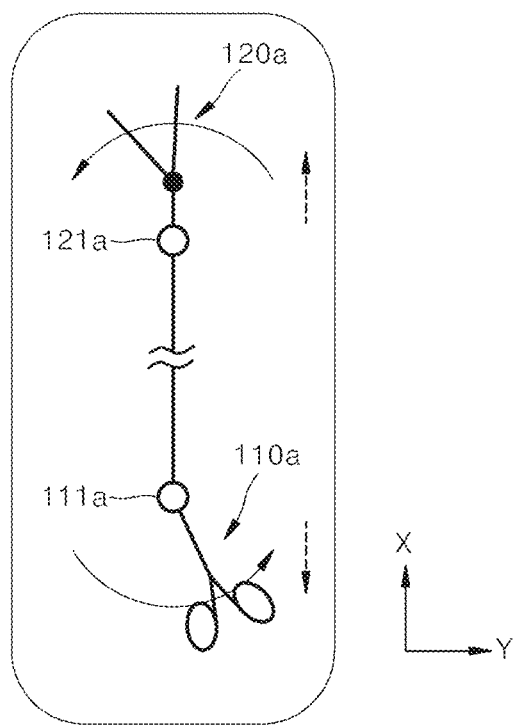
FIG. 1B is a schematic view illustrating a yaw motion of the instrument for surgery of the related art.

FIG. 1A is a schematic view illustrating pitch motion of an instrument for surgery of the related art, and FIG. 1B is a schematic view illustrating yaw motion of the instrument for surgery of the related art.

Referring to FIG. 1A, a pitch motion of the instrument for surgery of the related art is performed as follows. In a state in which an end tool 120*a* is in front of an end tool rotation center 121*a* and a manipulation part 110*a* is in back of a manipulation part rotation center 111*a*, if the manipulation part 110*a* is rotated clockwise, the end tool 120*a* is also rotated clockwise, and if the manipulation part 110*a* is rotated counterclockwise, the end tool 120*a* is also rotated counterclockwise. Referring to FIG. 1B, a yaw motion of the instrument for surgery of the related art is performed as follows. In a state in which the end tool 120*a* is in front of the end tool rotation center 121*a* and the manipulation part 110*a* is in back of the manipulation part rotation center 111*a*, if the manipulation part 110*a* is rotated clockwise, the end tool 120*a* is also rotated clockwise, and if the manipulation part 110*a* is rotated counterclockwise, the end tool 120*a* is also rotated counterclockwise. In this case, from the viewpoint of a horizontal direction of a user, when the user moves the manipulation part 110*a* to the left, the end tool 120*a* moves to the right, and when the user moves the manipulation part 110*a* to the right, the end tool 120*a* moves to the left. Consequently, since the manipulation direction of the user and the operation direction of the end tool are opposite each other, the user may make mistakes and have difficulty in manipulation.

Figure 1C:
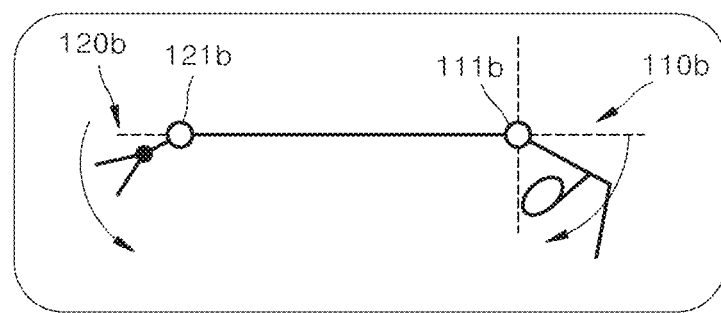
FIG. 1C is a schematic view illustrating a pitch motion of another instrument for surgery of the related art.
Figure 1D:
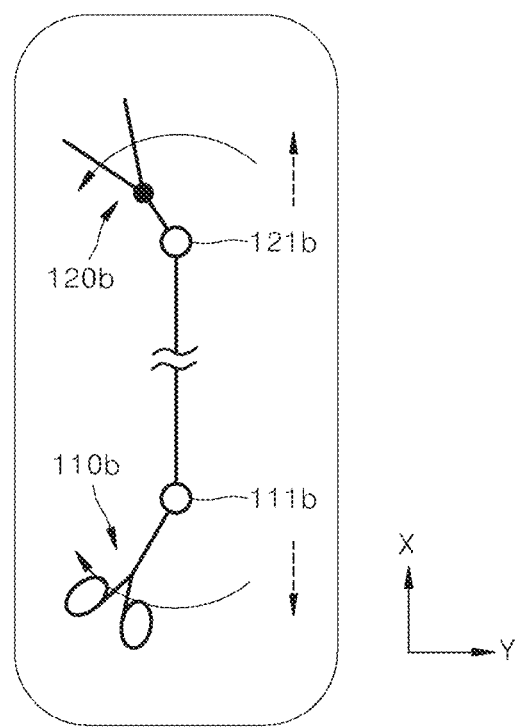
FIG. 1D is a schematic view illustrating a yaw motion of the other instrument for surgery of the related art.

FIG. 1C is a schematic view illustrating a pitch motion of another instrument for surgery of the related art, and FIG.

1D is a schematic view illustrating a yaw motion of the instrument for surgery of the related art.

Figure 1E:
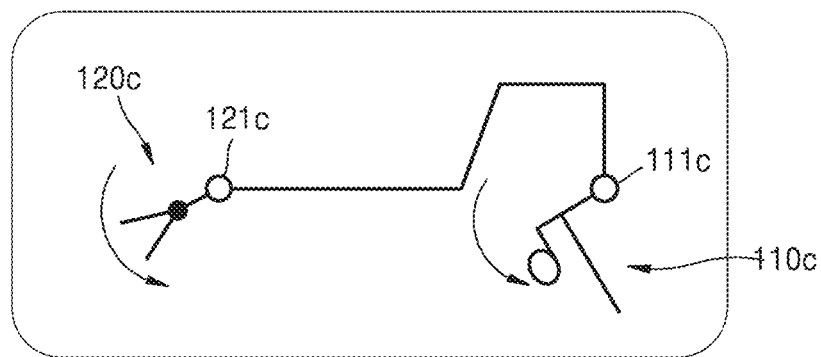
FIG. 1E is a schematic view illustrating a pitch motion of an instrument for surgery according to the present invention.
Figure 1F:
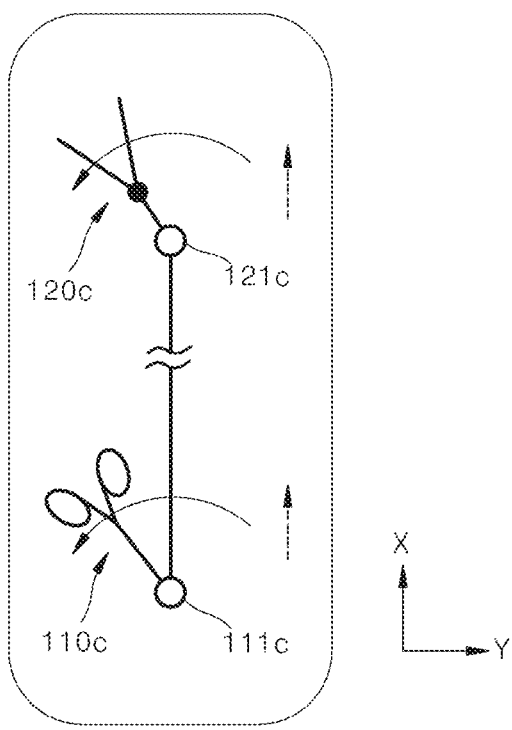
FIG. 1F is a schematic view illustrating a yaw motion of the instrument for surgery according to the present invention.

Referring to FIG. 1C, some instruments for surgery of the related art have a mirror-symmetric structure and perform a pitch motion as follows: in a state in which an end tool 120*b* is formed in front of an end tool rotation center 121*b* and an manipulation part 110*b* is formed in back of a manipulation part rotation center 111*b*, when the manipulation part 110*b* is rotated clockwise, the end tool 120*b* is rotated counterclockwise, and when the manipulation part 110*b* is rotated counterclockwise, the end tool 120*b* is rotated clockwise. In this case, from the viewpoint of the rotation directions of the manipulation part 110*b* and the end tool 120*b*, the direction in which a user rotates the manipulation part 110*b* is opposite the direction in which the end tool 120*b* is accordingly rotated. Consequently, the user may confuse manipulation directions, and the operation of a joint may not be intuitive, thereby causing mistakes. In addition, referring to FIG. 1D, a yaw motion is performed as follows. In a state in which the end tool 120*b* is in front of the end tool rotation center 121*b* and the manipulation part 110*b* is in back of the manipulation part rotation center 111*b*, if the manipulation part 110*b* is rotated clockwise, the end tool 120*b* is rotated counterclockwise, and if the manipulation part 110*b* is rotated counterclockwise, the end tool 120*b* is rotated clockwise. In this case, from the viewpoint of the rotation directions of the manipulation part 110*b* and the end tool 120*b*, the direction in which a user rotates the manipulation part 110*b* is opposite the direction in which the end tool 120*b* is accordingly rotated. Consequently, the user may confuse manipulation directions, and the operation of the joint may not be intuitive, thereby causing mistakes. As described above, when a user performs a pitch or yaw motion of an instrument for surgery of the related art, the manipulation direction of the user is not the same as the operation direction of an end tool from the viewpoint of the rotation directions or the horizontal direction. This is because an end tool and a manipulation part of an instrument for surgery of the related art have different joint structures. That is, the end tool is formed in front of the rotation center of the end tool, whereas the manipulation part is formed in back of the rotation center of the manipulation part. In order to address this problem, instruments for surgery according to embodiments of the present invention illustrated in FIGS. 1E and 1F are characterized in that an end tool 120*c* is provided in front of an end tool rotation center 121*c* and a manipulation part 110*c* is also provided in front of a manipulation part rotation center 111*c*, such that the operations of the manipulation part 110*c* and the end tool 120*c* are intuitively identical to each other. In other words, unlike the configuration example of the related art in which the manipulation part is adjacent to a user (i.e., distant from the end tool) based on a joint thereof as illustrated in FIGS. 1A, 1B, 1C, and 1D, the instruments for surgery according to the embodiments of the present invention illustrated in FIGS. 1E and 1F are configured such that at least a portion of the manipulation part may be more adjacent to the end tool based on a joint thereof (i.e., than the joint thereof is to the end tool) at at least a moment of manipulation.

In other words, in the case of an instrument for surgery of the related art as illustrated in FIGS. 1A, 1B, 1C, and 1D, since an end tool is located in front of a rotation center thereof but a manipulation part is located in back of a rotation center thereof, the end tool fixed at a rear side thereof and configured to be moved at a front side thereof is moved by the manipulation part fixed at a front side thereof and configured to be moved at a rear side thereof, and thus the structures of the manipulation part and the end tool are not intuitively identical to each other. Therefore, the manipulation of the manipulation part and the operation of the end tool are not identical to each other from the viewpoint of the horizontal direction or rotation directions, and thus a user may be confused and may not intuitively quickly manipulate the manipulation part, thereby making mistakes. However, in the case of the instruments for surgery according to the embodiments of the present invention, since each of the end tool and the manipulation part moves with respect to a rear rotation center thereof, it may be considered that the operations of the end tool and the manipulation part are structurally intuitively identical to each other. In other words, like the end tool having a portion movable based on the rear rotation center thereof, the manipulation part has a portion movable based on the rear rotation center thereof. Thus, it may be considered that the operations of the end tool and the manipulation part are structurally intuitively identical to each other. Consequently, a user may intuitively rapidly control the direction of the end tool, and the possibility that the user makes a mistake may be significantly reduced. A specific mechanism enabling this function will be described below.

Figure 2:
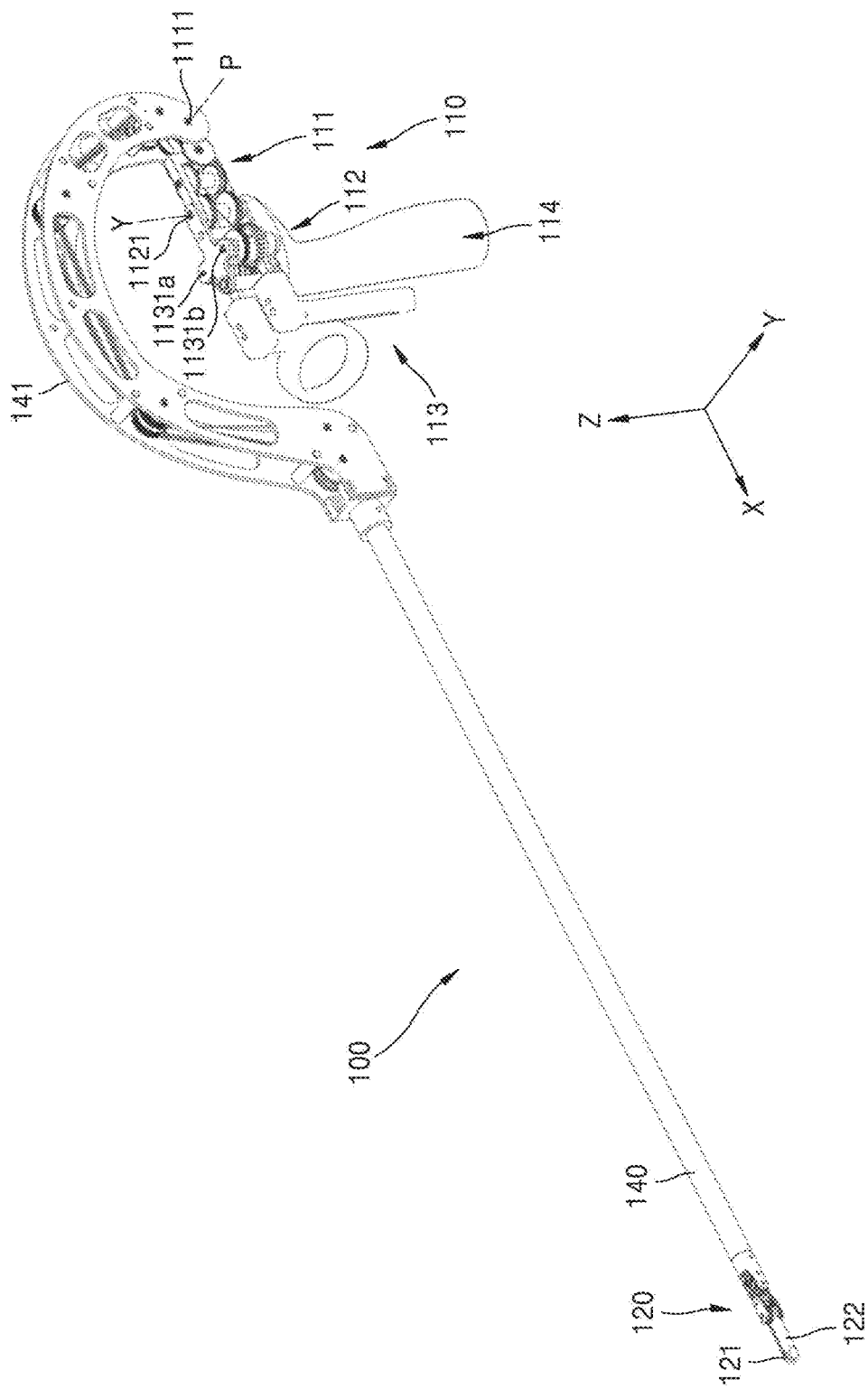
FIG. 2 is a perspective view illustrating an instrument for surgery according to a first embodiment of the present invention.
Figure 3:
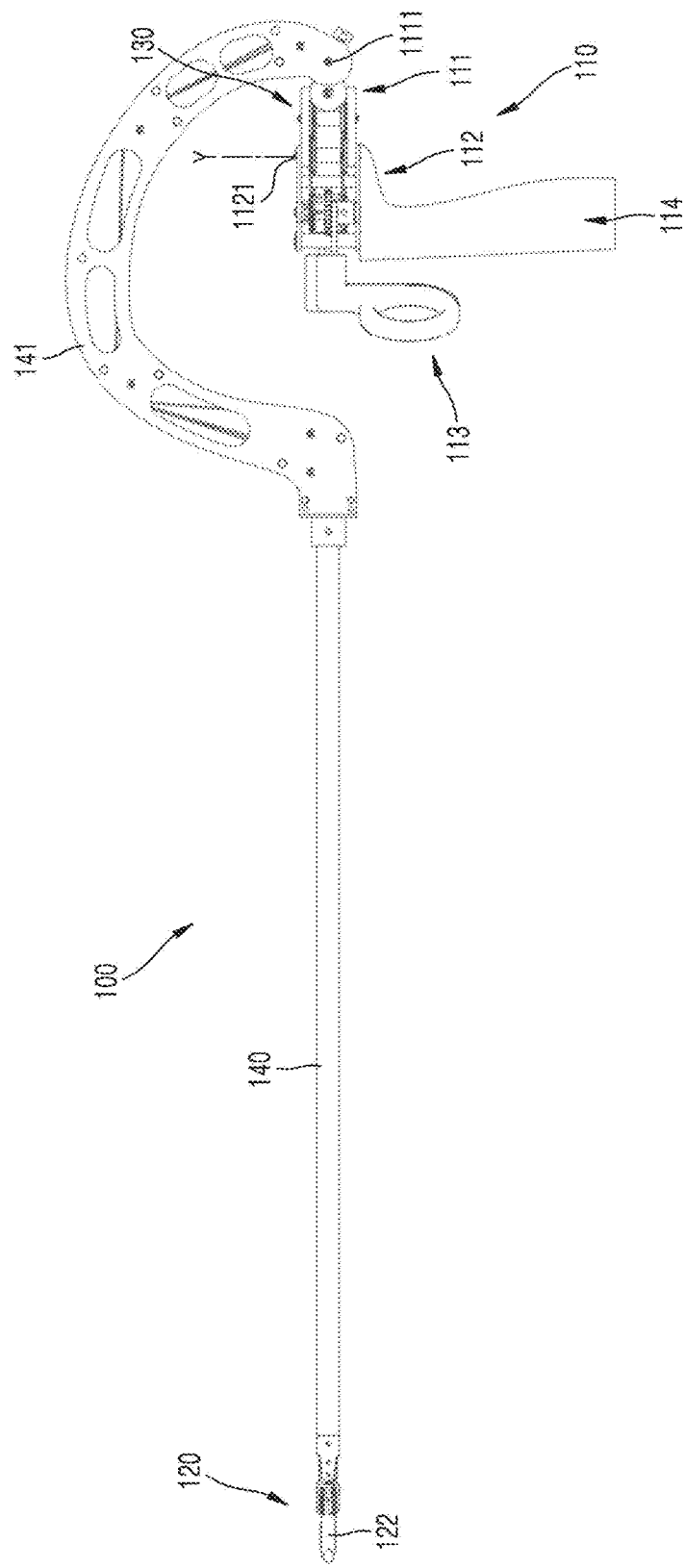
FIG. 3 is a side view illustrating the instrument for surgery shown in FIG. 2.

FIG. 2 is a perspective view illustrating an instrument for surgery according to a first embodiment of the present invention, and FIG. 3 is a side view illustrating the instrument for surgery shown in FIG. 2.

Referring to FIGS. 2, and 3, the instrument 100 for surgery according to the first embodiment of the present invention includes a manipulation part 110, an end tool 120, a power transmission part 130, and a connecting part 140. Here, the connecting part 140 may have a hollow shaft shape accommodating at least one wire (described later). The manipulation part 110 may be coupled to one end portion of the connecting part 140, and the end tool 120 may be coupled to the other end portion of the connecting part 140 such that the manipulation part 110 and the end tool 120 may be connected through the connecting part 140. Here, the connecting part 140 of the instrument 100 for surgery according to the first embodiment of the present invention is characterized by having a bent part 141 on a side of the manipulation part 110. As described above, an end portion of the connecting part 140 located on a side of the manipulation part 110 is bent such that a pitch manipulation part 111, a yaw manipulation part 112, and an actuation manipulation part 113 may be located on or adjacent to an extension line of the end tool 120. From another perspective, it may be stated that at least portions of the pitch manipulation part 111 and the yaw manipulation part 112 is accommodated in a concave region formed by the bent part 141. Owning to the shape of the bent part 141, the shapes and operations of the manipulation part 110 and the end tool 120 may be more intuitively identical to each other.

In addition, a plane formed by the bent part 141 may be substantially the same as a pitch plane, that is, an XZ plane shown in FIG. 2. In this manner, since the bent part 141 is provided on the same plane as the XZ plane, interference between manipulation parts may be reduced. Alternatively, any other configuration of the end tool and the manipulation part may be possible in addition to the XZ plane configuration.

The manipulation part 110 is provided on one end portion of the connecting part 140 and has an interface such as a tweezers shape, a stick shape, or a lever shape that a surgeon may directly manipulate, such that if an surgeon manipulates the interface, the end tool 120 connected to the interface and inserted into the body of a patient may be operated for surgery. Although FIG. 2 illustrates that the manipulation part 110 has a handle shape configured to be rotated by inserting a finger thereinto, the idea of the present invention is not limited thereto. That is, the manipulation part 110 may have any shape as long as the end tool 120 is connected to the manipulation part 110 and manipulated using the manipulation part 110.

The end tool 120 is provided on the other end portion of the connecting part 140 and is configured to be moved for surgery in a state in which that end tool 120 is inserted into a surgical site. As an example of the end tool 120, a pair of jaws 121 and 122 for gripping may be used as illustrated in FIG. 2. However, the idea of the present invention is not limited thereto. That is, various devices for surgery may be used as the end tool 120. For example, a device such as a one-armed cauter may be used as the end tool 120. The end tool 120 is connected to the manipulation part 110 through the power transmission part 130 to receive a driving force of the manipulation part 110 through the power transmission part 130, thereby performing a necessary surgical motion such as gripping, cutting, or suturing.

Herein, the end tool 120 of the instrument 100 for surgery of the first embodiment of the present invention is configured to rotate in at least two directions. For example, the end tool 120 may be capable of pitch motion around a Y axis of FIG. 2 and yaw motion and actuation motion around a Z axis of FIG. 2.

In the present invention, pitch, yaw, and actuation motions are defined as follows.

First, the pitch motion refers to upward and downward rotations of the end tool 120 with respect to an extension direction (the direction of an X axis in FIG. 2) of the connecting part 140, that is, rotation of the end tool 120 around the Y axis in FIG. 2. In other words, the pitch motion refers to upward and downward rotations of the end tool 120, which extends from the connecting part 140 in the extension direction (the X-axis direction in FIG. 2) of the connecting part 140, around the Y axis with respect to the connecting part 140. Next, the yaw motion refers to leftward and rightward rotations of the end tool 120 with respect to the extension direction (the X-axis direction in FIG. 2) of the connecting part 140, that is, rotation of the end tool 120 around the Z axis in FIG. 2. In other words, the yaw motion refers to leftward and rightward rotations of the end tool 120, which extends from the connecting part 140 in the extension direction (the X-axis direction in FIG. 2) of the connecting part 140, around the Z axis with respect to the connecting part 140. That is, the yaw motion refers to a motion in which the two jaws 121 and 122 of the end tool 120 are rotated around the Z axis in the same direction. In addition, the actuation motion refers to a motion in which the end tool 120 rotates around the same rotation axis as the yaw motion but the two jaws 121 and 122 rotate in opposite directions to move close to each other or away from each other. That is, the actuation motion refers to a motion in which the two jaws 121 and 122 rotate around the Z axis in opposite directions.

The power transmission part 130 may connect the manipulation part 110 and the end tool 120 to each other and transmit a driving force of the manipulation part 110 to the end tool 120. The power transmission part 130 may include a plurality of wires, pulleys, links, nodes, and gears. According to the embodiment of the present invention, the power transmission part 130 of the instrument 100 for surgery may include a pitch wire 130P, a first jaw wire 130J1, and a second jaw wire 130J2.

Hereinafter, parts of the instrument 100 for surgery shown in FIG. 2 such as the manipulation part 110, the end tool 120, and the power transmission part 130 will be described in more detail.

Figure 4:
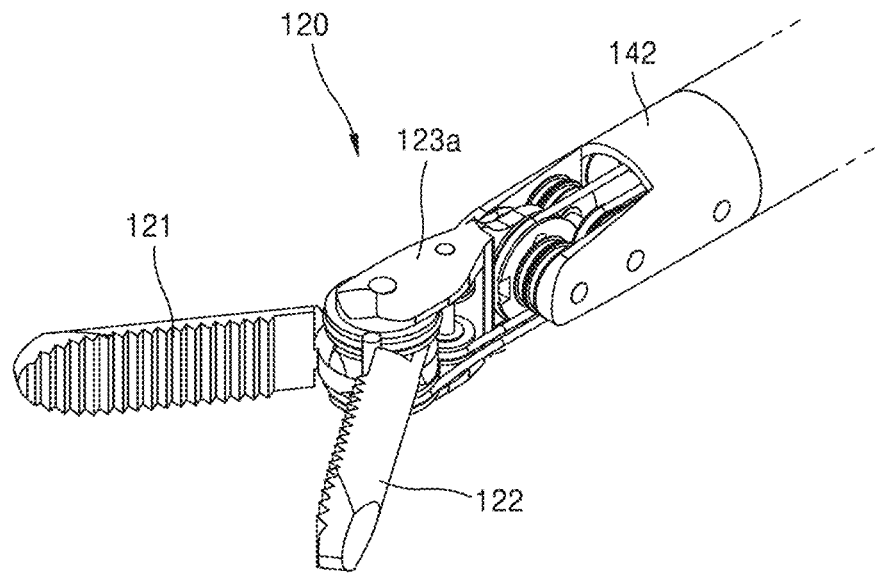
FIGS. 4 and 5 are perspective views illustrating an end tool of the instrument for surgery shown in FIG. 2.
Figure 5:
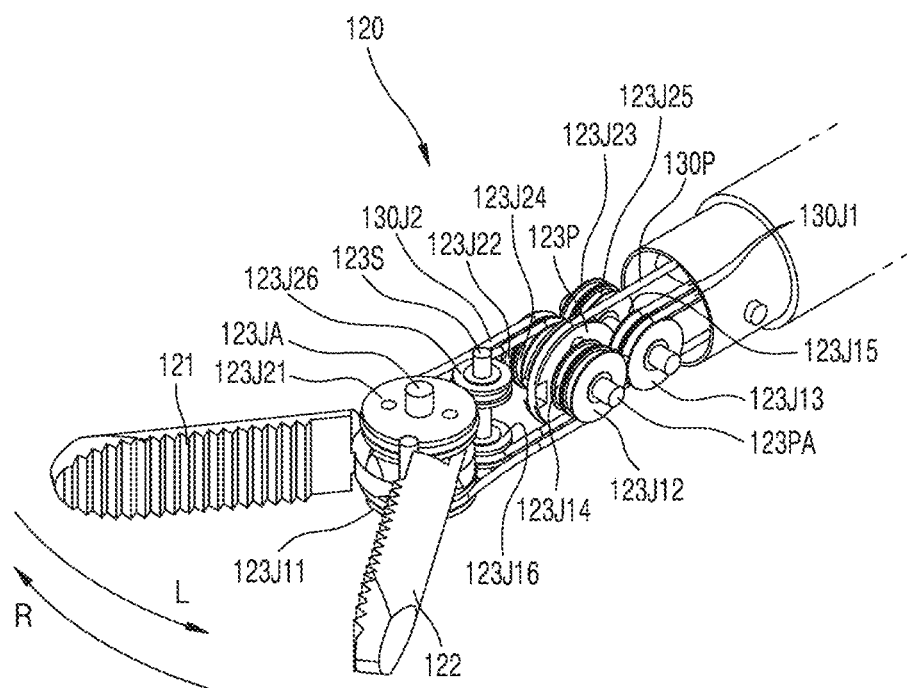
Figure 6A:
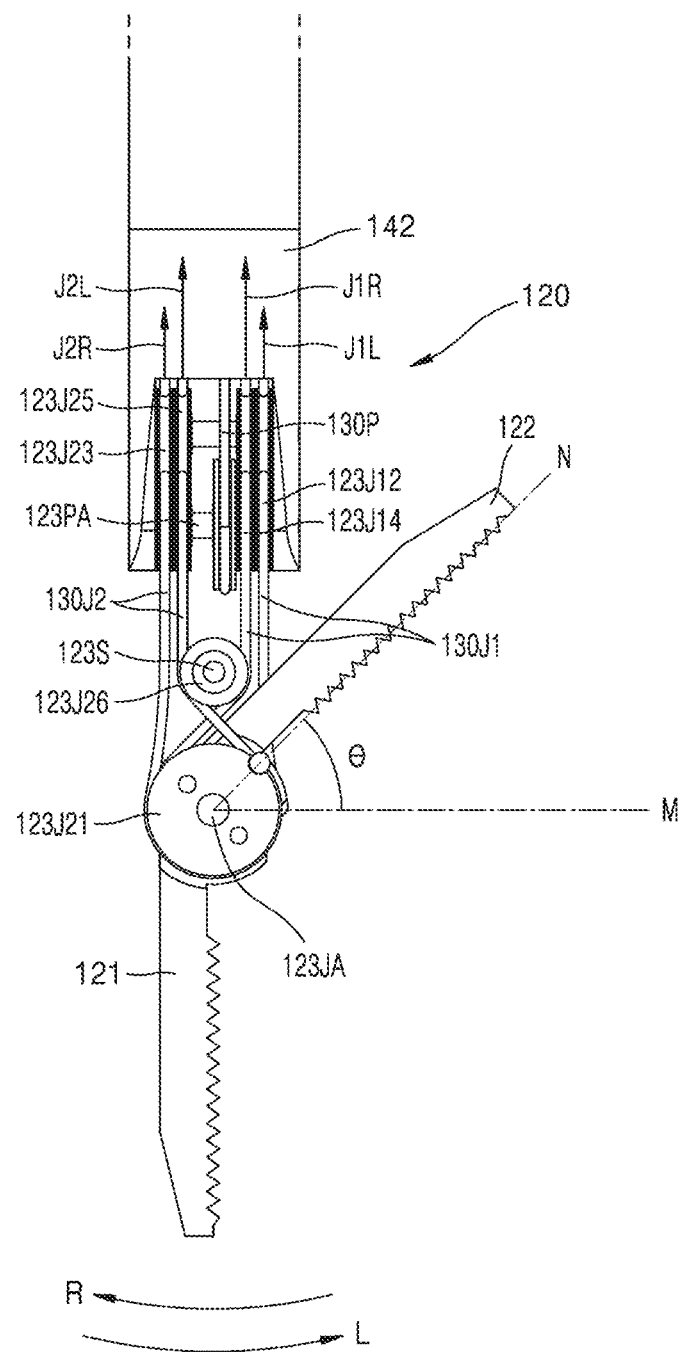
FIG. 6A is a plan view illustrating the end tool of the instrument for surgery shown in FIG. 2.

FIGS. 4 and 5 are perspective views illustrating the end tool of the instrument for surgery shown in FIG. 2, and FIG. 6A is a plan view illustrating the end tool of the instrument for surgery shown in FIG. 2.

Referring to FIGS. 4, 5 and 6A, the end the end tool 120 of the first embodiment of the present invention includes a pair of jaws 121 and 122, that is, a first jaw 121 and a second jaw 122 for gripping motion. In addition, the end tool 120 includes: a J11 pulley 123J11, a J12 pulley 123J12, a J13 pulley 123J13, a J14 pulley 123J14, and a J15 pulley 123J15 that are related to the rotation motion of the first jaw 121; and a J21 pulley 123J21, a J22 pulley 123J22, a J23 pulley 123J23, a J24 pulley 123J24, and a J25 pulley 123J25 that are related to the rotation motion of the second jaw 122. In this case, the first jaw 121, the J11 pulley 123J11, the J12 pulley 123J12, the J14 pulley 123J14, the second jaw 122, the J21 pulley 123J21, the J22 pulley 123J22, and the J24 pulley 123J24 may be configured to rotate around an end tool pitch rotation shaft 123PA.

In addition, A connecting part hub 142 is provided on an end portion of the connecting part 140 coupled to the end tool 120. The J12 pulley 123J12, the J13 pulley 123J13, the J14 pulley 123J14, the J15 pulley 123J15, the J22 pulley 123J22, the J23 pulley 123J23, the J24 pulley 123J24, and the J25 pulley 123J25 are connected to the connecting part hub 142.

Although it is illustrated that pulleys facing each other are parallel to each other, the idea of the present invention is not limited thereto. That is, the pulleys may have various positions and sizes suitable for the configuration of the end tool.

The J11 pulley 123J11 and the J21 pulley 123J21 face each other and rotate independently around a jaw rotation shaft 123JA. Here, the first jaw 121 may be fixedly coupled to the J11 pulley 123J11 so as to be rotated together with the J11 pulley 123J11, and the second jaw 122 may be fixedly coupled to the J21 pulley 123J21 so as to be rotated together with the J21 pulley 123J21. Yaw and actuation motions of the end tool 120 are performed as according to rotations of the J11 pulley 123J11 and the J21 pulley 123J21. That is, yaw motion is performed when the J11 pulley 123J11 and the J21 pulley 123J21 are rotated in the same direction, and actuation motion is performed when the J11 pulley 123J11 and the J21 pulley 123J21 are rotated in opposite directions.

In addition, a J16 pulley 123J16 and a J26 pulley 123J26 may be additionally provided as auxiliary pulleys on a side of the J11 pulley 123J11 and the J21 pulley 123J21, and the auxiliary pulleys may be rotatable on an auxiliary pulley shaft 123S. Although it is illustrated that the J16 pulley 123J16 and the J26 pulley 123J26 are configured to rotate on the single auxiliary pulley shaft 123S, the auxiliary pulleys may be configured to rotate on separate shafts, respectively. In other words, the J16 pulley 123J16 being an auxiliary pulley may be placed between the J11 pulley 123J11 and the J12 pulley 123J12/the J14 pulley 123J14. In addition, the J26 pulley 123J26 being an auxiliary pulley may be placed between the J21 pulley 123J21 and the J22 pulley 123J22/ the J24 pulley 123J24. The auxiliary pulleys will be described later in more detail.

Elements related to rotation of the J11 pulley 123J11 will be described below.

The J12 pulley 123J12 and the J14 pulley 123J14 are placed to face each other at a side of the J11 pulley 123J11.

In this case, the J12 pulley 123J12 and the J14 pulley 123J14 are independently rotatable about the end tool pitch rotation shaft 123PA. In addition, the J13 pulley 123J13 and the J15 pulley 123J15 are placed to face each other respectively at sides of the J12 pulley 123J12 and the J14 pulley 123J14. Here, the J13 pulley 123J13 and the J15 pulley 123J15 are independently rotatable around the Y-axis direction. Although it is illustrated that all of the J12 pulley 123J12, the J13 pulley 123J13, the J14 pulley 123J14, and the J15 pulley 123J15 are rotatable around the Y-axis direction, the idea of the present invention is not limited thereto, and the rotating axes of the respective pulleys may be oriented in various directions according to configurations thereof.

The first jaw wire 130J1 may be sequentially wound to make contact with at least portions of the J13 pulley 123J13, the J12 pulley 123J12, the J11 pulley 123J11, the J16 pulley 123J16, the J14 pulley 123J14, and the J15 pulley 123J15, and the first jaw wire 130J1 may move along the pulleys while rotating the pulleys.

Thus, when the first jaw wire 130J1 is pulled in the direction of an arrow J1R in FIG. 6A, the first jaw wire 130J1 rotates the J15 pulley 123J15, the J14 pulley 123J14, the J16 pulley 123J16, the J11 pulley 123J11, the J12 pulley 123J12, and the J13 pulley 123J13. At this time, as the J11 pulley 123J11 is rotated in the direction of an arrow R in FIG. 6A, the J11 pulley 123J11 rotates the first jaw 121.

On the other hand, when the first jaw wire 130J1 is pulled in the direction of an arrow J1L in FIG. 6A, the first jaw wire 130J1 rotates the J13 pulley 123J13, the J12 pulley 123J12, the J11 pulley 123J11, the J16 pulley 123J16, the J14 pulley 123J14, and the J15 pulley 123J15. At this time, as the J11 pulley 123J11 is rotated in the direction of an arrow L in FIG. 6A, the J11 pulley 123J11 rotates the first jaw 121.

Hereinafter, the auxiliary pulleys 123J16 and 123J26 will be described in more detail.

Figure 6B:
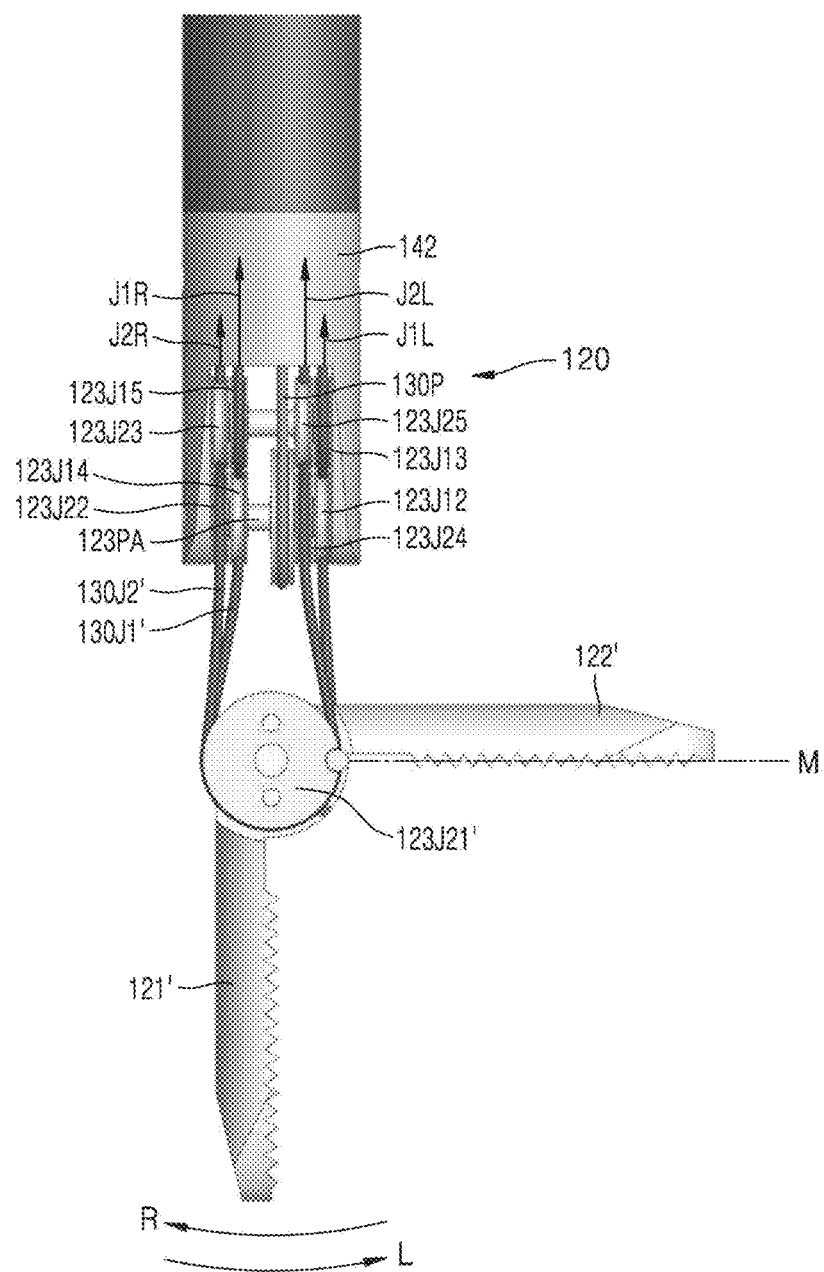
FIG. 6B is a plan view illustrating an end tool of an instrument for surgery of the related art.

The auxiliary pulleys 123J16 and 123J26 may be in contact with the first jaw wire 130J1 and the second jaw wire 130J2, thereby changing paths of the first jaw wire 130J1 and the second jaw wire 130J2 to some degree and extending the rotation radii of the first jaw 121 and the second jaw 122. That is, if no auxiliary pulley is placed as illustrated in FIG. 6B, the first jaw 121 and the second jaw 122 may be rotated up to a right angle to each other. However, according to the embodiment of the present invention, the auxiliary pulleys 123J16 and 123J26 are additionally provided such that the maximum rotation angle may be increased by θ as illustrated in FIG. 6A. This allows the two jaws of the end tool 120 to move away from each other for actuation motion in a state in which the two jaws are rotated together by 90° in yaw motion in the direction L. That is, this is because it is possible to further rotate the second jaw 122 by an additional angle θ as illustrated in FIG. 6A. Similarly actuation motion is also possible in a state in which the two jaws are rotated in yaw motion in the direction R. In other words, owing to the auxiliary pulleys 123J16 and 123J26, the range of yaw motion in which actuation motion is possible may be increased. This will now be described in more detail.

Referring to FIG. 6B, the first jaw wire 130J1 is fixedly coupled to the J11 pulley (not shown), and the second jaw wire 130J2 is fixedly coupled to the J21 pulley 123J21. Thus, if auxiliary pulleys are not arranged, each of the J11 pulley (not shown) and the J21 pulley 123J21 may only rotate to a line M in the direction of the arrow L as shown in FIG. 6B. In other words, rotation is possible only to about a right angle to prevent separation of the first jaw wire 130J1 from a fixation coupling part between the first jaw wire 130J1 and the J11 pulley 123J11. In this case, if actuation motion is performed in a state in which the first jaw 121 and the second jaw 122 are placed on the line M in FIG. 6B, the first jaw 121 may be rotated in the direction R, but the second jaw 122 may not be rotated away from the line M in the direction L. Therefore, in a state in which the first jaw 121 and the second jaw 122 are rotated to a certain angle or greater in yaw motion, actuation motion may not be smoothly performed.

In order to solve this problem, in the instrument 100 for surgery according to the embodiment of the present invention, the J16 pulley 123J16 and the J26 pulley 123J26 are additionally arranged as auxiliary pulleys at a side of the J11 pulley 123J11 and the J21 pulley 123J21. In this manner, since the J16 pulley 123J16 and the J26 pulley 123J26 are arranged to change the paths of the first jaw wire 130J1 and the second jaw wire 130J2 to some degree and thus to change tangential directions of the first jaw wire 130J1 and the second jaw wire 130J2, a fixation coupling part of the second jaw wire 130J2 and the J21 pulley 123J21 may be rotated up to a line N of FIG. 6A. That is, the fixation coupling part of the second jaw wire 130J2 and the J21 pulley 123J21 may be rotated until the coupling part is located on a common internal tangent of the J21 pulley 123J21 and the J26 pulley 123J26. Similarly, a coupling part of the first jaw wire 130J1 and the J11 pulley 123J11 may be rotated until the coupling part is located on an common internal tangent of the J11 pulley 123J11 and the J16 pulley 123J16, thereby extending the range of rotation in the direction R.

In this manner, according to the present invention, the rotation radii of the first jaw 121 and the second jaw 122 may be increased, thereby obtaining an effect of increasing the range of yaw motion in which actuation motion is normally performed for opening and closing.

Next, elements relating to the rotation of the J21 pulley 123J21 will be described.

The J22 pulley 123J22 and the J24 pulley 123J24 are placed to face each other at a side of the J21 pulley 123J21. Here, the J22 pulley 123J22 and the J24 pulley 123J24 are independently rotatable around the end tool pitch rotation shaft 123PA. In addition, the J23 pulley 123J23 and the J25 pulley 123J25 are placed to face each other at a side of the J22 pulley 123J22 and the J24 pulley 123J24. Here, the J23 pulley 123J23 and the J25 pulley 123J25 are independently rotatable around the Y-axis direction. Although it is illustrated that all of the J22 pulley 123J22, the J23 pulley 123J23, the J24 pulley 123J24, and the J25 pulley 123J25 are rotatable around the Y-axis direction, the idea of the present invention is not limited thereto, and the rotating axes of the respective pulleys may be oriented in various directions according to configurations thereof.

The second jaw wire 130J2 may be sequentially wound to make contact with at least portions of the J23 pulley 123J23, the J22 pulley 123J22, the J21 pulley 123J21, the J26 pulley 123J26, the J24 pulley 123J24, and the J25 pulley 123J25, and the second jaw wire 130J2 may move along the pulleys while rotating the pulleys.

Therefore, when the second jaw wire 130J2 is pulled in the direction of an arrow J2R of FIG. 6A, the second jaw wire 130J2 rotates the J23 pulley 123J23, the J22 pulley 123J22, the J21 pulley 123J21, the J26 pulley 123J26, the J24 pulley 123J24, and the J25 pulley 123J25. At this time, as the J21 pulley 123J21 is rotated in the direction of the arrow R of FIG. 6A, the J21 pulley 123J21 rotates the second jaw 122.

On the other hand, when the second jaw wire 130J2 is pulled in the direction of an arrow J2L of FIG. 6A, the second jaw wire 130J2 rotates the J25 pulley 123J25, the J24 pulley 123J24, the J26 pulley 123J26, the J21 pulley 123J21, the J22 pulley 123J22, and the J23 pulley 123J23. At this time, as the J21 pulley 123J21 is rotated in the direction of the arrow L of FIG. 6A, the J21 pulley rotates the second jaw 122.

In addition, if an end portion of the first jaw wire 130J1 is pulled in the direction of the arrow J1R of FIG. 6A, and at the same time the other end portion of the first jaw wire 130J1 is pulled in the direction of the arrow J1L of FIG. 6A (that is, if both end portions of the first jaw wire 130J1 are pulled), since the first jaw wire 130J1 is wound around lower portions of the J12 pulley 123J12 and the J14 pulley 123J14 that are rotatable around the end tool pitch rotation shaft 123PA as shown in FIG. 5, the J11 pulley 123J11 to which the first jaw wire 130J1 is fixedly coupled, the first jaw 121, the jaw rotation shaft 123JA, and an end tool hub 123a, and the second jaw 122 connected thereto are all rotated counterclockwise around the end tool pitch rotation shaft 123PA, and as a result, the end tool 120 is rotated downward in pitch motion. At this time, since the second jaw 122 and the second jaw wire 130J2 fixedly coupled to the second jaw 122 is wound around upper portions of the J22 pulley 123J22 and the J24 pulley 123J24 that are rotatable around the end tool pitch rotation shaft 123PA, both end portions of the second jaw wire 130J2 are respectively moved in directions opposite the directions of the arrows J2L and J2R.

In contract, if an end portion of the second jaw wire 130J2 is pulled in the direction of the arrow J2R of FIG. 6A, and at the same time the other end portion of the second jaw wire 130J2 is pulled in the direction of the arrow J2L of FIG. 6A, since the second jaw wire 130J2 is wound around the upper portions of the J22 pulley 123J22 and the J24 pulley 123J24 that are rotatable around the end tool pitch rotation shaft 123PA as shown in FIG. 5, the J21 pulley 123J21 to which the second jaw wire 130J1 is fixedly coupled, the second jaw 122, the jaw rotation shaft 123JA, and the end tool hub 123a, and the first jaw 121 connected thereto are all rotated clockwise around the end tool pitch rotation shaft 123PA, and as a result, the end tool 120 is rotated upward in pitch motion. At this time, since the first jaw 121 and the first jaw wire 130J1 fixedly coupled to the first jaw 121 are wound around the lower portions of the J12 pulley 123J12 and the J14 pulley 123J14 that are rotatable around the end tool pitch rotation shaft 123PA, both end portions of the first jaw wire 130J1 are respectively moved in directions opposite the directions of the arrows J1L and J1R.

In addition, the end tool 120 of the instrument 100b for surgery may further include a pitch pulley 123P, the manipulation part 110 may further include a pitch wire end pulley 115P, and the power transmission part 130 may further include the pitch wire 130P. In detail, the pitch pulley 123P of the end tool 120 may be rotatable about the end tool pitch rotation shaft 123PA and may be fixedly coupled to the end tool hub 123a. In addition, a pitch pulley of the manipulation part may be rotatable about a pitch rotation shaft and may be fixedly coupled to a pitch manipulation part (not shown). In addition, the pitch wire 130P may connect the pitch pulley 123P of the end tool 120 to the pitch pulley of the manipulation part.

Thus, if a user rotates a first handle 114 around a pitch rotation shaft 1111 while holding the first handle 114 of the manipulation part 110, a pitch pulley coupled to the first handle 114 is rotated around the pitch rotation shaft 1111, and the rotation of the pitch pulley is transmitted to the pitch pulley 123P of the end tool 120 through the pitch wire 130P to rotate the pitch pulley 123P. As a result, the end tool 120 is rotated, and a pitch motion is performed.

That is, since the instrument 100 for surgery according to the first embodiment of the present invention includes the pitch pulley 123P of the end tool 120, the pitch wire end pulley 115P of the manipulation part 110, and the pitch wire 130P of the power transmission part 130, a pitch motion driving force of the pitch manipulation part 111 may be more completely transmitted to the end tool 120, and thus reliability of motion may be improved.

Figure 6C:
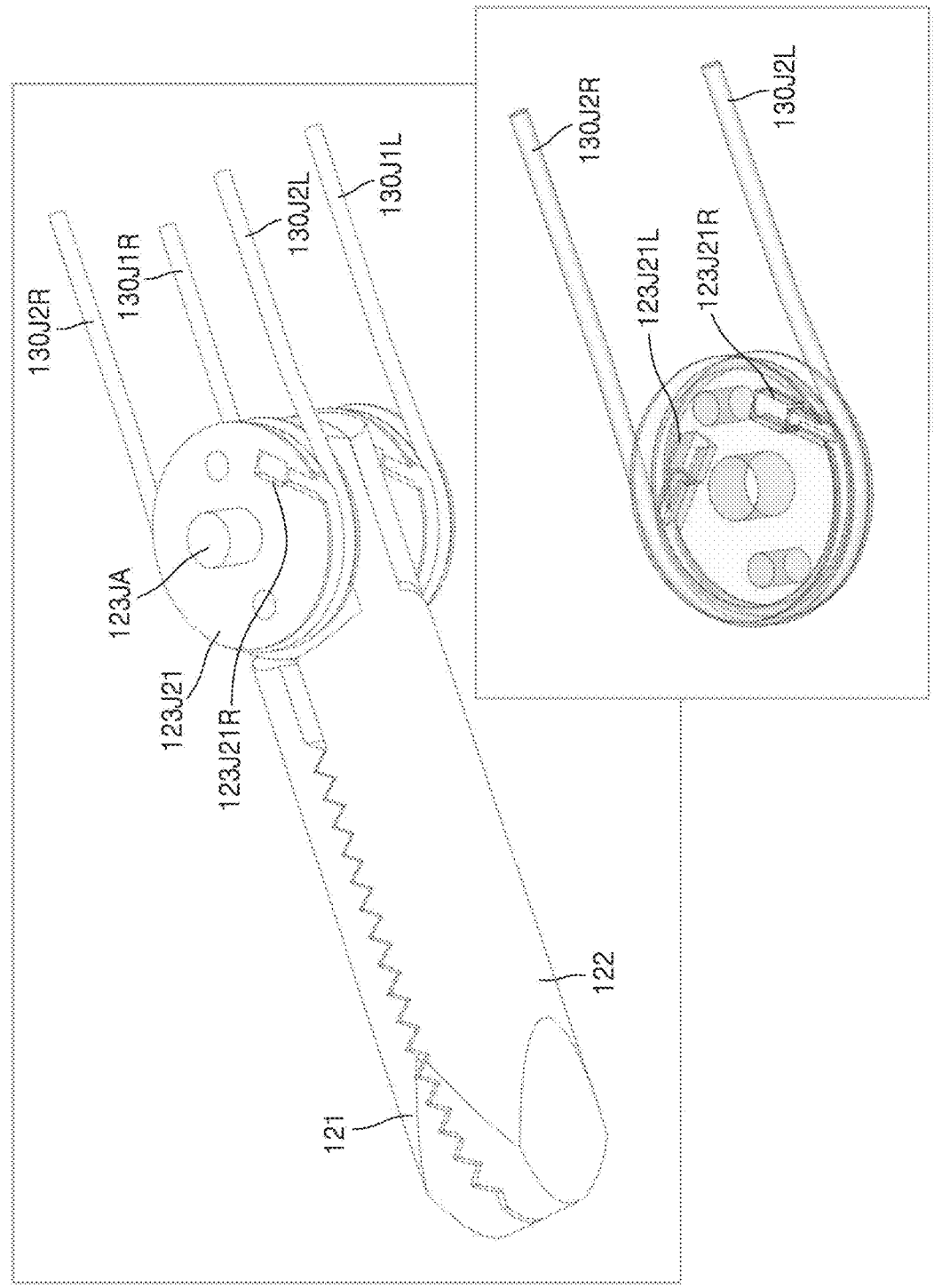
FIG. 6C is a view illustrating a modification of the end tool shown in FIG. 6A.

FIG. 6C is a view illustrating a modification of the coupling structure of the end tool and wires.

Referring to FIG. 6C, the second jaw wire 130J2 is coupled to the J21 pulley 123J21 as follows. The second jaw wire 130J2 is divided into two wires based on the J21 pulley 123J21: a second jaw R wire 130J2R and a second jaw L wire 130J2L, and ends of the second jaw R and L wires 130J2R and 130J2L are respectively coupled to the J21 pulley 123J21. That is, an end portion of the second jaw R wire 130J2R is coupled to a first coupling part 123J21R of the J21 pulley 123J21, and an end portion of the second jaw L wire 130J2L is coupled to a second coupling part 123J21L of the J21 pulley 123J21.

In this case, the coupling parts 123J21R and 123J21L of the J21 pulley 123J21 are positioned to overlap the R and L wires 130J2R and 130J2L. Thus, the rotation radius of the second jaw 122 limited to 90° in FIG. 6B may be increased. That is, the rotation radius of the second jaw 122 may be increased as shown in FIG. 6A.

Similarly, the first jaw wire 130J1 may be fixedly coupled to the J11 pulley 123J11, and thus the rotation radius of the first jaw 121 may be increased. In this manner, the range of yaw motion in which normal opening/closing actuation motion is possible may be increased.

Figure 6D:
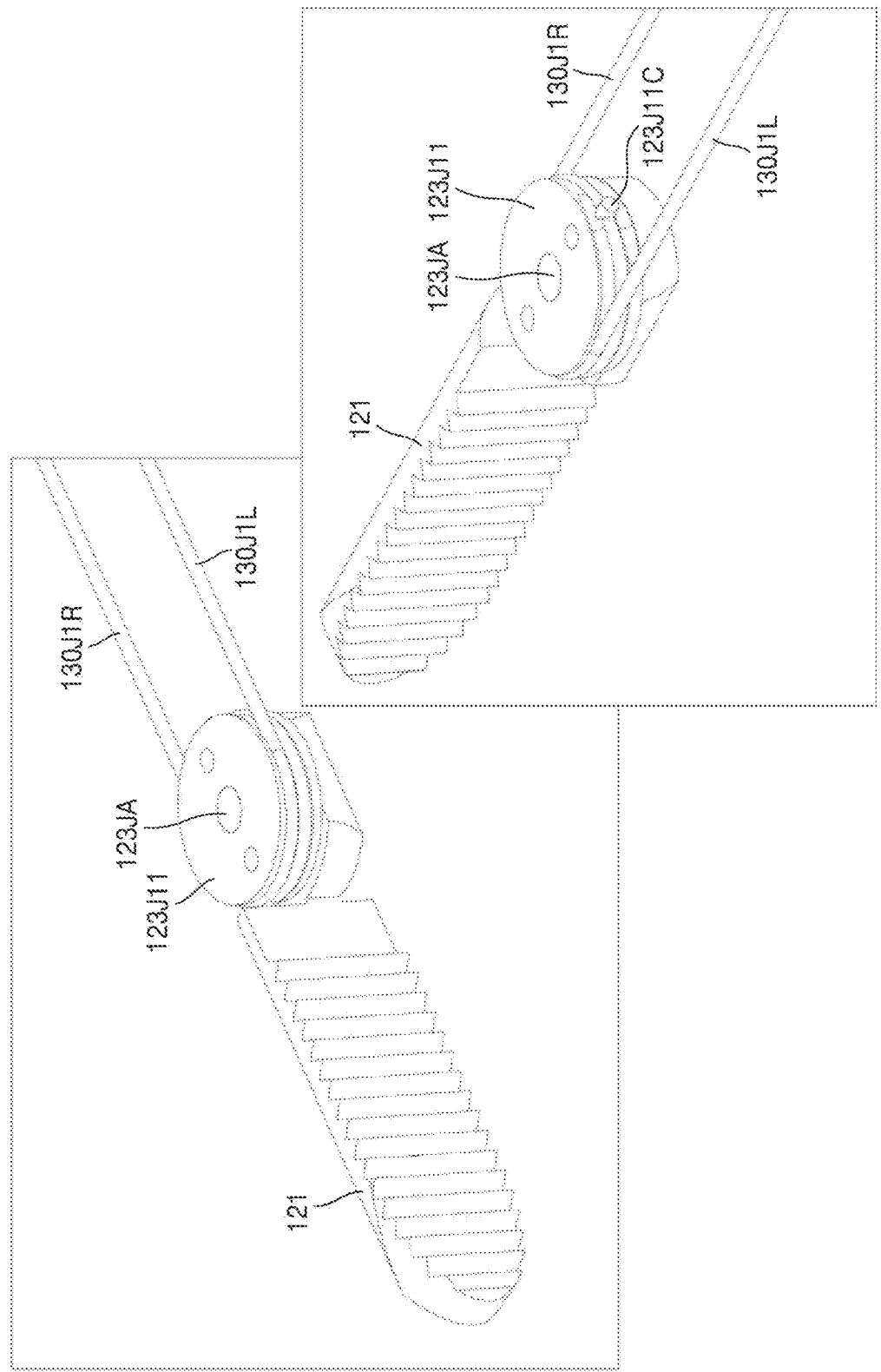
FIG. 6D is a view illustrating a modification of the end tool shown in FIG. 6A.

FIG. 6D is a view illustrating another modification of the coupling structure of the end tool and wires.

Referring to FIG. 6D, the first jaw wire 130J1 is coupled to the J11 pulley 123J11 as follows. The first jaw wire 130J1 is divided into two wires based on the J11 pulley 123J11: a first jaw R wire 130J1R and a first jaw L wire 130J1L, and ends of the first jaw R and L wires 130J1R and 130J1L are respectively coupled to a coupling member 123J11C of the J11 pulley 123J11. In this case, the coupling member 123J21C is provided on a side of the J11 pulley 123J11 opposite the first jaw 121, wherein an end portion of the first jaw R wire 130J1R is coupled to a side of the coupling member 123J21C, and an end portion of the first jaw L wire 130J1L is coupled to the other side of the coupling member 123J21C.

In this case, the position of the coupling member 123J21C of the J11 pulley 123J11 is determined such that the R and L wires 130J1R and 130J1L may be further wound a half turn. This increases the rotation radius of the second jaw 122 limited to 90° in FIG. 6B, and thus the second jaw 122 may have an increased rotation radius as shown in FIG. 6A.

In the same manner, the second jaw wire 130J2 may be fixedly coupled to the J21 pulley 123J21, and thus the rotation radius of the second jaw 122 may be increased. In this manner, the range of yaw motion in which normal opening/closing actuation motion is possible may be increased.

(Manipulation Part)

Figure 7A:
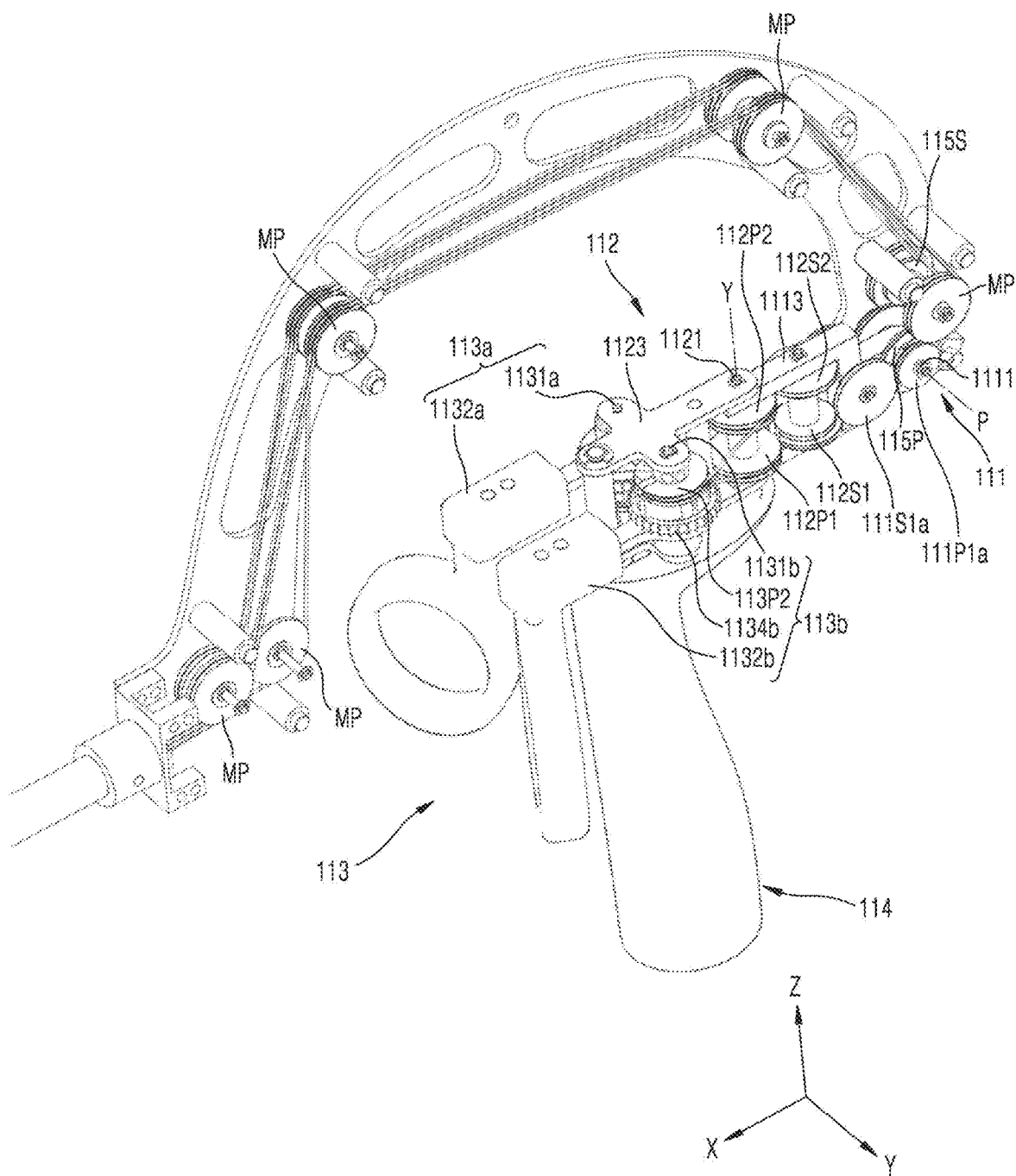
FIGS. 7A and 7B are perspective views illustrating a manipulation part of the instrument for surgery shown in FIG. 2.
Figure 7B:
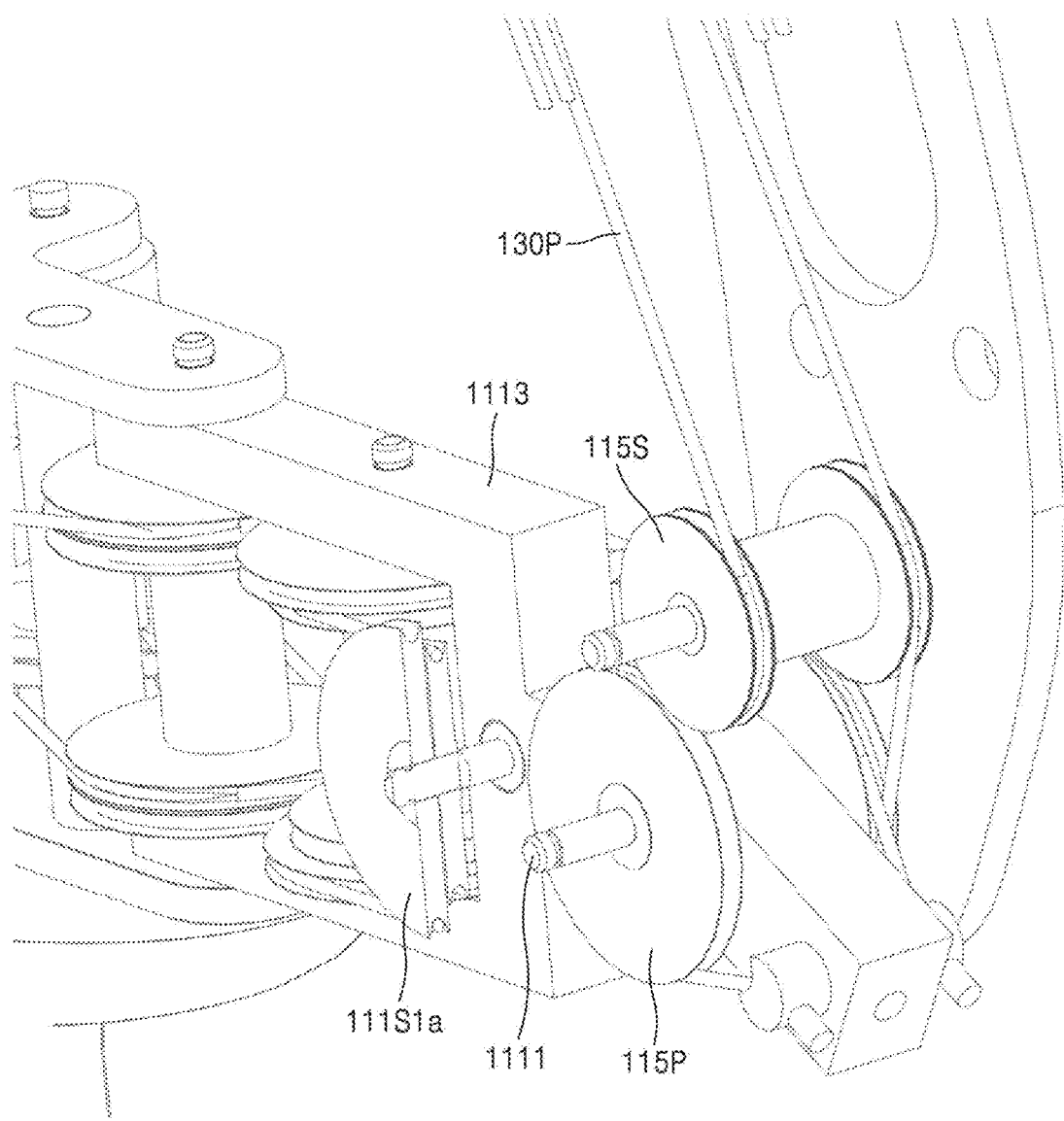

FIG. 7A is a perspective view illustrating the manipulation part of the instrument for surgery shown in FIG. 2, and FIG. 7B is a rear perspective view illustrating the instrument for surgery shown in FIG. 2.

Referring to FIG. 2 to FIG. 7, the manipulation part 110 of the instrument 100 for surgery includes the first handle 114 which a user may grip, the actuation manipulation part 113 configured to control actuation motion of the end tool 120, the yaw manipulation part 112 configured to control yaw motion of the end tool 120, and the pitch manipulation part 111 configured to control pitch motion of the end tool 120.

First, an example operation of the instrument 100 for surgery shown in FIG. 2 will be described. In a state in which a user holds the first handle 114 with his/her palm, the user may perform a pitch motion by rotating the first handle 114 around the Y axis (that is, around the pitch rotation shaft 1111) and a yaw motion by rotating the first handle 114 around the Z axis (that is, around a yaw rotation shaft 1121). In addition, in a state in which the user inserts his/her thumb or index finger in the actuation manipulation part 113, the user may rotate the actuation manipulation part 113 to perform an actuation motion.

Here, when the manipulation part 110 of the instrument 100 for surgery is rotated in a direction with respect to the connecting part 140, the end tool 120 is rotated intuitively in the same direction as the direction in which the manipulation part 110 is manipulated. In other words, if the first handle 114 of the manipulation part 110 is rotated in a certain direction, the end tool 120 is also rotated intuitively in the same direction as the certain direction, and thus a pitch motion or a yaw motion is performed. Here, the expression "intuitively in the same direction" may be used to denote that the direction in which a finger of a user holding the manipulation part 110 is moved is substantially the same as the direction in which a distal end portion of the end tool 120 is moved. The expression "intuitively in same direction" may not refer to completely in the same direction in a three-dimensional coordinate system. For example, it may be understood that the expression refers to sameness to the following extend: if a finger of a user is moved leftward, the distal end portion of the end tool 120 is also be moved leftward, and if the finger of the user is moved downward, the distal end portion of the end tool 120 is also moved downward.

To this end, in the instrument 100 for surgery of the first embodiment of the present invention, the manipulation part 110 and the end tool 120 are provided in the same direction with respect to a plane perpendicular to an extension axis (the X axis) of the connecting part 140. That is, when viewed based on a YZ plane of FIG. 2, the manipulation part 110 extends in a positive (+) X-axis direction, and the end tool 120 also extends in the positive (+) X-axis direction. In other words, it may be stated that the formation direction of the end tool 120 on an end portion of the connecting part 140 is the same as the formation direction of the manipulation part 110 on the other end portion of the connecting part 140 based on the YZ plane. Furthermore, in other words, it may be stated that the manipulation part 110 is located in a direction away from the body of a user holding the manipulation part 110, that is, in a direction in which the end tool 120 is provided. That is, in the case of parts such as the first handle 114 and actuation rotation parts 1132a and 1132b which a user holds and moves for actuation, yaw, and pitch motions, each moving portion extends from the rotation center of a corresponding joint for the motions in the positive (+) X-axis direction. In this manner, the manipulation part 110 may be configured like the end tool 120 in which each moving portion extends from the rotation center of a corresponding joint for the motions in the positive (+) X-axis direction, and as described with reference to FIG. 1, a manipulation direction of a user may be identical to an operation direction of the end tool from the viewpoint of rotation directions and leftward and rightward directions. As a result, intuitively the same manipulation may be performed.

In detail, in the case of an instrument for surgery of the related art, a direction in which a user manipulate a manipulation part is different from a direction in which the end tool is actually operated, that is, intuitively different from the direction in which the end tool is actually operated. Thus, surgeons may not easily intuitively manipulate the instrument for surgery and may spend a long time to learn a skill of operating the end tool in desired directions. In some cases, patients may suffer from malfunctions.

In order to solve such problems, the instrument 100 for surgery of the first embodiment of the present invention is configured such that the manipulation direction of the manipulation part 110 and the operation direction of the end tool 120 are intuitively identical to each other. To this end, the manipulation part 110 is configured like the end tool 120. That is, in the manipulation part 110, portions that are actually moved for actuation, yaw, and pitch motions extend respectively from rotation centers of corresponding joints in the positive (+) X-axis direction. This will now be described in more detail.

The first handle 114 may be configured such that a user may grip the first handle 114 with his/her hand. In particular, a user may grip the first handle 114 by holding around the first handle 114 with his/her palm. In addition, the actuation manipulation part 113 and the yaw manipulation part 112 are provided above the first handle 114, and the pitch manipulation part 111 is provided at a side of the yaw manipulation part 112. In addition, another end portion of the pitch manipulation part 111 is connected to the bent part 141 of the connecting part 140.

The actuation manipulation part 113 includes a first actuation manipulation part 113a and a second actuation manipulation part 113b. The first actuation manipulation part 113a includes a first actuation rotation shaft 1131a, a first actuation rotation part 1132a, a first actuation pulley 113P1, and a first actuation gear 1134a. The second actuation manipulation part 113b includes a second actuation rotation shaft 1131b, a second actuation rotation part 1132b, a second actuation pulley 113P2, and a second actuation gear 1134b. Here, the first and second actuation rotation parts 1132a and 1132b may function as a second handle.

Here, the actuation rotation shafts 1131a and 1131b may make a predetermined angle with an XY plane on which the connecting part 140 is located. For example, the actuation rotation shafts 1131a and 1131b may be parallel with the Z axis. In this state, if the pitch manipulation part 111 or the yaw manipulation part 112 is rotated, the coordinate system of the actuation manipulation part 113 may be relatively varied. However, the idea of the present invention is not limited thereto, and the actuation rotation shafts 1131a and 1131b may be oriented in various directions according to ergonomic designs for the hand structure of a user holding the actuation manipulation part 113.

In addition, the first actuation rotation part 1132a, the first actuation pulley 113P1, and the first actuation gear 1134a may be fixedly coupled to each other so as to be rotated together around the first actuation rotation shaft 1131a. Here, the first actuation pulley 113P1 may include a single pulley or two pulleys fixedly coupled to each other.

Similarly, the second actuation rotation part 1132b, the second actuation pulley 113P2, and the second actuation gear 1134b may be fixedly coupled to each other so as to be rotated together around the second actuation rotation shaft 1131*b*. Here, the second actuation pulley 113P2 may include a single pulley or two pulleys fixedly coupled to each other.

Here, the first actuation gear 1134*a* and the second actuation gear 1134*b* may be engaged with each other, and thus if one of the first and second actuation gears 1134*a* and 1134*b* is rotated, the first and second actuation gears 1134*a* and 1134*b* may be rotated together in opposite directions.

The yaw manipulation part 112 may include a yaw rotation shaft 1121, a first jaw yaw pulley 112P1, a second jaw yaw pulley 112P2, and a yaw frame 1123. In addition, the yaw manipulation part 112 may further include a first jaw yaw auxiliary pulley 112S1 provided on a side of the first jaw yaw pulley 112P1, and a second jaw yaw auxiliary pulley 112S2 provided on a side of the second jaw yaw pulley 112P2. Here, the first jaw yaw auxiliary pulley 112S1 and the second jaw yaw auxiliary pulley 112S2 may be coupled to a pitch frame 1113 (described later).

In the drawings, it is illustrated that the yaw manipulation part 112 includes the first jaw yaw pulley 112P1 and the second jaw yaw pulley 112P2, and each of the first jaw yaw pulley 112P1 and the second jaw yaw pulley 112P2 includes two pulleys facing each other and independently rotatable. However, the idea of the present invention is not limited thereto. That is, according to the configuration of the yaw manipulation part 112, the yaw manipulation part 112 may include one or more pulleys having the same diameter or different diameters.

Specifically, the yaw rotation shaft 1121 is provided on a side of the actuation manipulation part 113 above the first handle 114. In this case, the first handle 114 is rotatable around the yaw rotation shaft 1121.

Here, the yaw rotation shaft 1121 may make a predetermined angle with the XY plane in which the connecting part 140 is provided. For example, the yaw rotation shaft 1121 may be oriented in a direction parallel to the Z axis, and in this state, if the pitch manipulation part 111 is rotated, the coordinate system of the yaw rotation shaft 1121 may be relatively varied as described above. However, the idea of the present invention is not limited thereto, and the yaw rotation shaft 1121 may be oriented in various directions according to ergonomic designs for the hand structure of a user holding the manipulation part 110.

In addition, the first jaw yaw pulley 112P1 and the second jaw yaw pulley 112P2 are coupled to the yaw rotation shaft 1121 such that the first jaw yaw pulley 112P1 and the second jaw yaw pulley 112P2 may be rotated on the yaw rotation shaft 1121. In addition, the first jaw wire 130J1 may be wound around the first jaw yaw pulley 112P1, and the second jaw wire 130J2 may be wound around the second jaw yaw pulley 112P2. In this case, each of the first jaw yaw pulley 112P1 and the second jaw yaw pulley 112P2 may include two pulleys facing each other and independently rotatable. Therefore, an inward wire and an outward wire may be respectively wound around separate pulleys and thus may not interfere with each other.

The yaw frame 1123 connects the first handle 114, the yaw rotation shaft 1121, the first actuation rotation shaft 1131*a*, and the second actuation rotation shaft 1131*b* such that the first handle 114, the yaw manipulation part 112, and the actuation manipulation part 113 may be rotated together around the yaw rotation shaft 1121.

The pitch manipulation part 111 may include the pitch rotation shaft 1111, a first jaw pitch pulley-a 111P1*a*, a first jaw pitch pulley-b 111P1*b*, a second jaw pitch pulley-a 111P2*a*, a second jaw pitch pulley-b 111P2*b*, and the pitch frame 1113. In addition, the pitch manipulation part 111 may further include a first jaw pitch auxiliary pulley-a 111S1*a* provided at a side of the first jaw pitch pulley-a 111P1*a*, a first jaw pitch auxiliary pulley-b 111S1*b* provided at a side of the first jaw pitch pulley-b 111P1*b*, a second jaw pitch auxiliary pulley-a 111S2*a* provided at a side of the second jaw pitch pulley-a 111P2*a*, and a second jaw pitch auxiliary pulley-b 111S2*b* provided at a side of the second jaw pitch pulley-b 111P2*b*. The pitch manipulation part 111 is connected to a bent part 141 of a connecting part 140 through the pitch rotation shaft 1111.

In detail, the pitch frame 1113 serves as a base frame of the pitch manipulation part 111, and the yaw rotation shaft 1121 is rotatably coupled to an end portion of the pitch frame 1113. That is, the yaw frame 1123 is rotatable around the yaw rotation shaft 1121 with respect to the pitch frame 1113.

As described above, the yaw frame 1123 connects the first handle 114, the yaw rotation shaft 1121, the first actuation rotation shaft 1131*a*, and the second actuation rotation shaft 1131*b* to each other, and is also connected to the pitch frame 1113. Therefore, if the pitch frame 1113 is rotated around the pitch rotation shaft 1111, the yaw frame 1123, the first handle 114, the yaw rotation shaft 1121, the first actuation rotation shaft 1131*a*, and the second actuation rotation shaft 1131*b* connected to the pitch frame 1113 are rotated together. That is, if the pitch manipulation part 111 is rotated around the pitch rotation shafts 1111, the actuation manipulation part 113 and the yaw manipulation part 112 are rotated together with the pitch manipulation part 111. In other words, if a user rotates the first handle 114 around the pitch rotation shaft 1111, the actuation manipulation part 113, the yaw manipulation part 112, and the pitch manipulation part 111 are moved together.

The pitch manipulation part 111, the first jaw pitch pulley-a 111P1*a*, the first jaw pitch pulley-b 111P1*b*, the second jaw pitch pulley-a 111P2*a*, and the second jaw pitch pulley-b 111P2*b* are coupled to the pitch frame 1113. In this case, the first jaw pitch pulley-a 111P1*a*, the first jaw pitch pulley-b 111P1*b*, the second jaw pitch pulley-a 111P2*a*, and the second jaw pitch pulley-b 111P2*b* are coupled to the pitch rotation shaft 1111 in a manner rotatable around the pitch rotation shaft 1111.

Here, the first jaw pitch pulley-a 111P1*a* and the first jaw pitch pulley-b 111P1*b* may face each other and may be independently rotated. Therefore, an inward wire and an outward wire may be respectively wound around separate pulleys and thus may not interfere with each other. Similarly, the second jaw pitch pulley-a 111P2*a* and the second jaw pitch pulley-b 111P2*b* may face each other and may be independently rotated. Therefore, an inward wire and an outward wire may be respectively wound around separate pulleys and thus may not interfere with each other.

Referring to FIG. 7B, the pitch wire end pulley 115P is fixedly coupled to the pitch frame 1113 and rotatable together with the pitch frame 1113. In addition, the pitch wire 130P is fixedly coupled to the pitch frame 1113 through a pitch wire auxiliary pulley 115S and the pitch wire end pulley 115P. As a result, the pitch frame 1113 and the pitch wire end pulley 115P may be rotated together around the pitch rotation shaft 1111 by pitch rotation.

The pitch wire 130P is operated as follows.

The pitch pulley 123P is fixedly coupled to the end tool hub 123*a* of the end tool 120, and the manipulation part 110 includes the pitch wire end pulley 115P, wherein the pitch pulley 123P and the pitch wire end pulley 115P are connected to each other through the pitch wire 130P such that pitch motion of the end tool 120 may be easily performed by pitch-manipulating the manipulation part 110. Here, both ends of the pitch wire 130P are fixedly coupled to the pitch frame 1113 respectively through the pitch wire auxiliary pulley 115S and the pitch wire end pulley 115P, and the pitch wire end pulley 115P is also fixedly coupled to the pitch frame 1113. That is, the pitch frame 1113 and the pitch wire end pulley 115P are rotated together about the pitch rotation shaft 1111 by pitch rotation of the manipulation part, and as a result, both sides of the pitch wire 130P are also moved in opposite directions such that additional power for pitch rotation may be transmitted independently of pitch motion of the end tool by the first jaw wire 130J1 and the second jaw wire 130J2.

The first handle 114, the pitch manipulation part 111, the yaw manipulation part 112, and the actuation manipulation part 113 are connected as follows. The actuation rotation shafts 1131a and 1131b, the yaw rotation shaft 1121, and the pitch rotation shaft 1111 may be provided on the first handle 114. In this case, since the actuation rotation shafts 1131a and 1131b are directly provided on the first handle 114, and the first handle 114 and the actuation manipulation part 113 may be directly connected to each other. In addition, since the yaw rotation shaft 1121 is directly provided on the first handle 114, the first handle 114 and the yaw manipulation part 112 may be directly connected to each other. However, since the pitch manipulation part 111 is provided at a side of the yaw manipulation part 112 and connected to the yaw manipulation part 112, the pitch manipulation part 111 may not be directly connected to the first handle 114 but may be indirectly connected to the first handle 114 through the yaw manipulation part 112.

Referring to the drawings, in the instrument 100 for surgery according to the first embodiment of the present invention, the pitch manipulation part 111 and the end tool 120 may be provided on the same axis or on parallel axes (to the X axis). That is, the pitch rotation shaft 1111 of the pitch manipulation part 111 is provided on an end portion of the bent part 141 of the connecting part 140, and the end tool 120 is provided on the other end portion of the connecting part 140.

In addition, one or more relay pulleys MP may be placed on a middle portion of the connecting part 140, particularly, on the bent part 141 of the connecting part 140 to change paths of wires or guide wires. At least portions of wires may be wound around the relay pulleys MP, thereby guiding paths of the wires and arranging the wires along a bent shape of the bent part 141.

In the drawings, it is illustrated that the connecting part 140 includes the bent part 141 and has a curved shape with a predetermined radius of curvature. However, the idea of the present invention is not limited thereto. If necessary, the connecting part 140 may have a straight shape or may be bent at least one time, and even in this case, it may be stated that the pitch manipulation part 111 and the end tool 120 are provided substantially on the same axis or parallel axes. In addition, although FIG. 3 illustrates that the pitch manipulation part 111 and the end tool 120 are provided on an axis parallel to the X axis, the idea of the present invention is not limited thereto. For example, the pitch manipulation part 111 and the end tool 120 may be provided on different axes.

Actuation, yaw, and pitch motions in the present embodiment are described below.

First, actuation motion is described below.

In a state in which a user inserts his/her index finger in the first actuation rotation part 1132a and his/her thumb in the second actuation rotation part 1132b, if the user rotates the actuation rotation parts 1132a and 1132b using one or both of his/her index finger and thumb, the first actuation pulley 113P1 and the first actuation gear 1134a fixedly coupled to the first actuation rotation part 1132a are rotated around the first actuation rotation shaft 1131a, and the second actuation pulley 1133b and the second actuation gear 1134b fixedly coupled to the second actuation rotation part 1132b are rotated around the second actuation rotation shaft 1131b. At this time, the first actuation pulley 113P1 and the second actuation pulley 113P2 are rotated in opposite directions, and thus the first jaw wire 130J1 fixedly coupled to the first actuation pulley 113P1 at an end portion thereof and the second jaw wire 130J2 fixedly coupled to the second actuation pulley 113P2 at an end portion thereof are also moved in opposite directions. Then, rotating force is transmitted to the end tool 120 through the power transmission part 130, and two jaws 121 and 122 of the end tool 120 perform an actuation motion. Here, as described above, the actuation motion refers to a motion in which the two jaws 121 and 122 is splayed or closed while being rotated in opposite directions. That is, if the actuation rotation parts 1132a and 1132b of the actuation manipulation part 113 are rotated toward each other, the first jaw 121 is rotated counterclockwise, and the second jaw 122 is rotated clockwise, thereby closing the end tool 120. If the actuation rotation parts 1132a and 1132b of the actuation manipulation part 113 are rotated away from each other, the first jaw 121 is rotated clockwise, and the second jaw 122 is rotated counterclockwise, thereby opening the end tool 120. In the present embodiment, the first and second actuation rotation parts 1132a and 1132b function as a second hand for actuation motion, and the second handle may be manipulated by gripping the second handle two fingers. However, the actuation manipulation part 113 for actuation motion in which two jaws of the end tool 120 are opened or closed may be configured in a manner different from the aforementioned manner. In a modification example, the first actuation pulley 113P1 and the second actuation pulley 113P2 may be oppositely driven using a single actuation rotation part.

Next, yaw motion will be described below.

If a user rotates the first handle 114 around the yaw rotation shaft 1121 while holding the first handle 114, the actuation manipulation part 113 and the yaw manipulation part 112 are rotated around the yaw rotation shaft 1121 in yaw motion. That is, if the first actuation pulley 113P1 of the first actuation manipulation part 113a to which the first jaw wire 130J1 is fixedly coupled is rotated around the yaw rotation shaft 1121, the first jaw wire 130J1 wound around the first jaw yaw pulley 112P1 is moved. Likewise, if the second actuation pulley 113P2 of the second actuation manipulation part 113b to which the second jaw wire 130J2 is fixedly coupled is rotated around the yaw rotation shaft 1121, the second jaw wire 130J2 wound around the second jaw yaw pulley 112P2 is moved. At this time, the first jaw wire 130J1 connected to the first jaw 121 and the second jaw wire 130J2 connected to the second jaw 122 are wound around the first jaw yaw pulley 112P1 and the second jaw yaw pulley 112P2 in such a manner that the first jaw 121 and the second jaw 122 are rotated in the same direction in the yaw motion. Then, rotating force is transmitted to the end tool 120 via the power transmission part 130, and thus the two jaws 121 and 122 of the end tool 120 are rotated in the same direction in yaw motion.

At this time, since the yaw frame 1123 connects the first handle 114, the yaw rotation shaft 1121, the first actuation rotation shaft 1131a, and the second actuation rotation shaft 1131b to each other, the first handle 114, the yaw manipulation part 112, and the actuation manipulation part 113 are rotated together around the yaw rotation shaft 1121.

Next, pitch motion will be described below.

If a user rotates the first handle 114 around the pitch rotation shaft 1111 while holding the first handle 114, the actuation manipulation part 113, the yaw manipulation part 112, and the pitch manipulation part 111 are rotated around the pitch rotation shaft 1111 in pitch motion. That is, if the first actuation pulley 113P1 of the first actuation manipulation part 113a to which the first jaw wire 130J1 is fixedly coupled is rotated around the pitch rotation shaft 1111, the first jaw wire 130J1 wound around the first jaw pitch pulley-a 111P1a and the first jaw pitch pulley-b 111P1b is moved. Likewise, if the second actuation pulley 113P2 of the second actuation manipulation part 113b to which the second jaw wire 130J2 is fixedly coupled is rotated around the pitch rotation shaft 1111, the second jaw wire 130J2 wound around the second jaw pitch pulley-a 111P2a and the second jaw pitch pulley-b 111P2b is moved. At this time, as described with reference to FIG. 5, while both strands of the first jaw wire 130J1 are rotated in the same direction, and both strands of the second jaw wire 130J2 are rotated in the same direction, the first jaw wire 130J1 and the second jaw wire 130J2 are wound around the first jaw pitch pulleys 111P1a and 111P1b and the second jaw pitch pulleys 111P2a and 111P2b such that the first jaw 121 and the second jaw 122 may be pitch-rotated. Then, rotating force is transmitted to the end tool 120 via the power transmission part 130, and thus the two jaws 121 and 122 of the end tool 120 perform a pitch motion.

At this time, since the pitch frame 1113 is connected to the yaw frame 1123 and the yaw frame 1123 connects the first handle 114, the yaw rotation shaft 1121, the first actuation rotation shaft 1131a, and the second actuation rotation shaft 1131b to each other, if the pitch frame 1113 is rotated around the pitch rotation shaft 1111, the yaw frame 1123, the first handle 114, the yaw rotation shaft 1121, the first actuation rotation shaft 1131a, and the second actuation rotation shaft 1131b connected to the pitch frame 1113 are rotated together. That is, if the pitch manipulation part 111 is rotated around the pitch rotation shaft 11111, the actuation manipulation part 113 and the yaw manipulation part 112 are rotated together with the pitch manipulation part 111.

In short, according to the instrument 100 for surgery of the embodiment of the present invention, pulleys are respectively provided on joint points (a actuation joint, a yaw joint, and a pitch joint), wires (the first jaw wire or the second jaw wire) are wound around the pulleys, such that if the manipulation part is rotated (actuation rotation, yaw rotation, or pitch rotation), each wire is moved for a desired motion of the end tool 120. Furthermore, an auxiliary pulley may be provided at a side of each pulley, and a wire may not be wound several times around the pulley owing to the auxiliary pulley.

Figure 8:
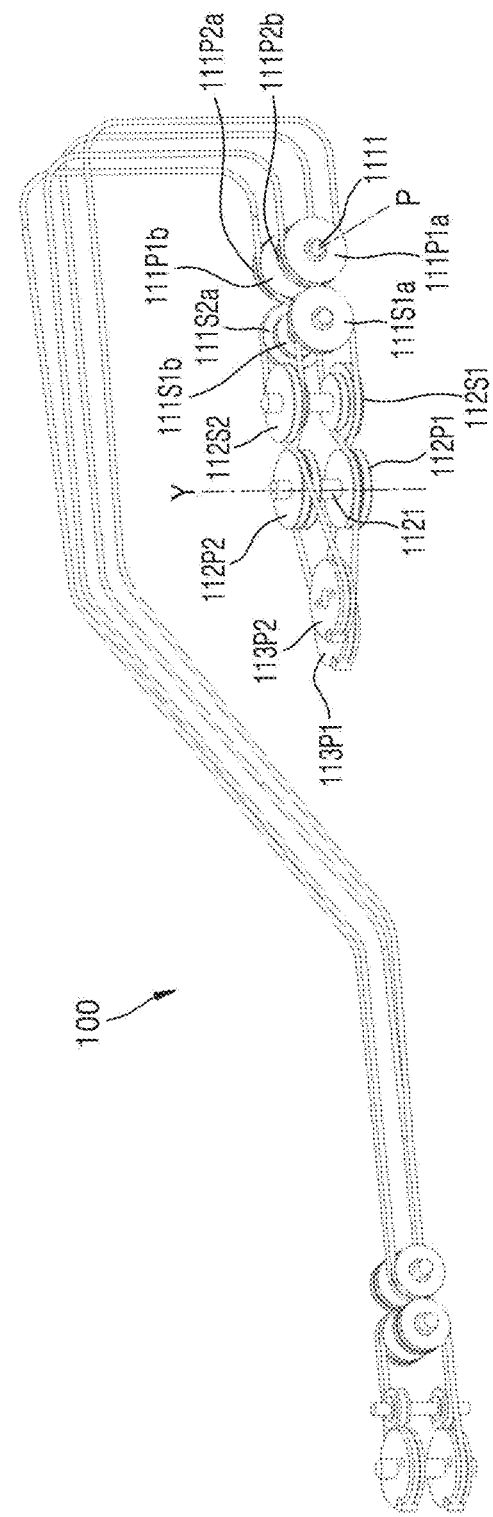
FIG. 8 is a schematic view illustrating only a configuration of pulleys and wires of the instrument for surgery shown in FIG. 7, according to the embodiment of the present invention.

FIG. 8 is a view simply illustrating only the configuration of pulleys and wires making up joints of the instrument 100 for surgery shown in FIG. 7 according to the embodiment of the present invention. In FIG. 8, relay pulleys changing paths of wires and not related to the operation of joints are not illustrated.

Referring to FIG. 8, the manipulation part 110 may include the first actuation pulley 113P1, the first jaw yaw pulley 112P1, the first jaw yaw auxiliary pulley 112S1, the first jaw pitch pulley-a 111P1a, the first jaw pitch pulley-b 111P1b, the first jaw pitch auxiliary pulley-a 111S1a, and the first jaw pitch auxiliary pulley-b 111S1b that are related to rotation of the first jaw 121.

In addition, the manipulation part 110 may include the second actuation pulley 113P2, the second jaw yaw pulley 112P2, the second jaw yaw auxiliary pulley 112S2, the second jaw pitch pulley-a 111P2a, the second jaw pitch pulley-b 111P2b, the second jaw pitch auxiliary pulley-a 111S2a, and the second jaw pitch auxiliary pulley-b 111S2b that are related to rotation of the second jaw 122 (the arrangement and structure of the pulleys of the manipulation part 100 are the same in principle as the arrangement and structure of the pulleys of the end tool 120, and some of reference numerals are omitted in the drawings).

The first jaw yaw pulley 112P1 and the second jaw yaw pulley 112P2 may be independently rotated around the same axis, that is, the yaw rotation shaft 1121. In this case, each of the first jaw yaw pulley 112P1 and the second jaw yaw pulley 112P2 may include two pulleys facing each other and configured to be independently rotated.

The first jaw yaw auxiliary pulley 112S1 and the second jaw yaw auxiliary pulley 112S2 may be independently rotated around the same axis. In this case, the first jaw yaw auxiliary pulley 112S1 may include two pulleys facing each other and configured to be independently rotated, and the two pulleys may have different diameters. Similarly, the second jaw yaw auxiliary pulley 112S2 may include two pulleys facing each other and configured to be independently rotated, and the two pulleys may have different diameters.

The first jaw pitch auxiliary pulley-a 111S1a, the first jaw pitch auxiliary pulley-b 111S1b, the second jaw pitch auxiliary pulley-a 111S2a, and the second jaw pitch auxiliary pulley-b 111S2b may be independently rotatable around the same axis. In this case, the first jaw pitch auxiliary pulley-a 111S1a and the first jaw pitch auxiliary pulley-b 111S1b may have different diameters. Further, the second jaw pitch auxiliary pulley-a 111S2a and the second jaw pitch auxiliary pulley-b 111S2b may have different diameters.

The first jaw pitch pulley-a 111P1a, the first jaw pitch pulley-b 111P1b, the second jaw pitch pulley-a 111P2a, and the second jaw pitch pulley-b 111P2b may be independently rotatable around the same axis, that is, the pitch rotation shaft 1111.

The first jaw wire 130J1 may be wound around the first actuation pulley 113P1 after being sequentially laid along the first jaw pitch pulley-a 111P1a, the first jaw pitch auxiliary pulley-a 111S1a, the first jaw yaw auxiliary pulley 112S1, and the first jaw yaw pulley 112P1 of the manipulation part 110, and then may be sequentially laid along the first jaw yaw pulley 112P1, the first jaw yaw auxiliary pulley 112S1, the first jaw pitch auxiliary pulley-b 111S1b, and the first jaw pitch pulley-b 111P1b, such that the first jaw wire 130J1 may move along the pulleys while rotating the pulleys. In this case, the first jaw wire 130J1 may be fixedly coupled to a point of the first actuation pulley 113P1.

The second jaw wire 130J2 may be wound around the second actuation pulley 113P2 after being sequentially laid along the second jaw pitch pulley-a 111P2a, the second jaw pitch auxiliary pulley-a 111S2a, the second jaw yaw auxiliary pulley 112S2, and the second jaw yaw pulley 112P2 of the manipulation part 110, and then may be sequentially laid along the second jaw yaw pulley 112P2, the second jaw yaw auxiliary pulley 112S2, the second jaw pitch auxiliary pulley-b 111S2b, and the second jaw pitch pulley-b 111P2b, such that the second jaw wire 130J2 may move along the pulleys while rotating the pulleys. In this case, the second jaw wire 130J2 may be fixedly coupled to a point of the second actuation pulley 113P2.

Figure 9:
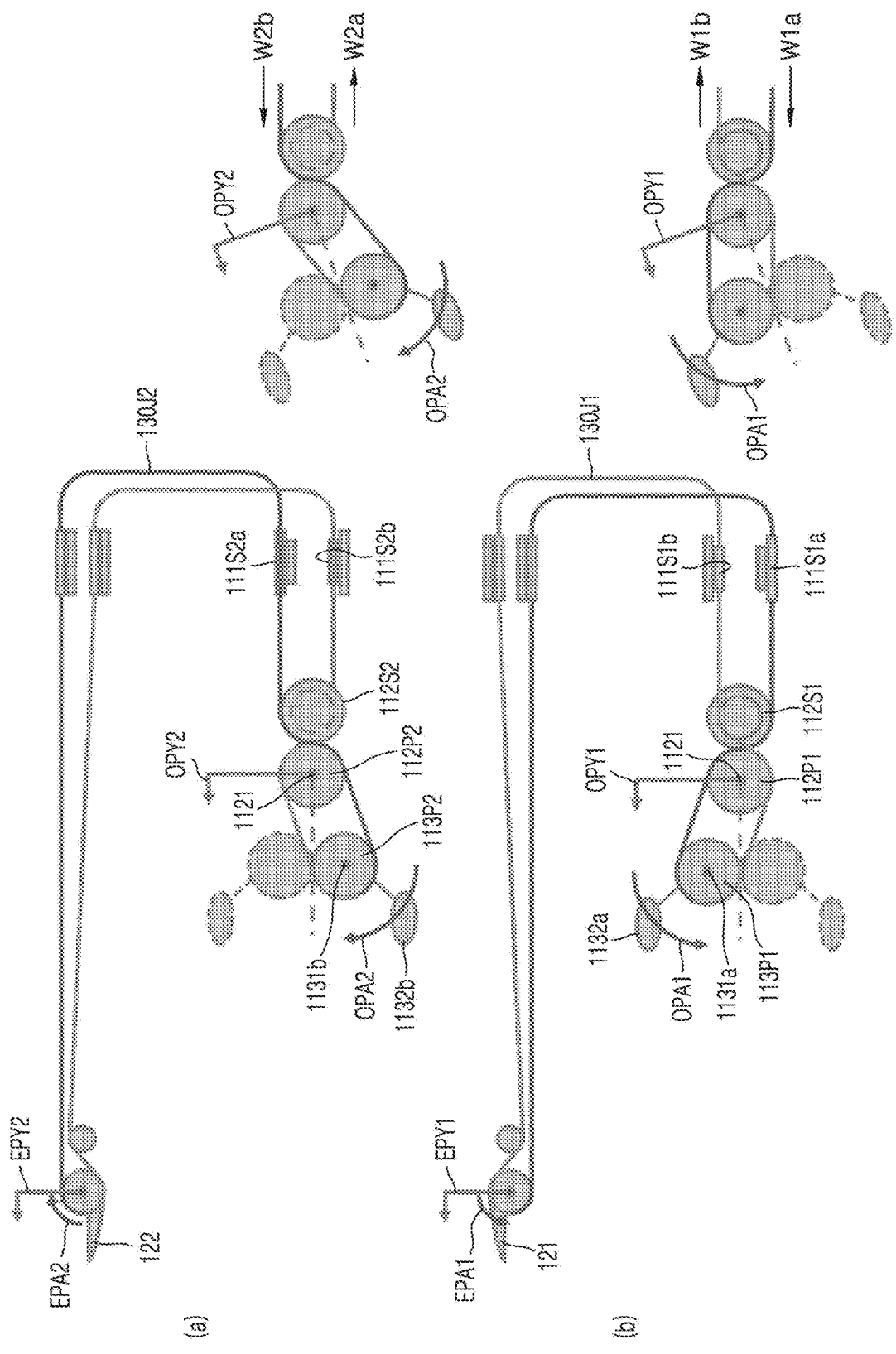
FIG. 9 is a view illustrating configurations of pulleys and wires relating to actuation motion and yaw motion of the instrument shown in FIG. 7 separately with respect to a first jaw and a second jaw, according to the embodiment of the present invention.
Figure 10:
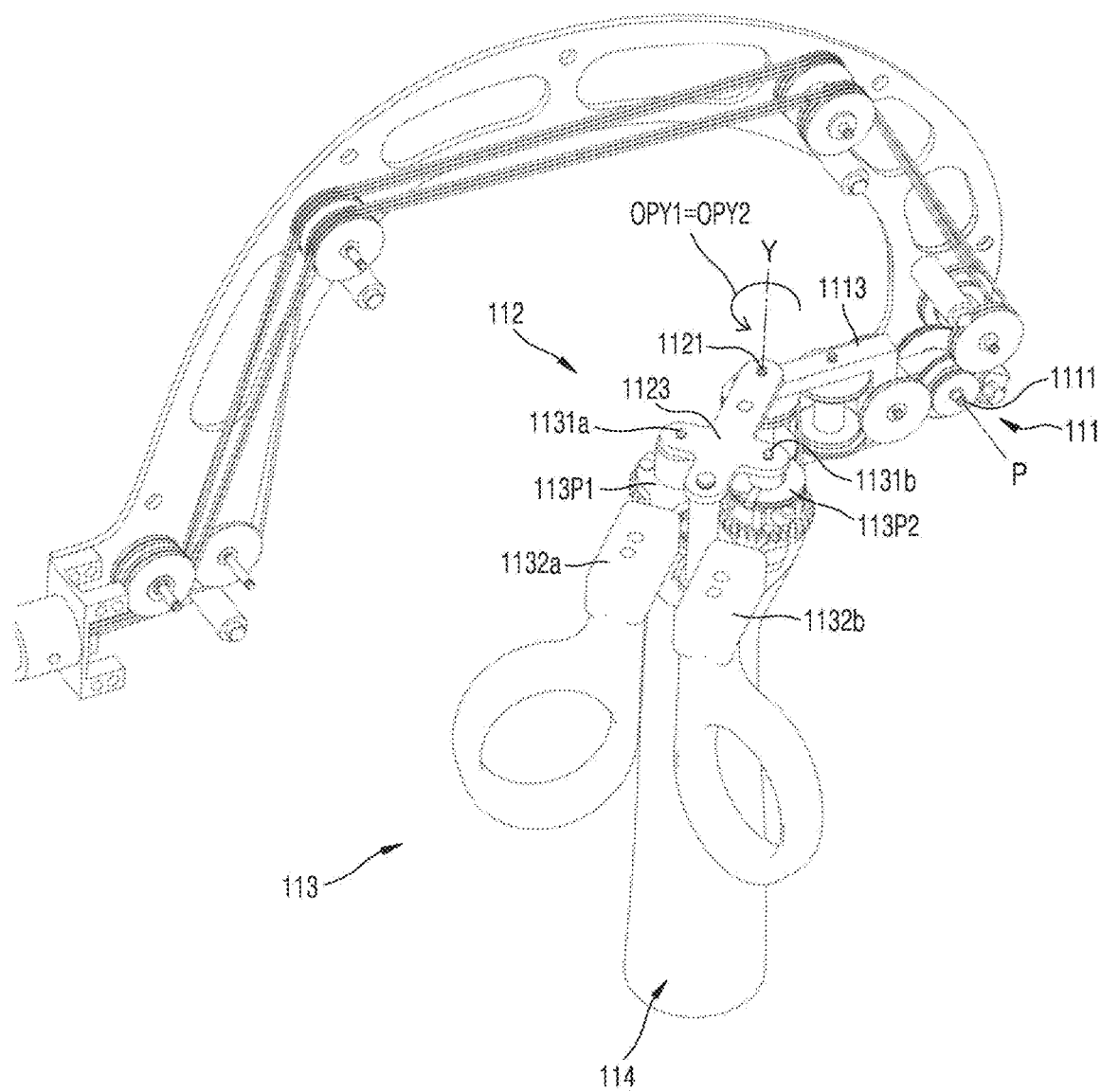
FIG. 10 is a perspective view illustrating a yaw motion of the instrument for surgery shown in FIG. 7.

FIG. 9 is a view illustrating the configurations of pulleys and wires relating to actuation motion and yaw motion of the instrument 100 for surgery shown in FIG. 7 separately with respect to a first jaw and a second jaw, according to the embodiment of the present invention. FIG. 9A is a view illustrating only pulleys and wires relating to the second jaw, and FIG. 9B is view illustrating only pulleys and wires relating to the first jaw. In addition, FIG. 10 is a perspective view illustrating a yaw motion of the instrument for surgery shown in FIG. 7.

First, the operation of wires in actuation motion will be described.

Referring to FIG. 9B, if the first actuation rotation part 1132a is rotated around the first actuation rotation shaft 1131a in the direction of an arrow OPA1, the first actuation pulley 113P1 connected to the first actuation rotation part 1132a is rotated, and both strands of the first jaw wire 130J1 wound around the first actuation pulley 113P1 are moved in directions W1a and W1b, thereby rotating the first jaw 121 of the manipulation part in the direction of an arrow EPA1.

Referring to FIG. 9A, if the second actuation rotation part 1132b is rotated around the second actuation rotation shaft 1131b in the direction of an arrow OPA2, the second actuation pulley 113P2 connected to the second actuation rotation part 1132b is rotated, and both strands of the second jaw wire 130J2 wound around the second actuation pulley 113P2 are moved in directions W2a and W2b, thereby rotating the second jaw 122 of the manipulation part in the direction of an arrow EPA2. Therefore, if a user manipulates the first actuation rotation part 1132a and the second actuation rotation part 1132b in approaching directions, the first jaw 121 and the second jaw 122 are moved close to each other.

Next, the operation of wires in yaw motion will be described.

First, since the yaw rotation shaft 1121, the first actuation rotation shaft 1131a, and the second actuation rotation shaft 1131b are connected to each other through the yaw frame 1123 (refer to FIG. 7), the yaw rotation shaft 1121, the first actuation rotation shaft 1131a, and the second actuation rotation shaft 1131b are rotated together.

Referring to FIG. 9B, if the first handle 114 is rotated around the yaw rotation shaft 1121 in the direction of an arrow OPY1, the first actuation pulley 113P1, the first jaw yaw pulley 112P1, and the first jaw wire 130J1 wound around the first actuation pulley 113P1 and the first jaw yaw pulley 112P1 are all rotated around the yaw rotation shaft 1121, and thus both strands of the first jaw wire 130J1 wound around the first jaw yaw pulley 112P1 are moved respectively in the directions W1a and W1b, thereby rotating the first jaw 121 of the end tool 120 in the direction of an arrow EPY1.

Referring to FIG. 9A, if the first handle 114 is rotated around the yaw rotation shaft 1121 in the direction of an arrow OPY2, the second actuation pulley 113P2, the second jaw yaw pulley 112P2, and the second jaw wire 130J2 wound around the second actuation pulley 113P2 and the second jaw yaw pulley 112P2 are all rotated around the yaw rotation shaft 1121, and thus both strands of the second jaw wire 130J2 wound around the second jaw yaw pulley 112P2 are moved respectively in a direction opposite the direction W1a and a direction opposite the direction W1b, thereby rotating the first jaw 121 of the end tool 120 in the direction of an arrow EPY2.

Figure 12:
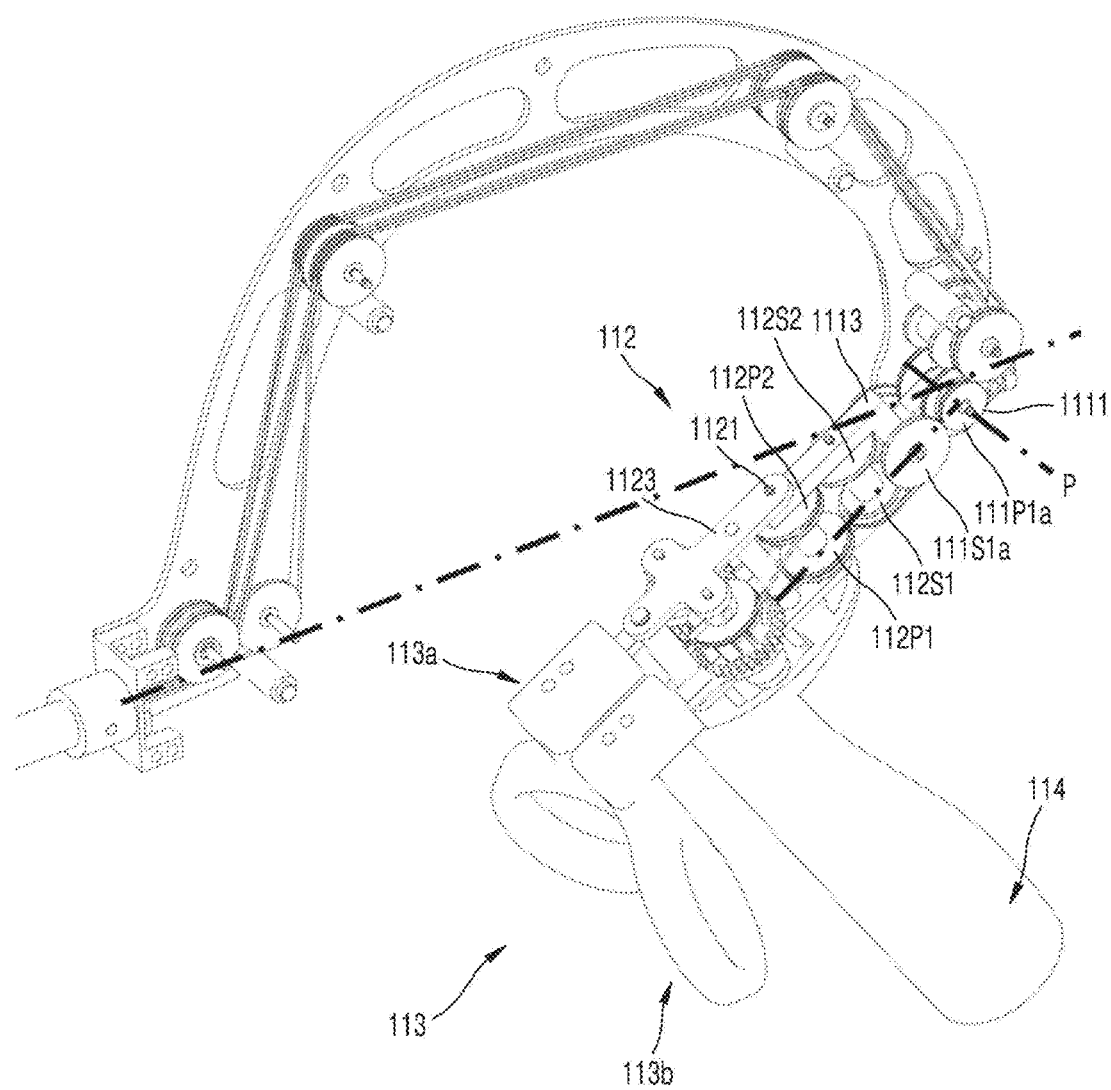
FIG. 12 is a perspective view illustrating a pitch motion of the instrument for surgery shown in FIG. 7.

FIG. 11 is a view illustrating the configurations of pulleys and wires relating to pitch motion of the instrument 100 for surgery shown in FIG. 7 separately with respect to the first jaw and the second jaw, according to the embodiment of the present invention. FIG. 11A is a view illustrating only pulleys and wires relating to the second jaw, and FIG. 11B is view illustrating only pulleys and wires relating to the first jaw. As shown in FIG. 8, pulleys relating to pitch motion are paired, and both strands of each wire are wound in the same path. Thus, in FIG. 11, both strands of each wire are illustrated with one line. In addition, FIG. 12 is a perspective view illustrating a pitch motion of the instrument for surgery shown in FIG. 7.

Referring to FIG. 11B, if the first handle 114 is rotated around the pitch rotation shaft 1111 in the direction of an arrow OPP1, parts such as the first actuation pulley 113P1, the first jaw pitch auxiliary pulleys 111S1a and 111S1b, and the first jaw pitch pulleys 111P1a and 111P1b, and the first jaw wire 130J1 wound therearound are all rotated around the pitch rotation shaft 1111. At this time, since both strands of the first jaw wire 130J1 are wound around upper portions of the first jaw pitch pulleys 111P1a and 111P1b as shown in FIG. 8, the first jaw wire 130J1 is moved in the direction of an arrow W1. Accordingly, as described with reference to FIG. 5, the first jaw 121 of the end tool 120 is rotated in the direction of an arrow EPP1.

Referring to FIG. 11A, if the first handle 114 is rotated around the pitch rotation shaft 1111 in the direction of an arrow OPP2, parts such as the second actuation pulley 113P2, the second jaw pitch auxiliary pulleys 111S2a and 111S2b, and the second jaw pitch pulleys 111P2a and 111P2b, and the second jaw wire 130J2 wound therearound are all rotated around the pitch rotation shaft 1111. At this time, since both strands of the second jaw wire 130J2 are wound around lower portions of the second jaw pitch pulleys 111P2a and 111P2b, the second jaw wire 130J2 is moved in the direction of an arrow W2. Accordingly, as described with reference to FIG. 5, the second jaw 122 of the end tool 120 is rotated in the direction of an arrow EPP2.

Thus, operational principles in the first embodiment shown in FIG. 7 may be explained with reference to FIGS. 8, 9, 10, 11, and 12, and actuation manipulation, yaw manipulation, and pitch manipulation may be independently performed.

As described with reference to FIG. 1, the actuation manipulation part 113, the yaw manipulation part 112, and the pitch manipulation part 111 are configured such that a rotation shaft is located behind each manipulation part like the joint configuration of the end tool, and thus a user may intuitively perform manipulations.

Particularly, in the instrument 100 for surgery of the embodiment of the present invention, a pulley provided on each joint point (an actuation joint, an yaw joint, and a pitch joint), a wire (the first jaw wire or the second jaw wire) is wound around the pulley, and if a manipulation part is rotated (actuation rotation, yaw rotation, or pitch rotation), the wire is moved to induce a desired motion of the end tool 120. Furthermore, an auxiliary pulley may be provided on a side of each pulley. Owing to the auxiliary pulley, a wire may not be wound several times around the pulley, wires wound around the pulley may not be in contact with each other, and a path for a wire running toward the pulley and wound around the pulley and a path in which a wire is wound around the pulley and leaves the pulley may be safely formed, thereby improving factors such as safety and efficient in power transmission.

In addition, as described above, the yaw manipulation part 112 and the actuation manipulation part 113 are directly provided on the first handle 114. Thus, if the first handle 114 is rotated about the pitch rotation shaft 1111, the yaw manipulation part 112 and the actuation manipulation part 113 are also rotated together with the first handle 114. Thus, the coordinate systems of the yaw manipulation part 112 and the actuation manipulation part 113 are not fixed, but relatively vary according to the rotation of the first handle 114. That is, drawings such as FIG. 2 illustrate that the yaw manipulation part 112 and the actuation manipulation part 113 are parallel with the Z axis. However, if the first handle 114 is rotated, the yaw manipulation part 112 and the actuation manipulation part 113 are not parallel with the Z axis. That is, the coordinate systems of the yaw manipulation part 112 and the actuation manipulation part 113 may change according to the rotation of the first handle 114. However, unless described otherwise, the coordinate systems of the yaw manipulation part 112 and the actuation manipulation part 113 are described based on the case in which the first handle 114 is perpendicular to the connecting part 140 as shown in FIG. 2 for ease of description.

<Various Modifications of Joints>

Joint structures for yaw rotation or pulley rotation made up of a main joint pulley and an additional auxiliary pulley may be modified according to the configuration of pulleys, and may be classified into a direct type and an indirect type.

(Direct-Type Joint and Indirect-Type Joint—Yaw Joint)

FIG. 13 is a view illustrating a direct-type joint as an example of a yaw joint, and FIG. 14 is a view illustrating an indirect-type joint as an example of a yaw joint. FIGS. 13A and 14A are views illustrating only pulleys and wires relating to the second jaw, and FIGS. 13B and 14B are view illustrating only pulleys and wires relating to the first jaw.

Herein, the direct-type joint means that in a relationship between a pulley corresponding to a joint position and an auxiliary pulley in a structure including two adjacent pulleys for joint movement, when a joint part is rotated around a corresponding rotation axis, the auxiliary pulley is not rotated around the rotation shaft corresponding to the joint part but only the pulley corresponding to the joint position is rotated around the rotation axis of the joint part. On the other hand, the indirect-type joint means that when a joint part is rotated around a corresponding rotation axis, not only a pulley corresponding to a joint position but also an auxiliary pulley is rotated around the rotation axis of the joint part.

In the direct-type joint shown in FIG. 13, the first jaw yaw pulley 112P1 and the first jaw yaw auxiliary pulley 112S1 are arranged to neighbor each other for yaw motion of the first jaw 121, and the first jaw yaw pulley 112P1 is a pulley located on the yaw rotation shaft 1121 at a left side in the drawing so as to be rotated around the yaw rotation shaft 1121 for yaw rotation. In this case, the first jaw yaw auxiliary pulley 112S1 is located at a right side in the drawing and is not rotated around the yaw rotation shaft 1121 during yaw rotation.

Meanwhile, in the indirect-type joint shown in FIG. 14, the first jaw yaw pulley 112P1 and the first jaw yaw auxiliary pulley 112S1 are arranged to neighbor each other for yaw motion of the first jaw 121, and the first jaw yaw pulley 112P1 is a pulley located on the yaw rotation shaft 1121 at a right side in the drawing so as to be rotated around the yaw rotation shaft 1121 for yaw rotation. In this case, the first jaw yaw auxiliary pulley 112S1 is located at a left side in the drawing and is not rotated around the yaw rotation shaft 1121 during yaw rotation.

The direct-type joint and the indirect-type joint are different from each other in the movement direction of a wire when a joint is rotated in the same direction. That is, in the direct-type joint shown in FIG. 13, if the yaw rotation shaft 1121 is rotated in a direction OPY, portions of the first jaw wire 130J1 and the second jaw wire 130J2 are moved in the direction of an arrow D1. However, in the indirect-type join shown in FIG. 14, if the yaw rotation shaft 1121 is rotated in the direction OPY, the portions of the first jaw wire 130J1 and the second jaw wire 130J2 are moved in the direction of an arrow D2 which is opposite the direction of the arrow D1.

As described above, depending on whether the direct-type joint or the indirect-type joint is selected as a joint structure, the movement direction of a wire may be changed to the opposite direction without changing the direction of yaw rotation.

(Direct-Type Joint and Indirect-Type Joint—Pitch Joint)

Figure 15:
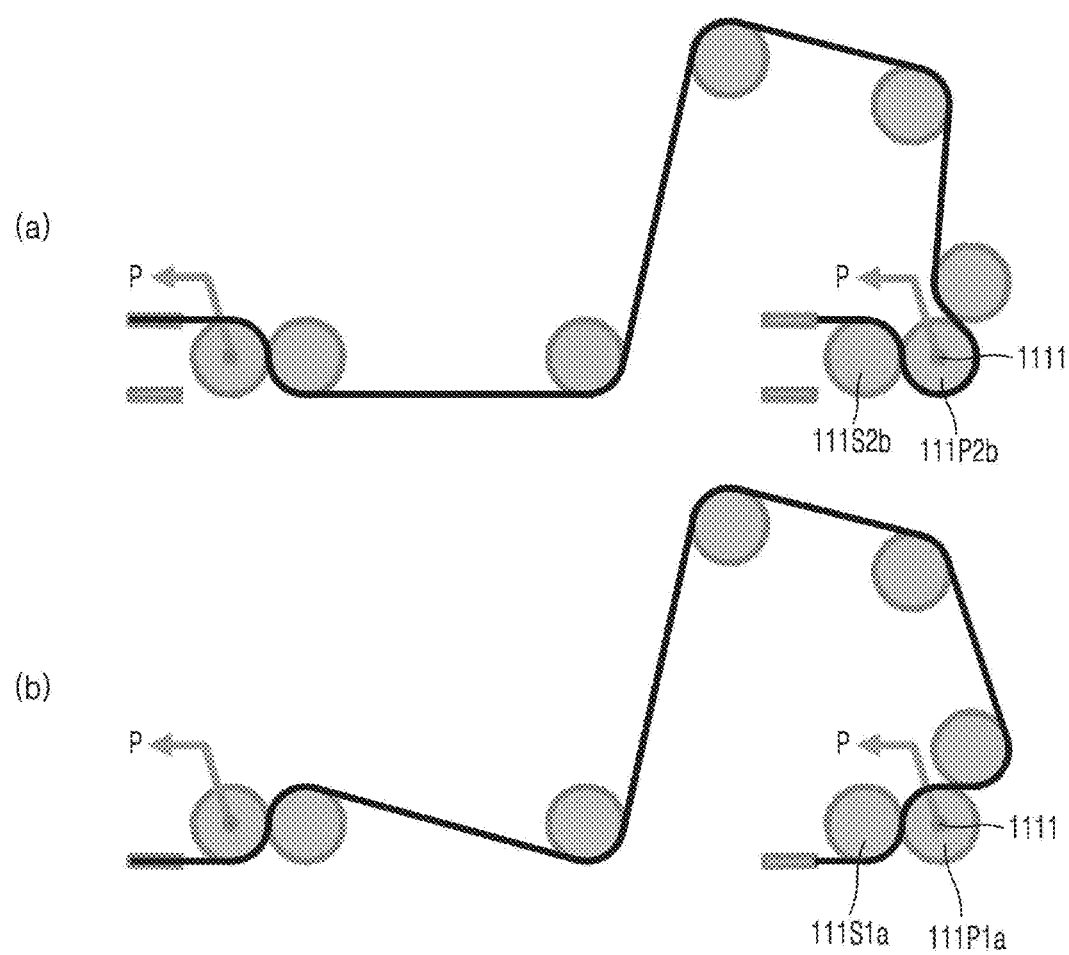
FIG. 15 is a view illustrating an example of an indirect-type pitch joint.
Figure 16:
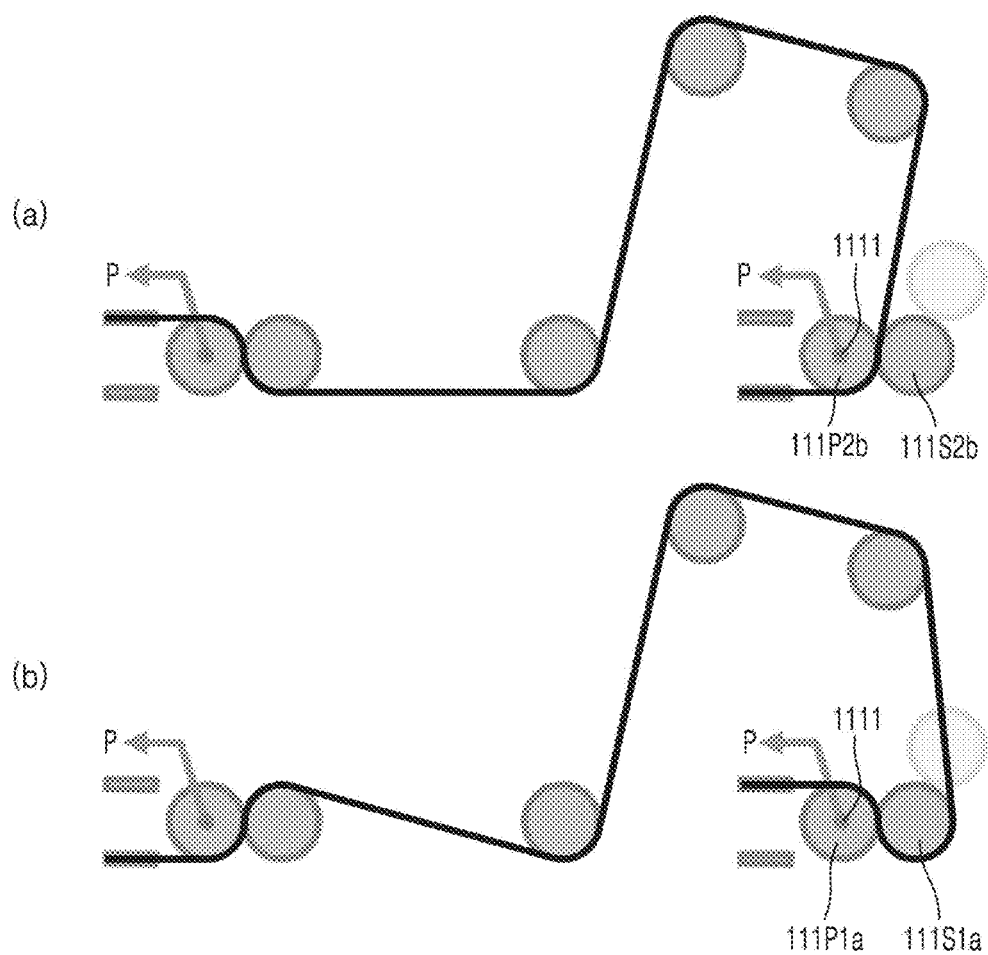
FIG. 16 is a view illustrating an example of a direct-type pitch joint.

FIG. 15 is a view illustrating an indirect-type joint as an example of a pitch joint, and FIG. 16 is a view illustrating a direct-type joint as an example of a pitch joint. FIGS. 15A and 16A are views illustrating only pulleys and wires relating to the second jaw, and FIGS. 15B and 16B are view illustrating only pulleys and wires relating to the first jaw.

The indirect-type joint shown in FIG. 15B includes the first jaw pitch pulley-a 111P1a and the first jaw pitch auxiliary pulley-a 111S1a neighboring each other for pitch motion of the first jaw 121, and the first jaw pitch pulley-a 111P1a is located at a right side in FIG. 15B.

The direct-type joint shown in FIG. 16B includes the first jaw pitch pulley-a 111P1a and the first jaw pitch auxiliary pulley-a 111S1a neighboring each other for pitch motion of the first jaw 121, and the first jaw pitch pulley-a 111P1a is located at a left side in FIG. 15B.

As described above, depending on whether the direct-type joint or the indirect-type joint is selected as a joint structure, the movement direction of a wire may be changed to the opposite direction without changing the direction of pitch rotation, and the winding direction of a wire around a pitch pulley may be changed.

(Various Modifications in the Configuration of Pulleys and Wires)

The configuration of pulleys and wires relating to the actuation motion and yaw motion of the instrument 100 for surgery shown in FIG. 9 according to the first embodiment of the present invention may be variously modified by changing the paths of wires, the sizes and arrangement of joint pulleys, the configuration of manipulation parts, the configuration of the end tool, etc. Hereinafter, various possible modifications in the configuration of pulleys and wires will be described.

Figure 17:
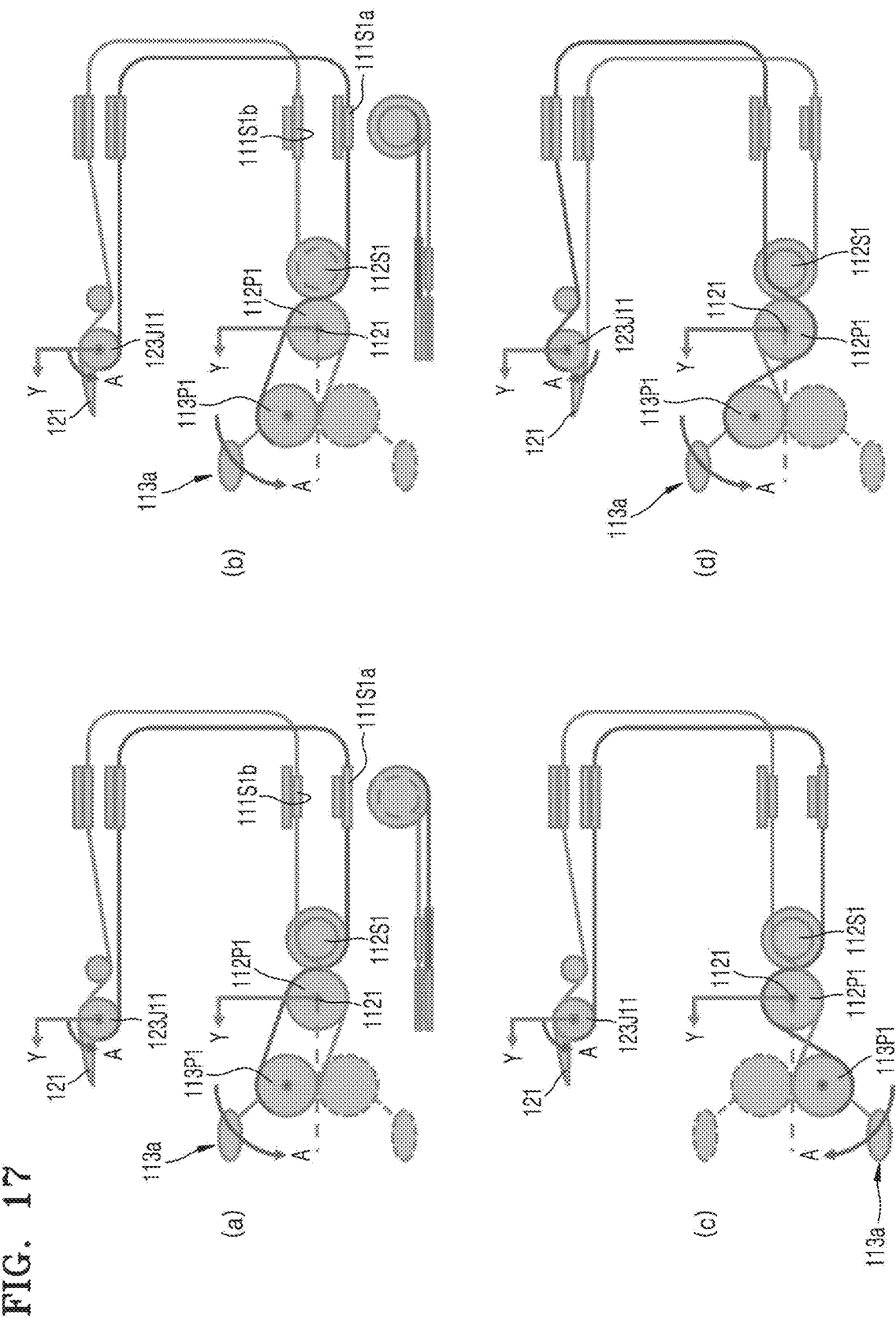
FIG. 17 is a view illustrating configurations of pulleys and wires of the instrument for surgery shown in FIG. 9, relating to the operation of the first jaw, and modifications thereof, according to the embodiment of the present invention.

FIG. 17 is a view illustrating the configuration of pulleys and wires of the instrument 100 for surgery shown in FIG. 9 relating to the operation of the first jaw, and modifications thereof, according to the embodiment of the present invention.

Referring to FIG. 17A, in the instrument 100 for surgery of the embodiment of the present invention, wires basically do not cross each other in the connecting part 140. That is, in the connecting part 140 connecting the end tool 120 and the manipulation part 110, both strands of the first jaw wire 130J1 do not cross each other, and both strands of the second jaw wire 130J2 also do not cross each other.

Referring to FIG. 17A, in the instrument 100 for surgery according to the embodiment of the present invention, each wire spreads out in the connecting part 140. In other words, since the interval between both strands of the first jaw wire 130J1 is smaller at the end tool 120 than in a region connected to a relay pulley MP owing to the sizes of pulleys and the gaps between pulleys, the interval between both strands of the first jaw wire 130J1 increases in a direction from the end tool 120 to the relay pulley MP, and thus the first jaw wire 130J1 spreads out as a whole.

Referring to FIG. 17A, in the instrument 100 for surgery according to the embodiment of the present invention, the manipulation part 110 has a direct-type yaw joint. That is, the instrument 100 for surgery includes the first jaw yaw pulley 112P1 and the first jaw yaw auxiliary pulley 112S1 neighboring each other for yaw motion of the first jaw 121, wherein the first jaw yaw pulley 112P1 is located at a left side in the drawing, and a rotation axis of the first jaw yaw pulley 112P1 is a yaw rotation axis. In this case, the first jaw yaw auxiliary pulley 112S1 may include two pulleys facing each other and configured to be independently rotated, and the two pulleys may have different diameters. In this case, each of the first jaw yaw pulley 112P1 and the first jaw yaw auxiliary pulley 112S1 may include two pulleys, and both strands of the first jaw wire 130J1 may have a height difference, so that a wire wound around the first jaw yaw pulley 112P1 and the first jaw yaw auxiliary pulley 112S1 in a crossing manner may not have overlapping paths. In addition, to this end, two pitch auxiliary pulleys having different diameters (the first jaw pitch auxiliary pulley-a 111S1a and the first jaw pitch auxiliary pulley-b 111S1b) may be used such that the first jaw wire 130J1 may be smoothly wound around pulleys having a height difference.

Referring to FIG. 17B, the sizes and arrangement of the pitch auxiliary pulleys (the first jaw pitch auxiliary pulley-a 111S1a and the first jaw pitch auxiliary pulley-b 111S1b) connected to the first jaw yaw auxiliary pulley 112S1 are different from those shown in FIG. 17A. Therefore, as shown in a lower region of FIG. 17B, the height of a wire wound around the first jaw pitch auxiliary pulley-a 111S1a and the height of a wire wound around the first jaw pitch auxiliary pulley-b 111S1b may be opposite, and thus a vertical relationship between both strands of the first jaw wire 130J1 may be reversed compared to that shown in FIG. 17A.

Referring to FIG. FIG. 17C, the first actuation manipulation part 113a for operating the first jaw is configured differently from the case shown in FIG. 17A, and the first jaw wire 130J1 connecting the first jaw yaw pulley 112P1 and the first actuation pulley 113P1 to each other may have a crossing structure such that motions of the end tool 120 by actuation and yaw manipulations of the manipulation part 110 may be performed in the same manner as that shown in FIG. 17A.

Referring to FIG. 17D, the configuration of the first jaw 121 and the J11 pulley 123J11 is modified such that the first jaw 121 may be oriented in a direction different from that shown in FIG. 17A. In this case, the rotation direction of the first jaw 121 for yaw motion is the same as that shown in FIG. 17A, but the rotation direction of the first jaw 121 and the J11 pulley 123J11 for actuation motion is opposite that shown in FIG. 17A. To this end, the first jaw wire 130J1 connecting the first jaw yaw pulley 112P1 and the first actuation pulley 113P1 to each other may have a crossing structure such that the first jaw wire 130J1 may be moved by manipulation of the first actuation manipulation part 113a in a direction opposite the direction shown in FIG. 17A.

This configuration may include two yaw pulleys, two yaw auxiliary pulleys, two pitch pulleys, and two pitch auxiliary pulleys, and a wire that looks like having a crossing structure in the drawing is actually laid in different paths without physical contact, thereby improving the safety and efficiency of power transmission using the wire.

The above description is for the actuation and yaw motions of the first jaw, and the drawings are also for describing the actuation and yaw motions of the first jaw. Although relay pulleys and pulleys relating to pitch motion are not described, these pulleys may be sufficiently understood, and thus these pulleys are not illustrated in the drawings. In addition, the second jaw may be sufficiently understood from the drawings and description of the first jaw, and thus drawings and a description of the second jaw are omitted.

Figure 18:
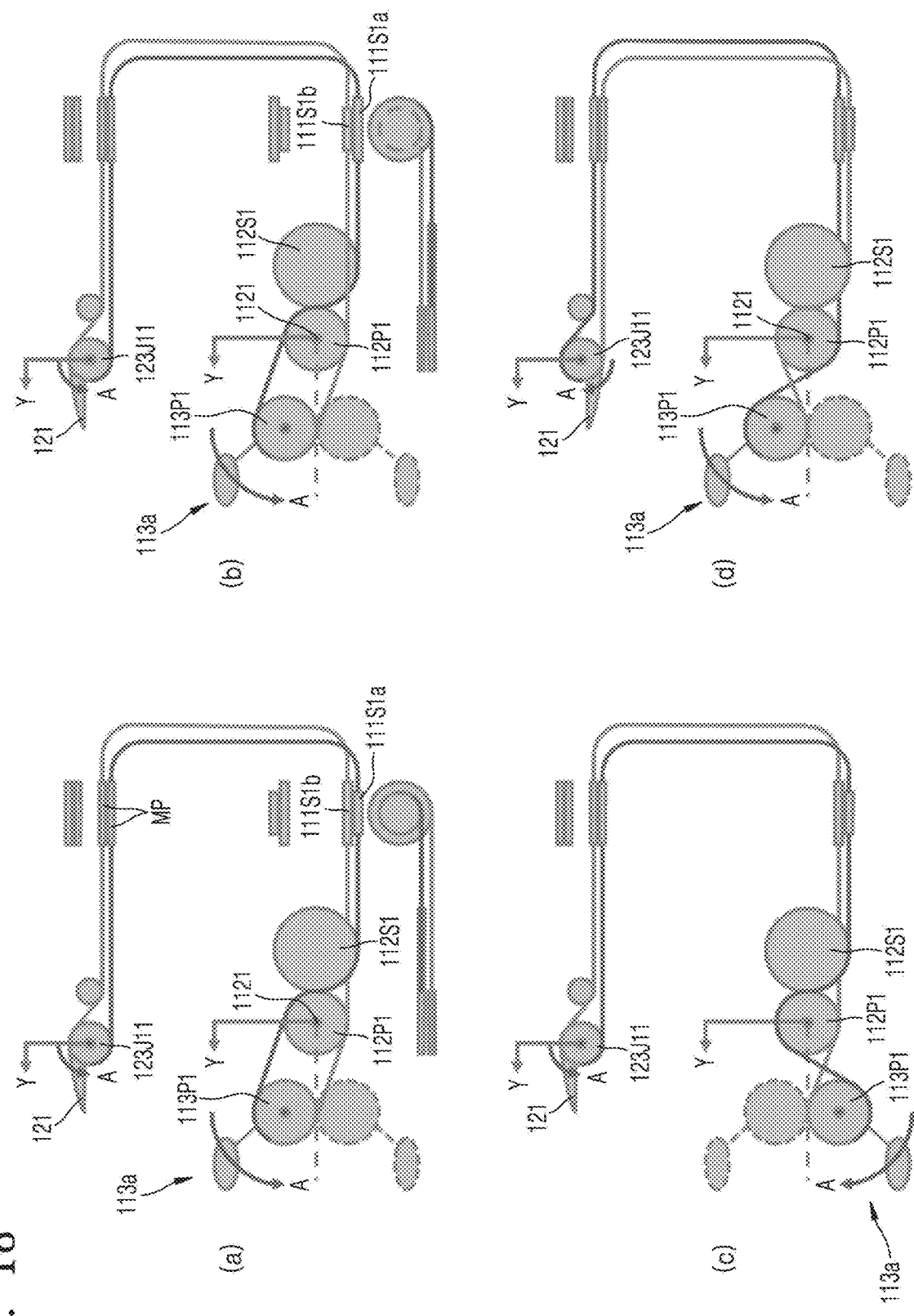
FIG. 18 is a view illustrating another modification of the embodiment shown in FIG. 17.

FIG. 18 is view illustrating modifications of the embodiment shown in FIG. 17. For example, wire paths shown in FIG. 17 are modified.

In the modification shown in FIG. 18A, unlike the configuration of the first embodiment, both strands of the first jaw wire 130J1 wound around the first jaw 121 are configured to pass over two connection-part relay pulleys MP that are adjacent to each other, and parts such as the first jaw yaw auxiliary pulley 112S1 are modified for performing the same operation as in the first embodiment.

To this end, pitch auxiliary pulleys (the first jaw pitch auxiliary pulley-a 111S1a and the first jaw pitch auxiliary pulley-b 111S1b) having different sizes and which the first jaw wire 130J1 passes over are arranged adjacent to each other side by side, wherein the first jaw wire 130J1 passing over the first jaw pitch auxiliary pulley-a 111S1a is wound around the first jaw yaw auxiliary pulley 112S1, and the first jaw wire 130J1 passing over the first jaw pitch auxiliary pulley-b 111S1b is directly wound around the first jaw yaw pulley 112P1 without being wound around a yaw auxiliary pulley. Therefore, the modification shown in FIG. 18A allows for the same operation as that in the first embodiment. The configuration shown in FIG. 18A may be variously modified by changing the paths of wires, the sizes and arrangement of joint pulleys, the configuration of manipulation parts, the configuration of the end tool, etc.

Referring to FIG. 18B, the size of a pitch auxiliary pulley connected to a yaw auxiliary pulley is varied compared to the case shown in FIG. 18A, and thus as shown in a lower region of FIG. 18B, a wire wound around the first jaw pitch auxiliary pulley-a 111S1a and a wire wound around the first jaw pitch auxiliary pulley-b 111S1b are opposite each other in height. As a result, both strands of the first jaw wire 130J1 may be opposite compared to the case shown in FIG. 18A. Referring to FIG. 18C, the actuation manipulation part 113a for operating the first jaw is configured differently from the case shown in FIG. 18A, and the first jaw wire 130J1 connecting the first jaw yaw pulley 112P1 and the first actuation pulley 113P1 may have a crossing structure such that motions of the end tool 120 by actuation and yaw manipulations of the manipulation part 110 may be performed in the same manner as that shown in FIG. 18A.

Referring to FIG. 18D, the configuration of the first jaw 121 and the J11 pulley 123J11 is modified such that the first jaw 121 may be oriented in a direction different from that shown in FIG. 18A. In this case, the rotation direction of the first jaw 121 for yaw motion is the same as that shown in FIG. 18A, but the rotation direction of the first jaw 121 and the J11 pulley 123J11 for actuation motion is opposite that shown in FIG. 18A. To this end, the first jaw wire 130J1 connecting the first jaw yaw pulley 112P1 and the first actuation pulley 113P1 to each other may have a crossing structure such that the first jaw wire 130J1 may be moved by manipulation of the first actuation manipulation part 113a in a direction opposite the direction shown in FIG. 18A.

This configuration may include two yaw pulleys, a yaw auxiliary pulley, two pitch pulleys, and two pitch auxiliary pulleys, and a wire that looks like having a crossing structure in the drawing is actually laid in different paths without physical contact, thereby improving the safety and efficiency of power transmission using the wire.

The above description is for the actuation and yaw motions of the first jaw, and the drawings are also for describing the actuation and yaw motions of the first jaw.

Although relay pulleys and pulleys relating to pitch motion are not described, these pulleys may be sufficiently understood, and thus these pulleys are not illustrated in the drawings. In addition, the second jaw may be sufficiently understood from the drawings and description of the first jaw, and thus drawings and a description of the second jaw are omitted.

Figure 19:
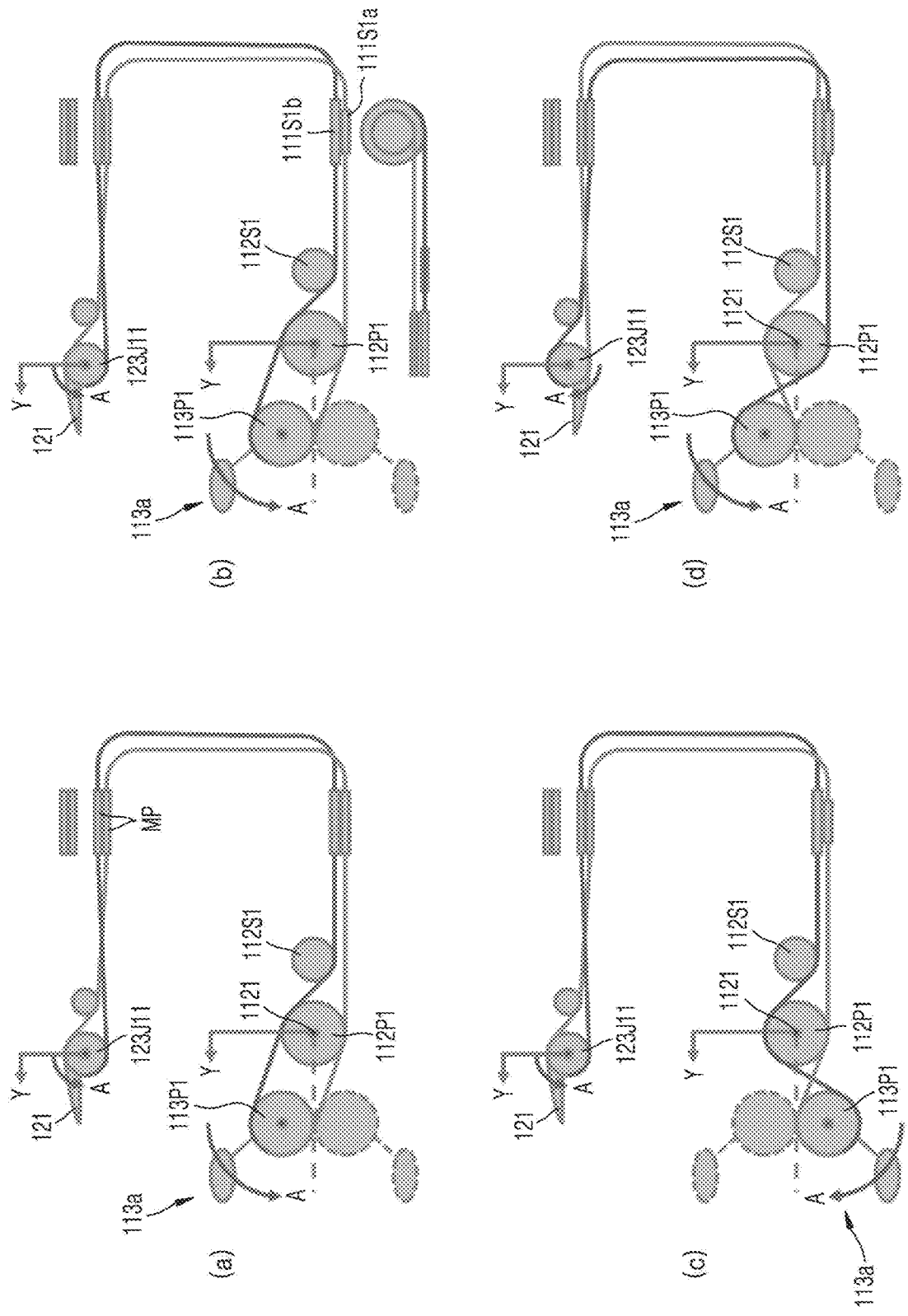
FIG. 19 is a view illustrating another modification of the embodiment shown in FIG. 17.

FIG. 19 is view illustrating modifications of the embodiment shown in FIG. 17. For example, wire paths shown in FIG. 17 are modified.

In the modification shown in FIG. 19A, unlike the configuration of the first embodiment, both strands of the first jaw wire 130J1 wound around the first jaw 121 are configured to cross each other and pass over two connection-part relay pulleys MP that are adjacent to each other, and parts such as the first jaw yaw auxiliary pulley 112S1 are modified for performing the same operation as in the first embodiment.

In addition, unlike the configuration of the first embodiment, in the case shown in FIG. 19A, wires cross each other at least once inside the connecting part 140. That is, in the connecting part 140 connecting the end tool 120 and the manipulation part 110, both strands of the first jaw wire 130J1 cross each other, and both strands of the second jaw wire 130J2 also cross each other. Although both strands of each wire look like crossing each other in a two-dimensional plane of the drawing, the wires may be arranged without actual physical contact with each other by properly three-dimensionally positioning relay pulleys to which the wires are connected.

In addition, the first jaw pitch auxiliary pulley-a 111S1a and the first jaw pitch auxiliary pulley-b 11151b have the same diameter, and the first jaw wire 13071 wound around the first jaw pitch auxiliary pulley-b 11151b is configured to be wound around the first jaw yaw pulley 112P1 through the first jaw yaw auxiliary pulley 112S1. In addition, the first jaw wire 130J1 wound around the first jaw pitch auxiliary pulley-a 11151a may be directly wound around the first jaw yaw pulley 112P1 without an intervening yaw auxiliary pulley, and owing to this, the modification shown in FIG. 19A allows for the same operation as in the first embodiment.

The configuration shown in FIG. 19A may be variously modified by changing the paths of wires, the sizes and arrangement of joint pulleys, the configuration of manipulation parts, the configuration of the end tool, etc.

Referring to FIG. 19B, the size of a pitch auxiliary pulley connected to a yaw auxiliary pulley is varied compared to the case shown in FIG. 19A. That is, the first jaw pitch auxiliary pulley-a 111S1a and the first jaw pitch auxiliary pulley-b 111S1b have different diameters. Thus, as shown in a lower region of FIG. 19B, two pulleys of the first jaw yaw pulley 112P1 may be arranged at different heights. This may be easily applied to a configuration in which the first jaw wire 130J1 has a crossing structure between the first actuation pulley 113P1 and the first jaw yaw pulley 112P1 as shown in FIG. 19C (described later), and both sides of the first jaw wire 130J1 may not make actual physical contact with each other.

Referring to FIG. 19C, the actuation manipulation part 113a for operating the first jaw is configured differently from the case shown in FIG. 19A, and the first jaw wire 130J1 connecting the first jaw yaw pulley 112P1 and the first actuation pulley 113P1 may have a crossing structure such that motions of the end tool 120 by actuation and yaw manipulations of the manipulation part 110 may be performed in the same manner as that shown in FIG. 19A.

Referring to FIG. 19D, the configuration of the first jaw 121 and the J11 pulley 123J11 is modified such that the first jaw 121 may be oriented in a direction different from that shown in FIG. 19A. In this case, the rotation direction of the first jaw 121 for yaw motion is the same as that shown in FIG. 19A, but the rotation direction of the first jaw 121 and the J11 pulley 123J11 for actuation motion is opposite that shown in FIG. 19A. To this end, the first jaw wire 130J1 connecting the first jaw yaw pulley 112P1 and the first actuation pulley 113P1 to each other may have a crossing structure such that the first jaw wire 130J1 may be moved by manipulation of the first actuation manipulation part 113a in a direction opposite the direction shown in FIG. 19A.

This configuration may include one or two yaw pulleys, a yaw auxiliary pulley, two pitch pulleys, and two pitch auxiliary pulleys, and a wire that looks like having a crossing structure in the drawing is actually laid in different paths without physical contact, thereby improving the safety and efficiency of power transmission using the wire.

In addition, it is also possible to arrange pitch pulleys in place of the pitch auxiliary pulleys shown in the drawing.

The above description is for the actuation and yaw motions of the first jaw, and the drawings are also for describing the actuation and yaw motions of the first jaw. Although relay pulleys and pulleys relating to pitch motion are not described, these pulleys may be sufficiently understood, and thus these pulleys are not illustrated in the drawings. In addition, the second jaw may be sufficiently understood from the drawings and description of the first jaw, and thus drawings and a description of the second jaw are omitted.

Figure 20:
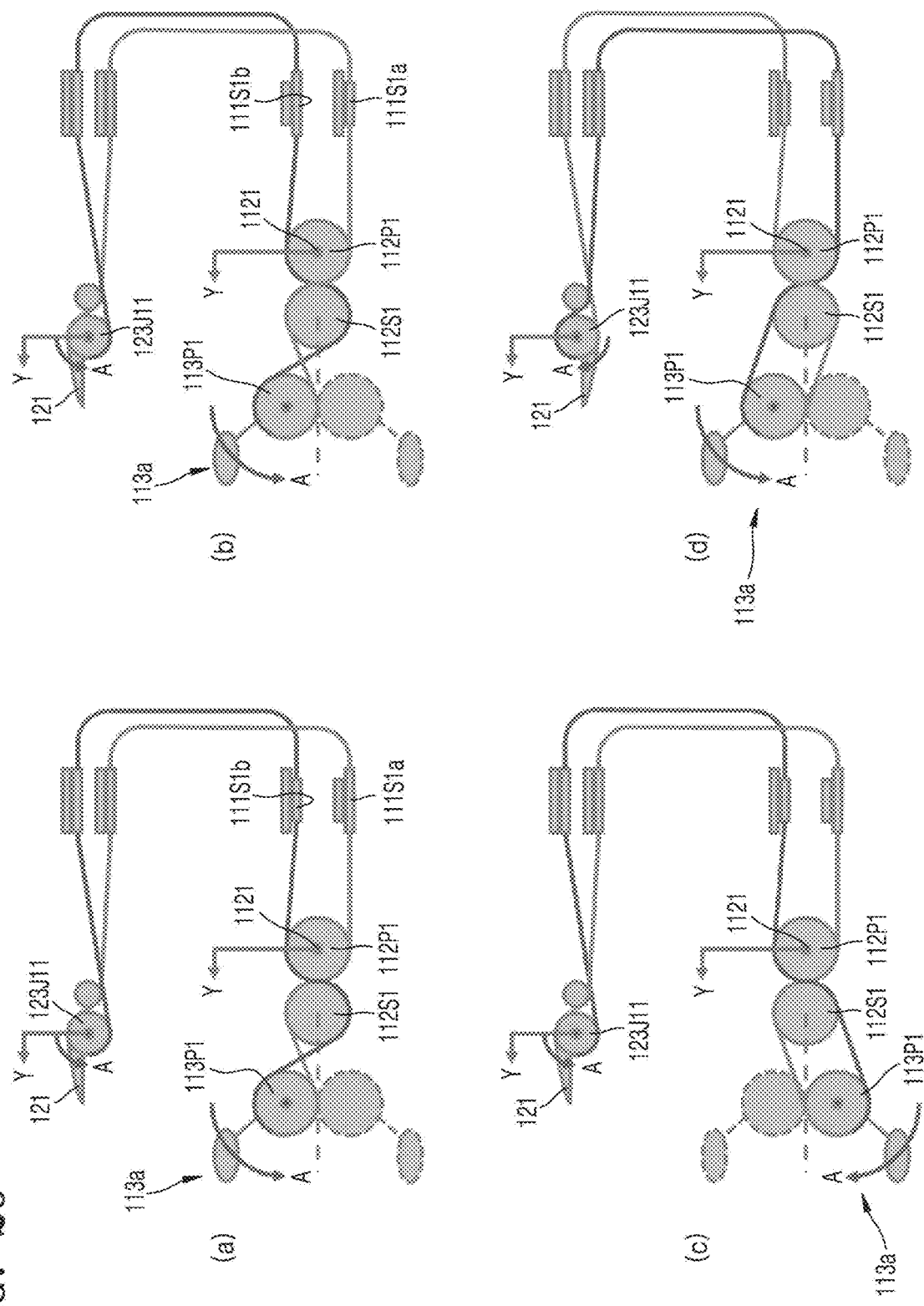
FIG. 20 is a view illustrating another modification of the embodiment shown in FIG. 17.

FIG. 20 is view illustrating modifications of the embodiment shown in FIG. 17. For example, wire paths shown in FIG. 17 are modified.

In the modification shown in FIG. 20A, unlike the configuration of the first embodiment, both strands of the first jaw wire 130J1 wound around the first jaw 121 are configured to cross each other and pass over two connection-part relay pulleys MP that are not adjacent to each other, and parts such as the first jaw yaw auxiliary pulley 112S1 are modified for performing the same operation as in the first embodiment.

In addition, unlike the configuration of the first embodiment, in the case shown in FIG. 20A, wires cross each other at least once inside the connecting part 140. That is, in the connecting part 140 connecting the end tool 120 and the manipulation part 110, both strands of the first jaw wire 130J1 cross each other, and both strands of the second jaw wire 130J2 also cross each other. Although both strands of each wire look like crossing each other in a two-dimensional plane of the drawing, the wires may be arranged without actual physical contact with each other by properly three-dimensionally adjusting relay pulleys to which the wires are connected.

In addition, pitch auxiliary pulleys having different sizes (the first jaw pitch auxiliary pulley-a 111S1a and the first jaw pitch auxiliary pulley-b 111S1b) are arranged, and the first jaw pitch auxiliary pulley-a 111S1a being an outer pitch auxiliary pulley is relatively large such that a wire wound around the outer pitch auxiliary pulley may be wound around the first jaw yaw auxiliary pulley 112S1 located at a lower height.

In addition, referring to FIG. 20A, in the instrument 100 for surgery according to the embodiment of the present invention, the manipulation part 110 has a indirect-type yaw joint. That is, the instrument 100 for surgery includes the first jaw yaw pulley 112P1 and the first jaw yaw auxiliary pulley 112S1 neighboring each other for yaw motion of the first jaw 121, wherein the first jaw yaw pulley 112P1 is located at a right side in the drawing, and a rotation axis of the first jaw yaw pulley 112P1 is a yaw rotation axis. In this case, the first jaw wire 130J1 connecting the first jaw yaw auxiliary pulley 112S1 and the first actuation pulley 113P1 may be configured to have a crossing structure so as to operate the end tool in the same manner as that shown in FIG. 17A by actuation and yaw manipulations of the manipulation part 110.

The configuration shown in FIG. 20A may be variously modified by changing the paths of wires, the sizes and arrangement of joint pulleys, the configuration of manipulation parts, the configuration of the end tool, etc.

Referring to FIG. 20B, the sizes and arrangement of the pitch auxiliary pulleys (the first jaw pitch auxiliary pulley-a 111S1a and the first jaw pitch auxiliary pulley-b 111S1b) connected to the first jaw yaw auxiliary pulley 112S1 are different from those shown in FIG. 20A. Therefore, the height of a wire wound around the first jaw pitch auxiliary pulley-a 111S1a and the height of a wire wound around the first jaw pitch auxiliary pulley-b 111S1b may be opposite, and thus a vertical relationship between both strands of the first jaw wire 130J1 may be reversed compared to that shown in FIG. 20A.

Referring to FIG. 20C, the actuation manipulation part 113a for operating the first jaw is configured differently from the case shown in FIG. 20A, and the first jaw wire 130J1 connecting the first jaw yaw auxiliary pulley 112S1 and the first actuation pulley 113P1 may not have a crossing structure such that motions of the end tool 120 by actuation and yaw manipulations of the manipulation part 110 may be performed in the same manner as that shown in FIG. 20A.

Referring to FIG. 20D, the configuration of the first jaw 121 and the J11 pulley 123J11 is modified such that the first jaw 121 may be oriented in a direction different from that shown in FIG. 20A. In this case, the rotation direction of the first jaw 121 for yaw motion is the same as that shown in FIG. 20A, but the rotation direction of the first jaw 121 and the J11 pulley 123J11 for actuation motion is opposite that shown in FIG. 20A. To this end, the first jaw wire 130J1 connecting the first jaw yaw auxiliary pulley 112S1 and the first actuation pulley 113P1 to each other may not have a crossing structure such that the first jaw wire 130J1 may be moved by manipulation of the first actuation manipulation part 113a in a direction opposite the direction shown in FIG. 20A.

This configuration may include two yaw pulleys, two yaw auxiliary pulleys, two pitch pulleys, and two pitch auxiliary pulleys, and a wire that looks like having a crossing structure in the drawing is actually laid in different paths without physical contact, thereby improving the safety and efficiency of power transmission using the wire.

The above description is for the actuation and yaw motions of the first jaw, and the drawings are also for describing the actuation and yaw motions of the first jaw. Although relay pulleys and pulleys relating to pitch motion are not described, these pulleys may be sufficiently understood, and thus these pulleys are not illustrated in the drawings. In addition, the second jaw may be sufficiently understood from the drawings and description of the first jaw, and thus drawings and a description of the second jaw are omitted.

Figure 21:
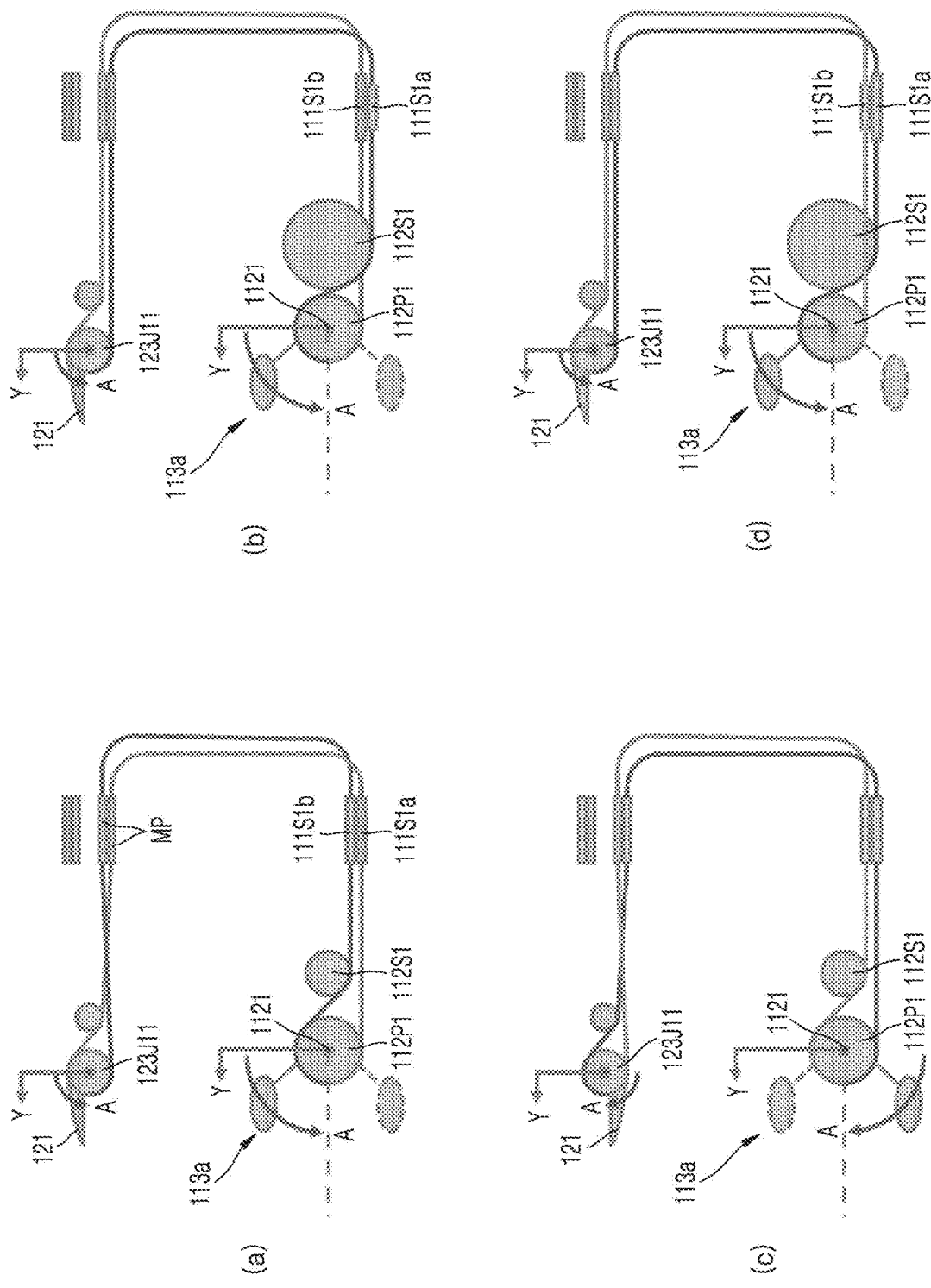
FIG. 21 is a view illustrating another modification of the embodiment shown in FIG. 17.

FIG. 21 is view illustrating modifications of the embodiment shown in FIG. 17. For example, wire paths shown in FIG. 17 are modified.

In the modification shown in FIG. 21A, unlike the configuration of the first embodiment, both strands of the first jaw wire 130J1 wound around the first jaw 121 are configured to cross each other and pass over two connection-part relay pulleys MP that are adjacent to each other, and both strands of the second jaw wire 130J2 also cross each other.

In addition, the first jaw pitch auxiliary pulley-a 111S1a and the first jaw pitch auxiliary pulley-b 111S1b have the same diameter, and the first jaw wire 13071 wound around the first jaw pitch auxiliary pulley-b 111S1b is configured to be wound around the first jaw yaw pulley 112P1 through the first jaw yaw auxiliary pulley 112S1. In addition, the first jaw wire 130J1 wound around the first jaw pitch auxiliary pulley-a 111S1a may be directly wound around the first jaw yaw pulley 112P1 without an intervening yaw auxiliary pulley, and owing to this, the modification shown in FIG. 21A allows for the same operation as in the first embodiment.

Here, in the case of FIG. 21A, a yaw pulley and an actuation pulley are not separately provided, but a common yaw pulley is used. In this case, the yaw pulley and the actuation manipulation part may be connected through gears or the like to implement actuation motion (refer to a second embodiment).

The configuration shown in FIG. 20A may be variously modified by changing the paths of wires, the sizes and arrangement of joint pulleys, the configuration of manipulation parts, the configuration of the end tool, etc.

Referring to FIG. 21B, the sizes and arrangement of the pitch auxiliary pulleys (the first jaw pitch auxiliary pulley-a 111S1a and the first jaw pitch auxiliary pulley-b 111S1b) connected to the first jaw yaw auxiliary pulley 112S1 are different from those shown in FIG. 21A, and the first jaw yaw auxiliary pulley 112S1 may be configured to be larger than the first jaw yaw pulley 112P1 to obtain an effect of crossing both strands of the first jaw wire 130J1. Therefore, in the connecting part 140 connecting the end tool 120 and the manipulation part 110, both strands of the first jaw wire 130J1 may be passed over two connection-part relay pulleys MP adjacent to each other without crossing both strands of the first jaw wire 130J1.

Referring to FIG. 21C, the actuation manipulation part 113 for operating the first jaw is configured differently from the case shown in FIG. 21A, and along with this, the configuration of the first jaw 121 and the J11 pulley 123J11 is changed so as to orient the first jaw 121 in a direction different from the direction shown in FIG. 21A.

Referring to FIG. 21D, the sizes and arrangement of the pitch auxiliary pulleys (the first jaw pitch auxiliary pulley-a 111S1a and the first jaw pitch auxiliary pulley-b 111S1b) connected to the first jaw yaw auxiliary pulley 112S1 are different from those shown in FIG. 21B. Therefore, the height of a wire wound around the first jaw pitch auxiliary pulley-a 111S1a and the height of a wire wound around the first jaw pitch auxiliary pulley-b 111S1b may be opposite, and thus a vertical relationship between both strands of the first jaw wire 130J1 may be reversed compared to that shown in FIG. 21B.

This configuration may include one or two yaw pulleys, a yaw auxiliary pulley, two pitch pulleys, and two pitch auxiliary pulleys, and a wire that looks like having a crossing structure in the drawing is actually laid in different paths without physical contact, thereby improving the safety and efficiency of power transmission using the wire. In addition, it is also possible to arrange pitch pulleys in place of the pitch auxiliary pulleys shown in the drawing.

The above description is for the actuation and yaw motions of the first jaw, and the drawings are also for describing the actuation and yaw motions of the first jaw. Although relay pulleys and pulleys relating to pitch motion are not described, these pulleys may be sufficiently understood, and thus these pulleys are not illustrated in the drawings. In addition, the second jaw may be sufficiently understood from the drawings and description of the first jaw, and thus drawings and a description of the second jaw are omitted.

Figure 22:
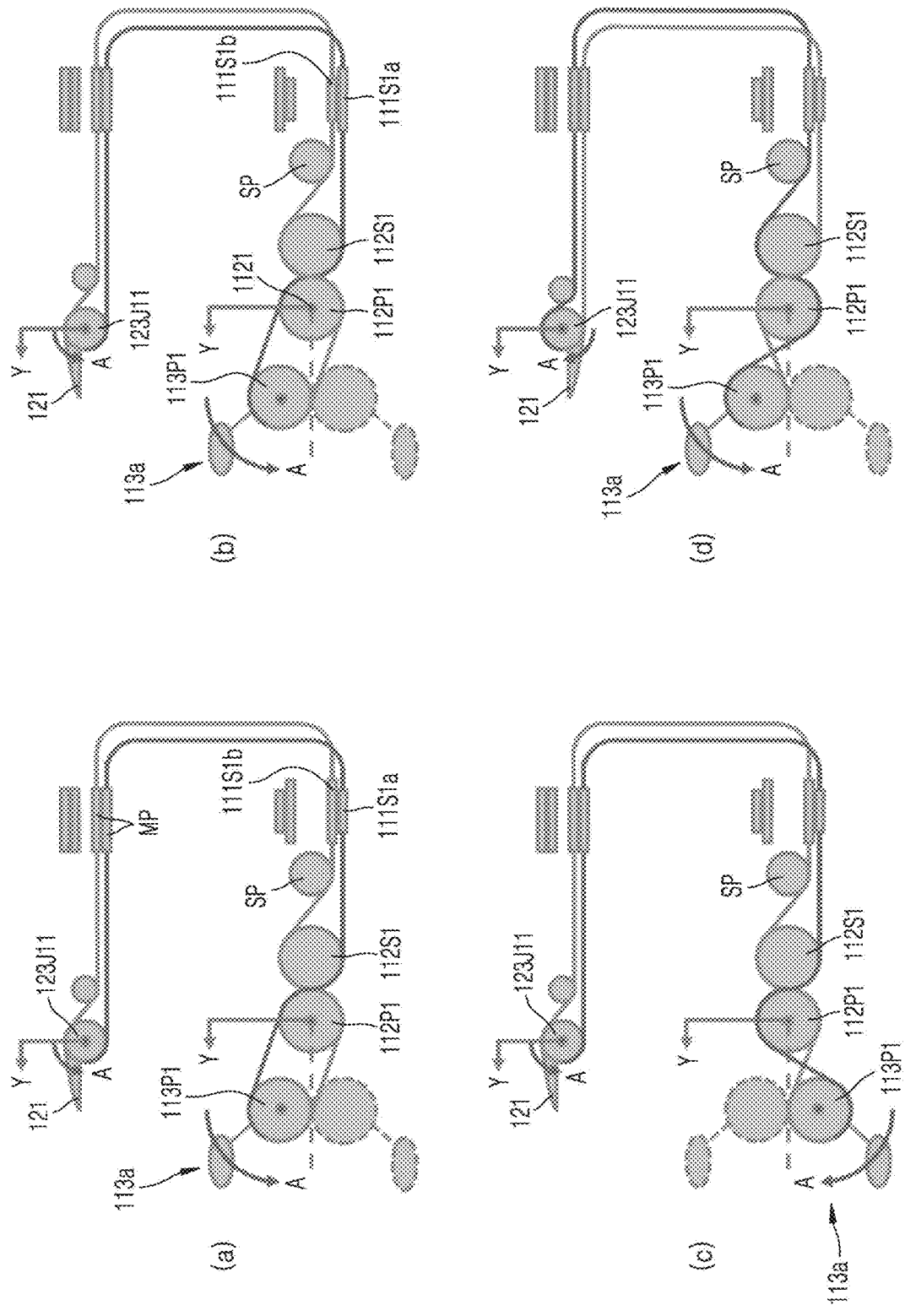
FIG. 22 is a view illustrating another modification of the embodiment shown in FIG. 17.

FIG. 22 is view illustrating modifications of the embodiment shown in FIG. 17. For example, wire paths shown in FIG. 17 are modified.

In the modification shown in FIG. 22A, unlike the configuration of the first embodiment, both strands of the first jaw wire 130J1 wound around the first jaw 121 are configured to pass over two connection-part relay pulleys MP that are adjacent to each other, and parts such as the first jaw yaw auxiliary pulley 112S1 are modified for performing the same operation as in the first embodiment.

To this end, pitch auxiliary pulleys (the first jaw pitch auxiliary pulley-a 111S1a and the first jaw pitch auxiliary pulley-b 111S1b) having different sizes and which the first jaw wire 130J1 passes over are arranged adjacent to each other side by side, wherein the first jaw wire 130J1 passing over the first jaw pitch auxiliary pulley-a 111S1a is wound around the first jaw yaw auxiliary pulley 112S1, and the first jaw wire 130J1 passing over the first jaw pitch auxiliary pulley-b 111S1b is wound around the first jaw yaw auxiliary pulley 112S1 after passing over an auxiliary pulley SP. Therefore, the modification shown in FIG. 22A allows for the same operation as that in the first embodiment.

Here, when FIG. 22 is compared with FIG. 17, the first jaw pitch auxiliary pulley-b 111S1b is adjacent to the first jaw pitch auxiliary pulley-a 111S1a, and the auxiliary pulley SP is added between the first jaw yaw auxiliary pulley 112S1 and the pitch auxiliary pulleys, such that the first jaw wire 130J1 passing over the first jaw pitch auxiliary pulley-b 111S1b may be wound around the first jaw yaw auxiliary pulley 112S1 through the auxiliary pulley SP. That is, owing to the addition of the auxiliary pulley SP, in the connecting part 140 connecting the end tool 120 and the manipulation part 110 to each other, both strands of the first jaw wire 130J1 may pass over tow connection-part relay pulleys SP in parallel with each other, and the pitch auxiliary pulleys that the first jaw wire 130J1 may be adjacent to each other. In addition, if the first jaw yaw auxiliary pulley 112S1 include two pulleys, the two pulleys may have the same diameter.

The configuration shown in FIG. 22A may be variously modified by changing the paths of wires, the sizes and arrangement of joint pulleys, the configuration of manipulation parts, the configuration of the end tool, etc.

Referring to FIG. 22B, the size and arrangement of pitch auxiliary pulleys connected to a yaw auxiliary pulley is varied compared to the case shown in FIG. 22A, and thus a wire wound around the first jaw pitch auxiliary pulley-a 111S1a and a wire wound around the first jaw pitch auxiliary pulley-b 111S1b are opposite to each other in height. As a result, both strands of the first jaw wire 130J1 may be opposite compared to the case shown in FIG. 22A.

Referring to FIG. 22C, the actuation manipulation part 113a for operating the first jaw is configured differently from the case shown in FIG. 22A, and the first jaw wire 130J1 connecting the first jaw yaw pulley 112P1 and the first actuation pulley 113P1 may have a crossing structure such that motions of the end tool 120 by actuation and yaw manipulations of the manipulation part 110 may be performed in the same manner as that shown in FIG. 22A.

Referring to FIG. 22D, the configuration of the first jaw 121 and the J11 pulley 123J11 is modified such that the first jaw 121 may be oriented in a direction different from that shown in FIG. 22A. In this case, the rotation direction of the first jaw 121 for yaw motion is the same as that shown in FIG. 22A, but the rotation direction of the first jaw 121 and the J11 pulley 123J11 for actuation motion is opposite that shown in FIG. 22A. To this end, the first jaw wire 130J1 connecting the first jaw yaw pulley 112P1 and the first actuation pulley 113P1 to each other may have a crossing structure such that the first jaw wire 130J1 may be moved by manipulation of the first actuation manipulation part 113a in a direction opposite the direction shown in FIG. 22A.

This configuration may include two yaw pulleys, two yaw auxiliary pulleys, an auxiliary pulley, two pitch pulleys, and two pitch auxiliary pulleys, and a wire that looks like having a crossing structure in the drawing is actually laid in different paths without physical contact, thereby improving the safety and efficiency of power transmission using the wire.

The above description is for the actuation and yaw motions of the first jaw, and the drawings are also for describing the actuation and yaw motions of the first jaw. Although relay pulleys and pulleys relating to pitch motion are not described, these pulleys may be sufficiently understood, and thus these pulleys are not illustrated in the drawings. In addition, the second jaw may be sufficiently understood from the drawings and description of the first jaw, and thus drawings and a description of the second jaw are omitted.

Figure 23:
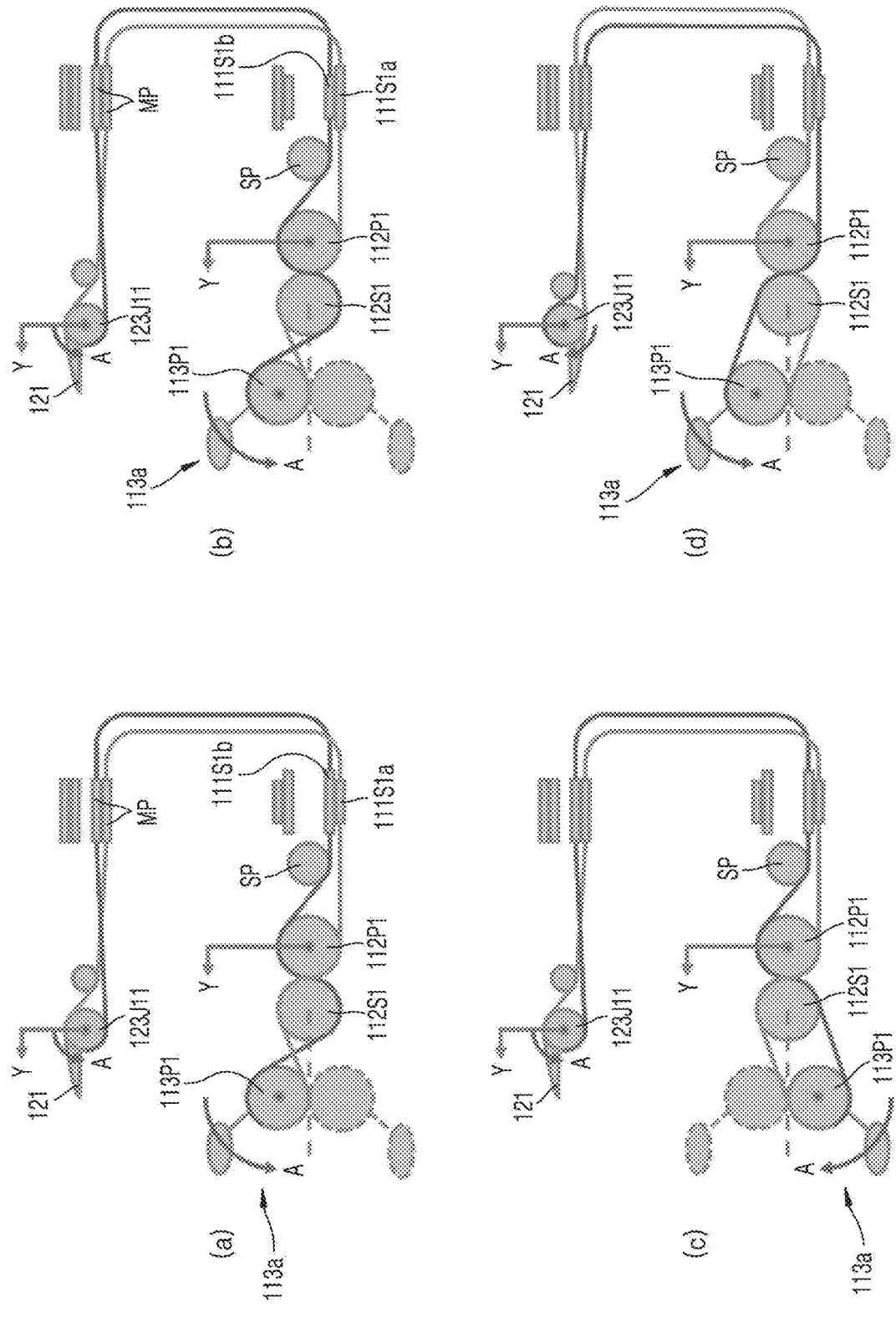
FIG. 23 is a view illustrating another modification of the embodiment shown in FIG. 17.

FIG. 23 is view illustrating modifications of the embodiment shown in FIG. 22. For example, wire paths shown in FIG. 22 are modified.

In the case of FIG. 22, the left one of the first jaw yaw pulley 112P1 and the first jaw yaw auxiliary pulley 112S1 neighboring each other for yaw motion of the first jaw 121 is the first jaw yaw pulley 112P1. However, in the case of FIG. 23, the first jaw yaw pulley 112P1 is placed on a right side, and the first jaw yaw auxiliary pulley 112S1 is placed on a left side. That is, it may be understood that FIG. 22 illustrates a direct-type yaw joint, and FIG. 12 illustrates an indirect-type yaw joint.

Due to this difference, the movement directions of both strands of the first jaw wire 130J1 by yaw rotation of the manipulation part 110 in the case of FIG. 12A are opposite those in the case of FIG. 22A. In this case, to operate the end tool 110 by actuation and yaw manipulations of the manipulation part 120 in the same manner as in the case shown in FIG. 22A, both strands of the first jaw wire 130J1 may be crossed each other and passed over two adjacent connection-part relay pulleys MP in the connecting part 140 connecting the end tool 120 and the manipulation part 110.

The configuration shown in FIG. 23A may be variously modified by changing the paths of wires, the sizes and arrangement of joint pulleys, the configuration of manipulation parts, the configuration of the end tool, etc.

Referring to FIG. 23B, the size and arrangement of pitch auxiliary pulleys connected to a yaw auxiliary pulley is varied compared to the case shown in FIG. 23A, and thus a wire wound around the first jaw pitch auxiliary pulley-a 111S1a and a wire wound around the first jaw pitch auxiliary pulley-b 111S1b are opposite to each other in height. As a result, both strands of the first jaw wire 130J1 may be opposite compared to the case shown in FIG. 23A.

Referring to FIG. 23C, the actuation manipulation part 113a for operating the first jaw is configured differently from the case shown in FIG. 23A, and the first jaw wire 130J1 connecting the first jaw yaw pulley 112P1 and the first actuation pulley 113P1 may not have a crossing structure such that motions of the end tool 120 by actuation and yaw manipulations of the manipulation part 110 may be performed in the same manner as that shown in FIG. 23A.

Referring to FIG. 23D, the configuration of the first jaw 121 and the J11 pulley 123J11 is modified such that the first jaw 121 may be oriented in a direction different from that shown in FIG. 23A. In this case, the rotation direction of the first jaw 121 for yaw motion is the same as that shown in FIG. 23A, but the rotation direction of the first jaw 121 and the J11 pulley 123J11 for actuation motion is opposite that shown in FIG. 23A. To this end, the first jaw wire 130J1 connecting the first jaw yaw pulley 112P1 and the first actuation pulley 113P1 to each other may not have a crossing structure such that the first jaw wire 130J1 may be moved by manipulation of the first actuation manipulation part 113a in a direction opposite the direction shown in FIG. 23A.

This configuration may include two yaw pulleys, two yaw auxiliary pulleys, an auxiliary pulley, two pitch pulleys, and two pitch auxiliary pulleys, and a wire that looks like having a crossing structure in the drawing is actually laid in different paths without physical contact, thereby improving the safety and efficiency of power transmission using the wire.

The above description is for the actuation and yaw motions of the first jaw, and the drawings are also for describing the actuation and yaw motions of the first jaw. Although relay pulleys and pulleys relating to pitch motion are not described, these pulleys may be sufficiently understood, and thus these pulleys are not illustrated in the drawings. In addition, the second jaw may be sufficiently understood from the drawings and description of the first jaw, and thus drawings and a description of the second jaw are omitted.

Figure 24:
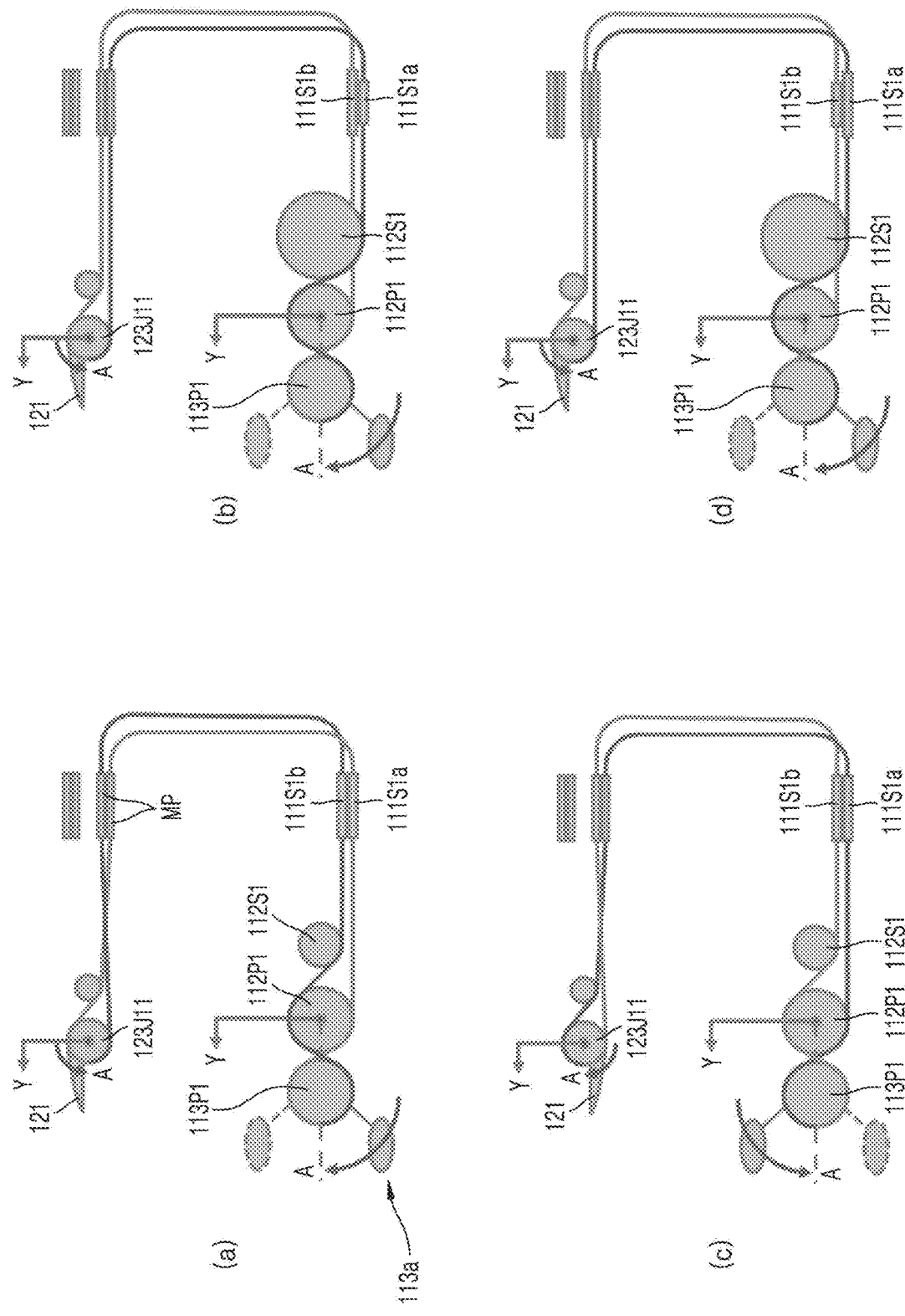
FIG. 24 is a view illustrating another modification of the embodiment shown in FIG. 17.

FIG. 24 is view illustrating modifications of the embodiment shown in FIG. 21. For example, wire paths shown in FIG. 21 are modified.

In the case of FIG. 21, a yaw pulley and an actuation pulley are not separately provided, but a common yaw pulley is used. However, in the case of FIG. 24A, the actuation pulley 113P1 is used in addition to the jaw yaw pulley 112P1. To this end, both strands of the first jaw wire 130J1 passing over the first jaw pitch auxiliary pulley-a 111S1a and the first jaw pitch auxiliary pulley-b 111S1b are wound around the jaw yaw pulley 112P1, crossed each other, and then wound around the actuation pulley 113P1. In this case, for the same operation in the modification example shown in FIG. 24A as in the example shown in FIG. 21, the position and rotation direction of the first actuation manipulation part 113a in the FIG. 24A may be opposite those shown in FIG. 21.

The configuration shown in FIG. 24A may be variously modified by changing the paths of wires, the sizes and arrangement of joint pulleys, the configuration of manipulation parts, the configuration of the end tool, etc.

Unlike the case shown in FIG. 24A, the first jaw yaw auxiliary pulley 112S1 may be larger than the first jaw yaw pulley 112P1, and in this case, an effect of crossing both strands of the first jaw wire 130J1 may be obtained. Therefore, in the connecting part 140 connecting the end tool 120 and the manipulation part 110, both strands of the first jaw wire 130J1 may be passed over two connection-part relay pulleys MP adjacent to each other without crossing both strands of the first jaw wire 130J1.

Referring to FIG. 24C, the actuation manipulation part 113 for operating the first jaw is configured differently from the case shown in FIG. 24A, and along with this, the configuration of the first jaw 121 and the J11 pulley 123J11 is changed so as to orient the first jaw 121 in a direction different from the direction shown in FIG. 24A.

Referring to FIG. 24D, the sizes and arrangement of the pitch auxiliary pulleys (the first jaw pitch auxiliary pulley-a 111S1a and the first jaw pitch auxiliary pulley-b 111S1b) connected to the first jaw yaw auxiliary pulley 112S1 are different from those shown in FIG. 24B. Therefore, the height of a wire wound around the first jaw pitch auxiliary pulley-a 111S1a and the height of a wire wound around the first jaw pitch auxiliary pulley-b 111S1b may be opposite, and thus a vertical relationship between both strands of the first jaw wire 130J1 may be reversed compared to that shown in FIG. 24B.

This configuration may commonly include one or two actuation pulleys, one or two yaw pulleys, a yaw auxiliary pulley, two pitch pulleys, and two pitch auxiliary pulleys, and a wire that looks like having a crossing structure in the drawing is actually laid in different paths without physical contact, thereby improving the safety and efficiency of power transmission using the wire. In addition, it is also possible to arrange pitch pulleys in place of the pitch auxiliary pulleys shown in the drawing.

The above description is for the actuation and yaw motions of the first jaw, and the drawings are also for describing the actuation and yaw motions of the first jaw. Although relay pulleys and pulleys relating to pitch motion are not described, these pulleys may be sufficiently understood, and thus these pulleys are not illustrated in the drawings. In addition, the second jaw may be sufficiently understood from the drawings and description of the first jaw, and thus drawings and a description of the second jaw are omitted.

Figure 25:
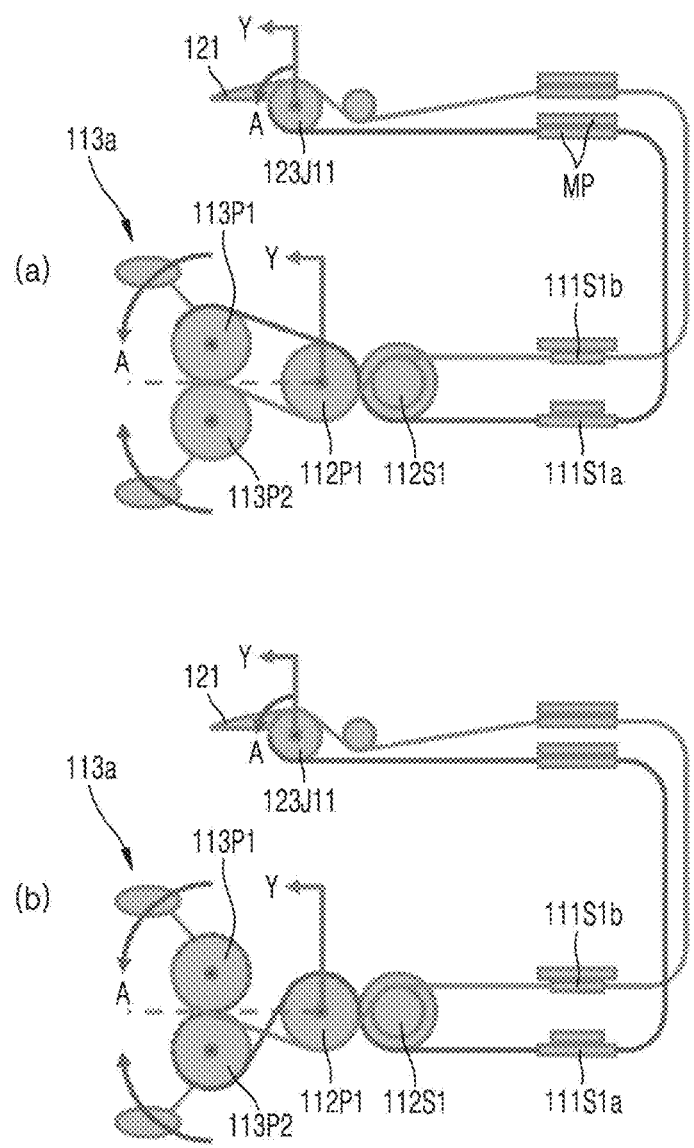
FIG. 25 is a view illustrating another modification of the embodiment shown in FIG. 17.

FIG. 25 is view illustrating modifications of the embodiment shown in FIG. 17. For example, wire paths shown in FIG. 17 are modified.

Here, the modifications are different from the embodiment shown in FIG. 17 in that ends of both strands of the first jaw wire 130J1 are not coupled to the same actuation pulley but are coupled to different actuation pulleys. That is, one end of the first jaw wire 130J1 is coupled to the first actuation pulley 113P1, and the other end of the first jaw wire 130J1 is coupled to the second actuation pulley 113P2. In this case, it is necessary that rotations of the two actuation pulleys are synchronized with each other using gears or the like. That is, the two actuation pulleys have to be connected in such a manner that if one of the actuation pulleys is rotated, the other of the actuation pulleys is accordingly rotated.

As described above, since rotations of the two actuation pulleys are synchronized with each other, although both strands of the first jaw wire 130J1 are not wound around one actuation pulley but are wound around different actuation pulleys, the same effect may be obtained.

In this structure, it may be considered that the first jaw wire 130J1 forms a virtual closed circuit as indicated using a dashed line in FIG. 25A, and the virtual closed circuit may be called a virtual loop.

The configuration shown in FIG. 25A may be variously modified by changing the paths of wires, the sizes and arrangement of joint pulleys, the configuration of manipulation parts, the configuration of the end tool, etc.

In FIG. 25B, the actuation pulleys around which both strands of the first jaw wire 130J1 are wound are configured differently from the configuration shown in FIG. 25A. That is, in this case, one end portion of the first jaw wire 130J1 coupled to the first actuation pulley 113P1 in FIG. 25A is coupled to the second actuation pulley 113P2. Similarly, in this case, the other end portion of the first jaw wire 130J1 coupled to the second actuation pulley 113P2 in FIG. 25A is coupled to the first actuation pulley 113P1.

As described above, when wires wound around yaw pulleys are connected to actuation pulleys, the wires may be coupled to any one of the actuation pulleys. This is because the two actuation pulleys are synchronized with each other using gears or the like. However, in winding around any actuation pulley, the direction of winding has to be properly determined according to the rotation direction of the actuation pulley so as to make actuation manipulation identical to a final actuation motion of the end tool.

The above description is for the actuation and yaw motions of the first jaw, and the drawings are also for describing the actuation and yaw motions of the first jaw. Although relay pulleys and pulleys relating to pitch motion are not described, these pulleys may be sufficiently understood, and thus these pulleys are not illustrated in the drawings. In addition, the second jaw may be sufficiently understood from the drawings and description of the first jaw, and thus drawings and a description relating to the operation of the second jaw are omitted.

Figure 26:
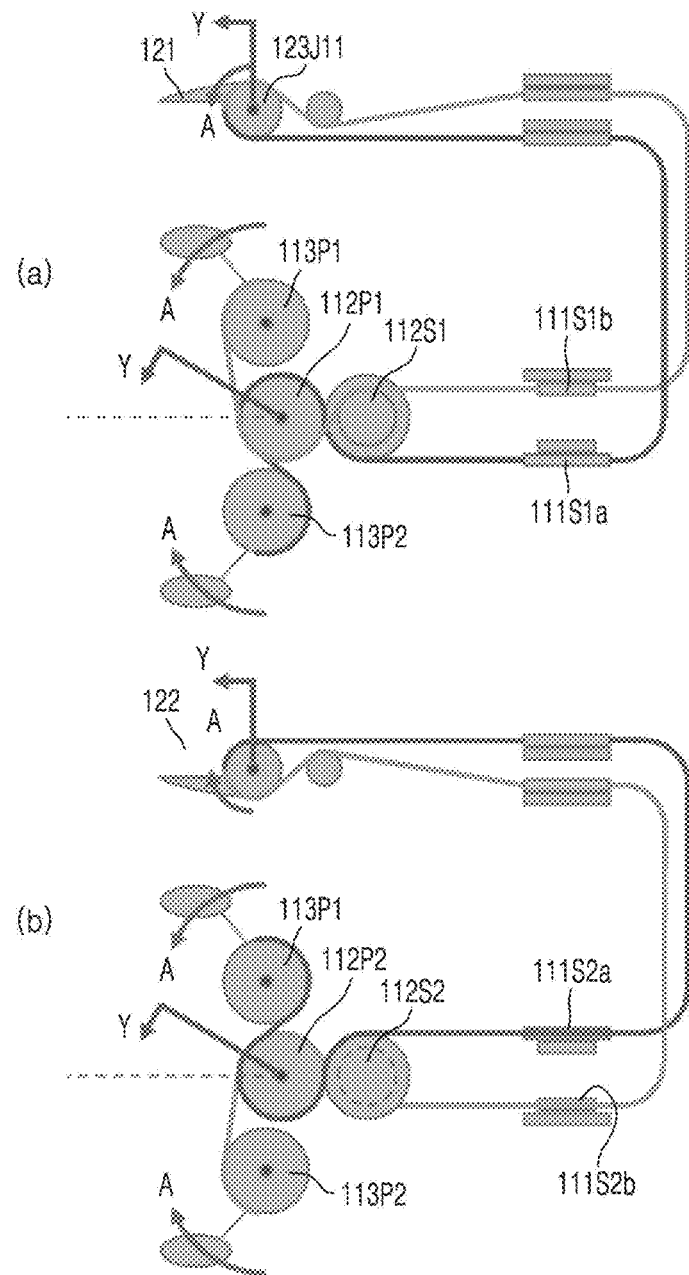
FIG. 26 is a view illustrating another modification of the embodiment shown in FIG. 17.

FIG. 26 is view illustrating modifications of the embodiment shown in FIG. 25. For example, the positions of actuation pulleys shown in FIG. 25 are modified.

Here, the modifications are different from the embodiment shown in FIG. 25 in that two actuation pulleys are not adjacent to each other but are spaced apart from each other and are opposite each other with respect to the first jaw yaw pulley 112P1. If the two actuation pulleys are synchronized with each other using gears or the like, the same operation as that explained with reference to FIG. 25 may be possible.

This configuration makes it possible to place the actuation pulleys at more rearward positions than in other embodiments. That is, a long actuation handle may be provided, and thus actuation manipulation may be more easily performed. The reason for this is that as the length of a handle increases, actuation manipulation is performed with less force owing to the principle of the lever.

FIG. 26A is a view illustrating actuation motion and yaw motion of the first jaw, and FIG. 26B is a view illustrating actuation motion and yaw motion of the second jaw.

The configurations shown in FIGS. 26A and 26B may be variously modified by changing the paths of wires, the sizes and arrangement of joint pulleys, the configuration of manipulation parts, the configuration of the end tool, etc.

Figure 27:
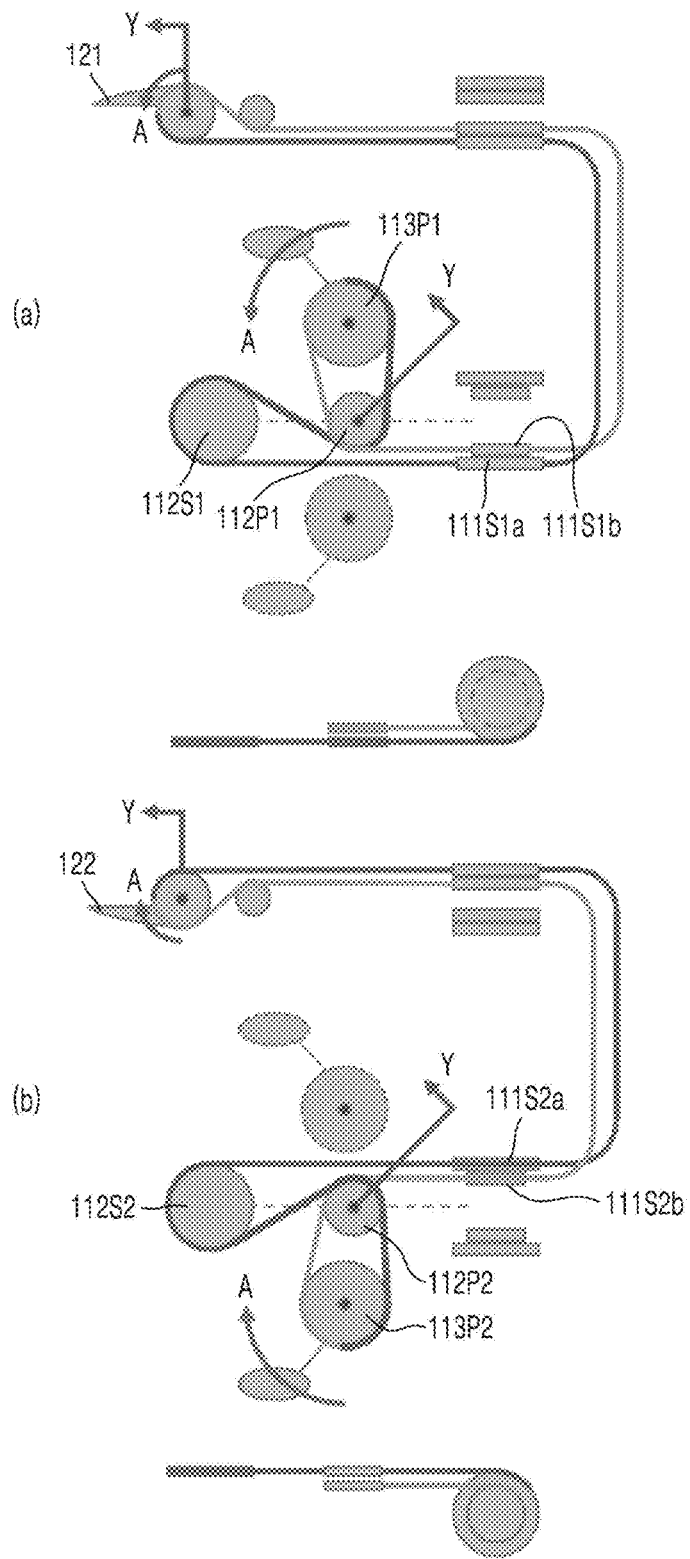
FIG. 27 is a view illustrating another modification of the embodiment shown in FIG. 17.

FIG. 27 is view illustrating modifications of the embodiment shown in FIG. 17. For example, the positions of actuation pulleys shown in FIG. 25 are modified.

Unlike the configured in the first embodiment, in the case shown in FIG. 27A, both strands of the first jaw wire 130J1 wound around the first jaw 121 pass over two adjacent connection-part relay pulleys MP, the first jaw yaw pulley 112P1 and the first jaw yaw auxiliary pulley 112S1 neighbor each other for yaw motion, the first jaw yaw pulley 112P1 is placed on a right side in the drawing, and the rotation axis of the first jaw yaw pulley 112P1 is a yaw rotation axis.

Here, the modifications are different from the embodiment shown in FIG. 17 in that two actuation pulleys are not adjacent to each other but are spaced apart from each other and are opposite each other with respect to a yaw pulley.

In addition, the modifications are different from the embodiments shown in FIGS. 17, 25, and 26 in that the positional relationship (front-rear positional relationship) between a yaw pulley and a yaw auxiliary pulley is modified. That is, even in a direct-type joint, the first jaw yaw pulley 112P1 is placed on a right side in the drawing, and the rotation axis of the first jaw yaw pulley 112P1 is a yaw rotation axis. To this end, the first jaw wire passing over the first jaw pitch auxiliary pulley-a 111S1a is wound around the first jaw yaw auxiliary pulley 112S1, passed over the first jaw yaw pulley 112P1, and fixedly coupled to the first actuation pulley 113P1. In addition, the first jaw wire passing over the first jaw pitch auxiliary pulley-b 111S1b is passed over the first jaw yaw pulley 112P1 and directly fixedly coupled to the first actuation pulley 113P1 without passing over the first jaw yaw auxiliary pulley 112S1.

In this configuration, a yaw rotation axis may be located closer to a pitch rotation axis than in other embodiments. As a result, a user may perform more natural, intuitive manipulation.

In addition, this configuration makes it possible to place the actuation pulleys at more rearward positions than in other embodiments. That is, a long actuation handle may be provided, and thus actuation motion may be more easily performed. The reason for this is that as the length of a handle increases, actuation manipulation is performed with less force owing to the principle of the lever.

FIG. 27A is a view illustrating actuation motion and yaw motion of the first jaw, and FIG. 27B is a view illustrating actuation motion and yaw motion of the second jaw.

The configurations shown in FIGS. 27A and 27B may be variously modified by changing the paths of wires, the sizes and arrangement of joint pulleys, the configuration of manipulation parts, the configuration of the end tool, etc.

Modification of Actuation Manipulation Part

Figure 28:
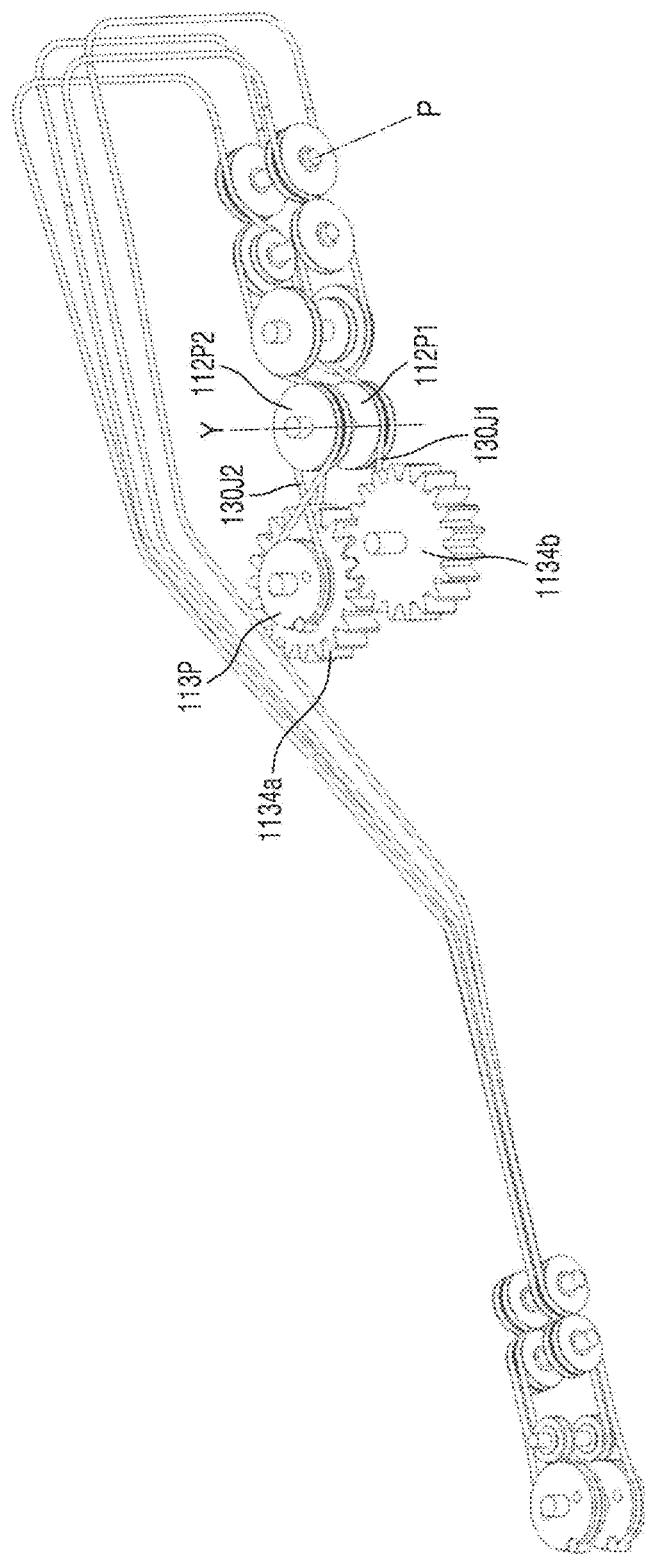
FIG. 28 is a view illustrating another modification of the embodiment shown in FIG. 8.

FIG. 28 is a view illustrating another modification of the embodiment shown in FIG. 8.

Here, an instrument for surgery according to this modification is characteristically different from the instrument 100 for surgery of the first embodiment of the present invention (refer to FIG. 8) in the configuration of an actuation pulley 113P of an manipulation part 110. That is, in the instrument 100 for surgery of FIG. 8, actuation pulleys are respectively provided on two actuation rotation shafts, and jaw wires are respectively wound around the actuation pulleys.

Specifically, in the instrument 100 for surgery of FIG. 8, the first actuation pulley 113P1 is provided on the first actuation rotation shaft 1131a, and the first jaw wire 130J1 is wound around the first actuation pulley 113P1. Similarly, the second actuation pulley 113P2 is provided on the second actuation rotation shaft 1131b, and the second jaw wire 130J2 is wound around the second actuation pulley 113P2.

However, the modification shown in FIG. 28 is characteristically different in that both two jaw wires are wound around one actuation rotation shaft. That is, the actuation pulley 113P is provided on an actuation rotation shaft 1131, a first jaw wire 130J1 is wound around a lower portion of the actuation pulley 113P, and a second jaw wire 130J2 is wound around an upper portion of the actuation pulley 113P. However, since the two wires 130J1 and 130J2 have to be rotated in opposite directions by rotation of the actuation rotation shaft 1131, one of the two wires 13071 and 130J2 has a crossing structure. In FIG. 28, the second jaw wire 130J2 is crossed between the actuation pulley 113P and a second jaw yaw pulley 112P2.

The structure of an actuation manipulation part except for the actuation rotation shaft and the actuation pulley is the same as above, that is, a first actuation rotation part (not shown), a first actuation gear 1134a, a second actuation rotation part (not shown), and a second actuation gear 1134b are provided. Here, the gears connect operations of the two actuation rotation parts to each other such that if one of two fingers holding the two actuation rotation parts is moved, the other finger may also be moved. In addition, owing to the gears, the amounts of rotation of the two actuation rotation parts may be equal. Instead of the gears, a link structure may be used to obtain the same effect.

Modification of Pitch Manipulation Part

Figure 29:
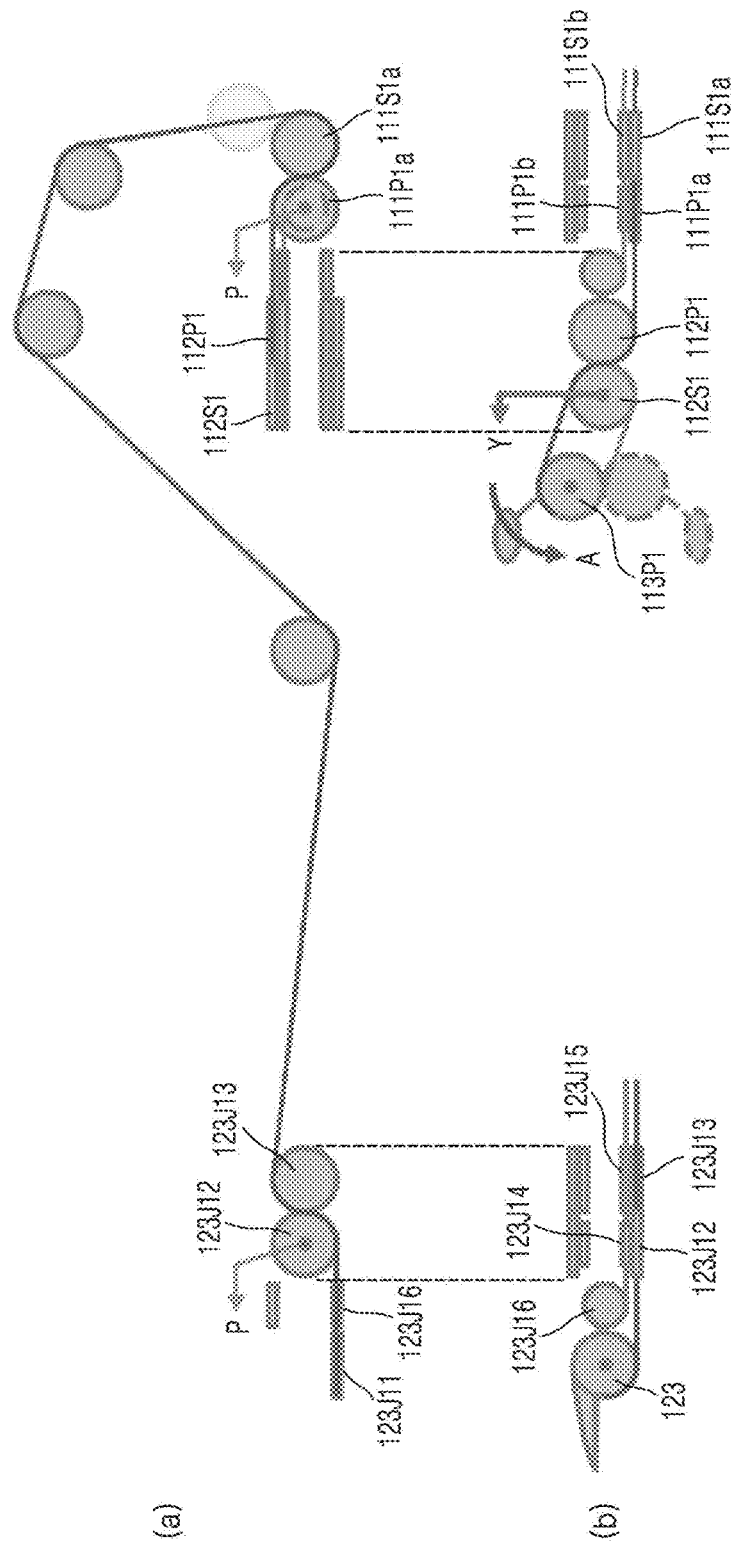
FIG. 29 is a view illustrating another modification of the embodiment shown in FIG. 16.

FIG. 29 is a view illustrating another modification of the embodiment shown in FIG. 16.

Here, FIG. 29A is a side view, and FIG. 29B is a plan view.

Here, an instrument for surgery according to this modification is characteristically different from the instrument 100 for surgery of the embodiment of the present invention (refer to FIG. 16) in the configuration of an manipulation part 110 and an end tool 120. That is, in the instrument 100 for surgery shown in FIG. 16, pitch pulleys have the same diameter. However, in FIG. 29, pitch pulleys have different diameters.

That is, the J12 pulley 123J12 and J14 pulley 123J14 of the end tool 120 face each other and have different diameters, and the first jaw pitch pulley-a 111P1a and the first jaw pitch pulley-b 111P1b of the manipulation part 110 face each other and have different diameters.

In this case, the ratio of the different diameters of the pitch pulleys of the end tool 120 (that is, the diameter ratio of the J12 pulley 123J12 and the J14 pulley 123J14) is set to be equal to the ratio of the different diameters of the pitch pulleys of the manipulation part 110 (that is, the diameter ratio of the first jaw pitch pulley-a 111P1a and the first jaw pitch pulley-b 111P1b) such that the amount of angular movement of both strands of a jaw wire by pitch rotation of the manipulation part 110 may be equal to the amount of angular movement of both strands of a wire by pitch rotation of the end tool 120, and thus pitch motion may be normally performed. Thus, even in the case of a direct-type pitch joint, pitch pulleys having different diameters may be used. This method may also be applied to a yaw joint. That is, the yaw pulleys of the manipulation part 110 may be configured to having different diameters and the J11 pulley 123J11 and the J21 pulley 123J21 of the end tool 120 may be configured to have different diameters, so as to provide a direct-type yaw joint constituted by yaw pulleys having different pulleys.

As described above, the instrument 100 for surgery according to the first embodiment of the present invention may be modified by variously modifying the yaw joint, the pitch joint, and the actuation joint to provide instruments for surgery according to various embodiments that have the same function as the instrument 100 for surgery of the first embodiment. The above-described modifications described as modification examples of each joint may be variously combined to provide various other modifications.

In addition, the idea of the present invention is not limited to those illustrated in the accompanying drawings. For example, various wires, pulleys, and joint constituted thereof may be combined to provide the same function as that of the instrument 100 for surgery of the first embodiment.

<Modification for Insulation>

Figure 30:
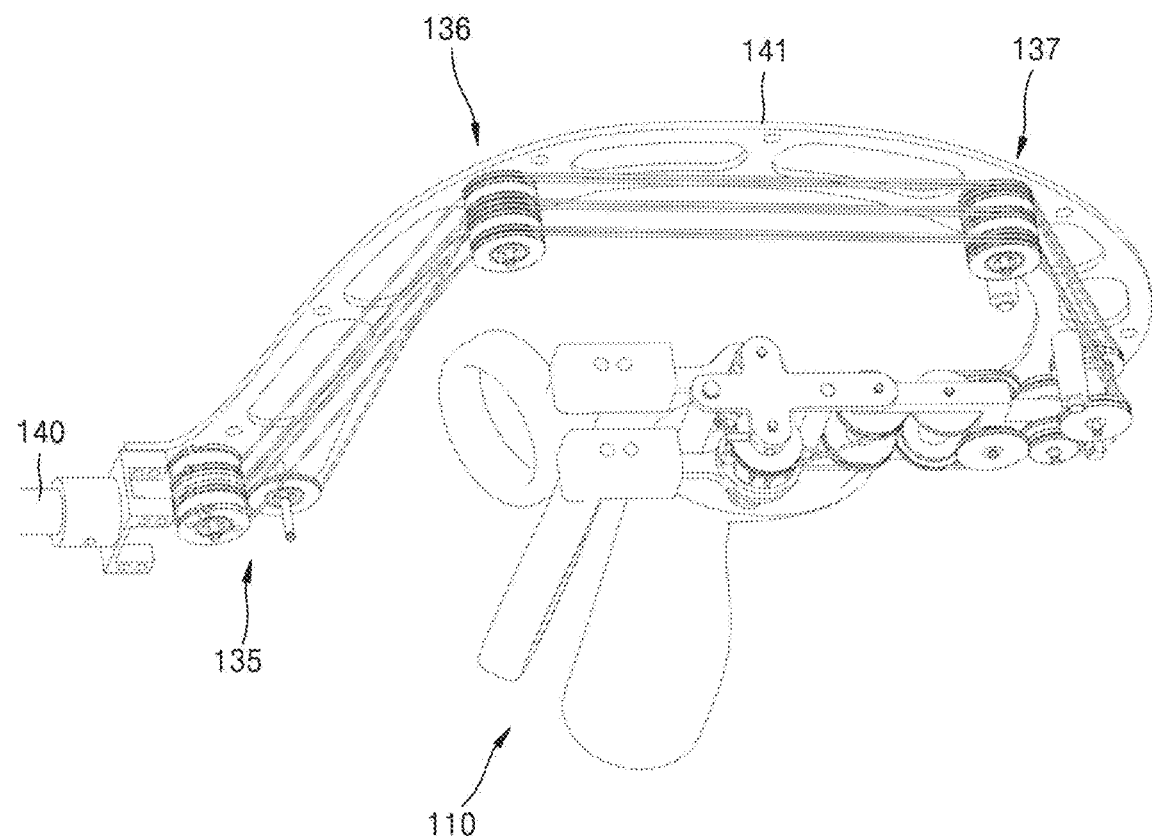
FIGS. 30 and 31 are views illustrating a modification relating to insulation.
Figure 31:
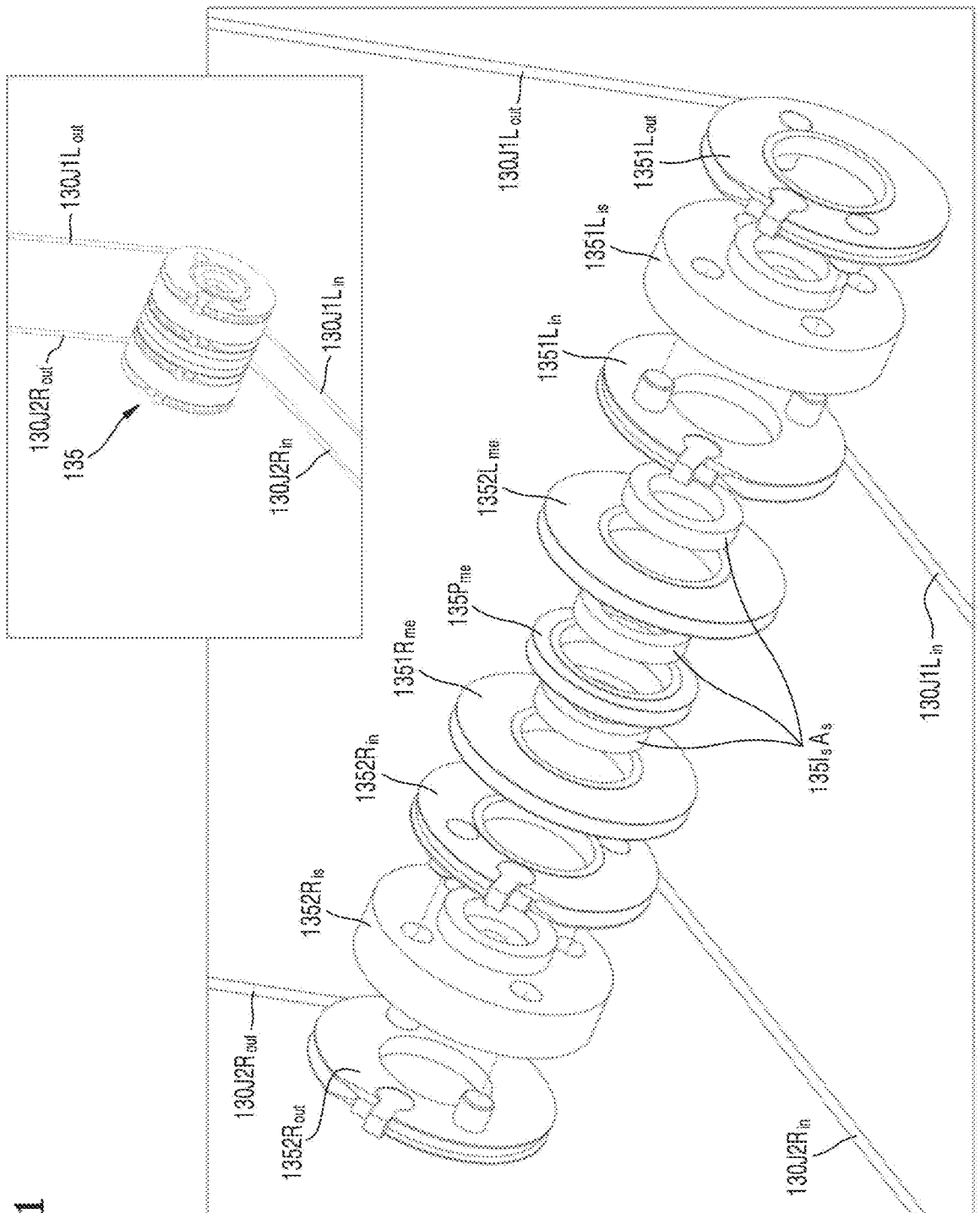

FIGS. 30 and 31 are views illustrating a modification relating to insulation.

Referring to FIGS. 30 and 31, an instrument for surgery according to the embodiment is characteristically different from the above-described instrument 100 for surgery of the present invention (refer to FIG. 2) in that the instrument for surgery further include an insulation assembly for insulating each wire. That is, an end tool and a manipulation part are separated for electrical insulation, and thus even when an additional electrical wire is connected to the end tool to use jaws of the end tool for electrical cautery, the manipulation part may be safely electrically insulated. To this end, an insulation assembly is provided on a middle portion of each wire physically connecting the end tool and the manipulation part for insulating the end tool and the manipulation part from each other. To this end, a first insulation assembly 135, a second insulation assembly 136, and a third insulation assembly 137 are sequentially arranged along a bent part 141 of a connecting part 140, and each insulation assembly sequentially insulates two wires.

In the drawings, the first insulation assembly 135, the second insulation assembly 136, and the third insulation assembly 137 are sequentially arranged from a side close to the end tool 120. However, the idea of the invention is not limited thereto, and if necessary, the structure and arrangement of each insulation assembly may be variously modified.

Hereinafter, the first insulation assembly 135 will be described in more detail.

Here, a second jaw R wire 130J2R refers to the right one of both strands of a second jaw wire 130J2, and the second jaw R wire 130J2R is divided into two: a second jaw R wire-in 130J2Rin entering the first insulation assembly 135 and a second jaw R wire-out 130J2Rout leaving the first insulation assembly 135.

In addition, a first jaw L wire 130J1L refers to the left one of both strands of a first jaw wire 130J1, and the first jaw L wire 130J1L is divided into two: a first jaw L wire-in 130J1Lin entering the first insulation assembly 135 and a first jaw L wire-out 130J1Lout leaving the first insulation assembly 135.

The first insulation assembly 135 includes a second jaw R wire-in pulley 1352Rin, a second jaw R wire-out pulley 1352Rout, and a second jaw R wire insulation pulley 1352Ris that relate to insulation of the second jaw R wire. Here, the second jaw R wire-in 130J2Rin is coupled to the second jaw R wire-in pulley 1352Rin, and the second jaw R wire-out 130J2Rout is coupled to the second jaw R wire-out pulley 1352Rout. In addition, the second jaw R wire insulation pulley 1352Ris is placed between the second jaw R wire-in pulley 1352Rin and the second jaw R wire-out pulley 1352Rout to insulate the second jaw wire-in pulley 1352Rin and the second jaw R wire-out pulley 1352Rout from each other and thus to insulate the second jaw R wire-in 130J2Rin and the second jaw R wire-out 130J2Rout from each other.

In this case, a recess is formed in one of the second jaw wire-in pulley 1352Rin and the second jaw R wire insulation pulley 1352Ris, and a protrusion formed on the other is coupled to the recess. In this case, a recess is formed in one of the second jaw wire-out pulley 1352Rout and the second jaw R wire insulation pulley 1352Ris, and a protrusion formed on the other is coupled to the recess. In this case, the protrusion (or recess) of the second jaw wire-in pulley 1352Rin and the protrusion (or recess) of the second jaw R wire-out pulley 1352Rout are isolated from each other for insulating the second jaw R wire-in 130J2Rin and the second jaw R wire-out 130J2Rout from each other.

That is, owing to the aforementioned configuration, although the second jaw R wire-in 130J2Rin, the second jaw wire-in pulley 1352Rin, the second jaw R wire-out 130J2Rout, and the second jaw R wire-out pulley 1352Rout is formed of a conductor such as a metal, the second jaw R wire-in 130J2Rin and the second jaw R wire-out 130J2Rout may be insulated from each other by forming the second jaw R wire insulation pulley 1352Ris using a nonconductor.

Owing to the configuration, the second jaw R wire-in 130J2Rin entering the first insulation assembly 135 may be electrically insulated from the second jaw R wire-out 130J2Rout leaving the first insulation assembly 135, and during the manipulation of the manipulation part and the operation of the end tool, power may be transmitted as if a single continuous wire is used for the power transmission.

In addition, the first insulation assembly 135 includes a first jaw L wire-in pulley 1351Lin, a first jaw L wire-out pulley 1351Lout, and a first jaw L wire insulation pulley 1351Lis that relate to insulation of the first jaw R wire. This configuration is the same in principle as that for insulating the first jaw R wire described above, and thus a detailed description thereof will be omitted.

In addition, the first insulation assembly 135 may include a first jaw R wire relay pulley 1351Rme, a second jaw L wire relay pulley 1352Lme, at least one pitch wire relay pulley 135Pme, and at least one auxiliary insulation pulley 135IsAs being a nonconductor. Here, auxiliary insulation pulleys 135IsAs are respectively inserted into a second jaw R wire relay pulley 1352Rme, the second jaw L wire relay pulley 1352Lme, the pitch wire relay pulley 135Pme, and another pitch wire relay pulley (not shown); the first jaw R wire (not shown) passes over the first jaw R wire relay pulley 1351Rme while being wound around the first jaw R wire relay pulley 1351Rme; a second jaw L wire (not shown) passes over the second jaw L wire relay pulley 1352Lme while being wound around the second jaw L wire relay pulley 1352Lme; and both strands of a pitch wire (not shown) pass over two pitch wire relay pulleys 135Pme while being wound around the two pitch wire relay pulleys 135Pme.

Owing to this configuration, wires connected to the first insulation assembly 135 from the end tool 120, and pulleys of the first insulation assembly 135 around which the wires are wound may be electrically separated from rotation shafts of the pulleys of the first insulation assembly 135 and wires.

In more detail, if wires and pulleys of the first insulation assembly are metallic, pulleys formed of an electrically insulative material may be placed between the metallic pulleys so as to electrically separate the end tool and the manipulation part as described above, and if only wires are metallic, elements of the first insulation assembly may be formed of an electrically insulative material so as to electrically separate the end tool and the manipulation part as described above.

In the same manner as in the first insulation assembly 135, the first jaw R wire and the second jaw L wire are separated and insulated in the second insulation assembly 136, and both strands of a pitch wire are separated and insulated in the third insulation assembly 137.

According to the configuration, each wire connecting the end tool and manipulation part is completely insulated, and thus the end tool and the manipulation part may be separately insulated for electrical safety of the manipulation part. Each insulation assembly described above is characterized in that the insulation assembly electrically disconnects an intermediate point of a wire connected from the end tool to the manipulation part for electrically insulating the end tool from the manipulation part. The above description is given for the case in which wires and pulleys of the insulation assemblies are metallic. However, if the pulleys (such as the first jaw L wire-in pulley 1351Lin and the first jaw L wire-out pulley 1351Lout) are formed of a nonconductor that does not conduct electricity, the first jaw L wire-in pulley 1351Lin, the first jaw L wire-out pulley 1351Lout, and the first jaw L wire insulation pulley 1351Lis may not be separate and may constitute a single nonconductor pulley. This modification may be sufficiently deduced from the above description, and thus a detailed description thereof will be omitted.

MODE OF THE INVENTION

<Second Embodiment of Instrument for Surgery>

Hereinafter, an instrument 200 for surgery will be described according to a second embodiment of the present invention. Here, the instrument 200 for surgery of the second embodiment of the present invention is characteristically different in the configuration of a manipulation part 210 of the instrument 200 from the instrument 100 for surgery (refer to FIG. 2) of the first embodiment of the present invention. That is, in the instrument 200 for surgery of the second embodiment of the present invention, the modification shown in FIG. 21 is specifically embodied. This difference in the configuration from the first embodiment will be described later in detail.

Figure 32:
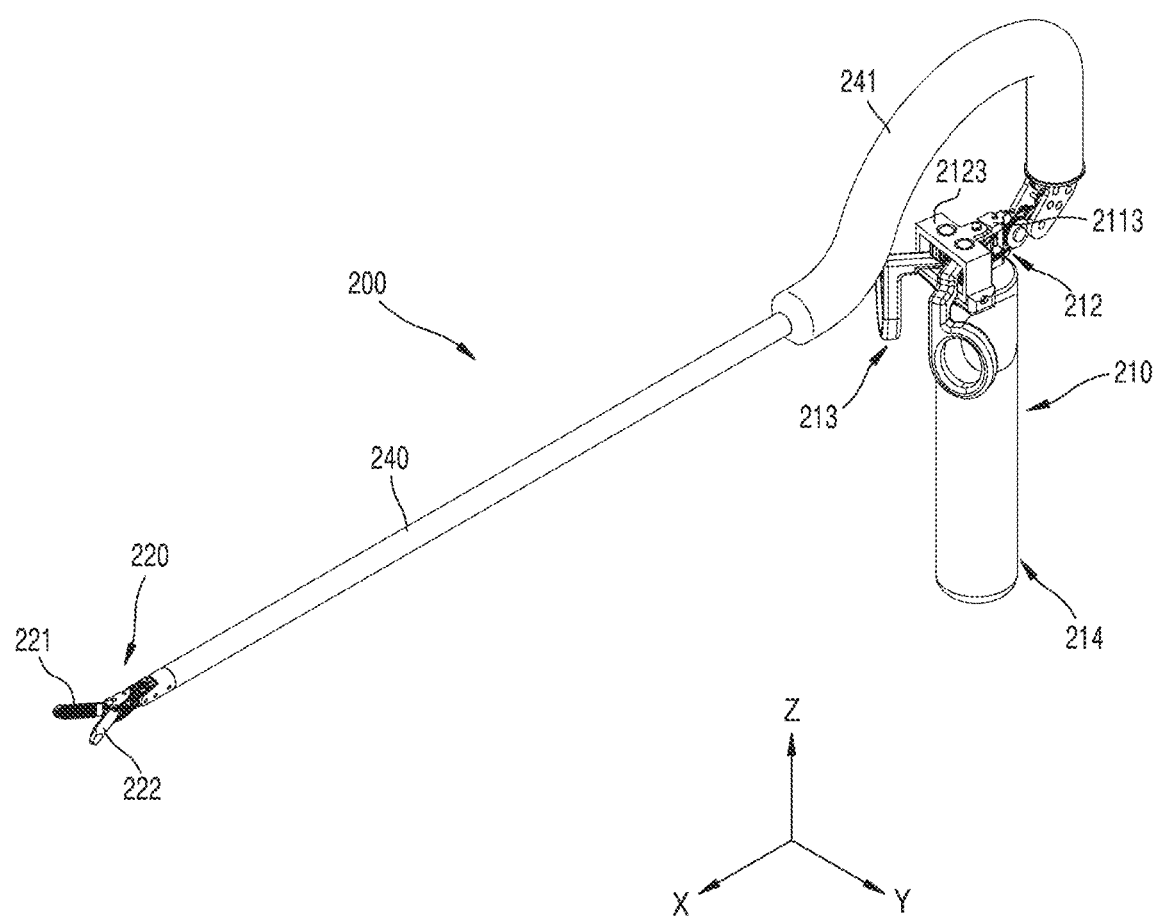
FIG. 32 is a perspective view illustrating an instrument for surgery according to a second embodiment of the present invention.
Figure 33:
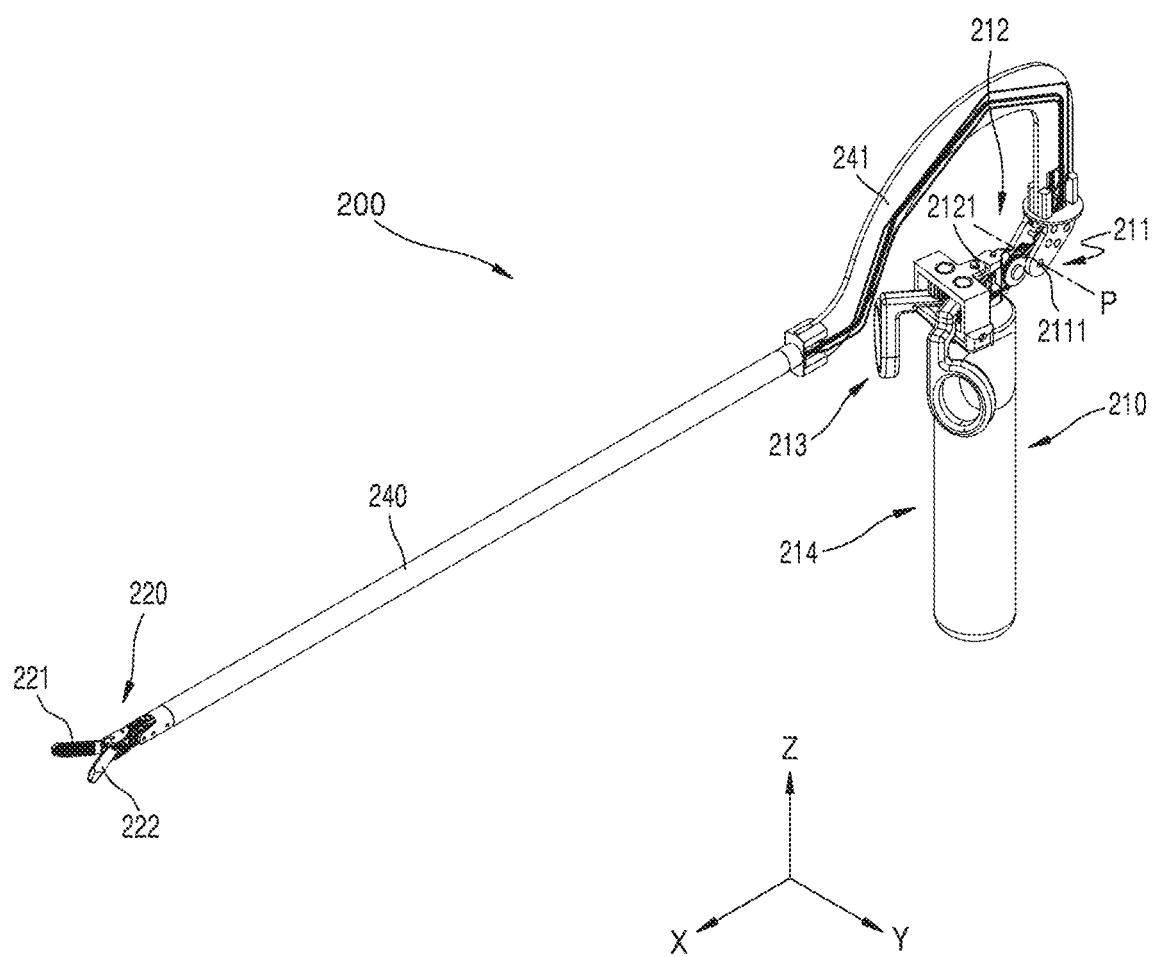
FIG. 33 is an inside perspective view illustrating the instrument for surgery shown in FIG. 32.
Figure 34:
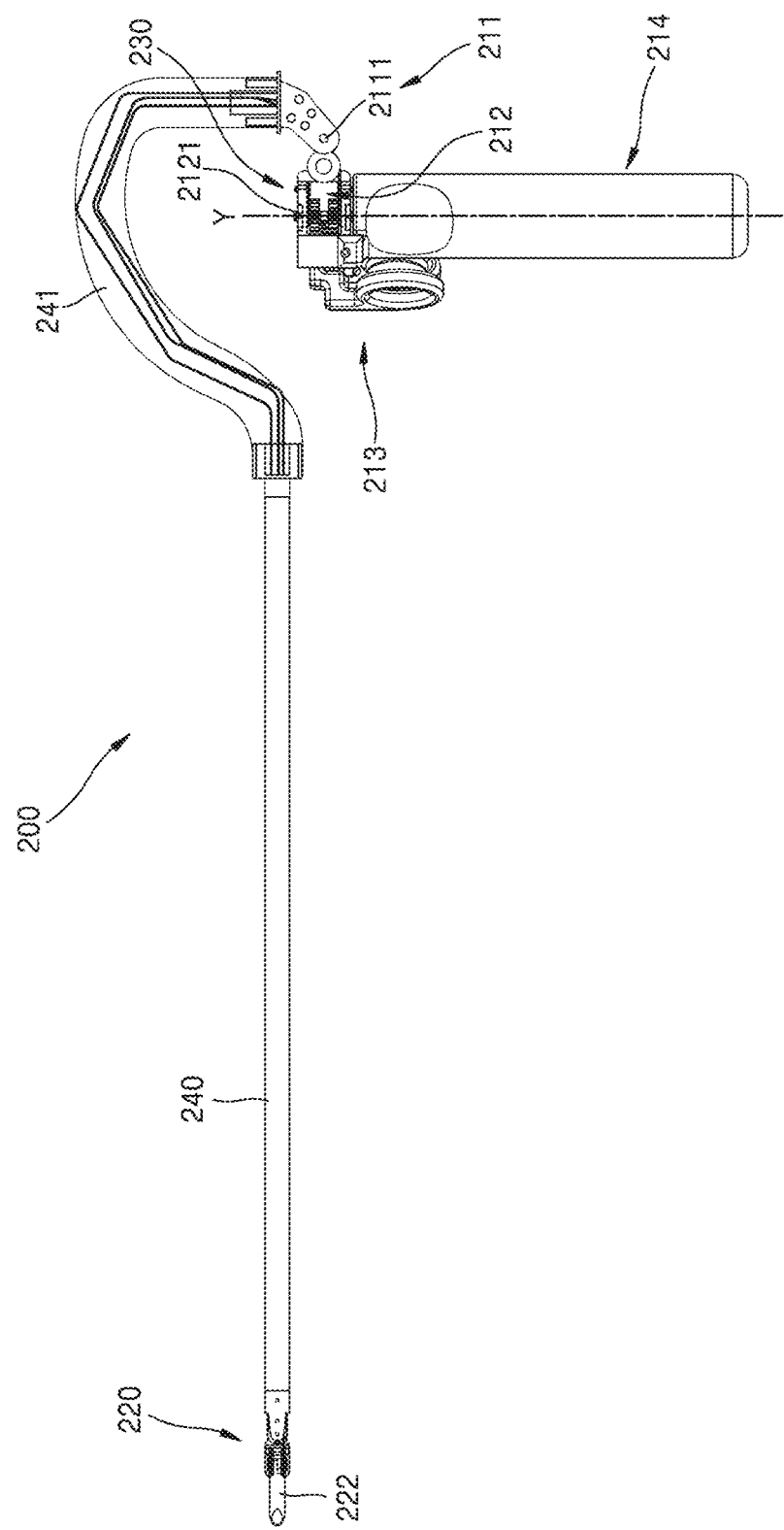
FIG. 34 is a side view illustrating the instrument for surgery shown in FIG. 33.
Figure 35:
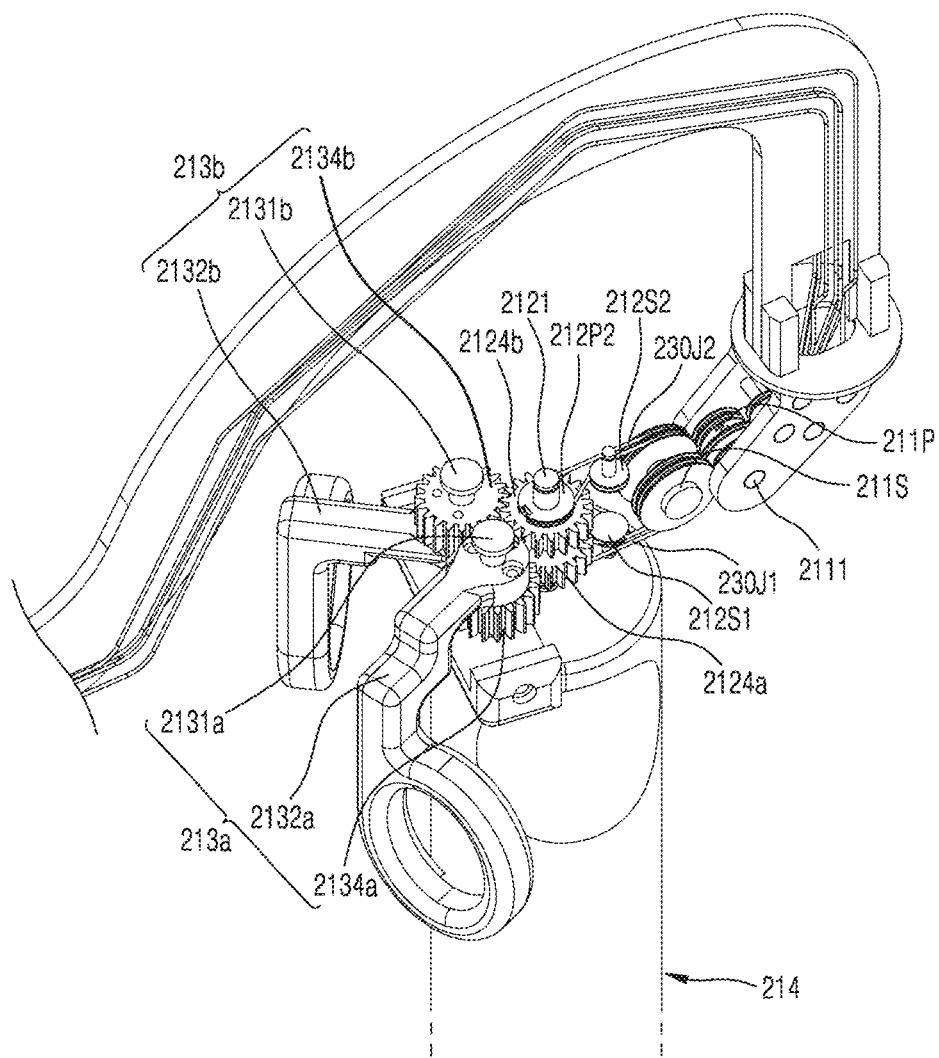
FIGS. 35 and 36 are perspective views illustrating a manipulation part of the instrument for surgery shown in FIG. 33.
Figure 36:
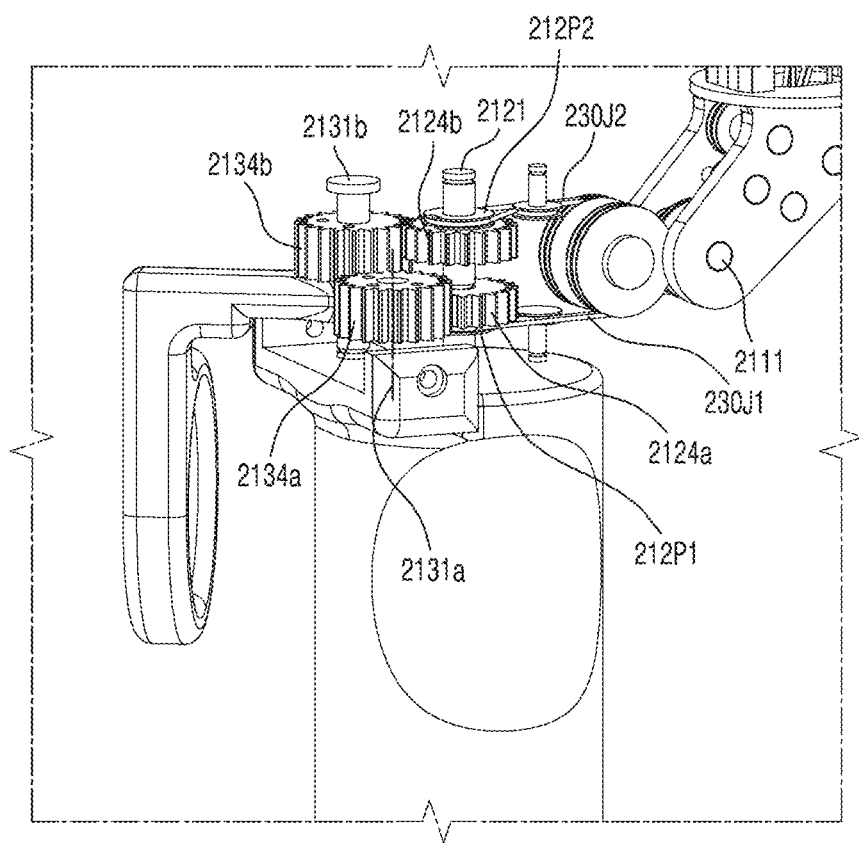
Figure 37:
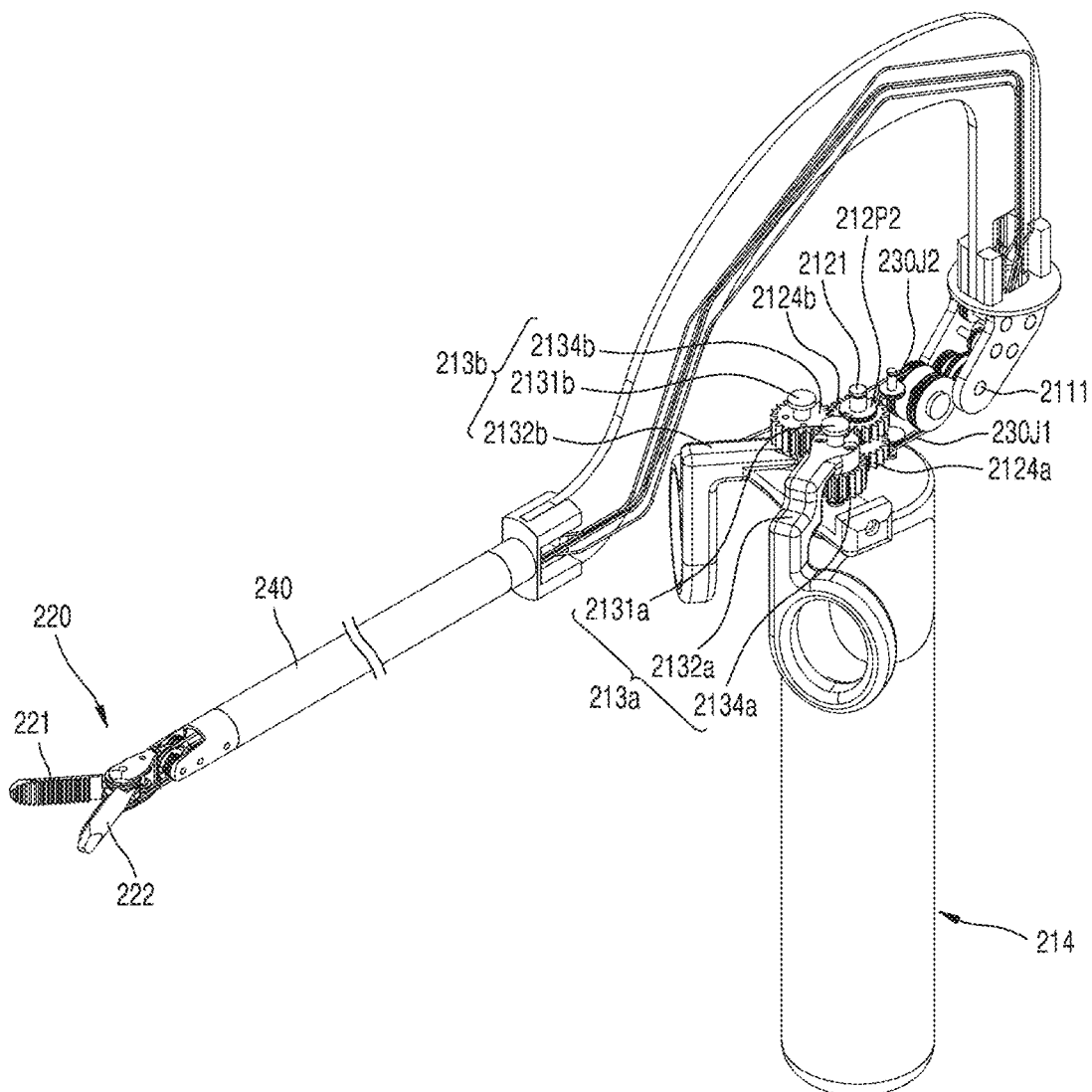
FIGS. 37 and 38 are perspective views illustrating a yaw motion of the instrument for surgery shown in FIG. 33.
Figure 38:
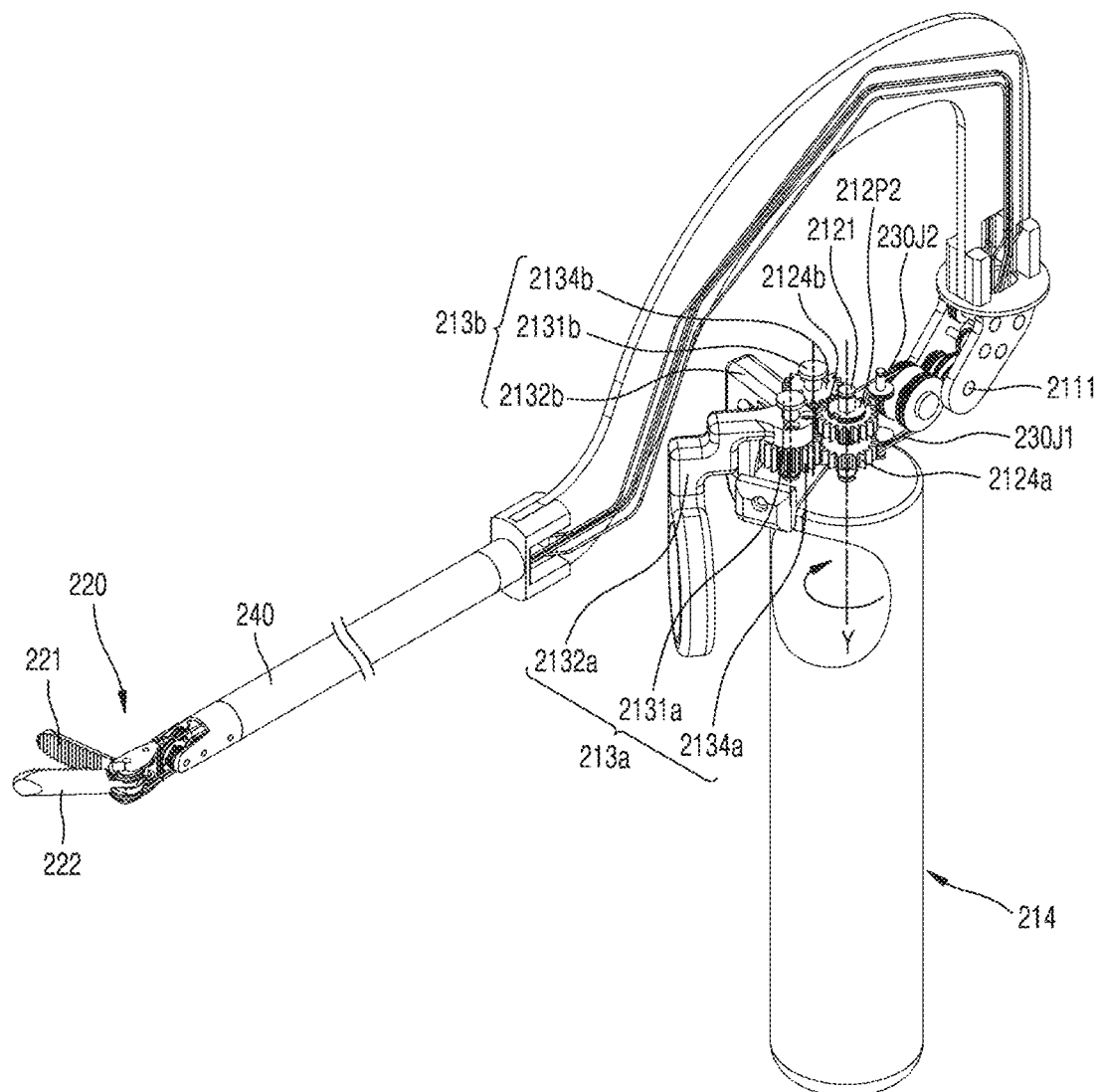
Figure 39:
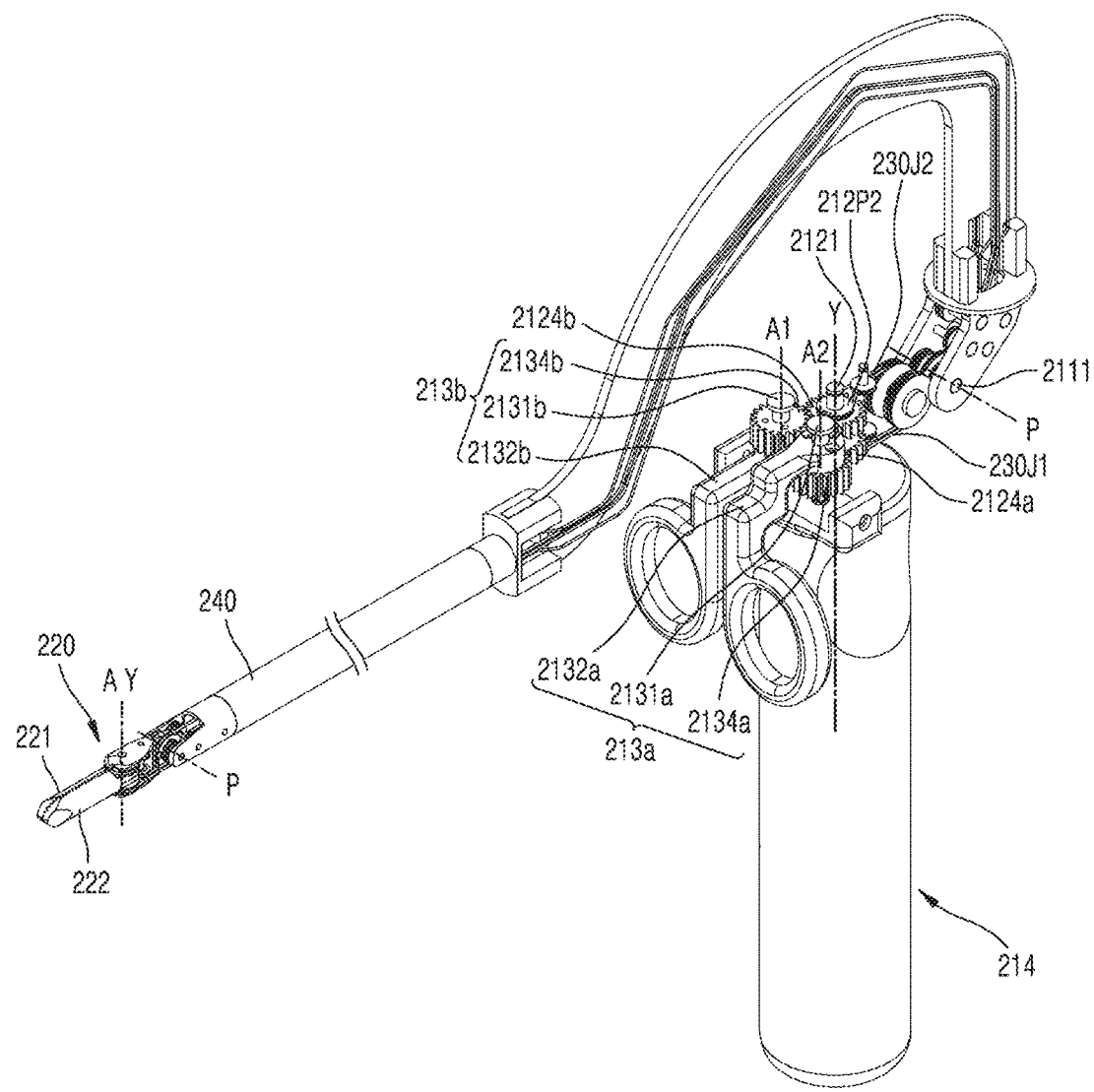
FIGS. 39 and 40 are perspective views illustrating an actuation motion of the instrument for surgery shown in FIG. 33.
Figure 40:
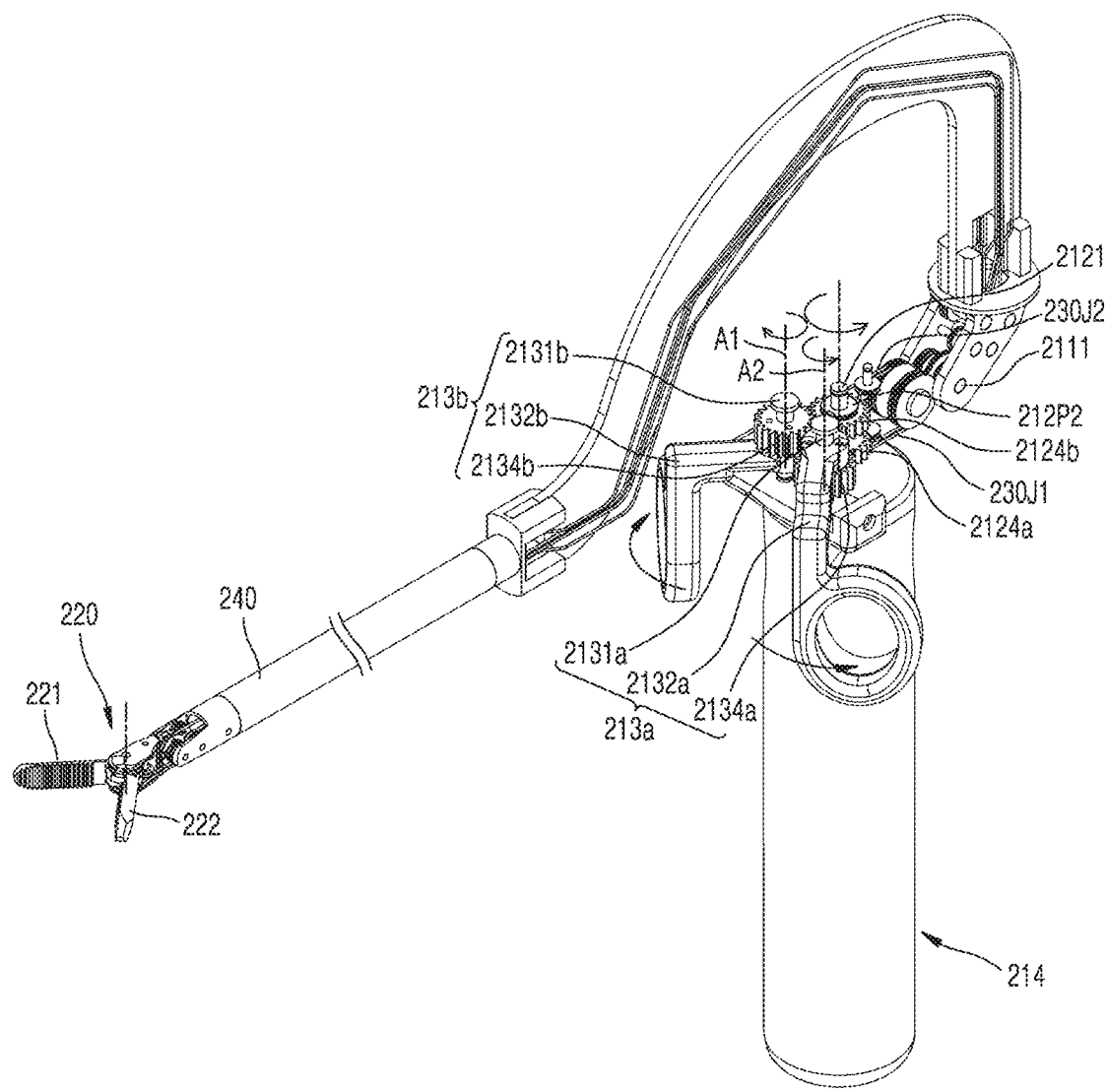

FIG. 32 is a perspective view illustrating the instrument for surgery according to the second embodiment of the present invention, FIG. 33 is an inside perspective view illustrating the instrument for surgery of FIG. 32, and FIG. 34 is a side view of the instrument for surgery of FIG. 33. In addition, FIGS. 35 and 36 are perspective views illustrating the manipulation part of the instrument for surgery shown in FIG. 33.

Referring to FIG. 32 to FIG. 40, according to the second embodiment of the present invention, the manipulation part 210 of the instrument 200 for surgery includes a pitch manipulation part 211 configured to control pitch motion of an end tool 220, a yaw manipulation part 212 configured to control yaw motion of the end tool 220, an actuation manipulation part (actuation operator) 213 configured to control actuation motion of the end tool 220, and a first handle 214 that a user may hold.

First, an example operation of the instrument 200 for surgery shown in FIG. 32 will be described. In a state in which a user holds the first handle 214 with his/her palm, the user may perform a pitch motion by rotating the first handle 214 around an Y axis (that is, around a pitch rotation shaft 2111) and a yaw motion by rotating the first handle 214 around a Z axis (that is, around a yaw rotation shaft 2121), and in a state in which the user inserts his/her thumb and index finger into the actuation manipulation part 213, the user may perform an actuation motion by rotating the actuation manipulation part 213.

Here, the instrument 200 for surgery of the second embodiment of the present invention also has the feature in which the end tool 120 and the manipulation part 110 of the instrument 100 for surgery of the first embodiment of the present invention are rotated in intuitively the same direction.

To this end, the manipulation part 210 is configured like the end tool 220. That is, in the manipulation part 210, portions that are actually moved for actuation, yaw, and pitch motions extend respectively from rotation centers of corresponding joints in a positive (+) X-axis direction.

In detail, the first handle 214 may be configured such that a user may grip the first handle 214 with his/her hand. In particular, a user may grip the first handle 214 by holding around the first handle 214 with his/her palm. In addition, the actuation manipulation part 213 and the yaw manipulation part 212 are provided above the first handle 214, and the pitch manipulation part 211 is provided at a side of the yaw manipulation part 212. In addition, another end portion of the pitch manipulation part 211 is connected to the bent part 241 of the connecting part 240.

The actuation manipulation part 213 includes a first actuation manipulation part 213a and a second actuation manipulation part 213b. The first actuation manipulation part 213a includes a first actuation rotation shaft 2131a, a first actuation rotation part 2132a, and a first actuation gear 2134a. The second actuation manipulation part 213b includes a second actuation rotation shaft 2131b, a second actuation rotation part 2132b, and a second actuation gear 2134b. Here, the first and second actuation rotation parts 2132a and 2132b may function as a second handle.

Here, the actuation rotation shafts 2131a and 2131b may make a predetermined angle with an XY plane in which the connecting part 240 is located. For example, the actuation rotation shafts 2131a and 2131b may be parallel with the Z axis. In this state, if the pitch manipulation part 211 or the yaw manipulation part 212 is rotated, the coordinate system of the actuation manipulation part 213 may be relatively varied. However, the idea of the present invention is not limited thereto, and the actuation rotation shafts 2131a and 2131b may be oriented in various directions according to ergonomic designs for the hand structure of a user holding the actuation manipulation part 213.

In addition, the first actuation rotation part 2132a and the first actuation gear 2134a may be fixedly coupled to each other so as to be rotated together around the first actuation rotation shaft 2131a.

Similarly, the second actuation rotation part 2132b and the second actuation gear 2134b may be fixedly coupled to each other so as to be rotated together around the second actuation rotation shaft 2131b.

Here, the first actuation gear 2134a and the second actuation gear 2134b may be engaged with each other, and thus if one of the first and second actuation gears 2134a and 2134b is rotated, the first and second actuation gears 2134a and 2134b may be rotated together in opposite directions.

The yaw manipulation part 212 may include a yaw rotation shaft 2121, a first jaw yaw pulley 212P1, a second jaw yaw pulley 212P2, and a yaw frame 2123. Here, in the drawings, it is illustrated that the yaw manipulation part 212 includes two pulleys: the first jaw yaw pulley 212P1 and the second jaw yaw pulley 212P2. However, the idea of the present invention is not limited thereto. That is, according to the configuration of the yaw manipulation part 212, the yaw manipulation part 212 may include one or more pulleys having the same diameter or different diameters.

Specifically, the yaw rotation shaft 2121 is provided on a side of the actuation manipulation part 213 above the first handle 214. In this case, the first handle 214 is rotatable around the yaw rotation shaft 2121.

Here, the yaw rotation shaft 2121 may make a predetermined angle with the XY plane in which the connecting part 240 is provided. For example, the yaw rotation shaft 2121 may be oriented in a direction parallel to the Z axis, and in this state, if the pitch manipulation part 211 is rotated, the coordinate system of the yaw rotation shaft 2121 may be relatively varied as described above. However, the idea of the present invention is not limited thereto, and the yaw rotation shaft 2121 may be oriented in various directions according to ergonomic designs for the hand structure of a user holding the manipulation part 210.

In addition, the first jaw yaw pulley 212P1 and the second jaw yaw pulley 212P2 are coupled to the yaw rotation shaft 2121 such that the first jaw yaw pulley 212P1 and the second jaw yaw pulley 212P2 may be rotated on the yaw rotation shaft 2121. In addition, a first jaw wire 230J1 may be wound around the first jaw yaw pulley 212P1, and a second jaw wire 230J2 may be wound around the second jaw yaw pulley 212P2.

The yaw frame 2123 connects the first handle 214, the yaw rotation shaft 2121, the first actuation rotation shaft 2131a, and the second actuation rotation shaft 2131b such that the first handle 214, the yaw manipulation part 212, and the actuation manipulation part 213 may be rotated together around the yaw rotation shaft 2121.

In addition, the yaw manipulation part 212 may further include a first yaw gear 2124a and a second yaw gear 2124b that are independently rotatable around the yaw rotation shaft 2121. In this case, the first yaw gear 2124a may be fixedly coupled to the first jaw yaw pulley 212P1 and rotatable together with the first jaw yaw pulley 212P1, and the second yaw gear 2124b may be fixedly coupled to the second jaw yaw pulley 212P2 and rotatable together with the second jaw yaw pulley 212P2.

Here, the first actuation gear 2134a and the second actuation gear 2134b are engaged with each other, and thus if one of the first and second actuation gears 2134a and 2134b is rotated, the first and second actuation gears 2134a and 2134b are rotated together in opposite directions. In addition, the first actuation gear 2134a and the first yaw gear 2124a are engaged with each other, and thus if one of the first actuation gear 2134a and the first yaw gear 2124a is rotated, the first actuation gear 2134a and the first yaw gear 2124a are rotated together in opposite directions. In addition, the first actuation gear 2134a and the second yaw gear 2124b are engaged with each other, and thus if one of the first actuation gear 2134a and the second yaw gear 2124b is rotated, the first actuation gear 2134a and the second yaw gear 2124b are rotated together in opposite directions.

In the example described with reference to FIG. 21A illustrating actuation and yaw motions of the first jaw 121, a handle of the manipulation part 110 is located in an upper region in the drawing. However, in the manipulation part 210 of the instrument 200 for surgery of the second embodiment of the present invention, the first actuation manipulation part 213a located in a lower region in FIG. 31 functions as a handle for operating a first jaw 221 by moving the first jaw wire 230J1. Since the first yaw gear 2124a and the first actuation gear 2134a are engaged with each other, the first actuation rotation part 2132a has to be rotated clockwise in FIG. 31 for an actuation motion. However, in the case shown in FIG. 21A, the upper handle is rotated counterclockwise. These two operations are both for closing two jaws 221 and 222 of the end tool 220 and may be considered to be the same operation, and the configuration of other substantive pulleys and wires is not changed. Thus, the instrument 200 for surgery of the second embodiment of the present invention may be considered to be substantially the same as the example shown in FIG. 21A.

The pitch manipulation part 211 may include a pitch rotation shaft 2111, a pitch pulley 211P, a pitch auxiliary pulley 211S, and a pitch frame 2113. The pitch manipulation part 211 is connected to a bent part 241 of a connecting part 240 through the pitch rotation shaft 2111.

In detail, the pitch frame 2113 serves as a base frame of the pitch manipulation part 211, and the yaw rotation shaft 2121 is rotatably coupled to an end portion of the pitch frame 1113. That is, the yaw frame 2123 is rotatable around the yaw rotation shaft 2121 with respect to the pitch frame 2113.

As described above, the yaw frame 2123 connects the first handle 214, the yaw rotation shaft 2121, the first actuation rotation shaft 2131a, and the second actuation rotation shaft 2131b to each other, and is also connected to the pitch frame 2113. Therefore, if the pitch frame 2113 is rotated around the pitch rotation shaft 2111, the yaw frame 2131, the first handle 214, the yaw rotation shaft 2121, the first actuation rotation shaft 2131a, and the second actuation rotation shaft 2131b connected to the pitch frame 2113 are rotated together. That is, if the pitch manipulation part 211 is rotated around the pitch rotation shaft 2111, the actuation manipulation part 213 and the yaw manipulation part 212 are rotated together with the pitch manipulation part 211. In other words, if a user rotates the first handle 214 around the pitch rotation shaft 2111, the actuation manipulation part 213, the yaw manipulation part 212, and the pitch manipulation part 211 are moved together.

The pitch rotation shaft 2111 and the pitch pulley 211P are coupled to the pitch frame 2113. In this case, the pitch pulley 211P is coupled to the pitch rotation shaft 2111 in such a manner that the pitch pulley 211P is rotatable around the pitch rotation shaft 2111. The pitch auxiliary pulley 211S is placed at a side of the pitch pulley 211P.

The first handle 214, the pitch manipulation part 211, the yaw manipulation part 212, and the actuation manipulation part 213 are connected as follows. The actuation rotation shafts 2131a and 2131b, the yaw rotation shaft 2121, and the pitch rotation shaft 2111 may be provided on the first handle 214. In this case, since the actuation rotation shafts 2131a and 2131b are directly provided on the first handle 214, the first handle 214 and the actuation manipulation part 213 may be directly connected to each other. In addition, since the yaw rotation shaft 2121 is directly provided on the first handle 214, the first handle 214 and the yaw manipulation part 212 may be directly connected to each other. However, since the pitch manipulation part 211 is provided at a side of the yaw manipulation part 212 and connected to the yaw manipulation part 212, the pitch manipulation part 211 may not be directly connected to the first handle 214 but may be indirectly connected to the first handle 214 through the yaw manipulation part 212.

Hereinafter, elements for transmitting the operation of the manipulation part 210 to the end tool 220 will be described in more detail.

The first jaw wire 230J1 for controlling the operation of the first jaw 221 of the end tool 220 is fixedly coupled to a point on the first jaw yaw pulley 212P1 of the manipulation part 210 and is wound around the first jaw yaw pulley 212P1. Similarly, the second jaw wire 230J2 for controlling the operation of a second jaw 222 of the end tool 220 is fixedly coupled to a point on the second jaw yaw pulley 212P2 of the manipulation part 210 and is wound around the second jaw yaw pulley 212P2.

As described with reference to FIG. 21, yaw and actuation motions of the end tool 220 are controlled by rotating the first jaw yaw pulley 212P1 and the second jaw yaw pulley 212P2. That is, the first jaw yaw pulley 212P1 and the second jaw yaw pulley 212P2 are rotated in the same direction so as to rotate the first jaw 221 and the second jaw 222 in the same direction for yaw motion and rotate the first jaw 221 and the second jaw 222 in different directions for actuation motion.

To this end, a structure is required to rotate the first jaw yaw pulley 212P1 and the second jaw yaw pulley 212P2 in the same direction or different directions according to a user's yaw manipulation or actuation manipulation.

To this end, the first jaw yaw pulley 212P1 and the second jaw yaw pulley 212P2 are configured to be rotated around the same yaw rotation shaft 2121, and the first jaw yaw pulley 212P1 and the second jaw yaw pulley 212P2 are connected to each other through at least one gear.

In detail, the first yaw gear 2124a which is fixedly coupled to the first jaw yaw pulley 212P1 and rotatable together with the first jaw yaw pulley 212P1 around the yaw rotation shaft 2121 is engaged with the first actuation gear 2134a, and in this case, the first actuation gear 2134a may be fixedly coupled to the first actuation manipulation part 213a and rotatable together with the first actuation manipulation part 213a around the first actuation rotation shaft 2131a. The first actuation gear 2134a is engaged with the second actuation gear 2134b, and in this case, the second actuation gear 2134b may be fixedly coupled to the second actuation manipulation part 213b and rotatable together with the second actuation manipulation part 213b around the second actuation rotation shaft 2131b. The second actuation gear 2134b is engaged with the second yaw gear 2124b, and in this case, the second yaw gear 2124b may be fixedly coupled to the second jaw yaw pulley 212P2 and rotatable together with the second jaw yaw pulley 212P2 around the yaw rotation shaft 2121.

Owing to this configuration, if an actuation manipulation in which the first actuation manipulation part 213a and the second actuation manipulation part 213b are rotated in opposite directions is performed, the first jaw yaw pulley 212P1 and the second jaw yaw pulley 212P2 are rotated in opposite directions, and thus the first jaw 221 and the second jaw 222 of the end tool 220 are rotated in opposite directions.

The first handle 214 is directly coupled to the yaw frame 2123, and the first actuation manipulation part 213a and the second actuation manipulation part 213b are also connected to the yaw frame 2123. That is, if the first handle 214 is yaw rotated around the yaw rotation shaft 2121, the yaw frame 2123, the first actuation manipulation part 213a, the second actuation manipulation part 213b, the first actuation gear 2134a, and the second actuation gear 2134b are rotated together around the yaw rotation shaft 2121, and as a result, the first yaw gear 2124a, the second yaw gear 2124b, the first jaw yaw pulley 212P1, and the second jaw yaw pulley 212P2 are rotated in the same direction around the yaw rotation shaft 2121. In this manner, the first jaw 221 and the second jaw 222 of the end tool 220 are yaw rotated in the same direction.

That is, owing to at least one gear, the first actuation manipulation part 213a and the second actuation manipulation part 213b may be rotated by the same amount in opposite directions, and along with this, the first jaw yaw pulley 212P1 and the second jaw yaw pulley 212P2 may be accordingly rotated in opposite directions. In addition, it is possible to rotate the first jaw yaw pulley 212P1 and the second jaw yaw pulley 212P2 in the same direction by yaw rotation of the manipulation part 210.

In this manner, the first jaw yaw pulley 212P1 and the second jaw yaw pulley 212P2 may be rotated by actuation manipulation and yaw manipulation. In particular, the structure for rotating the first jaw yaw pulley 212P1 and the second jaw yaw pulley 212P2 in different manners by actuation manipulation and yaw manipulation may be implemented by various methods such as a method of using a link structure as well as a method of using gears.

Actuation, yaw, and pitch motions in the present embodiment are described below.

First, actuation motion is described below.

Since the first actuation gear 2134a rotating together with the first actuation manipulation part 213a is engaged with the second actuation gear 2134b rotating together with the second actuation manipulation part 213b, if one of the first actuation manipulation part 213a and the second actuation manipulation part 213b is rotated, the other of the first actuation manipulation part 213a and the second actuation manipulation part 213b is also rotated.

If the first actuation manipulation part 213a and the first actuation gear 2134a are rotated clockwise, the first yaw gear 2124a engaged with the first actuation gear 2134a is rotated counterclockwise. In addition, if the first actuation manipulation part 213a and the first actuation gear 2134a are rotated clockwise, the second actuation gear 2134b engaged with the first actuation gear 2134a is rotated counterclockwise, and the second yaw gear 2124b engaged with the second actuation gear 2134b is rotated clockwise.

As a result, the first jaw yaw pulley 212P1 connected to the first yaw gear 2124a, and the second jaw yaw pulley 212P2 connected to the second yaw gear 2124b are rotated in opposite directions. Thus, the first jaw 221 connected to the first jaw yaw pulley 212P1, and the second jaw 222 connected to the second jaw yaw pulley 212P2 are rotated in opposite directions, thereby performing an actuation motion.

Next, yaw motion will be described below.

In addition, if the first handle 214 is rotated around the yaw rotation shaft 2121 in one direction, the actuation manipulation part 213 provided on an end of the first handle 214 is also rotated together with the first handle 214 around the yaw rotation shaft 2121.

At this time, since the entire actuation manipulation part 213 is rotated around the yaw rotation shaft 2121, the first actuation gear 2134a and the second actuation gear 2134b are not rotated relative to each other, and thus the first yaw gear 2124a and the second yaw gear 2124b respectively engaged with the first actuation gear 2134a and the second actuation gear 2134b are also not rotated relative to each other.

That is, the first handle 214, the actuation manipulation part 213, the first actuation gear 2134a, the second actuation gear 2134b, the first yaw gear 2124a, and the second yaw gear 2124b are simultaneously rotated around the yaw rotation shaft 2121 as if a single rigid body is rotated. Therefore, the first jaw yaw pulley 212P1 connected to the first yaw gear 2124a, and the second jaw yaw pulley 212P2 connected to the second yaw gear 2124b are rotated together in one direction, thereby performing an yaw motion in which the first jaw 221 and the second jaw 222 are rotated in the same direction.

Next, pitch motion will be described below.

If a user rotates the first handle 214 around the pitch rotation shaft 2111 while holding the first handle 214, the actuation manipulation part 213, the yaw manipulation part 212, and the pitch manipulation part 211 are pitch rotated around the pitch rotation shaft 2111. That is, if the first jaw yaw pulley 212P1 of the yaw manipulation part 212 to which the first jaw wire 230J1 is fixedly coupled is rotated around the pitch rotation shaft 2111, the first jaw wire 230J1 wound around the pitch pulley 211P is moved. Similarly, if the second jaw yaw pulley 212P2 of the yaw manipulation part 212 to which the second jaw wire 230J2 is fixedly coupled is rotated around the pitch rotation shaft 2111, the second jaw wire 230J2 wound around the pitch pulley 211P is moved. Then, rotating force is transmitted to the end tool 220 via the power transmission part 230, and thus the two jaws 221 and 222 of the end tool 220 perform a pitch motion.

At this time, since the pitch frame 2113 is connected to the yaw frame 2123 and the yaw frame 2123 connects the first handle 214, the yaw rotation shaft 2121, the first actuation rotation shaft 2131a, and the second actuation rotation shaft 2131b to each other, if the pitch frame 2113 is rotated around the pitch rotation shaft 2111, the yaw frame 2131, the first handle 214, the yaw rotation shaft 2121, the first actuation rotation shaft 2131a, and the second actuation rotation shaft 2131b connected to the pitch frame 2113 are rotated together. That is, if the pitch manipulation part 211 is rotated around the pitch rotation shaft 21111, the actuation manipulation part 213 and the yaw manipulation part 212 are rotated together with the pitch manipulation part 211.

In short, according to the instrument 200 for surgery of the embodiment of the present invention, pulleys are respectively provided on joint points (a actuation joint, a yaw joint, and a pitch joint), wires (the first jaw wire or the second jaw wire) are wound around the pulleys, such that if the manipulation part is rotated (actuation rotation, yaw rotation, or pitch rotation), each wire is moved for a desired motion of the end tool 220. Furthermore, an auxiliary pulley may be provided at a side of each pulley, and a wire may not be wound several times around the pulley owing to the auxiliary pulley.

<Third Embodiment of Instrument for Surgery>

Hereinafter, an instrument 300 for surgery will be described according to a third embodiment of the present invention. The instrument 300 for surgery of the third embodiment of the present invention is characteristically different in the configuration of a manipulation part 310 of the instrument 300 from the instrument 200 for surgery (refer to FIG. 32) of the second embodiment of the present invention. This different configuration from the third embodiment will now be described in detail.

Figure 41:
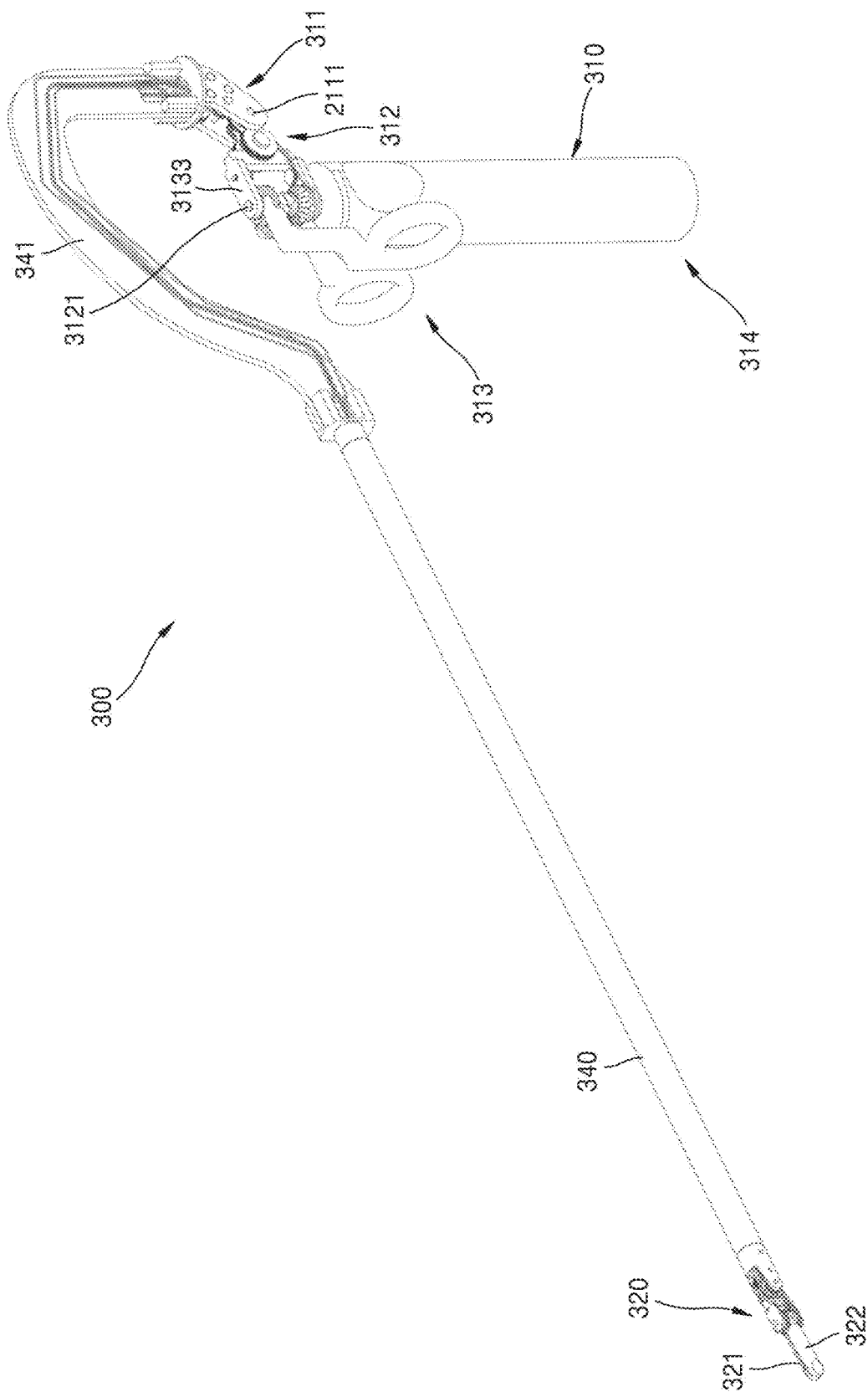
FIG. 41 is a perspective view illustrating an instrument for surgery according to a third embodiment of the present invention.
Figure 42:
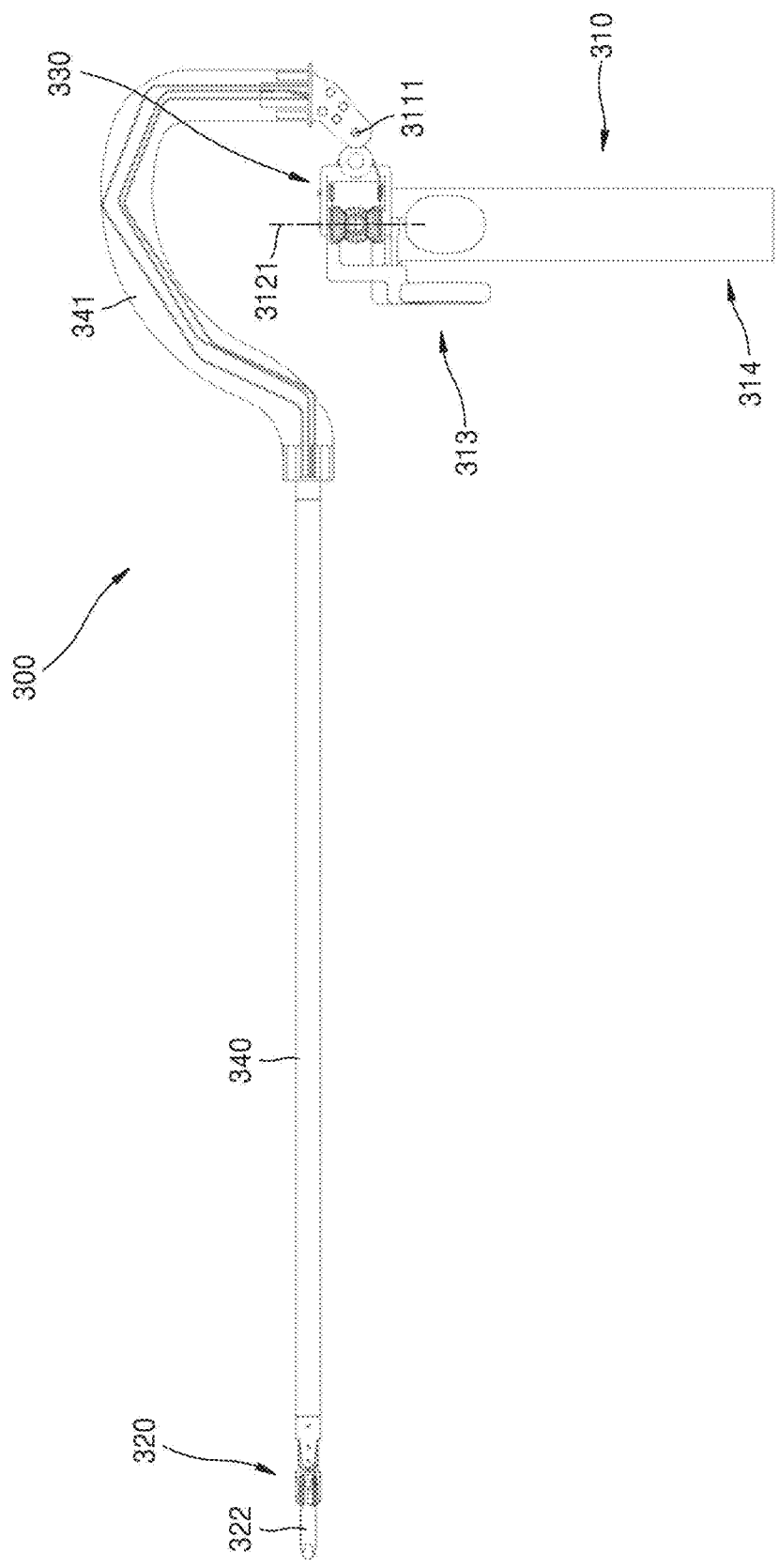
FIG. 42 is a side view illustrating the instrument for surgery shown in FIG. 41.
Figure 43:
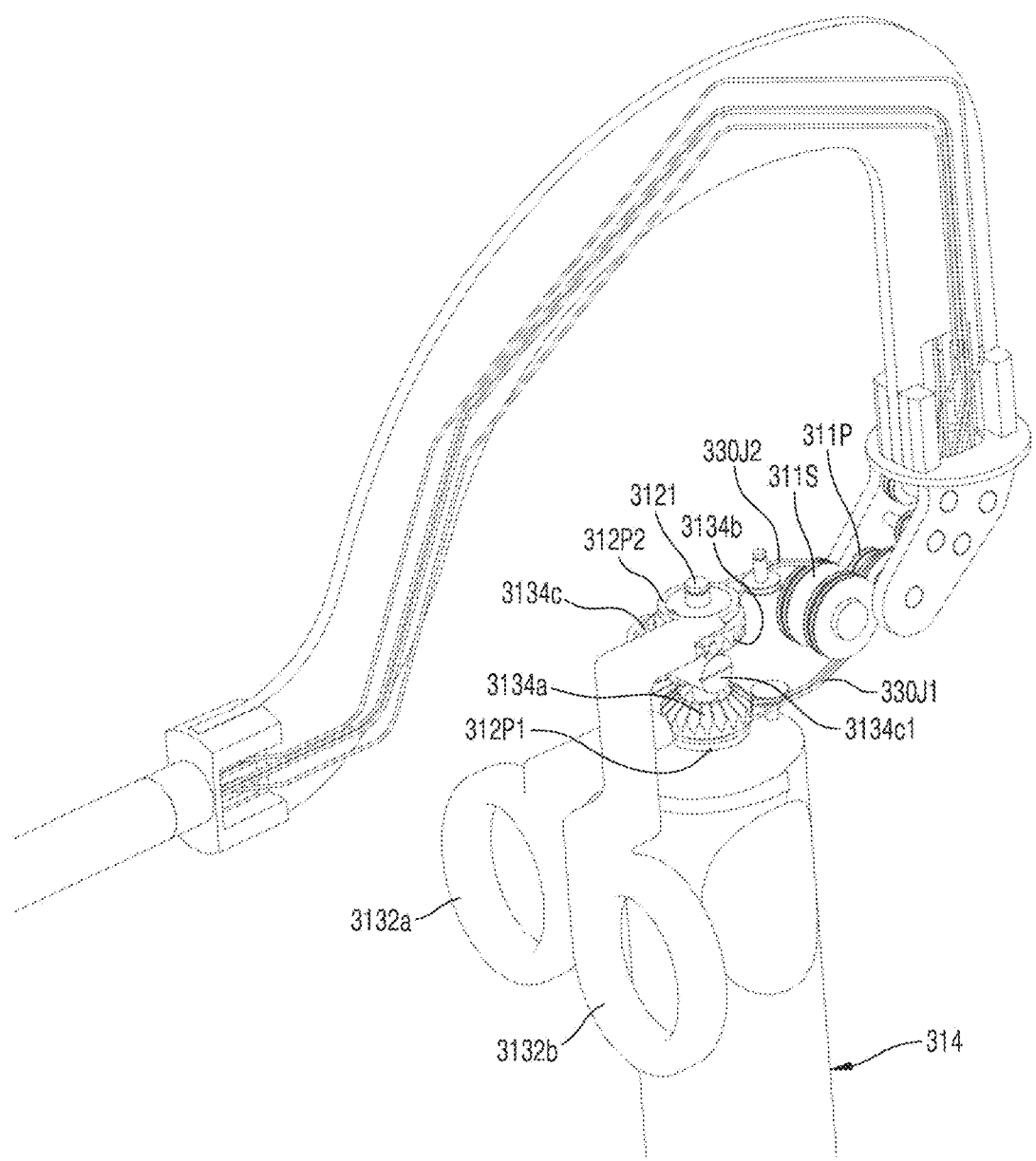
FIG. 43 is a perspective view illustrating a manipulation part of the instrument for surgery shown in FIG. 42.

FIG. 41 is a perspective view illustrating the instrument for surgery according to the third embodiment of the present invention, FIG. 42 is a plan view illustrating the instrument for surgery of FIG. 41, and FIG. 43 is a perspective view illustrating the manipulation part of the instrument for surgery of FIG. 42.

Referring to FIGS. 41, 42, and 43, in the instrument 300 for surgery of the third embodiment of the present invention, an actuation manipulation part and a yaw manipulation part that include a first yaw gear, a second yaw gear, a first actuation gear, and a second actuation gear are modified. However, ultimately, the instrument 300 for surgery of the third embodiment has the same motion mechanism as that in the second embodiment.

An actuation manipulation part 313 includes a first actuation manipulation part 313a and a second actuation manipulation part 313b. The first actuation manipulation part 313a includes a first actuation rotation part 3132a and a first actuation gear 3134a. The second actuation manipulation part 313b includes a second actuation rotation part 3132b and a second actuation gear 3134b. Here, the first actuation rotation part 3132a and the second actuation rotation part 3132b may function as a second handle. In addition, the actuation manipulation part 313 further includes a third actuation gear 3134c.

In addition, the first actuation rotation part 3132a and the first actuation gear 3134a may be fixedly coupled to each other and may be rotated together around a yaw rotation shaft 3121. Similarly, the second actuation rotation part 3132b and the second actuation gear 3134b may be fixedly coupled to each other and may be rotated together around the yaw rotation shaft 3121.

Here, the first actuation gear 3134a and the second actuation gear 3134b may be engaged with each other through the third actuation gear 3134c, and if one of the first and second actuation gears 3134a and 3134b is rotated, the first and second actuation gears 3134a and 3134b may be rotated together in opposite directions.

A yaw manipulation part 312 may include a yaw rotation shaft 3121, a first jaw yaw pulley 312P1, and a second jaw yaw pulley 312P2. In addition, the first jaw yaw pulley 312P1 and the second jaw yaw pulley 312P2 are connected to the yaw rotation shaft 3121 such that the first jaw yaw pulley 312P1 and the second jaw yaw pulley 312P2 may be rotated around the yaw rotation shaft 3121. The first jaw yaw pulley 312P1 may be fixedly coupled to the first actuation gear 3134a and rotatable together with the first actuation gear 3134a, and the second jaw yaw pulley 312P2 may be fixedly coupled to the second actuation gear 3134b and rotatable together with the second actuation gear 3134b. In addition, a first jaw wire 330J1 may be wound around the first jaw yaw pulley 312P1, and a second jaw wire 330J2 may be wound around the second jaw yaw pulley 312P2. In this case, each of the first jaw yaw pulley 312P1 and the second jaw yaw pulley 312P2 may include two pulleys facing each other and independently rotatable. A rotation shaft of the third actuation gear 3134c is connected to a first handle 314, and thus if the first handle 314 is rotated, the third actuation gear 3134c may also be rotated.

Actuation and yaw motions in the present embodiment are described below.

Figure 46:
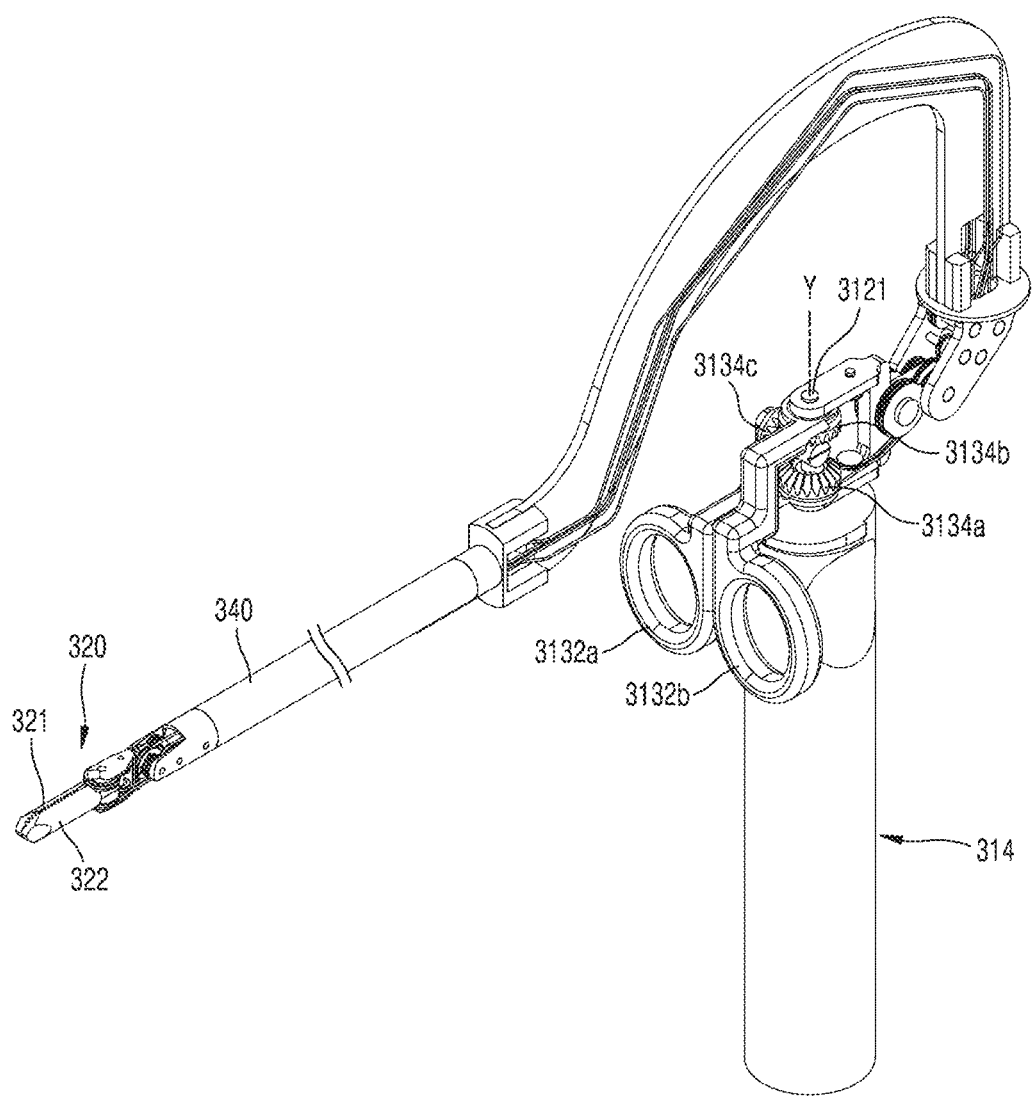
FIGS. 46 and 47 are perspective views illustrating an actuation motion of the instrument for surgery shown in FIG. 41.
Figure 47:
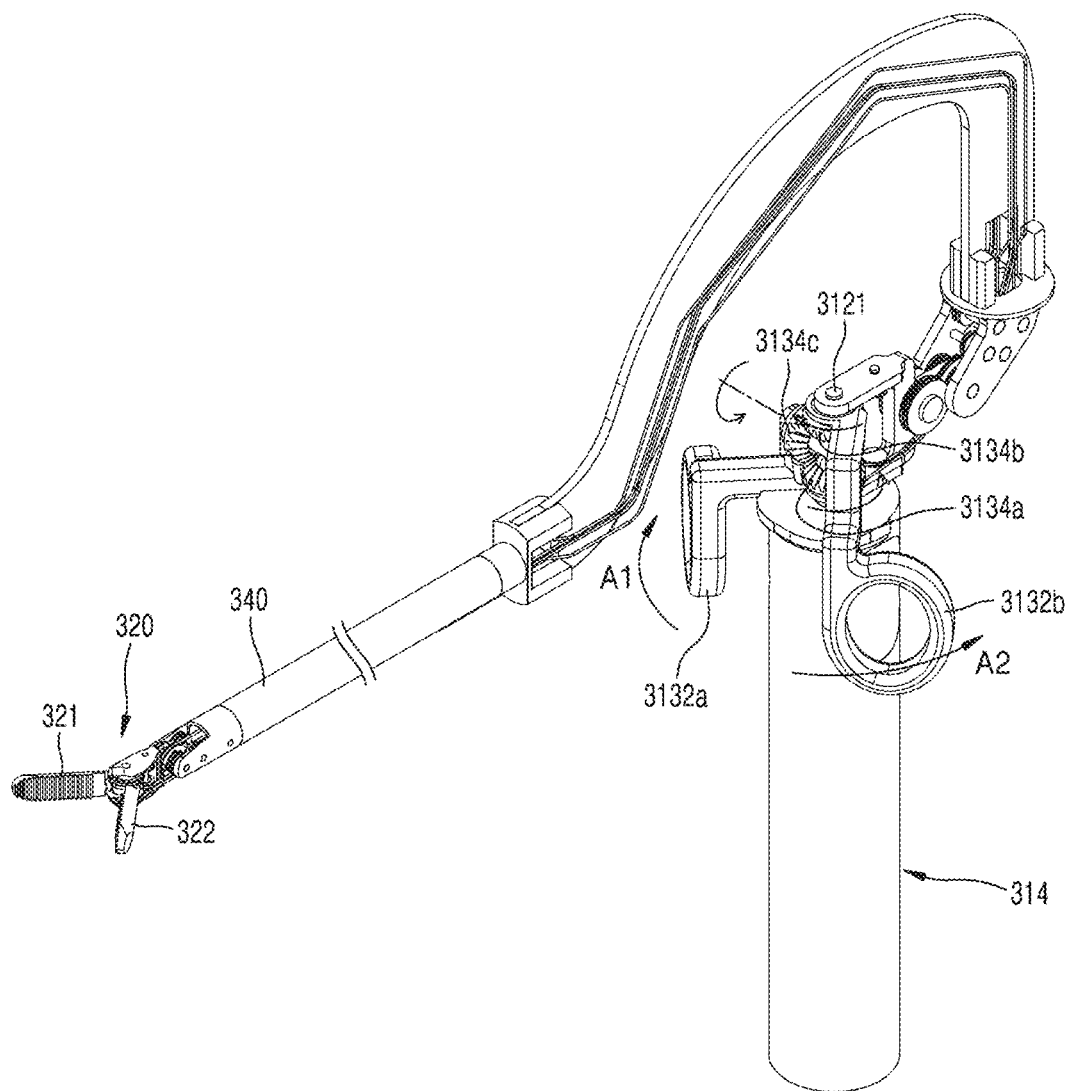

First, actuation motion will now be described. FIGS. 46 and 47 are views illustrating an actuation motion of the instrument for surgery shown in FIG. 41.

Referring to FIGS. 46 and 47, Since the first actuation gear 3134a rotating together with the first actuation rotation part 3132a is engaged with the second actuation gear 3134b rotating together with the second actuation rotation part 3132b, if one of the first actuation rotation part 3132a and the second actuation rotation part 3132b is rotated, the other of the first actuation rotation part 3132a and the second actuation rotation part 3132b is also rotated. If the first actuation rotation part 3132a and the first actuation gear 3134a is rotated around the yaw rotation shaft 3121 In the direction of an arrow A1, the third actuation gear 3134c engaged with the first actuation gear 3134a is rotated on its axis, and then the second actuation gear 3134b engaged with the third actuation gear 3134c is rotated around the yaw rotation shaft 3121 in the direction of an arrow A2.

As a result, the first jaw yaw pulley 312P1 connected to the first actuation gear 3134a, and the second jaw yaw pulley 312P2 connected to the second actuation gear 3134b are rotated in opposite directions. Thus, a first jaw 321 connected to the first jaw yaw pulley 312P1, and a second jaw 322 connected to the second jaw yaw pulley 312P2 are rotated in opposite directions, thereby performing an actuation motion.

Figure 44:
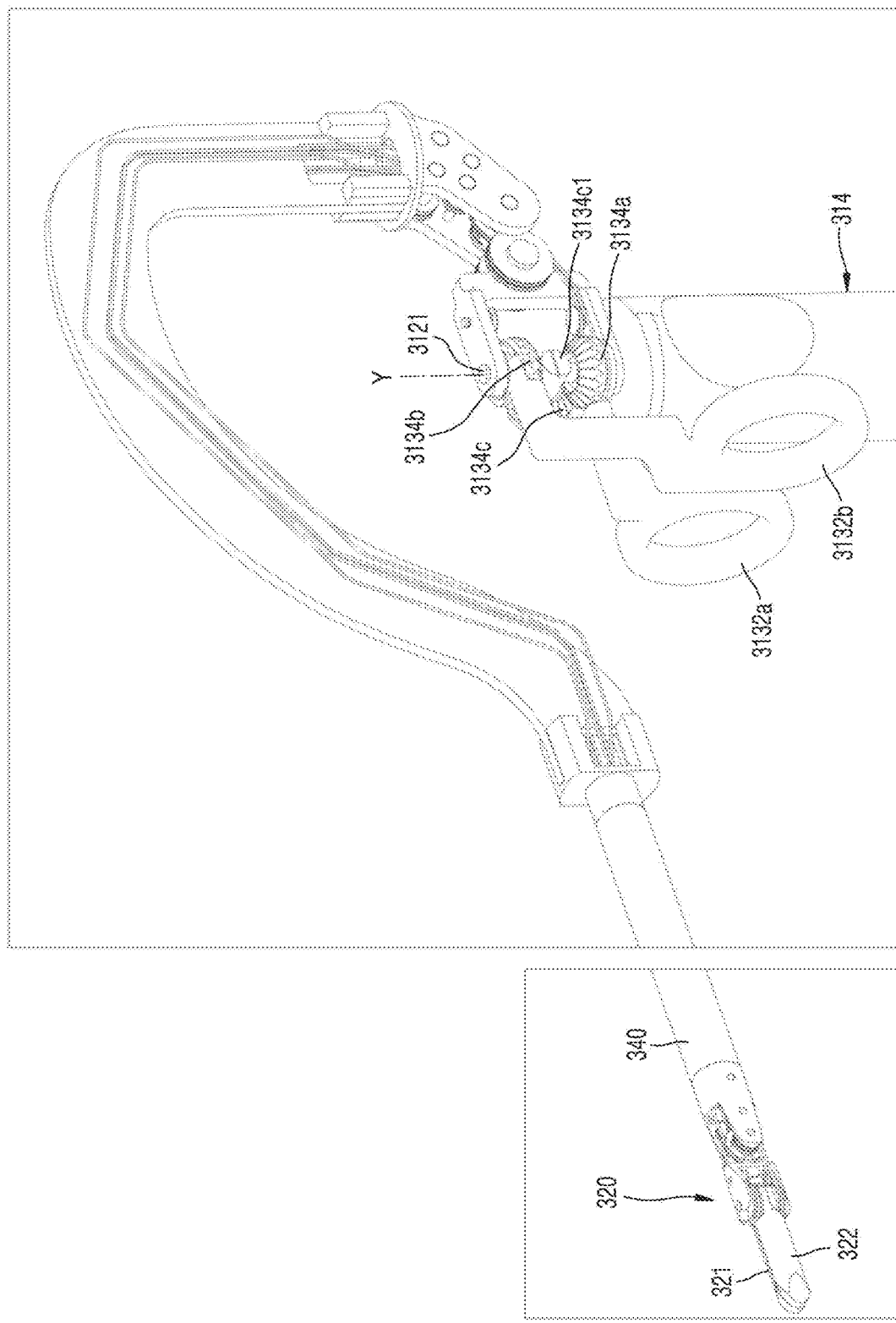
FIGS. 44 and 45 are perspective views illustrating a yaw motion of the instrument for surgery shown in FIG. 41.
Figure 45:
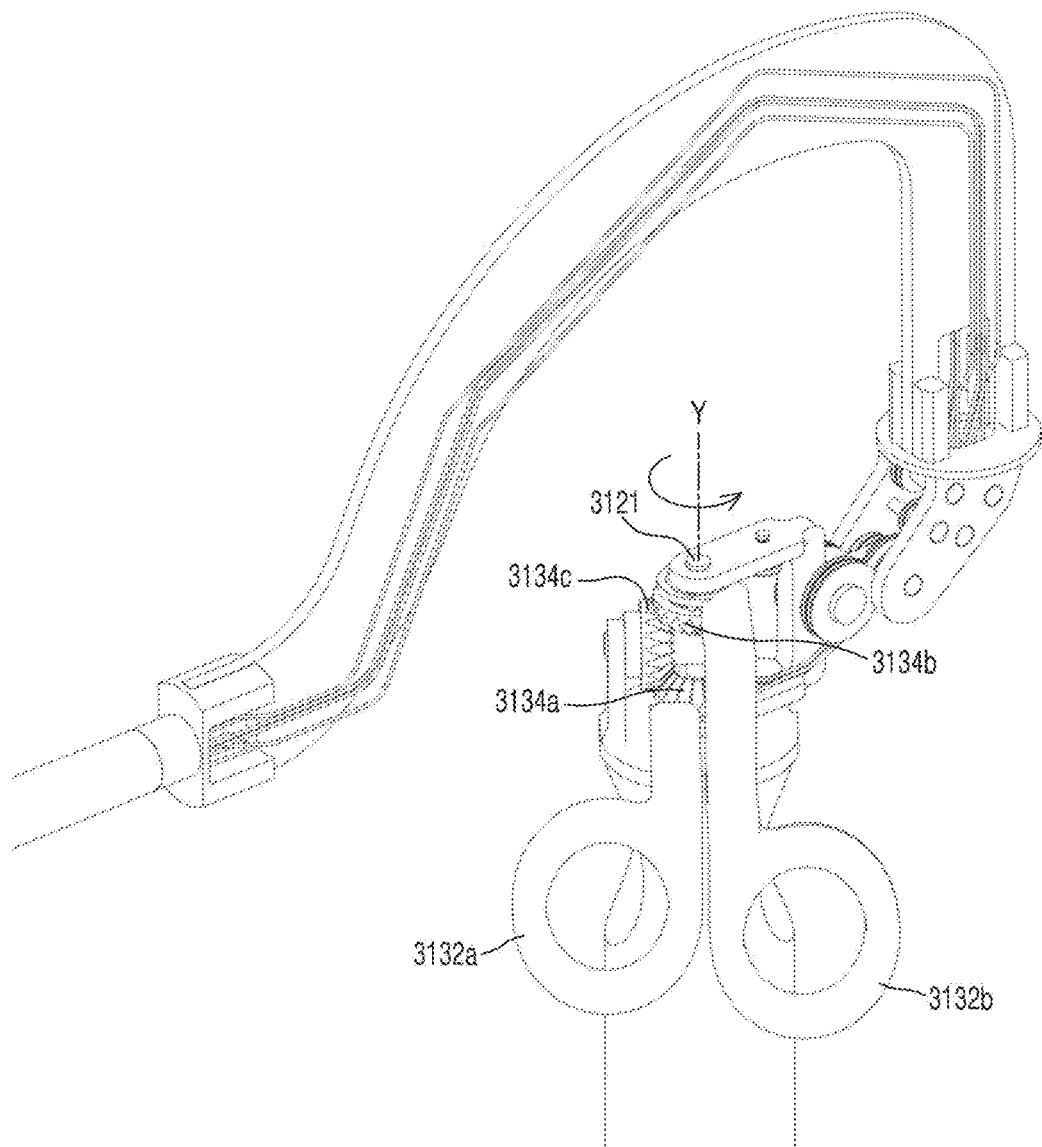

Next, yaw motion will now be described. FIGS. 44 and 45 are views illustrating a yaw motion of the instrument for surgery shown in FIG. 41.

Referring to FIGS. 44 and 45, if the first handle 314 is rotated around the yaw rotation shaft 3121, a third actuation gear center shaft 3134c1 connected to the first handle 314 is rotated around the yaw rotation shaft 3121, and the third actuation gear 3134c provided on the third actuation gear center shaft 3134c1 is revolved around the yaw rotation shaft 3121. Therefore, the first actuation gear 3134a and the second actuation gear 3134b connected to the third actuation gear 3134c are simultaneously rotated in the direction of an arrow Y.

Then, the first jaw yaw pulley 312P1 connected to the first actuation gear 3134a, and the second jaw yaw pulley 312P2 connected to the second actuation gear 3134b are rotated in the same direction. Thus, the first jaw 321 connected to the first jaw yaw pulley 312P1, and the second jaw 322 connected to the second jaw yaw pulley 312P2 are rotated in the same direction, thereby performing a yaw motion.

The configuration and operational characteristics of other parts are the same as those in the second embodiment, and thus descriptions thereof will be omitted.

<Fourth Embodiment of Instrument for Surgery>

Hereinafter, an instrument 400 for surgery will be described according to a fourth embodiment of the present invention. The instrument 400 for surgery of the fourth embodiment of the present invention is characteristically different in the configuration of a manipulation part 410 of the instrument 400 from the instrument 300 for surgery (refer to FIG. 41) of the third embodiment of the present invention. This different configuration from the third embodiment will now be described in detail.

Figure 48:
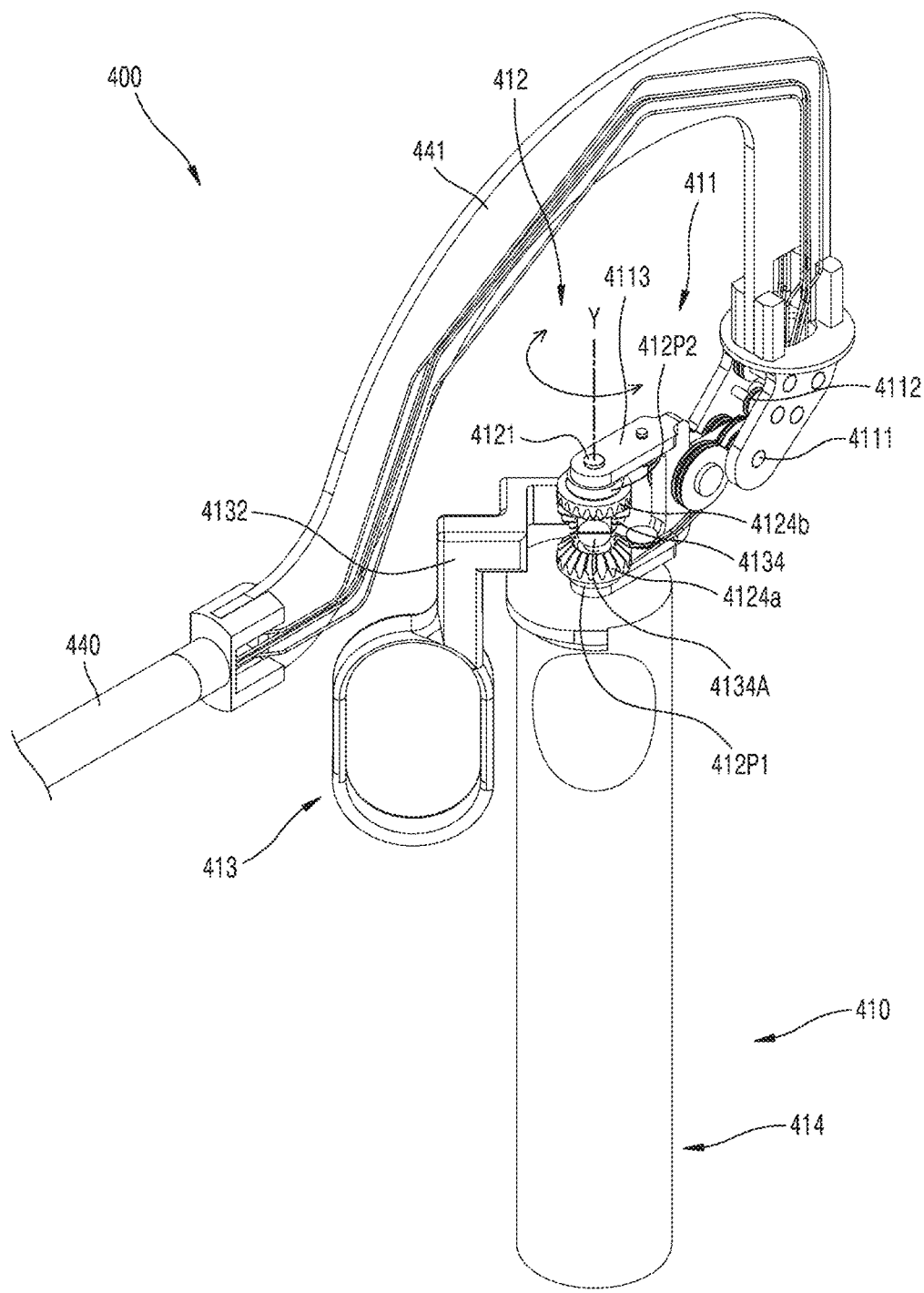
FIG. 48 is a perspective view illustrating a yaw motion of an instrument for surgery according to a fourth embodiment of the present invention.
Figure 49:
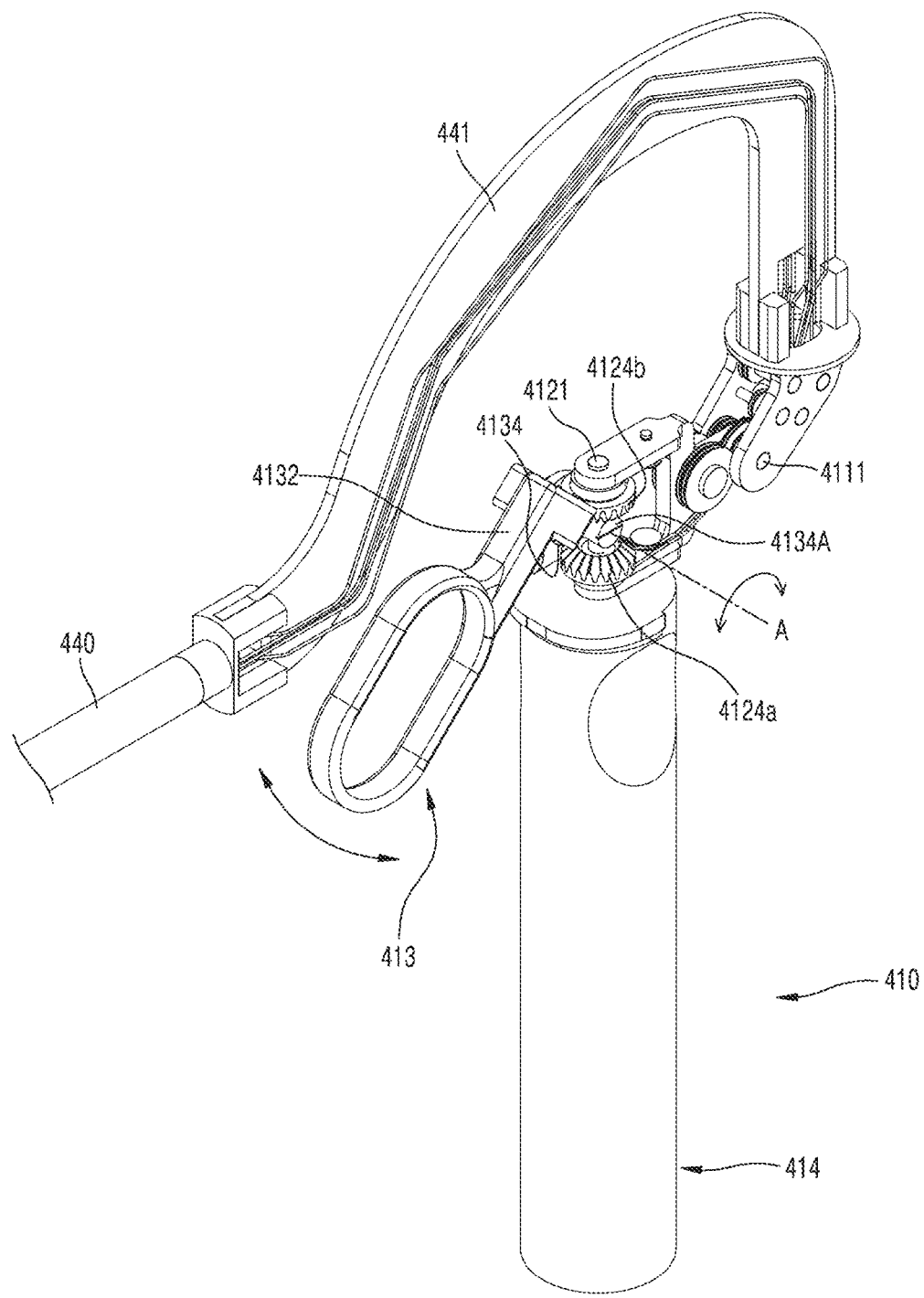
FIG. 49 is a perspective view illustrating an actuation motion of the instrument for surgery according to the fourth embodiment of the present invention.

FIG. 48 is a perspective view illustrating a yaw motion of the instrument for surgery according to the fourth embodiment of the present invention, FIG. 49 is a view illustrating an actuation motion of the instrument for surgery according to the fourth embodiment of the present invention.

The instrument 400 for surgery of the fourth embodiment of the present invention is different from the third embodiment in that a yaw manipulation part 412 and an actuation manipulation part 413 including a first actuation gear 4124a, a second actuation gear 4124b, and a third actuation gear 4134 are modified. In the third embodiment, the first actuation rotation part 3132a is fixedly coupled to the actuation gear 3134a, and the second actuation rotation part 3132b is fixedly coupled to the second actuation gear 3134b. However, in the fourth embodiment, a first actuation rotation part 4132 is fixedly coupled to the third actuation gear 4134. In addition, in the fourth embodiment, actuation manipulation is performed by rotating only the first actuation rotation part 4132. For ease of description, the first actuation gear, the second actuation gear, the third actuation gear, and the first actuation rotation part of the third embodiment are referred to as a first yaw gear, a second yaw gear, an actuation gear, and an actuation rotation part in the fourth embodiment.

Actuation and yaw motions in the present embodiment are described below.

First, actuation motion will now be described. FIG. 49 is a view illustrating an actuation motion of the instrument for surgery shown in FIG. 48.

If the actuation rotation part 4132 and the actuation gear 4134 connected thereto are rotated in the direction of an arrow A in FIG. 49, the first yaw gear 4124a and the second yaw gear 4124b engaged with the actuation gear 4134 are rotated around a yaw rotation shaft 4121 in opposite directions.

As a result, a first jaw yaw pulley 412P1 fixedly coupled to the first yaw gear 4124a, and a second jaw yaw pulley 412P2 fixedly coupled to the second yaw gear 4124b are rotated in opposite directions. Thus, a first jaw 421 connected to the first jaw yaw pulley 412P1, and a second jaw 422 connected to the second jaw yaw pulley 412P2 are rotated in opposite directions, thereby performing an actuation motion.

Next, yaw motion will now be described.

If a first handle 414 is rotated around the yaw rotation shaft 4121, an actuation gear center shaft 4134A connected to the first handle 414 is rotated around the yaw rotation shaft 4121, and the actuation gear 4134 provided on the actuation gear center shaft 4134A is revolved around the yaw rotation shaft 4121. Therefore, the first yaw gear 4124a and the second yaw gear 4134b connected to the actuation gear 4134 are simultaneously rotated in the direction of an arrow Y.

Then, the first jaw yaw pulley 412P1 fixedly coupled to the first yaw gear 4124a, and the second jaw yaw pulley 412P2 fixedly coupled to the second yaw gear 4124b are rotated in the same direction. Thus, the first jaw 421 connected to the first jaw yaw pulley 412P1, and the second jaw 422 connected to the second jaw yaw pulley 412P2 are rotated in the same direction, thereby performing a yaw motion.

The configuration and operational characteristics of other parts are the same as those in the third embodiment, and thus descriptions thereof will be omitted.

<Fifth Embodiment of Instrument for Surgery>

Hereinafter, an instrument 500 for surgery will be described according to a fifth embodiment of the present invention. The instrument 500 for surgery of the third embodiment of the present invention is characteristically different in the configuration of a manipulation part 510 of the instrument 500 from the instrument 200 for surgery (refer to FIG. 32) of the second embodiment of the present invention. This different configuration from the fifth embodiment will now be described in detail.

Figure 53:
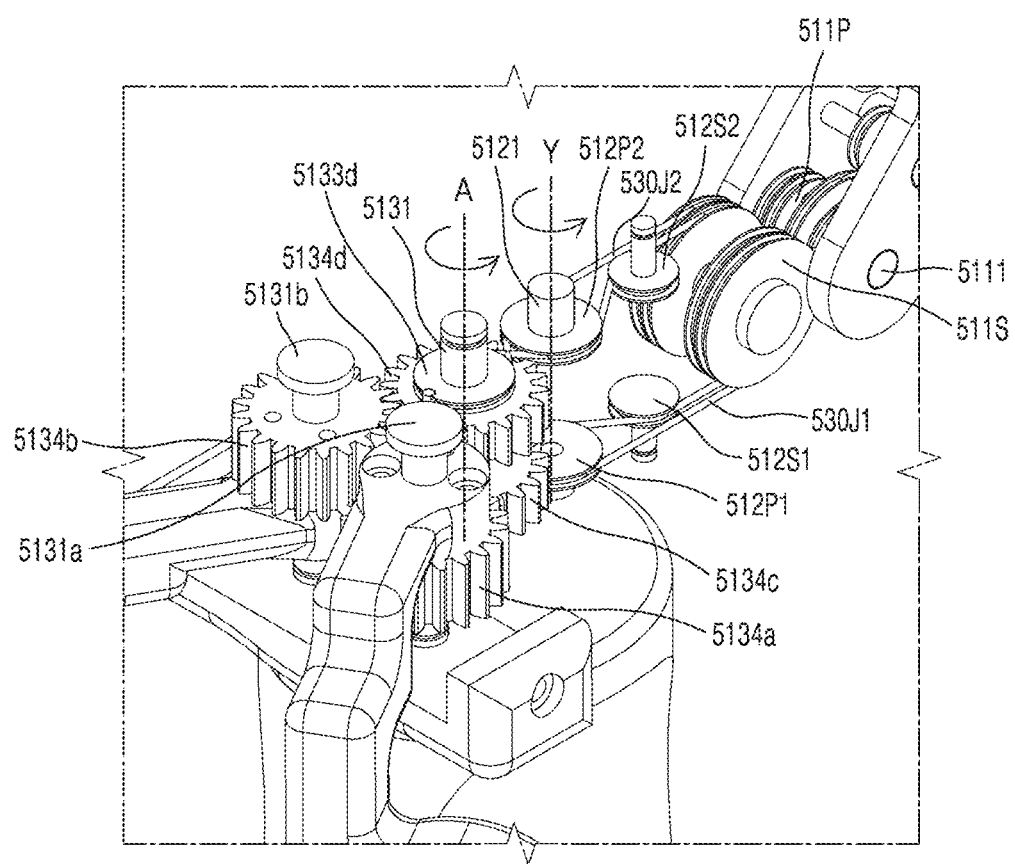

In the instrument for surgery 500 of the fifth embodiment of the present invention, the modification shown in FIG. 24 is specifically embodied. That is, the first jaw yaw auxiliary pulley 112S1 of FIG. 24A corresponds to a first jaw yaw auxiliary pulley 512S1 of FIG. 53, the first jaw yaw pulley 112P1 of FIG. 24A corresponds to a first jaw yaw pulley 512P1 of FIG. 53, and the first actuation pulley 113P1 of FIG. 24A corresponds to a first actuation pulley (not shown) of FIG. 53.

Figure 50:
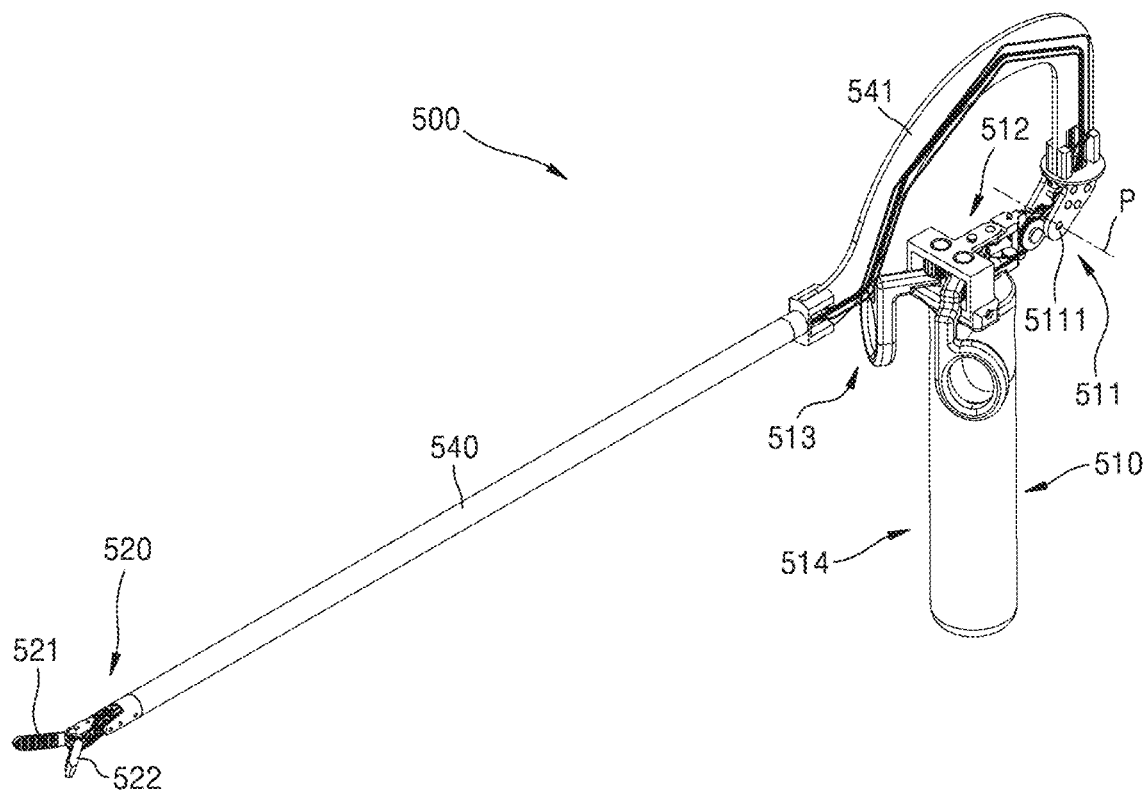
FIG. 50 is a perspective view illustrating an instrument for surgery according to a fifth embodiment of the present invention.
Figure 51:
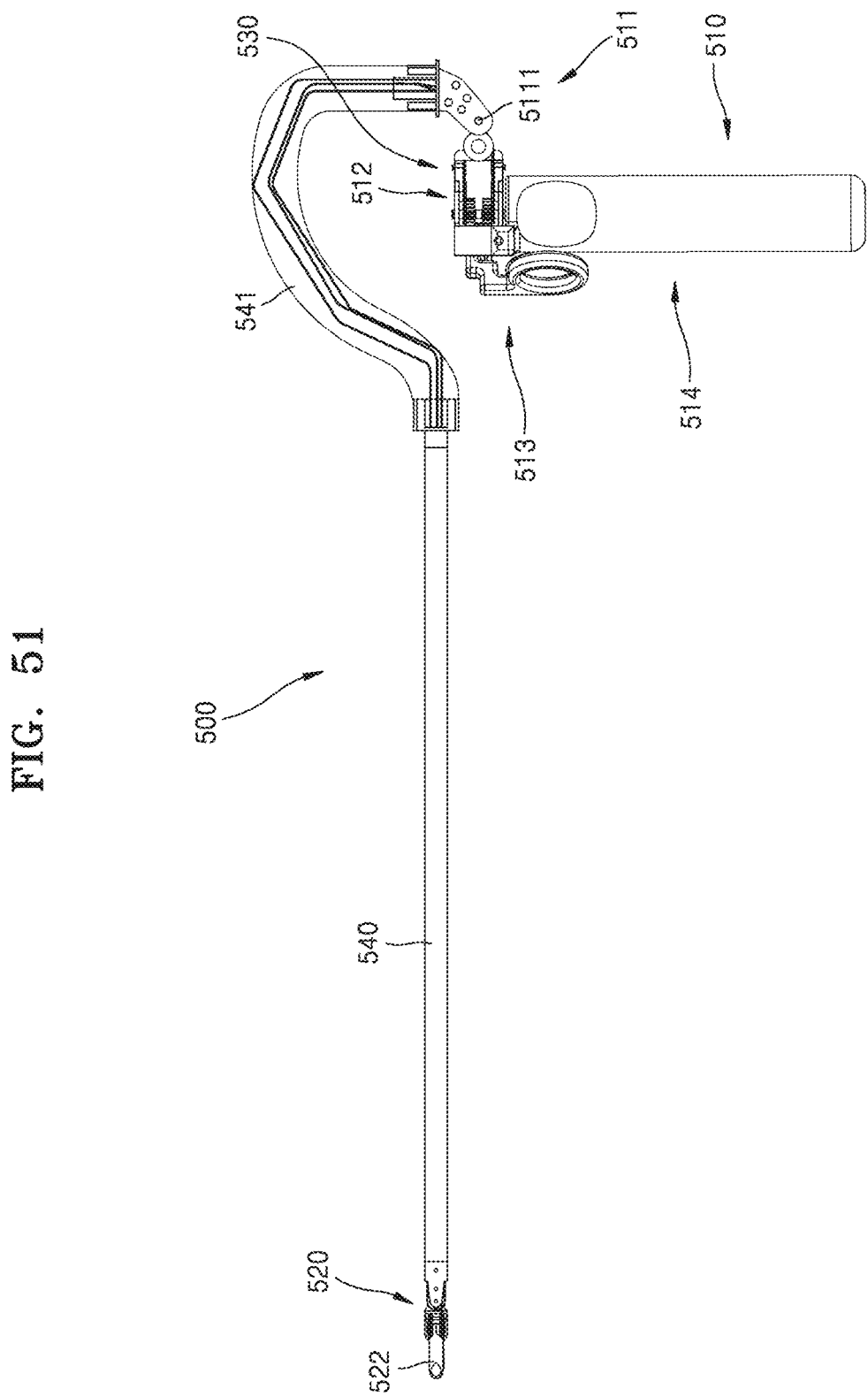
FIG. 51 is a side view illustrating the instrument for surgery shown in FIG. 50.
Figure 52:
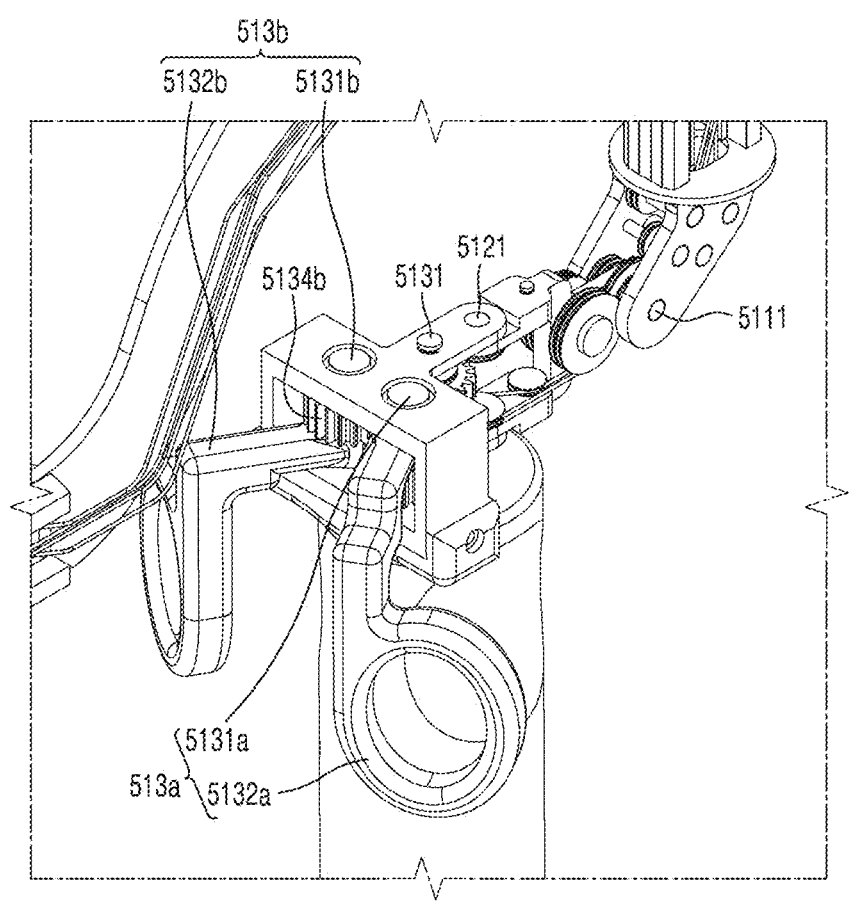
FIGS. 52 and 53 are perspective views illustrating a manipulation part of the instrument for surgery shown in FIG. 51.

FIG. 50 is a perspective view illustrating the instrument for surgery according to the fifth embodiment of the present invention, FIG. 51 is a plan view illustrating the instrument for surgery of FIG. 50, and FIG. 52 is a perspective view illustrating the manipulation part of the instrument for surgery of FIG. 51.

An actuation manipulation part 513 includes an actuation rotation shaft 5131, a first actuation manipulation part 513a, and a second actuation manipulation part 513b. The first actuation manipulation part 513a includes a first actuation rotation shaft 5131a, a first actuation rotation part 5132a, and a first actuation gear 5134a. The second actuation manipulation part 513b includes a second actuation rotation shaft 5131b, a second actuation rotation part 5132b, and a second actuation gear 5134b. Here, the first and second actuation rotation parts 5132a and 5132b may function as a second handle.

In this case, the first actuation rotation part 5132a and the first actuation gear 5134a may be fixedly coupled to each other so as to be rotated together around the first actuation rotation shaft 5131a. Similarly, the second actuation rotation part 5132b and the second actuation gear 5134b may be fixedly coupled to each other so as to be rotated together around the second actuation rotation shaft 5131b.

In addition, the first actuation gear 5134a and the second actuation gear 5134b may be engaged with each other, and thus if one of the first and second actuation gears 5134a and 5134b is rotated, the first and second actuation gears 5134a and 5134b may be rotated together in opposite directions.

A third actuation gear 5134c and a fourth actuation gear 5134d are provided on the actuation rotation shaft 5131, and the third actuation gear 5134c and the fourth actuation gear 5134d are independently rotatable around the actuation rotation shaft 5131.

In addition, a third actuation pulley (not shown) may be provided on a side of the third actuation gear 5134c, the third actuation pulley being fixedly coupled to the third actuation gear 5134c and rotatable together with the third actuation gear 5134c. A fourth actuation pulley 5133d may be provided on a side of the fourth actuation gear 5134d, the fourth actuation pulley 5133d being fixedly coupled to the fourth actuation gear 5134d and rotatable together with the fourth actuation gear 5134d.

The first actuation gear 5134a and the third actuation gear 5134c are engaged with each other, and thus if one of the first actuation gear 5134a and the third actuation gear 5134c is rotated, the first and third actuation gears 5134a and 5134c are rotated together in opposite directions. In addition, the second actuation gear 5134b and the fourth actuation gear 5134d are engaged with each other, and thus if one of the second actuation gear 5134b and the fourth actuation gear 5134d is rotated, the second actuation gear 5134b and the fourth actuation gear 5134d are rotated together in opposite directions.

In addition, the first jaw yaw pulley 512P1 is provided on a side of the third actuation gear 5134c and the third actuation pulley (not shown), and the third actuation pulley (not shown) and the first jaw yaw pulley 512P1 are connected through a first jaw wire 530J1, such that if the third actuation gear 5134c is rotated, the first jaw yaw pulley 512P1 may also be rotated. At this time, the first jaw wire 530J1 may be wound and fixedly coupled to a point of the third actuation pulley (not shown) and wound around the first jaw yaw pulley 512P1 in a crossed manner, such that the first jaw yaw pulley 512P1 may be rotated in a direction opposite the direction in which the third actuation pulley (not shown) is rotated.

In addition, a second jaw yaw pulley 512P2 is provided on a side of the fourth actuation gear 5134d and the fourth actuation pulley 5133d, and the fourth actuation pulley 5133d and the second jaw yaw pulley 512P2 are connected through a second jaw wire 530J2, such that if the fourth actuation gear 5134d is rotated, the second jaw yaw pulley 512P2 may also be rotated. At this time, the second jaw wire 530J2 may be wound and fixedly coupled to a point of the fourth actuation pulley 5133d and wound around the second jaw yaw pulley 512P2 in a crossed manner, such that the second jaw yaw pulley 512P2 may be rotated in a direction opposite the direction in which the fourth actuation pulley 5133d is rotated.

In this case, the first jaw yaw pulley 512P1 and the second jaw yaw pulley 512P2 are independently rotatable around a yaw rotation shaft 5121.

A yaw manipulation part 512 may include the yaw rotation shaft 5121, the first jaw yaw pulley 512P1, and the second jaw yaw pulley 512P2. A pitch manipulation part 511 may include a pitch rotation shaft 5111, a pitch pulley 511P, a pitch auxiliary pulley 211S, and a pitch frame 5113. The pitch manipulation part 511 is connected to a bent part 541 of a connecting part 540 through the pitch rotation shaft 5111.

Actuation, yaw, and pitch motions in the present embodiment are described below.

First, actuation motion is described below.

Referring to FIGS. 50 to 55, Since the first actuation gear 5134a rotating together with the first actuation manipulation part 513a is engaged with the second actuation gear 5134b rotating together with the second actuation manipulation part 513b, if one of the first actuation manipulation part 513a and the second actuation manipulation part 513b is rotated, the other of the first actuation manipulation part 513a and the second actuation manipulation part 513b is also rotated.

If the first actuation manipulation part 513a and the first actuation gear 5134a are rotated around the first actuation rotation shaft 5131a in the direction of an arrow A1, the third actuation gear 5134c engaged with the first actuation gear 5134a is rotated in a direction opposite to the direction A1.

Likewise, the second actuation gear 5134b engaged with the first actuation gear 5134a is rotated in the direction of an arrow A2, and the fourth actuation gear 5134d engaged with the second actuation gear 5134b is rotated in a direction opposite the direction A2.

As a result, the third actuation pulley (not shown) fixedly coupled to the third actuation gear 5134c, and the fourth actuation pulley 5133d fixedly coupled to the fourth actuation gear 5134d are rotated in opposite directions. Thus, a first jaw 521 connected to the third actuation gear (not shown), and a second jaw 522 connected to the fourth actuation pulley 5133d are rotated in opposite directions, thereby performing an actuation motion.

Here, the present embodiment is characterized in that the yaw rotation shaft 5121 and the actuation rotation shaft 5131 are separately provided. In addition, the first jaw yaw pulley 512P1 and the second jaw yaw pulley 512P2 are independently rotatable around the yaw rotation shaft 5121.

That is, in the second embodiment, all of the first yaw gear 2124a, the second yaw gear 2124b, the first jaw yaw pulley 212P1, and the second jaw yaw pulley 212P2 are provided on the yaw rotation shaft 2121. However, in the present embodiment, the third actuation gear 5134c and the fourth actuation gear 5134d are provided on the actuation rotation shaft 5131, and the first jaw yaw pulley 512P1 and the second jaw pulley 512P2 are provided on the yaw rotation shaft 5121.

Therefore, the same operational characteristics as in the second embodiment may be obtained in the present embodiment as follows: the first jaw wire 530J1 is crossed once between the third actuation pulley (not shown) and the first jaw yaw pulley 512P1, and the second jaw wire 530J2 is crossed once between the fourth actuation pulley 5133d and the second jaw yaw pulley 512P2. As described above, when each of the first jaw wire 530J1 and the second jaw wire 530J2 is crossed once, the operation of the manipulation part 510 and the operation of an end tool 520 are intuitively identical to each other.

Figure 54:
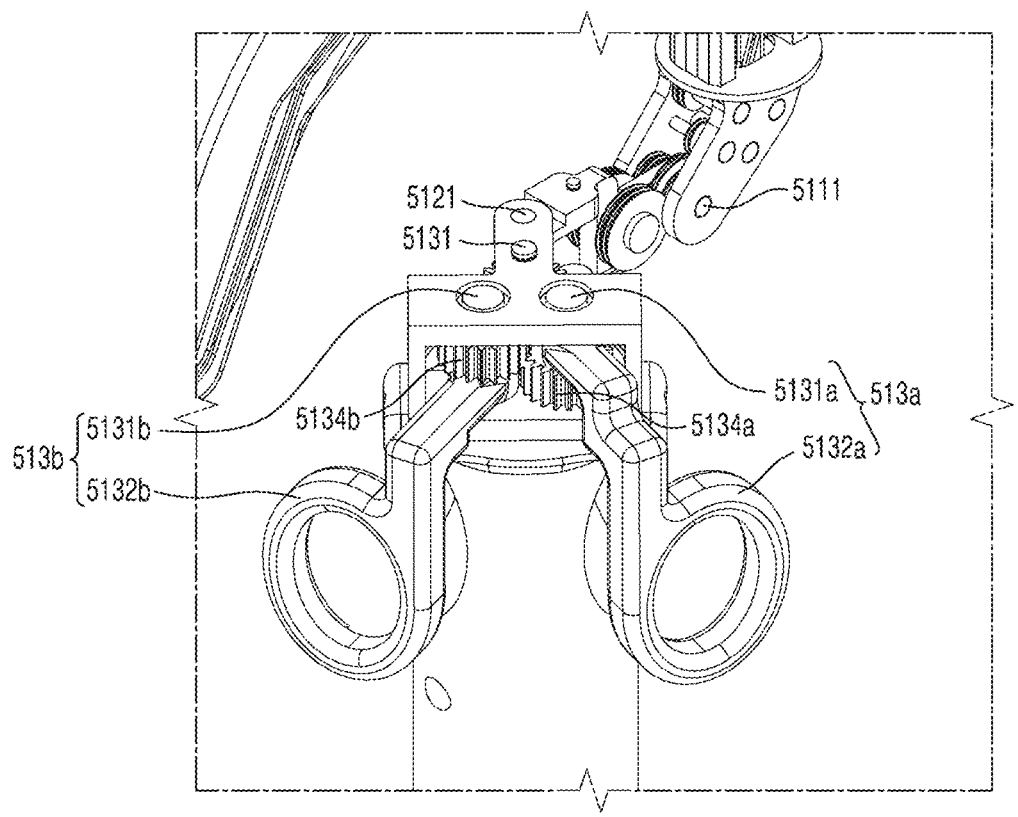
FIGS. 54 and 55 are perspective views illustrating a yaw motion of the instrument for surgery shown in FIG. 50.
Figure 55:
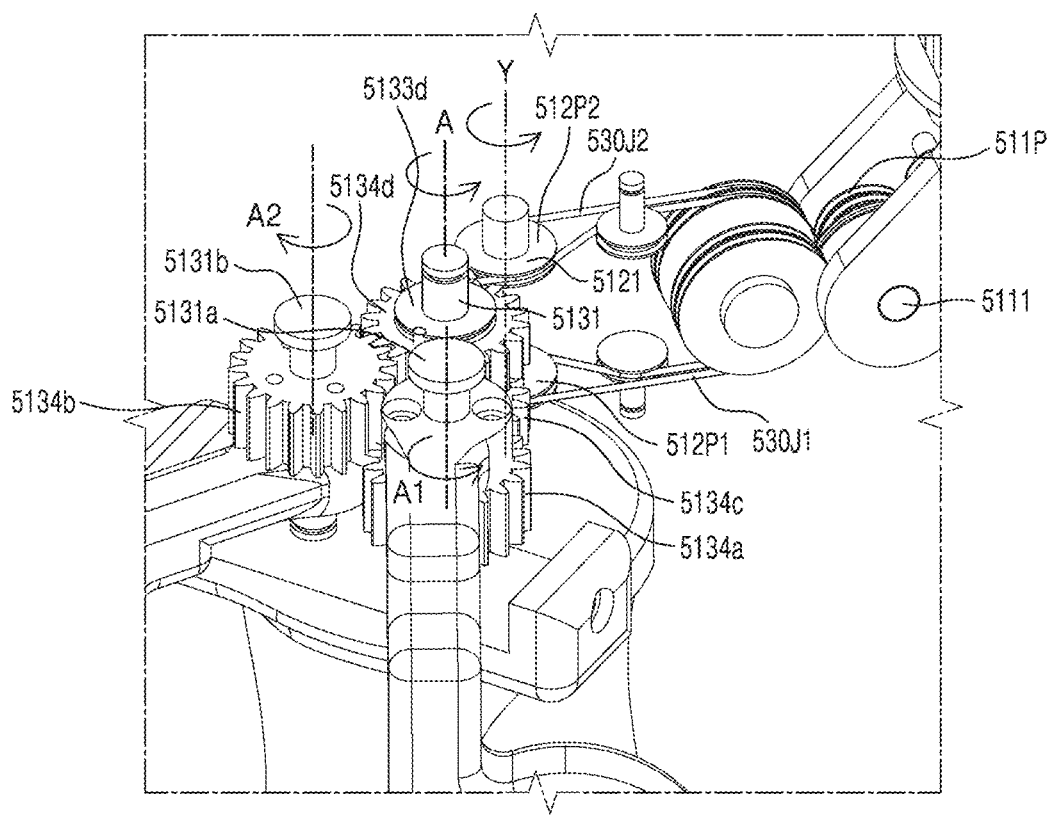

Next, yaw motion will now be described. FIGS. 54 and 55 are views illustrating a yaw motion of the instrument for surgery shown in FIG. 50.

Referring to FIGS. 50 to 55, if a first handle 514 is rotated in one direction around the yaw rotation shaft 5121, the actuation manipulation part 513 provided on an end of the first handle 514 is also rotated together with the first handle 514 around the yaw rotation shaft 5121. At this time, since the entire actuation manipulation part 513 is rotated around the yaw rotation shaft 5121, the first actuation gear 5134a and the second actuation gear 5134b are not rotated relative to each other, and thus the third actuation gear 5134c and the fourth actuation gear 5134d respectively engaged with the first actuation gear 5134a and the second actuation gear 5134b are also not rotated relative to each other.

That is, the first handle 514, the actuation manipulation part 513, the first actuation gear 5134a, the second actuation gear 5134b, the third actuation gear 5134c, the fourth actuation gear 5134d, the first jaw yaw pulley 512P1, and the second jaw yaw pulley 512P2 are simultaneously rotated around the yaw rotation shaft 5121 as if a single rigid body is rotated. Then, since the first jaw yaw pulley 512P1 and the second jaw yaw pulley 512P2 are rotated together in one direction as described above, the first jaw 521 and the second jaw 522 are rotated in the same direction, thereby performing a yaw motion.

The configuration and operational characteristics of other parts are the same as those in the second embodiment, and thus descriptions thereof will be omitted.

<Sixth Embodiment of Instrument for Surgery>

Hereinafter, an instrument 600 for surgery will be described according to a sixth embodiment of the present invention. The instrument 600 for surgery of the tenth embodiment of the present invention is characteristically different in the configuration of a manipulation part 610 of the instrument 600 from the instrument 100 for surgery (refer to FIG. 2) of the first embodiment of the present invention. This difference in the configuration from the first embodiment will be described later in detail.

Figure 56:
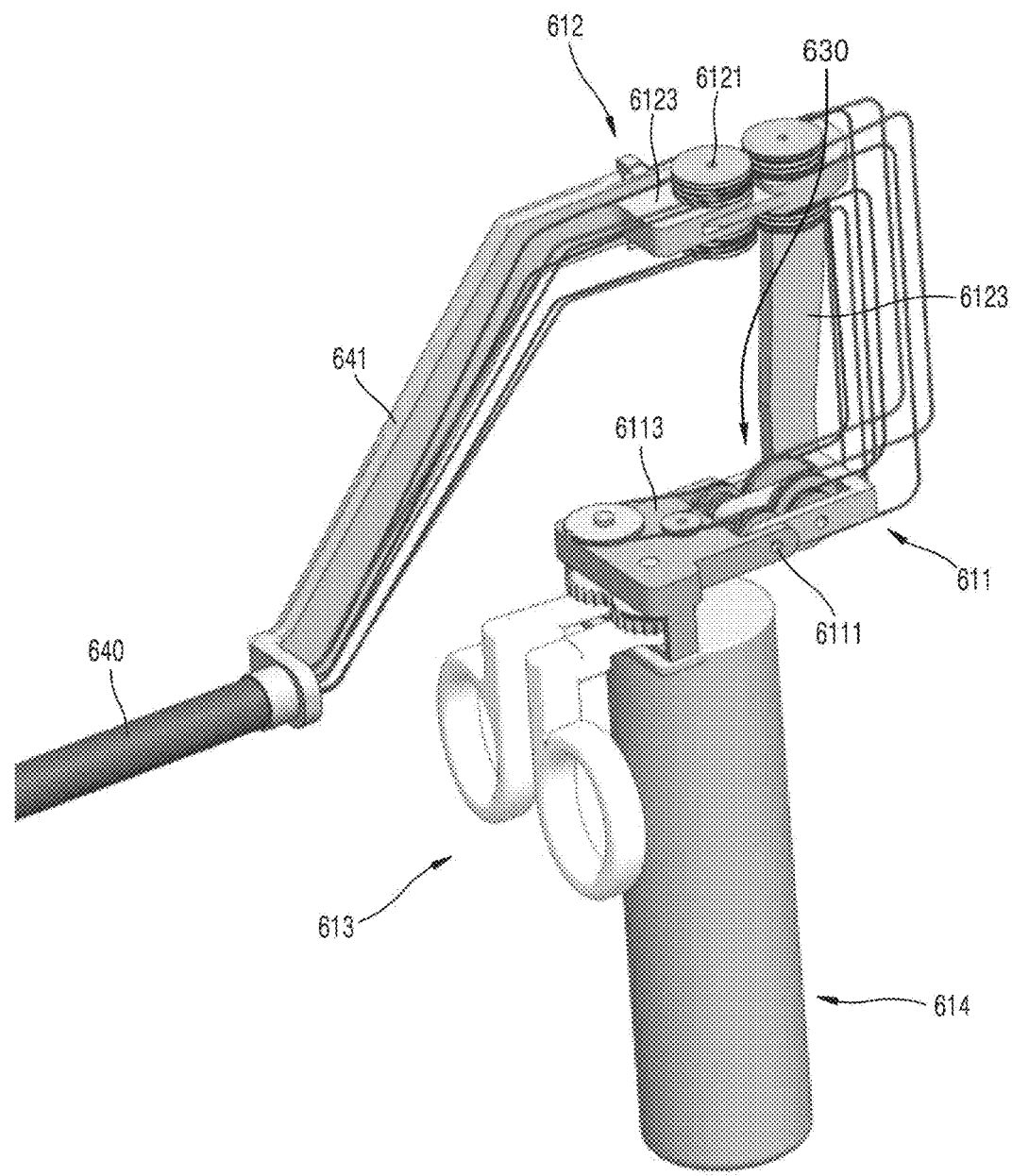
FIG. 56 is a perspective view illustrating an instrument for surgery according to a sixth embodiment of the present invention.
Figure 57:
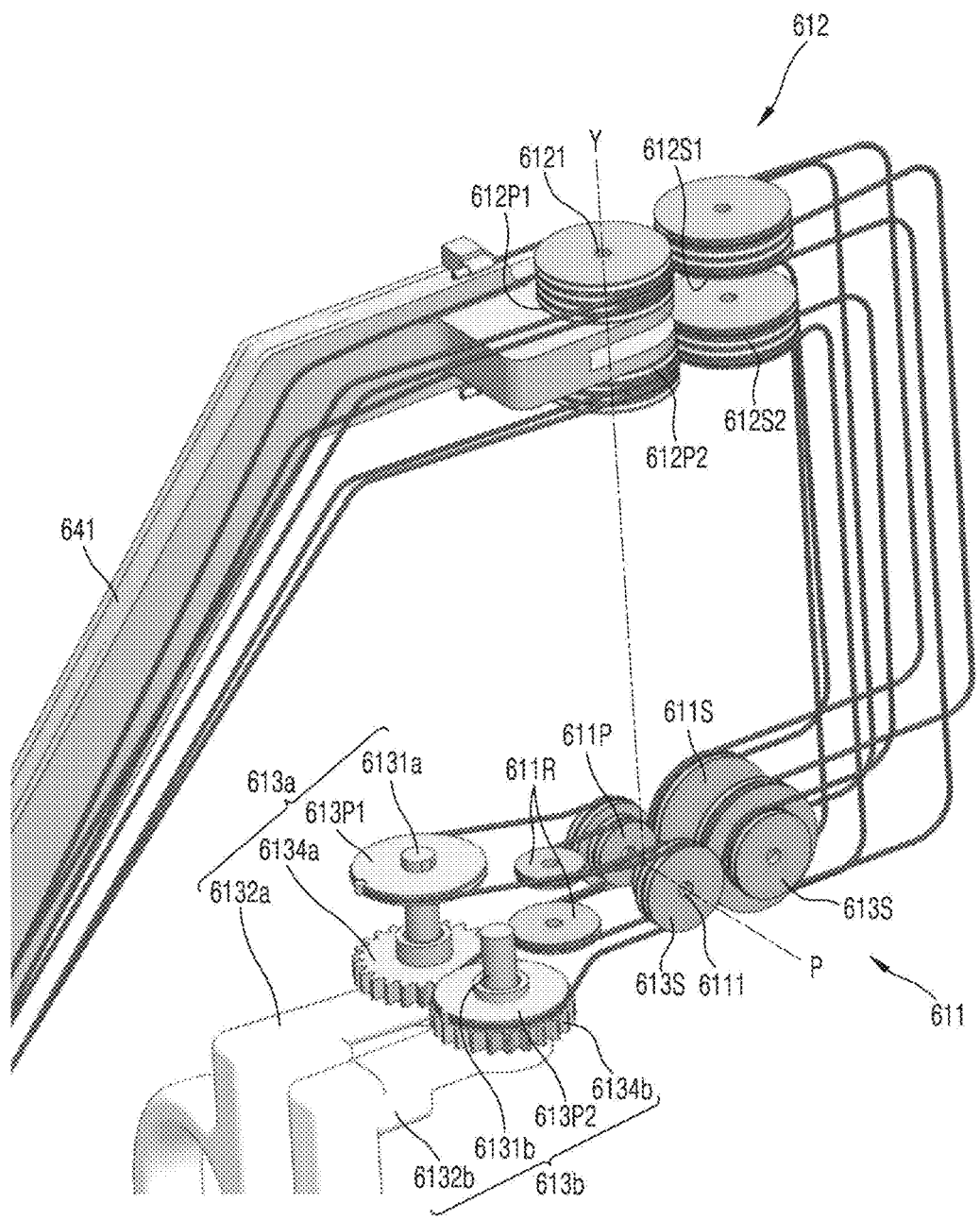
FIG. 57 is a perspective view illustrating a manipulation part of the instrument for surgery shown in FIG. 56.
Figure 58:
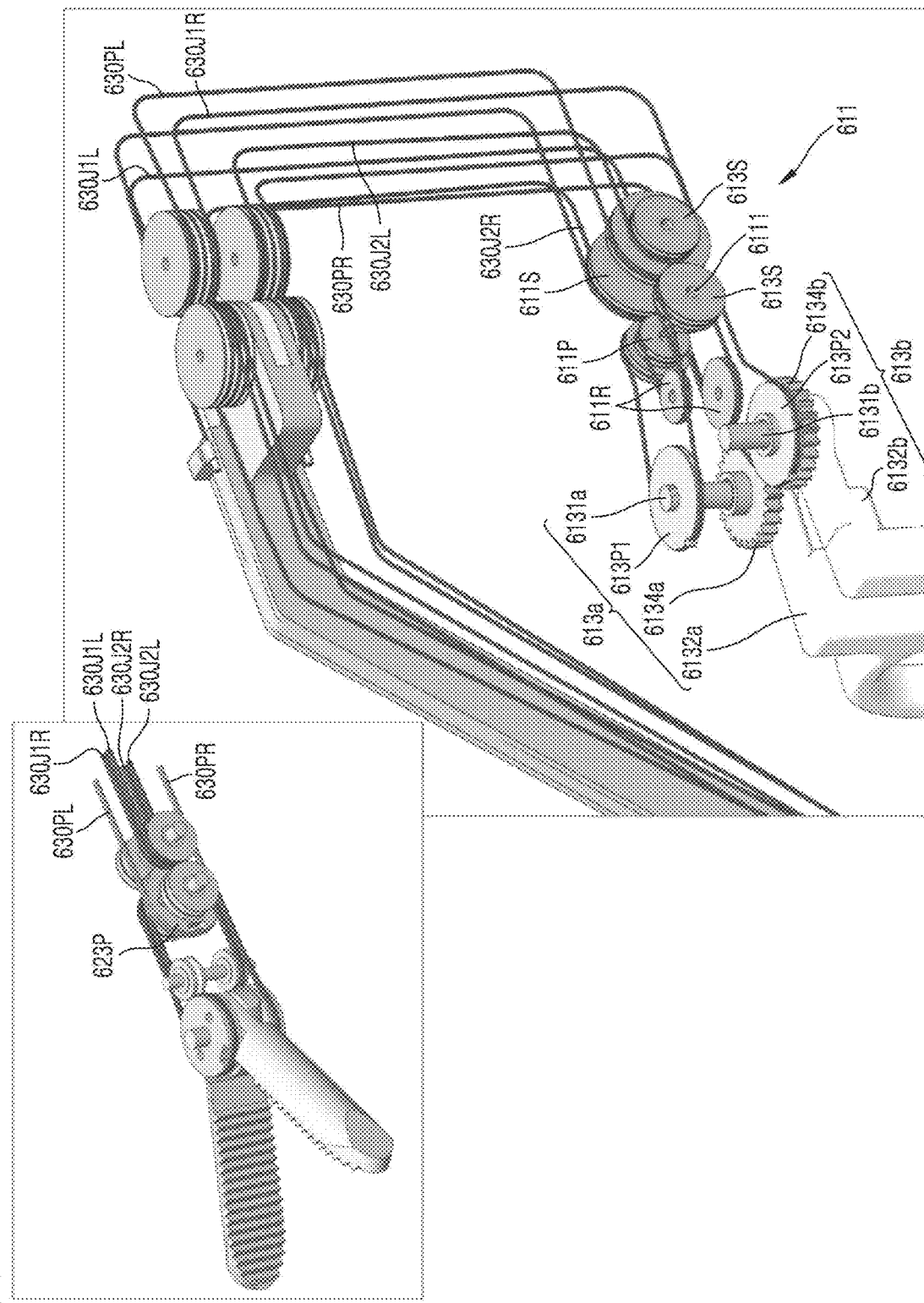
FIG. 58 is an inside perspective view illustrating a wiring structure of the instrument for surgery shown in FIG. 56.
Figure 59:
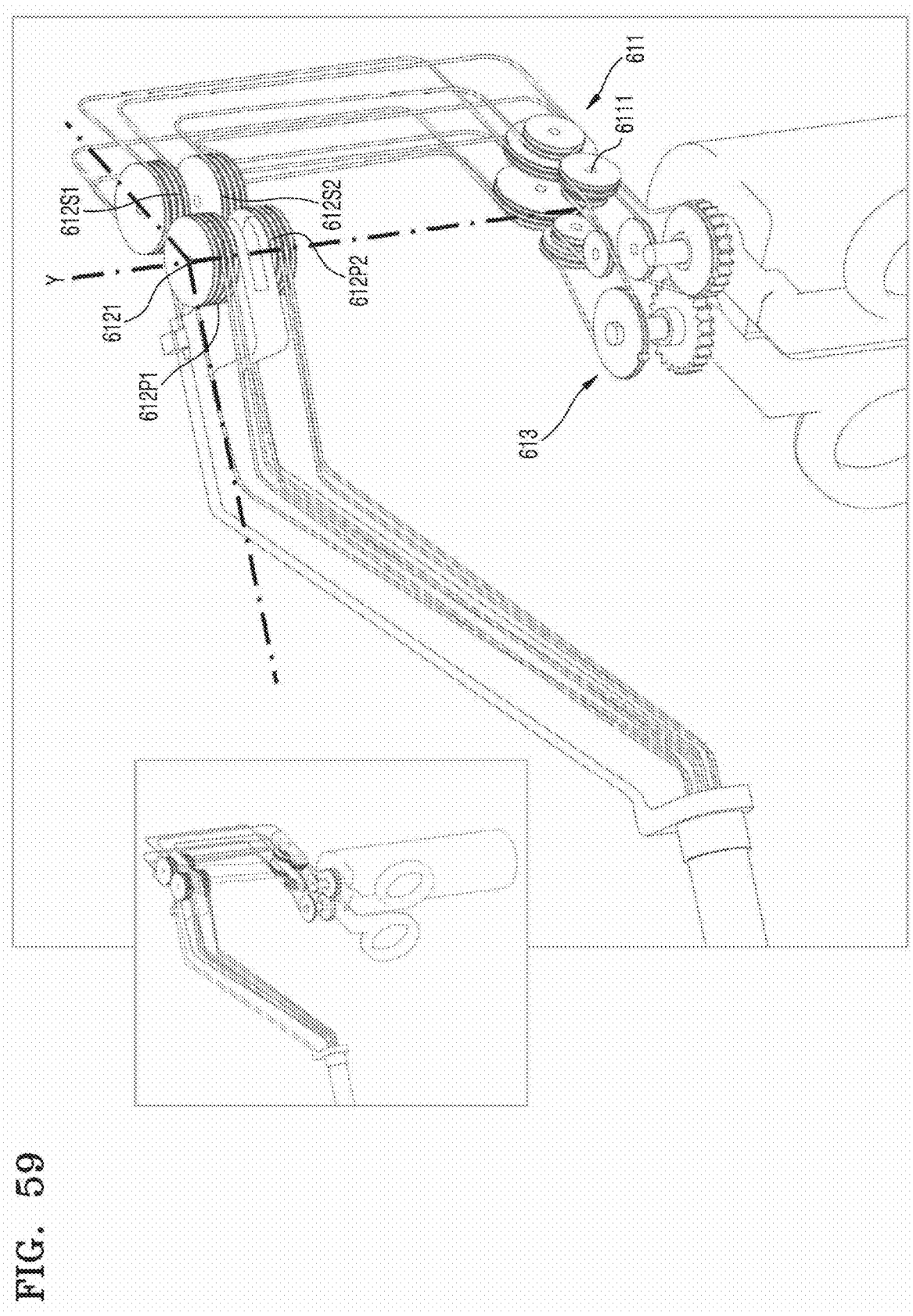
FIG. 59 is a perspective view illustrating a yaw motion of the instrument for surgery shown in FIG. 56.
Figure 60:
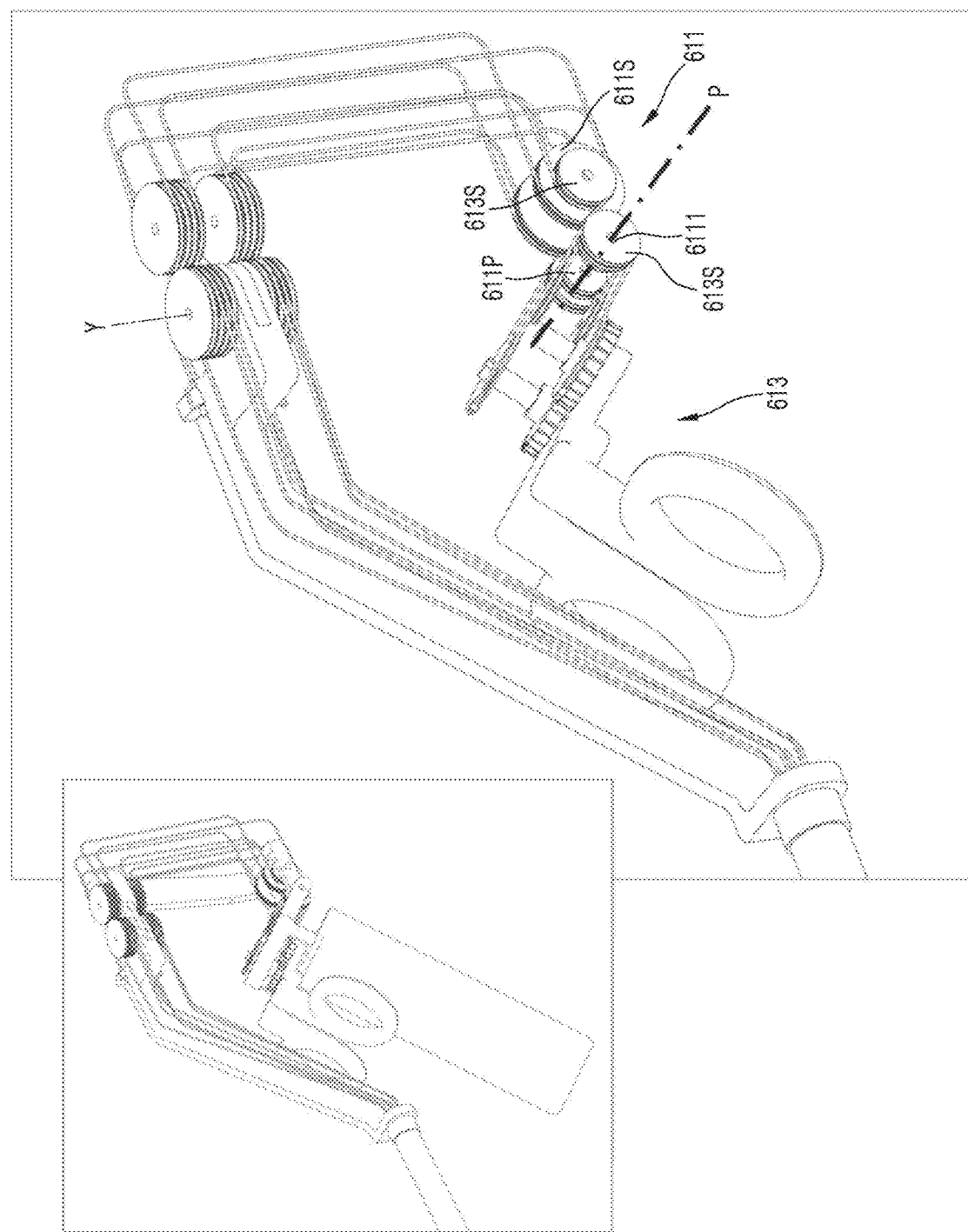
FIG. 60 is a perspective view illustrating a pitch motion of the instrument for surgery shown in FIG. 56.

FIG. 56 is a perspective view illustrating the instrument for surgery according to the sixth embodiment of the present invention, FIG. 57 is an inside perspective view illustrating the instrument for surgery of FIG. 56, and FIG. 58 is an inside perspective view illustrating a wiring structure of the instrument for surgery of FIG. 56. FIG. 59 is a perspective view illustrating a yaw motion of the instrument for surgery of FIG. 56, and FIG. 60 is a perspective view illustrating a pitch motion of the instrument for surgery of FIG. 56.

Referring to FIGS. 56 to 60, the instrument 600 for surgery according to the sixth embodiment of the present invention includes the manipulation part 610, an end tool 620, a power transmission part 630, and a connecting part 640. Herein, the connecting part 640 may have a hollow shaft shape accommodating at least one wire (described later). The manipulation part 610 may be coupled to one end portion of the connecting part 640, and the end tool 620 may be coupled to the other end portion of the connecting part 640 such that the manipulation part 610 and the end tool 620 may be connected through the connecting part 640. The connecting part 640 may include a bent part 641 at a side of the manipulation part 610.

According to the sixth embodiment of the present invention, the manipulation part 610 of the instrument 600 for surgery includes a pitch manipulation part 611 configured to control pitch motion of the end tool 620, a yaw manipulation part 612 configured to control yaw motion of the end tool 620, an actuation manipulation part (actuation operator) 613 configured to control actuation motion of the end tool 620, and a first handle 614 that a user may hold.

First, an example operation of the instrument 600 for surgery shown in FIG. 56 will be described. In a state in which a user holds the first handle 614 with his/her palm, the user may perform a pitch motion by rotating the first handle 614 around an Y axis (that is, around a pitch rotation shaft 6111) and a yaw motion by rotating the first handle 614 around a Z axis (that is, around a yaw rotation shaft 6121), and in a state in which the user inserts his/her thumb and index finger into the actuation manipulation part 613, the user may perform an actuation motion by rotating the actuation manipulation part 613.

Here, the instrument 600 for surgery according to the sixth embodiment of the present invention is configured such that the yaw manipulation part 612 is significantly spaced apart from the first handle 614 compared with the first embodiment. That is, although the actuation manipulation part 613 and the pitch manipulation part 611 are provided above the handle 614 and relatively close to the first handle 614, the yaw manipulation part 612 is connected to the pitch rotation shaft 6111 of the pitch manipulation part 611 through an I-shaped yaw frame 6123, and the yaw manipulation part 612 and the bent part 641 are connected to each other through the yaw rotation shaft 6121 provided on a side of the bent part 641. Therefore, the yaw manipulation part 612 is spaced apart from the first handle 614 in a Z-axis direction by the length of the yaw frame 6123. In other words, the yaw rotation shaft 6121 is provided above the actuation manipulation part 613 in the Z-axis direction instead of being provided on a side of the actuation manipulation part 613, and a plurality of pulleys are arranged between the yaw rotation shaft 6121 and the actuation manipulation part 613, such that if a user rotates the first handle 614 in yaw motion, the first handle 614, all of the actuation manipulation part 613, and the pitch manipulation part 611 may be rotated around the yaw rotation shaft 6121.

In the first embodiment, the joint structure of the manipulation part for operating the end tool includes a pitch joint and a yaw joint that are sequentially connected to each other. That is, wires for transmitting power to the end tool are first connected to a pitch joint part of the manipulation part via the bent part of the connecting part and is then connected to a yaw joint part.

However, the order of joints of the manipulation part in the sixth embodiment is different from that in the first embodiment, that is, a yaw joint and a pitch joint are sequentially connected. That is, if the difference is viewed from connection with the end tool, the yaw manipulation part is first provided, and then the pitch manipulation part and the actuation manipulation part are provided on the yaw manipulation part.

However, like the first embodiment, the sixth embodiment has the feature that the end tool is rotated intuitively in the same direction as the direction in which the manipulation part is manipulated. That is, as described with reference to FIG. 1, when a user moves a handle for actuation rotation, pitch rotation, or yaw rotation, the rotation axis of a manipulation part for the rotation is located at a rear side (a side of the user) like the end tool. In detail, the first handle 614 may be configured such that a user may grip the first handle 614 with his/her hand. In particular, a user may grip the first handle 614 by holding around the first handle 614 with his/her palm. In addition, the actuation manipulation part 613 is provided on the first handle 614, and the pitch manipulation part 611 is provided on a side of the actuation manipulation part 613. In addition, the pitch manipulation part 611 is connected to the yaw manipulation part 612 through the yaw frame 6123, and the yaw frame 6123 has a side connected to the pitch rotation shaft 6111 and another side connected to the yaw rotation shaft 6121.

The actuation manipulation part 613 includes a first actuation manipulation part 613*a* and a second actuation manipulation part 613*b*. The first actuation manipulation part 613*a* includes a first actuation rotation shaft 6131*a*, a first actuation rotation part 6132*a*, a first actuation pulley 613P1, and a first actuation gear 6134*a*. The second actuation manipulation part 613*b* includes a second actuation rotation shaft 6131*b*, a second actuation rotation part 6132*b*, a second actuation pulley 613P2, and a second actuation gear 6134*b*. Here, the first actuation rotation part 6132*a* and the second actuation rotation part 6132*b* may function as a second handle.

In addition, the first actuation rotation part 6132*a*, the first actuation pulley 613P1, and the first actuation gear 6134*a* may be fixedly coupled to each other so as to be rotated together around the first actuation rotation shaft 6131*a*.

Similarly, the second actuation rotation part 6132*b*, the second actuation pulley 613P2, and the second actuation gear 6134*b* may be fixedly coupled to each other so as to be rotated together around the second actuation rotation shaft 6131*b*.

Here, the first actuation gear 6134*a* and the second actuation gear 6134*b* may be engaged with each other, and thus if one of the first and second actuation gears 6134*a* and 6134*b* is rotated, the first and second actuation gears 6134*a* and 6134*b* may be rotated together in opposite directions.

The pitch manipulation part 611 may include a pitch rotation shaft 6111, a plurality of pitch pulleys 611P, a plurality of pitch auxiliary pulleys 611S, and a pitch frame 6113. In addition, the pitch manipulation part 611 may further include a plurality of pitch-wire pitch pulleys 611PP, a pitch-wire pitch auxiliary pulley 611PS, and a pitch-wire pitch return pulley 611PR.

The pitch rotation shaft 6111 and the pitch pulleys 611P are coupled to the pitch frame 6113. In this case, the pitch pulleys 611P are connected to the pitch rotation shaft 6111 in such a manner that the pitch pulleys 611P are rotatable around the pitch rotation shaft 6111.

The pitch frame 6113 is a base frame of the pitch manipulation part 611 and connects the pitch rotation shaft 6111, the first actuation rotation shaft 6131*a*, and the second actuation rotation shaft 6131*b*, thereby enabling the first handle 614, the actuation manipulation part 613, and the pitch manipulation part 611 to rotate together around the pitch rotation shaft 6111. That is, if the first handle 614 is rotated around the pitch rotation shaft 6111, the first actuation rotation shaft 6131*a* and the second actuation rotation shaft 6131*b* connected to the first handle 614 are rotated together. In other words, if a user rotates the first handle 614 around the pitch rotation shaft 6111, the actuation manipulation part 613 is moved together with the first handle 614.

The yaw manipulation part 612 may include the yaw rotation shaft 6121, a first jaw yaw pulley 612P1, a second jaw yaw pulley 612P2, and the yaw frame 6123. In addition, the yaw manipulation part 612 may further include a first jaw yaw auxiliary pulley 612S1 provided on a side of the first jaw yaw pulley 612P1, and a second jaw yaw auxiliary pulley 612S2 provided on a side of the second jaw yaw pulley 612P2.

Specifically, the yaw frame 6123 serves as a base frame of the yaw manipulation part 612 and may be formed as an I-shaped frame. A side of the yaw frame 6123 is connected to the pitch rotation shaft 6111, and another side of the yaw frame 6123 is connected to the yaw rotation shaft 6121. In addition, the yaw frame 6123 and the bent part 641 of the extension part 640 are rotatable relative to each other around the yaw rotation shaft 6121.

In addition, a first pitch wire yaw pulley 612PP1, a first pitch wire yaw auxiliary pulley 612PS1, a second pitch wire yaw pulley 612PP2, and a second pitch wire yaw auxiliary pulley 612PS2 may be respectively arranged at sides of the first jaw yaw pulley 612P1, the first jaw yaw auxiliary pulley 612S1, the second jaw yaw pulley 612P2, and the second jaw yaw auxiliary pulley 612S2 so as to wind a pitch wire 630P therearound.

Here, in the drawings, each of the first jaw yaw pulley 612P1, the second jaw yaw pulley 612P2, the first jaw yaw auxiliary pulley 612S1, the second jaw yaw auxiliary pulley 612S2, the first pitch wire yaw pulley 612PP1, the first pitch wire yaw auxiliary pulley 612PS1, the second pitch wire yaw pulley 612PP2, and the second pitch wire yaw auxiliary pulley 612PS2 of the yaw manipulation part 612 is illustrated as having two pulleys. However, the idea of the present invention is not limited thereto. That is, according to the configuration of the yaw manipulation part 612, the yaw manipulation part 612 may include one or more pulleys having the same diameter or different diameters.

In detail, the yaw rotation shaft 6121 is inserted through the bent part 641, the yaw frame 6123, the first jaw yaw pulley 612P1, and the second jaw yaw pulley 612P2. Therefore, the yaw frame 6123 is rotatable around the yaw rotation shaft 6121 with respect to the bent part 641. The pitch frame 6113 is coupled to the actuation manipulation part 613, and the actuation manipulation part 613 is coupled to the first handle 614. Therefore, as a result, if the first handle 614 is rotated around the yaw rotation shaft 6121, the first handle 614, the actuation manipulation part 613, the pitch frame 6113, and the yaw frame 6123 are rotated with respect to the bent part 641.

Owing to this structure, as shown in FIG. 57, the manipulation part is configured such that a rotation shaft of the yaw joint and a rotation shaft of the pitch joint may be placed close to each other, for example, to cross each other. As a result, users may perform more natural, intuitive manipulation.

In addition, the first jaw yaw pulley 612P1 and the second jaw yaw pulley 612P2 are connected to the yaw rotation shaft 6121 and rotatable around the yaw rotation shaft 6121. In addition, a first jaw wire 63071 may be wound around the first jaw yaw pulley 612P1, and a second jaw wire 630J2 may be wound around the second jaw yaw pulley 612P2. In this case, each of the first jaw yaw pulley 612P1 and the second jaw yaw pulley 612P2 may include two pulleys facing each other and independently rotatable. Therefore, an inward wire and an outward wire may be respectively wound around separate pulleys and thus may not interfere with each other.

Similarly, each of the first jaw yaw auxiliary pulley 612S1 and the second jaw yaw auxiliary pulley 612S2 may include two pulleys facing each other and independently rotatable. Therefore, an inward wire and an outward wire may be respectively wound around separate pulleys and thus may not interfere with each other.

The first handle 614, the pitch manipulation part 611, the yaw manipulation part 612, and the actuation manipulation part 613 are connected as follows. The actuation rotation shafts 6131a and 6131b, the yaw rotation shaft 6121, and the pitch rotation shaft 6111 may be provided on the first handle 614. In this case, since the actuation rotation shafts 6131a and 6131b are directly provided on the first handle 614, the first handle 614 and the actuation manipulation part 613 may be directly connected to each other. In addition, since the pitch rotation shaft 6111 is directly provided on the first handle 614, the first handle 614 and the pitch manipulation part 611 may be directly connected to each other. However, since the yaw manipulation part 612 is connected to the pitch manipulation part 611 through the yaw frame 6123, the yaw manipulation part 612 may not be directly connected to the first handle 614 but may be indirectly connected to the first handle 614 through the pitch manipulation part 611.

Actuation, yaw, and pitch motions in the present embodiment are described below.

First, actuation motion is described below.

In a state in which a user inserts his/her index finger in the first actuation rotation part 6132a and his/her thumb in the second actuation rotation part 6132b, if the user rotates the actuation rotation parts 6132a and 6132b using one or both of his/her index finger and thumb, the first actuation pulley 613P1 and the first actuation gear 6134a fixedly coupled to the first actuation rotation part 6132a are rotated around the first actuation rotation shaft 6131a, and the second actuation pulley 6133b and the second actuation gear 6134b fixedly coupled to the second actuation rotation part 6132b are rotated around the second actuation rotation shaft 6131b. At this time, the first actuation pulley 613P1 and the second actuation pulley 613P2 are rotated in opposite directions, and thus the first jaw wire 630J1 fixedly coupled to the first actuation pulley 613P1 at an end portion thereof and the second jaw wire 630J2 fixedly coupled to the second actuation pulley 613P2 at an end portion thereof are also moved in opposite directions. Then, rotating force is transmitted to the end tool 620 through the power transmission part 630, and two jaws 621 and 622 of the end tool 620 perform an actuation motion.

Next, pitch motion will be described below.

Referring to FIGS. 57 and 60, if a user rotates the first handle 614 around the pitch rotation shaft 6111 while holding the first handle 614, the actuation manipulation part 613 is pitch rotated around the pitch rotation shaft 6111. That is, if the first actuation pulley 613P1 of the first actuation manipulation part 613a to which the first jaw wire 630J1 is fixedly coupled is rotated around the pitch rotation shaft 6111, both strands 630J1R and 630J1L of the first jaw wire 630J1 wound around the pitch pulleys 611P are moved in the same direction. Similarly, if the second actuation pulley 613P2 of the second actuation manipulation part 613b to which the second jaw wire 630J1 is fixedly coupled is rotated around the pitch rotation shaft 6111, both strands 630J2R and 630J2L of the second jaw wire 630J2 wound around the pitch pulleys 611P are moved in the same direction. Then, rotating force is transmitted to the end tool 620 via the power transmission part 630, and thus the two jaws 620 and 621 of the end tool 622 perform a pitch motion.

In addition, as shown in FIG. 58, a pitch pulley 623P and the pitch wire 630P may be provided on the end tool 620, and thus pitch motion of the end tool 620 may be more easily performed as the manipulation part 610 is pitch manipulated.

Both strands 630PL and 630PR of the pitch wire 630P are wound around the pitch-wire pitch return pulley 611PR after passing through the yaw manipulation part 612 and the pitch manipulation part 611, and are then fixedly coupled to a point of the bent part after passing through the pitch manipulation part 611 and the yaw manipulation part 612.

If a user rotates the first handle 614 around the pitch rotation shaft 6111, the pitch-wire pitch return pulley 611PR is also rotated around the pitch rotation shaft 6111. In this case, since both strands 630PL and 630PR of the pitch wire 630P are wound in opposite directions around the pitch-wire pitch pulleys 611PP rotatable around the pitch rotation shaft 611, both strands 630PL and 630PR of the pitch wire 630P adjacent to the end tool 620 are moved in opposite directions, and thus additional pitch-rotation power may be transmitted independently of the pitch motion of the end tool 620 by the second jaw wire 630J1 and the second jaw wire 630J2.

Next, yaw motion will be described below.

Referring to FIGS. 57 and 59, if a user rotates the first handle 614 around the yaw rotation shaft 6121 while holding the first handle 614, the actuation manipulation part 613, the pitch manipulation part 611, and the yaw manipulation part 612 are yaw rotated around the yaw rotation shaft 6121. That is, if the first actuation pulley 613P1 of the first actuation manipulation part 613a to which the first jaw wire 630J1 is fixedly coupled is rotated around the yaw rotation shaft 6121, the first jaw wire 630J1 wound around the first jaw yaw pulley 612P1 is moved. Likewise, if the second actuation pulley 613P2 of the second actuation manipulation part 613b to which the second jaw wire 630J2 is fixedly coupled is rotated around the yaw rotation shaft 6121, the second jaw wire 630J2 wound around the second jaw yaw pulley 612P2 is moved. In this case, the first jaw wire 630J1 connected to the first jaw 621 and the second jaw wire 630J2 connected to the second jaw 622 may be configured such that the first jaw 621 and the second jaw 622 may be rotated in the same direction during yaw rotation. Then, rotating force is transmitted to the end tool 620 through the power transmission part 630, and the two jaws 621 and 622 of the end tool 620 perform a yaw motion.

Meanwhile, the pitch wire 630P for easily perform pitch motion may not affect the operation of the end tool 620 when the manipulation part 610 is manipulated for yaw motion. That is, both strands 630PL and 630PR of the pitch wire 630P may not move toward the end tool 620 when the manipulation part 620 is manipulated for yaw motion.

In the sixth embodiment, both strands 630PL and 630PR of the pitch wire 630P extending from the end tool 620 are correspondingly wound around the pitch wire yaw pulleys 612PP1 and 612PP2 and the pitch wire yaw auxiliary pulleys 612PS1 and 612PS2 in a crossed manner, and after passing through the pitch manipulation part 611 and the actuation manipulation part 613, both strands 630PL and 630PR of the pitch wire 630P are correspondingly wound around the pitch wire yaw auxiliary pulleys 612PS1 and 612PS2 and the pitch wire yaw pulleys 612PP1 and 612PP2 in a crossed manner. Then, each of the strands 630PL and 630PR of the pitch wire 630P is finally fixedly coupled to a point of the bent part 641. In this case, both strands 630PL and 630PR of the pitch wire 630P are wound such that each of the strands 630PL and 630PR of the pitch wire 630P approaches and leaves the pitch wire yaw pulleys 612PP1 and 612PP2 in opposite directions.

Thus, when a user rotates the first handle 614 around the yaw rotation shaft 6121, a portion of the pitch wire 630P wound around the pitch wire yaw pulleys 612PP1 and 612PP2 and extending toward the pitch manipulation part 611 is moved. In this case, however, a portion of the pitch wire 630P wound around the pitch wire yaw pulleys 612PP1 and 612PP2 and extending toward the end tool 620, that is, a portion of the pitch wire 630P extending from the end tool 620 and wound around the pitch wire yaw pulleys 612PP1 and 612PP2 and a portion of the pitch wire 630P extending outward from the pitch wire yaw pulleys 612PP1 and 612PP2 toward the point of the bent part 641 are not moved, thereby not affecting the operation of the end tool 620.

In short, according to the instrument 600 for surgery of the embodiment of the present invention, pulleys are respectively provided on joint points (a actuation joint, a yaw joint, and a pitch joint), wires (the first jaw wire or the second jaw wire) are wound around the pulleys, such that if the manipulation part is rotated (actuation rotation, yaw rotation, or pitch rotation), each wire is moved for a desired motion of the end tool 620. Furthermore, an auxiliary pulley may be provided at a side of each pulley, and a wire may not be wound several times around the pulley owing to the auxiliary pulley.

<Seventh Embodiment of Instrument for Surgery>

Hereinafter, an instrument 700 for surgery will be described according to a seventh embodiment of the present invention. The instrument 700 for surgery of the seventh embodiment of the present invention is characteristically different in the configuration of a manipulation part 710 of the instrument 700 from the instrument 100 for surgery (refer to FIG. 2) of the first embodiment of the present invention. This difference in the configuration from the first embodiment will be described later in detail.

Figure 61:
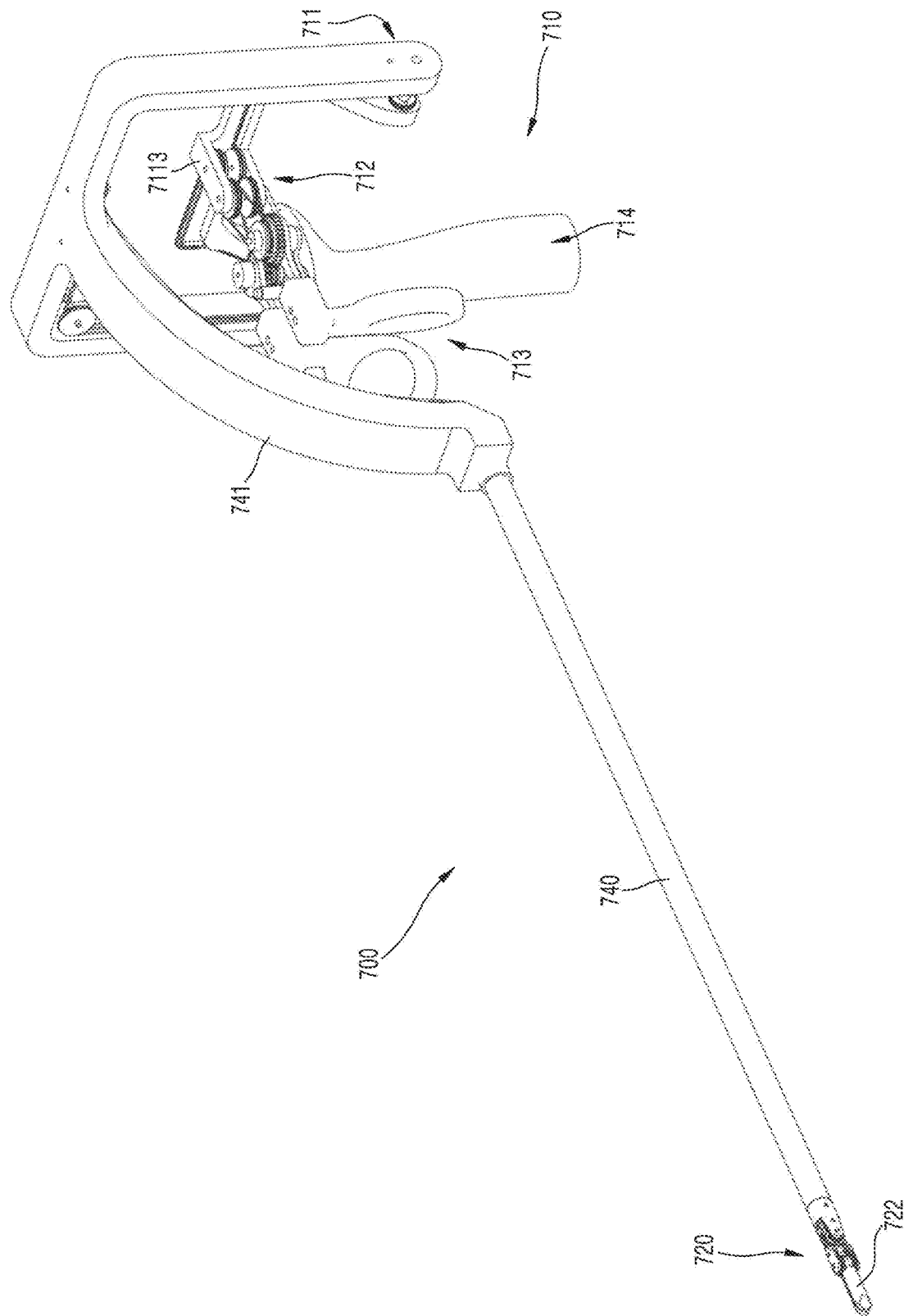
FIG. 61 is a perspective view illustrating an instrument for surgery according to a seventh embodiment of the present invention.
Figure 62:
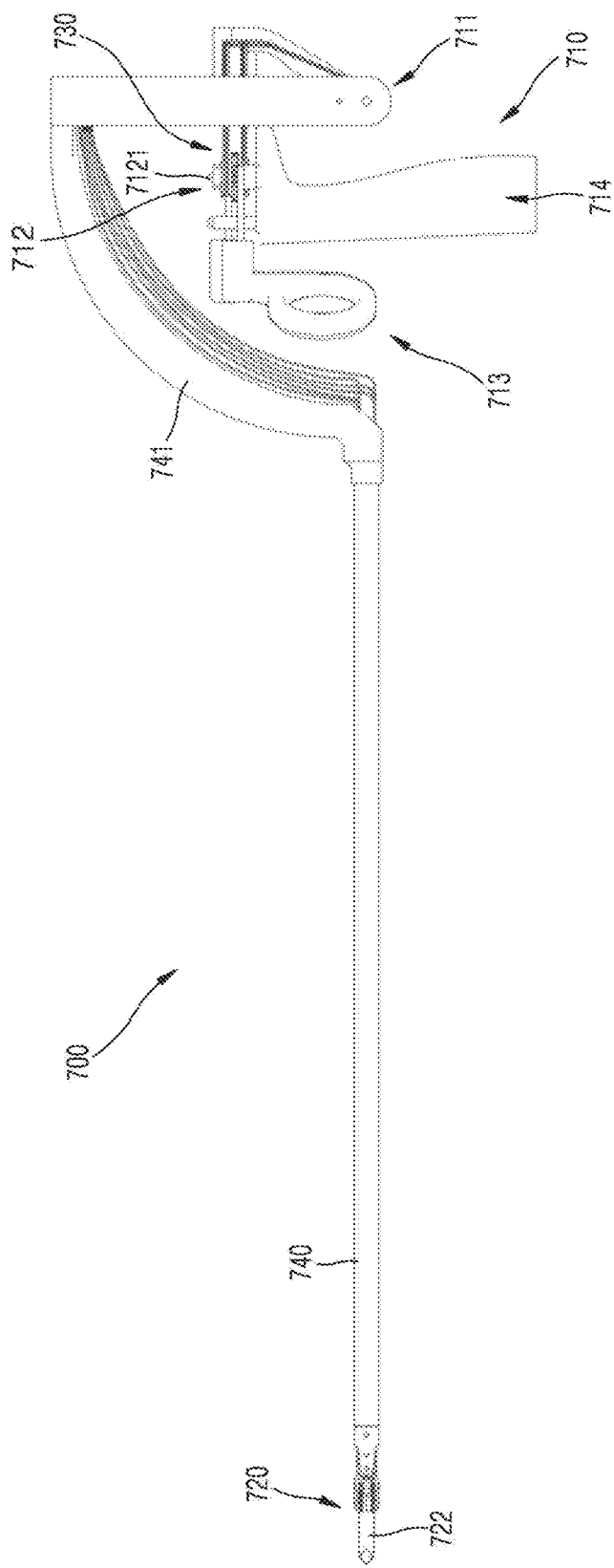
FIG. 62 is a side view illustrating the instrument for surgery shown in FIG. 61.
Figure 63:
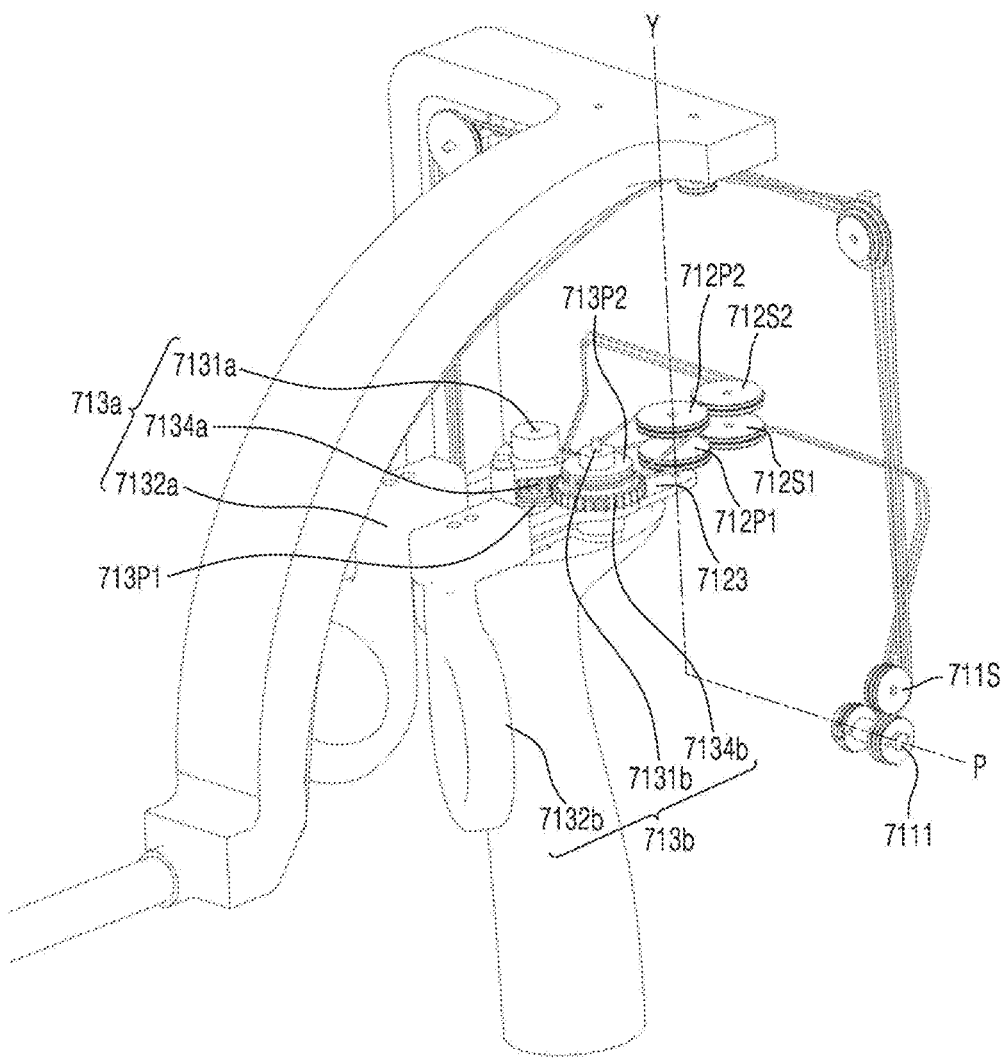
FIGS. 63 and 64 are perspective views illustrating a manipulation part of the instrument for surgery shown in FIG. 61.
Figure 65:
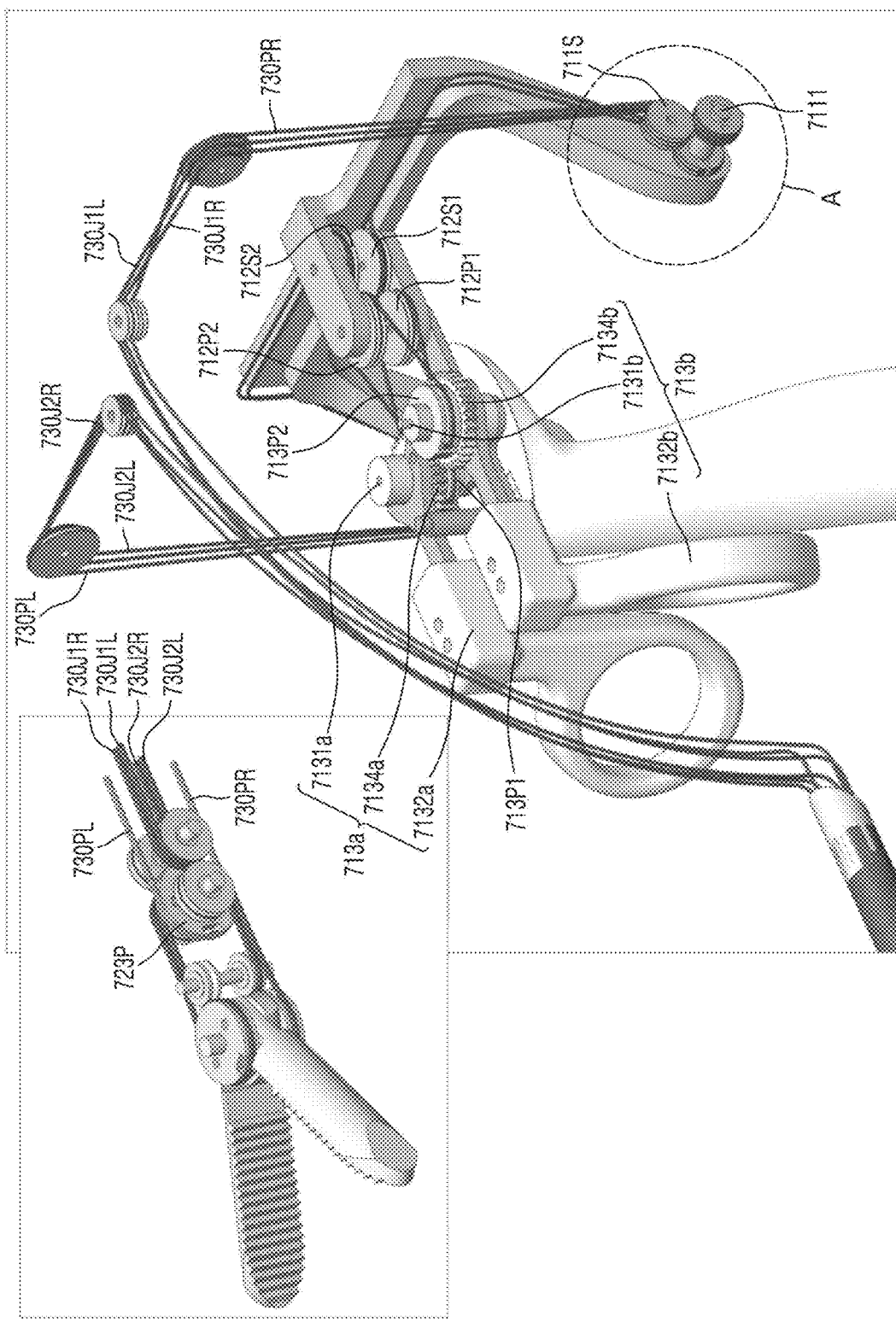
FIG. 65 is an inside perspective view illustrating a wiring structure of the instrument for surgery shown in FIG. 61.
Figure 66:
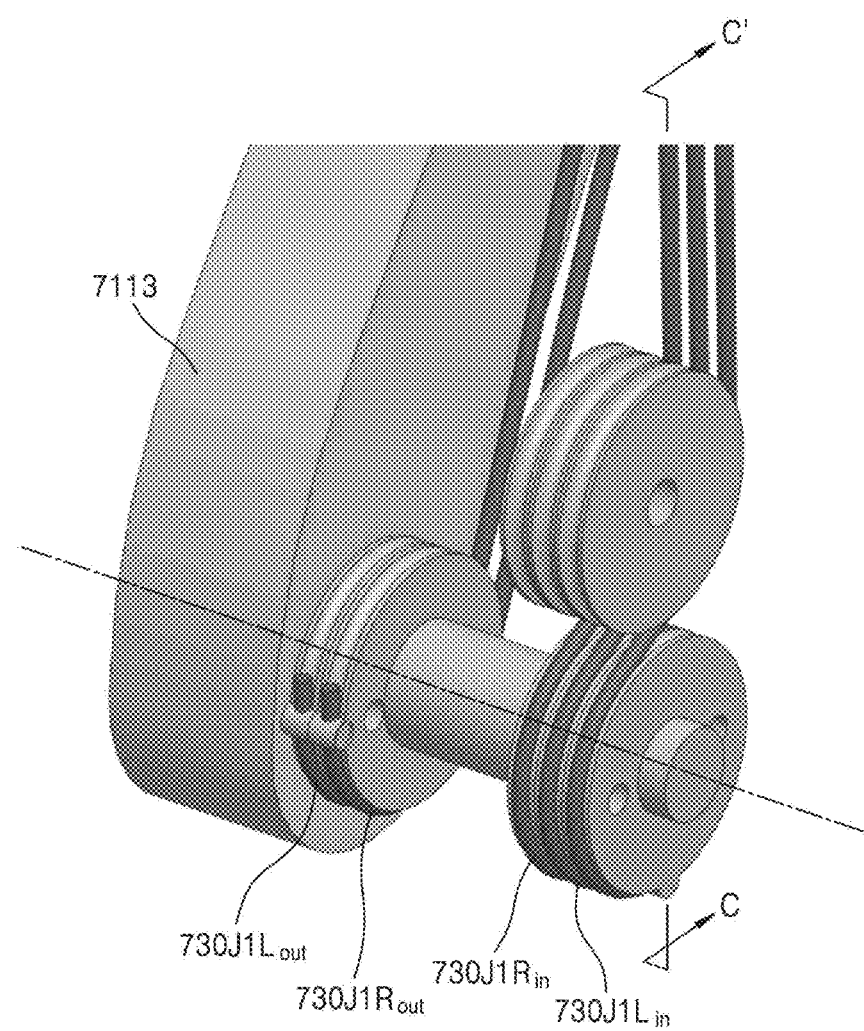
FIG. 66 is an enlarged view illustrating a portion A of FIG. 65.
Figure 67:
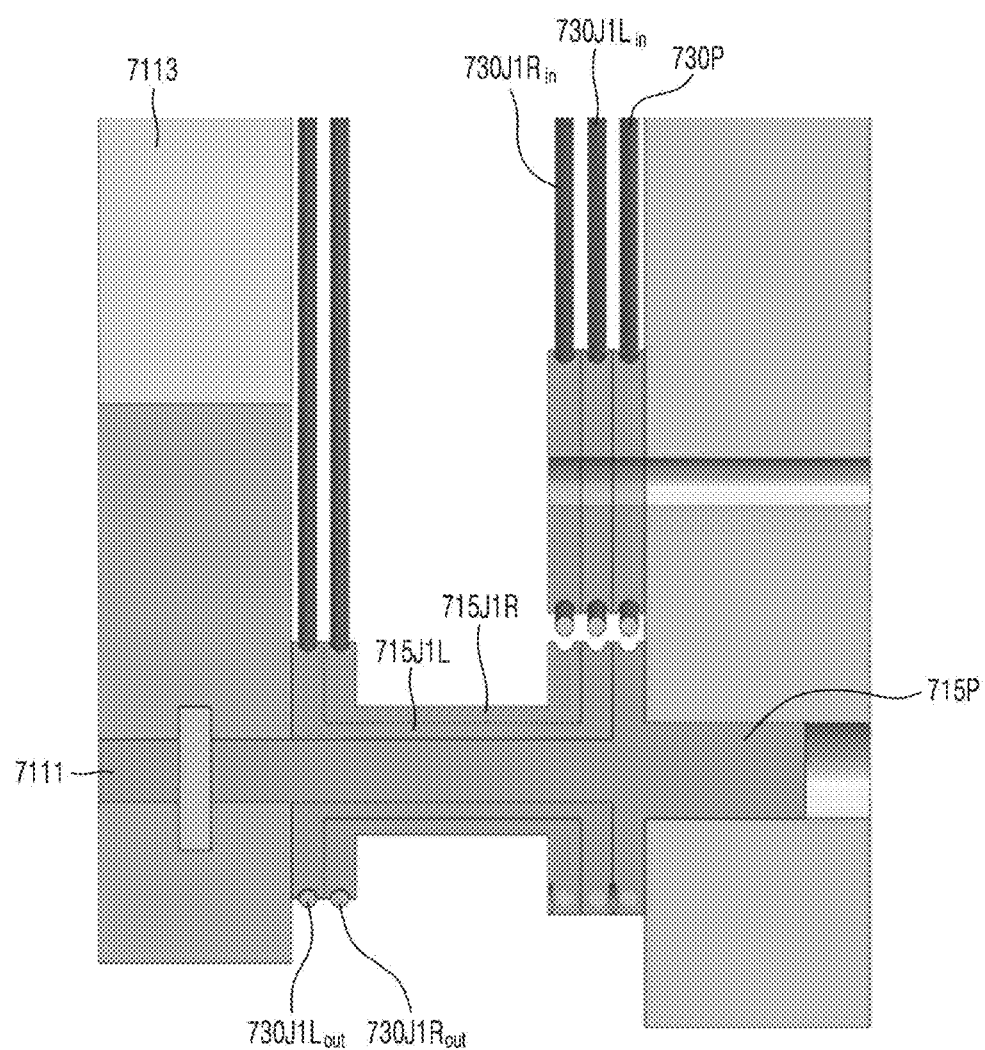
FIG. 67 is a cross-sectional view taken along line C-C' of FIG. 66.
Figure 68:
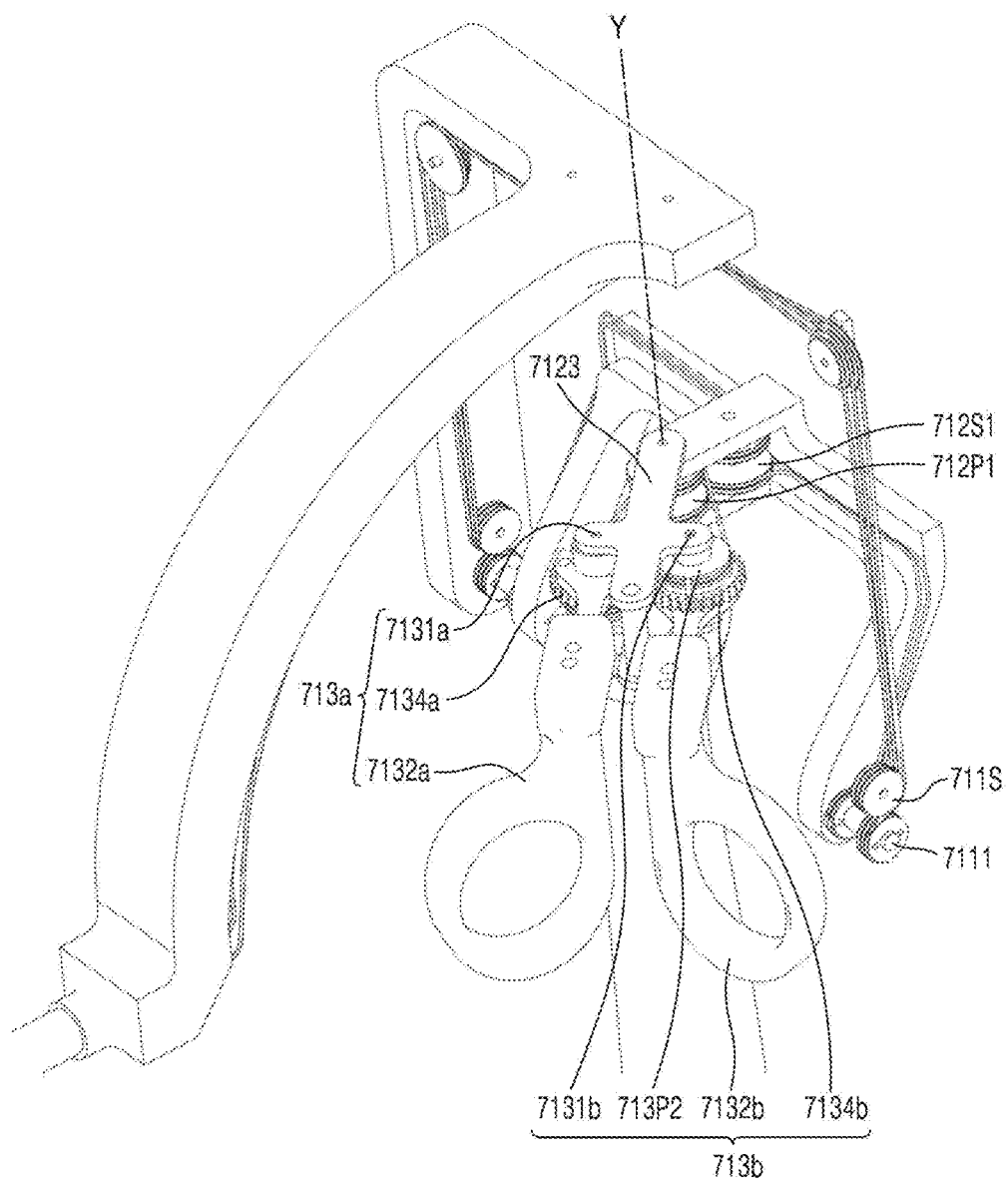
FIG. 68 is a perspective view illustrating a yaw motion of the instrument for surgery shown in FIG. 61.
Figure 69:
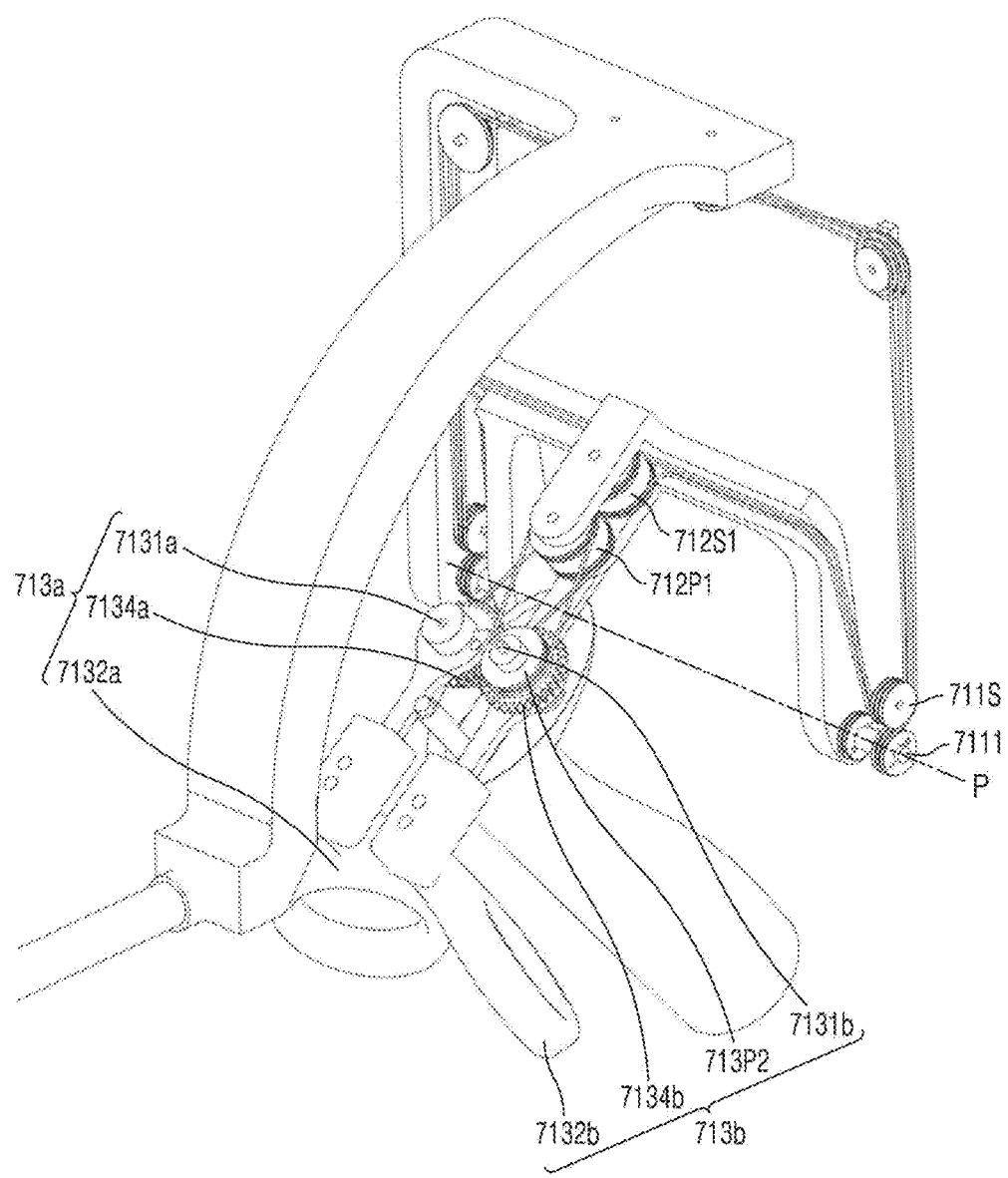
FIG. 69 is a perspective view illustrating a pitch motion of the instrument for surgery shown in FIG. 61.

FIG. 61 is a perspective view illustrating the instrument for surgery according to the seventh embodiment of the present invention, FIG. 62 is a side view illustrating the instrument for surgery of FIG. 61, FIG. 63 is an inside perspective view illustrating the instrument for surgery of FIG. 61, and FIG. 65 is an inside perspective view illustrating a wiring structure of the instrument for surgery of FIG. 61. FIG. 66 is an enlarged view illustrating a portion A in FIG. 65, and FIG. 67 is a cross-sectional view taken along line C-C' in FIG. 66. FIG. 68 is a perspective view illustrating a yaw motion of the instrument for surgery of FIG. 61, and FIG. 69 is a perspective view illustrating a pitch motion of the instrument for surgery of FIG. 61.

Referring to FIGS. 61 to 69, the instrument 700 for surgery of the seventh embodiment of the present invention includes the manipulation part 710, an end tool 720, a power transmission part 730, and a connecting part 740. Herein, the connecting part 740 may have a hollow shaft shape accommodating at least one wire (described later). The manipulation part 710 may be coupled to one end portion of the connecting part 740, and the end tool 720 may be coupled to the other end portion of the connecting part 640 such that the manipulation part 710 and the end tool 720 may be connected through the connecting part 740. The connecting part 740 may include a bent part 741 at a side of the manipulation part 710.

According to the sixth embodiment of the present invention, the manipulation part 710 of the instrument 700 for surgery includes a pitch manipulation part 711 configured to control pitch motion of the end tool 720, a yaw manipulation part 712 configured to control yaw motion of the end tool 720, an actuation manipulation part (actuation operator) 713 configured to control actuation motion of the end tool 720, and a first handle 714 that a user may hold.

First, an example operation of the instrument 700 for surgery shown in FIG. 61 will be described. In a state in which a user holds the first handle 714 with his/her palm, the user may perform a pitch motion by rotating the first handle 714 around an Y axis (that is, around a pitch rotation shaft 7111) and a yaw motion by rotating the first handle 714 around a Z axis (that is, around a yaw rotation shaft 7121), and in a state in which the user inserts his/her thumb and index finger into the actuation manipulation part 713, the user may perform an actuation motion by rotating the actuation manipulation part 713.

The instrument 700 for surgery of the seventh embodiment of the present invention is different from the first embodiment in that the bent part 741 is divided into left and right branch parts at a center portion to form an approximate '∩' shape, a pitch frame 7113 is also correspondingly divided into left and right branch parts to form an approximate '∩' shape, and pitch rotation shafts 7111 are respectively provided on both left and right branch end portions of the pitch frame 7113. As a result, the pitch rotation shafts 7111 are significantly spaced apart from the yaw rotation shaft 7121. That is, actuation rotation shafts 7131a and 7131b and the yaw rotation shaft 7121 are provided on or near the first handle 714 and are thus relatively close to the first handle 714. However, the pitch rotation shafts 7111 are provided on left and right branch end portions of the pitch frame 7113. Therefore, the pitch rotation shafts 7111 may be somewhat lower than the actuation rotation shaft 7131*a* and 7131*b* and the yaw rotation shaft 7121 in a Z-axis direction, and thus a portion of a user's hand may be placed in the pitch frame 7113 having a '∩' shape.

Figure 64:
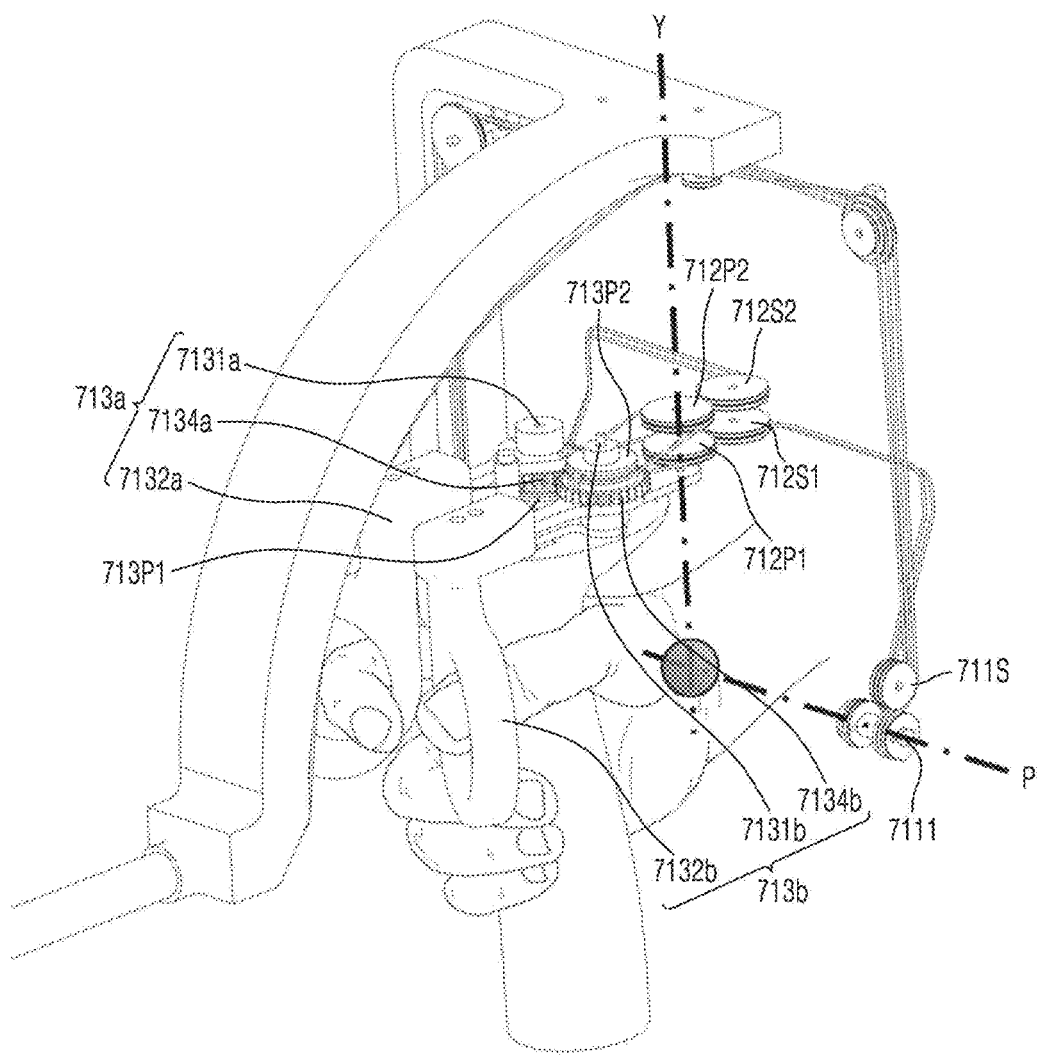

Owing to this configuration, as shown in FIG. 64, a rotation axis of a yaw joint and a rotation axis of a pitch joint of the manipulation part may be placed close to each other, for example, in a crossed manner. In addition, the rotation axis of the yaw joint and the rotation axis of the pitch joint may correspond to the wrist of a user performing yaw and pitch manipulations. Thus, as a result, users may perform more natural, intuitive manipulations.

In detail, the first handle 714 may be configured such that a user may grip the first handle 714 with his/her hand. In particular, a user may grip the first handle 714 by holding around the first handle 614 with his/her palm. In addition, the actuation manipulation part 713 is provided on the first handle 714, the yaw manipulation part 712 is provided on a side of the actuation manipulation part 713, the pitch manipulation part 711 is provided on a side of the yaw manipulation part 712, and the yaw manipulation part 712 and the pitch manipulation part 711 are connected to each other through the pitch frame 7113 having a '∩' shape. In addition, another end portion of the pitch manipulation part 711 is connected to the bent part 741 of the connecting part 740.

The actuation manipulation part 713 includes a first actuation manipulation part 713*a* and a second actuation manipulation part 713*b*. The first actuation manipulation part 713*a* includes a first actuation rotation shaft 7131*a*, a first actuation rotation part 7132*a*, a first actuation pulley 713P1, and a first actuation gear 7134*a*. The second actuation manipulation part 713*b* includes a second actuation rotation shaft 7131*b*, a second actuation rotation part 7132*b*, a second actuation pulley 713P2, and a second actuation gear 7134*b*. Here, the first and second actuation rotation parts 7132*a* and 7132*b* may function as a second handle.

In addition, the first actuation rotation part 7132*a*, the first actuation pulley 713P1, and the first actuation gear 7134*a* may be fixedly coupled to each other so as to be rotated together around the first actuation rotation shaft 7131*a*. Similarly, the second actuation rotation part 7132*b*, the second actuation pulley 713P2, and the second actuation gear 7134*b* may be fixedly coupled to each other so as to be rotated together around the second actuation rotation shaft 7131*b*. Here, the first actuation gear 7134*a* and the second actuation gear 7134*b* may be engaged with each other, and thus if one of the first and second actuation gears 7134*a* and 7134*b* is rotated, the first and second actuation gears 7134*a* and 7134*b* may be rotated together in opposite directions.

The yaw manipulation part 712 may include a yaw rotation shaft 7121, a first jaw yaw pulley 712P1, a second jaw yaw pulley 712P2, and a yaw frame 7123. In addition, the yaw manipulation part 712 may further include a first jaw yaw auxiliary pulley 712S1 provided on a side of the first jaw yaw pulley 712P1, and a second jaw yaw auxiliary pulley 712S2 provided on a side of the second jaw yaw pulley 712P2. Here, the first jaw yaw pulley 712P1, the second jaw yaw pulley 712P2, the first jaw yaw auxiliary pulley 712S1, and the second jaw yaw auxiliary pulley 712S2 may be corresponds to the pitch frame 7113 (described later).

Specifically, the yaw rotation shaft 7121 is provided on a side of the actuation manipulation part 714 above the first handle 714. In this case, the first handle 714 is rotatable around the yaw rotation shaft 7121. In addition, the first jaw yaw pulley 712P1 and the second jaw yaw pulley 712P2 are connected to the yaw rotation shaft 7121 and rotatable around the yaw rotation shaft 7121. In addition, a first jaw wire 730J1 may be wound around the first jaw yaw pulley 712P1, and a second jaw wire 730J2 may be wound around the second jaw yaw pulley 712P2. In this case, each of the first jaw yaw pulley 712P1 and the second jaw yaw pulley 712P2 may include two pulleys facing each other and independently rotatable. Therefore, an inward wire and an outward wire may be respectively wound around separate pulleys and thus may not interfere with each other.

The yaw frame 7123 connects the first handle 714, the yaw rotation shaft 7121, the first actuation rotation shaft 7131*a*, and the second actuation rotation shaft 731*b* such that the first handle 714, the yaw manipulation part 712, and the actuation manipulation part 713 may be rotated together around the yaw rotation shaft 7121.

The pitch manipulation part 711 may include the pitch frame 7113, a J1R relay pulley 715J1R, a J1L relay pulley 715J1L, a J2R relay pulley (not shown), and a J2L relay pulley (not shown). Here, the J1R relay pulley 715J1R and the J2R relay pulley (not shown) may be provided on the left and right branch end portions of the pitch frame 7113, and the J1L relay pulley 715J1L and the J2L relay pulley (not shown) may be respectively provided on the left and right branch end portions of the pitch frame 7113.

In this case, the J1R relay pulley 715J1R, the J1L relay pulley 715J1L, the J2R relay pulley 715J2R, and the J2L relay pulley 715J2L may have the function of pitch pulleys in the above-described embodiments, and may be rotatable around the pitch rotation shafts 7111.

In addition, a first jaw R wire 730J1R refers to the right one of both strands of the first jaw wire 730J1, and the first jaw R wire 730J1R is divided into two: a first jaw R wire-in 730J1Rin entering the pitch manipulation part 711 and a first jaw R wire-out 730J1Rout leaving the pitch manipulation part 711 and connected to the actuation manipulation part 713.

Similarly, a first jaw L wire 730J1L refers to the left one of both strands of the first jaw wire 730J1, and the first jaw L wire 730J1L is divided into two: a first jaw L wire-in 730J1Lin entering the pitch manipulation part 711 and a first jaw L wire-out 730J1Lout leaving the pitch manipulation part 711 and connected to the actuation manipulation part 713.

The J1R relay pulley 715J1R includes two pulleys facing each other and rotatable together. In addition, one of the two pulleys of the J1R relay pulley 715J1R is coupled to the first jaw R wire-in 730J1Rin, and the other pulley is coupled to the first jaw R wire-out 730J1Rout. In this case, as shown in FIG. 66, the direction in which the first jaw R wire-in 730J1Rin is wound around the J1R relay pulley 715J1R (counterclockwise in FIG. 66) is the same as the direction in which the first jaw R wire-out 730J1Rout is released from the J1R relay pulley 715J1R (counterclockwise in FIG. 66).

The J1L relay pulley 715J1L includes two pulleys facing each other and rotatable together. In addition, one of the two pulleys of the J1L relay pulley 715J1L is coupled to the first jaw L wire-in 730J1Lin, and the other pulley is coupled to the first jaw L wire-out 730J1Lout. In this case, as shown in FIG. 66, the direction in which the first jaw L wire-in 730J1Lin is wound around the J1L relay pulley 715J1L (counterclockwise in FIG. 66) is the same as the direction in which the first jaw L wire-out 730J1Lout is released from the J1L relay pulley 715J1L (counterclockwise in FIG. 66).

For example, if the first jaw R wire-in 730J1Rin is pushed or pulled, the J1R relay pulley 715J1R is rotated, and thus the first jaw R wire-out 730J1Rout connected through the J1R relay pulley 715J1R is pushed or pulled along the J1R relay pulley 715J1R in the same direction as the first jaw R wire-in 730J1Rin, that is, in the rotation direction of the J1R relay pulley 715J1R. That is, if the first jaw R wire-in 730J1Rin is moved toward the end tool 720 from the J1R relay pulley 715J1R, the first jaw R wire-out 730J1Rout may be moved in a direction from the yaw manipulation part 712 toward the J1R relay pulley 715J1R. This also applies to the first jaw L wire 730J1L. In this case, the J1R relay pulley 715J1R and the J1L relay pulley 715J1L may be independently rotatable around the pitch rotation shafts 7111. The second jaw wire may connect the end tool and the manipulation part in the same manner.

Pitch wire end pulleys 715P are fixedly coupled to the pitch rotation shafts 7111 and rotatable together with the pitch rotation shafts 7111, and the pitch rotation shafts 7111 are fixedly coupled to the pitch frame 7113. As a result, the pitch frame 7113, the pitch rotation shafts 7111, and the pitch wire end pulleys 715P may be rotated together by pitch rotation. In this case, each of the J1R relay pulley 715J1R, the J1L relay pulley 715J1L, the J2R relay pulley 715J2R, and the J2L relay pulley 715J2L may be independently rotated around the pitch rotation shafts 7111.

Actuation, yaw, and pitch motions in the present embodiment are described below.

First, actuation motion is described below.

In a state in which a user inserts his/her index finger in the first actuation rotation part 7132a and his/her thumb in the second actuation rotation part 7132b, if the user rotates the actuation rotation parts 7132a and 7132b using one or both of his/her index finger and thumb, the first actuation pulley 713P1 and the first actuation gear 7134a fixedly coupled to the first actuation rotation part 7132a are rotated around the first actuation rotation shaft 7131a, and the second actuation pulley 7133b and the second actuation gear 7134b fixedly coupled to the second actuation rotation part 7132b are rotated around the second actuation rotation shaft 7131b. At this time, the first actuation pulley 713P1 and the second actuation pulley 713P2 are rotated in opposite directions, and thus the first jaw wire 730J1 fixedly coupled to the first actuation pulley 713P1 at an end portion thereof and the second jaw wire 730J2 fixedly coupled to the second actuation pulley 713P2 at an end portion thereof are also moved in opposite directions. Then, rotating force is transmitted to the end tool 720 through the power transmission part 730, and two jaws 721 and 722 of the end tool 720 perform an actuation motion.

Next, yaw motion will be described below.

Referring to FIGS. 65 and 68, if a user rotates the first handle 714 around the yaw rotation shaft 7121 while holding the first handle 714, the actuation manipulation part 713 and the yaw manipulation part 712 are yaw rotated around the yaw rotation shaft 7121. That is, if the first actuation pulley 713P1 of the first actuation manipulation part 713a to which the first jaw wire 730J1 is fixedly coupled is rotated around the yaw rotation shaft 7121, the first jaw wire 730J1 wound around the first jaw yaw pulley 712P1 is moved. Likewise, if the second actuation pulley 713P2 of the second actuation manipulation part 713b to which the second jaw wire 730J2 is fixedly coupled is rotated around the yaw rotation shaft 7121, the second jaw wire 730J2 wound around the second jaw yaw pulley 712P2 is moved. In this case, the first jaw wire 730J1 connected to the first jaw 721 and the second jaw wire 730J2 connected to the second jaw 722 may be configured such that the first jaw 721 and the second jaw 722 may be rotated in the same direction during yaw rotation. Then, rotating force is transmitted to the end tool 720 through the power transmission part 730, and the two jaws 721 and 722 of the end tool 720 perform a yaw motion.

At this time, since the yaw frame 7123 connects the first handle 714, the yaw rotation shaft 7121, the first actuation rotation shaft 7131a, and the second actuation rotation shaft 7131b to each other, the first handle 714, the yaw manipulation part 712, and the actuation manipulation part 713 are rotated together around the yaw rotation shaft 7131.

Next, pitch motion will be described below.

Referring to FIGS. 65 and 69, if a user rotates the first handle 714 around the pitch rotation shafts 7111 while holding the first handle 714, the actuation manipulation part 713, the yaw manipulation part 712, and the pitch manipulation part 711 are pitch rotated around the pitch rotation shafts 7111. That is, if the first actuation pulley 713P1 of the first actuation manipulation part 713a to which the first jaw wire 730J1 is fixedly coupled is rotated around the pitch rotation shafts 7111, both strands 730J1R and 730J1L of the first jaw wire 730J1 coupled to the J1R relay pulley 715J1R and the J1L relay pulley 715J1L are moved in the same direction. Similarly, if the second actuation pulley 713P2 of the second actuation manipulation part 713b to which the second jaw wire 730J2 is fixedly coupled is rotated around the pitch rotation shafts 7111, both strands of the second jaw wire 730J2 coupled to the J2R relay pulley 715J2R and the J2L relay pulley 715J2L are moved in the same direction. At this time, the first jaw wire 730J1 and the second jaw wire 730J2 are moved in opposite directions. Then, rotating force is transmitted to the end tool 720 via the power transmission part 730, and thus the two jaws 721 and 722 of the end tool 720 perform a pitch motion.

At this time, since the pitch frame 7113 is connected to the yaw frame 7123 and the yaw frame 7123 connects the first handle 714, the yaw rotation shaft 7121, the first actuation rotation shaft 7131a, and the second actuation rotation shaft 7131b to each other, if the pitch frame 7113 is rotated around the pitch rotation shafts 7111, the yaw frame 7123, the first handle 714, the yaw rotation shaft 7121, the first actuation rotation shaft 7131a, and the second actuation rotation shaft 7131b connected to the pitch frame 7113 are rotated together. That is, if the pitch manipulation part 711 is rotated around the pitch rotation shafts 7111, the actuation manipulation part 713 and the yaw manipulation part 712 are rotated together with the pitch manipulation part 711.

In addition, a pitch pulley 723P may be provided on the end tool, the pitch wire end pulleys 715P may be provided on the manipulation part and connected to pitch wires 730P such that pitch motion of the end tool may be more easily performed by pitch manipulating the manipulation part. End portions of both strands of the pitch wires 730P are respectively fixedly coupled to the pitch wire end pulleys 715P, and each of the pitch wire end pulleys 715P is fixedly coupled to the pitch frame 7113. That is, the pitch frame 7113 and the pitch wire end pulleys 715P are rotated together around the pitch rotation shafts 7111 by pitch rotation of the manipulation part, and as a result, both strands of the pitch wires 730P are moved in opposite directions such that power for pitch rotation may be transmitted independently of pitch motion of the end tool by the first jaw wire 730J1 and the second jaw wire 730J2.

In short, according to the instrument 700 for surgery of the embodiment of the present invention, pulleys are respectively provided on joint points (a actuation joint, a yaw joint, and a pitch joint), wires (the first jaw wire or the second jaw wire) are wound around the pulleys, such that if the manipulation part is rotated (actuation rotation, yaw rotation, or pitch rotation), each wire is moved for a desired motion of the end tool 720. Furthermore, an auxiliary pulley may be provided at a side of each pulley, and a wire may not be wound several times around the pulley owing to the auxiliary pulley.

One of main features of the present embodiment is that since the bent part 741 and the manipulation part 710 are divided into two parts, a rotation axis of a yaw joint and a rotation axis of a pitch joint of the manipulation part may be placed as close as possible, for example, in a crossed manner as shown in FIG. 64, and a space may be formed at or near a crossing point to receive a user's hand or wrist. To this end, in the present embodiment, elements of the manipulation part 710 (such as pulleys and wires) are divided into two groups and arranged at both division sides. However, the configuration for the above-mentioned feature may be variously modified. That is, elements of the manipulation part 710 (such as pulleys and wires) may be arranged only at one of both division sides. Furthermore, instead of dividing the bent part 741 and the manipulation part 710 into both sides, the bent part 741 and the manipulation part 710 may be bent only at one side to form a space for accommodating a user's hand or wrist. That is, in the two-part division structure of the present embodiment, one part may be omitted. Such modifications may be sufficiently deduced from the above-description of the present embodiment, and thus detailed descriptions thereof will be omitted.

<Eighth Embodiment of Instrument for Surgery>

Hereinafter, an instrument 800 for surgery will be described according to a eighth embodiment of the present invention. The instrument 800 for surgery of the eighth embodiment of the present invention is characteristically different in the configuration of a manipulation part 810 of the instrument 800 from the instrument for surgery of the sixth embodiment of the present invention. As in the sixth embodiment, in the joint structure of the manipulation part 810 for manipulating the operation of an end tool 820, a yaw manipulation part 812 is first placed, and then a pitch manipulation part 811 and an actuation manipulation part 813 is provided on the yaw manipulation part 812 when viewed based on wires connected from the end tool 820 to the manipulation part 810. However, the difference between the eighth embodiment and the sixth embodiment is that, as in the seventh embodiment, a bent part 841 is divided into left and right branch parts at a center portion to form an approximate ' shape, a pitch frame 8113 is also divided into left and right branch parts to form an approximate' shape, and both left and right branch end portions of the pitch frame 8113 are connected to both left and right branch end portions of the bent part 841 through pitch rotation shafts 8111. Owning to this structure, as described in the seventh embodiment, a rotation axis of a yaw joint and a rotation axis of a pitch joint of the manipulation part 810 may be intuitively identical to a user's wrist joint performing yaw and pitch manipulations by holding a handle, such that the user may perform more natural, intuitive manipulations.

Figure 70:
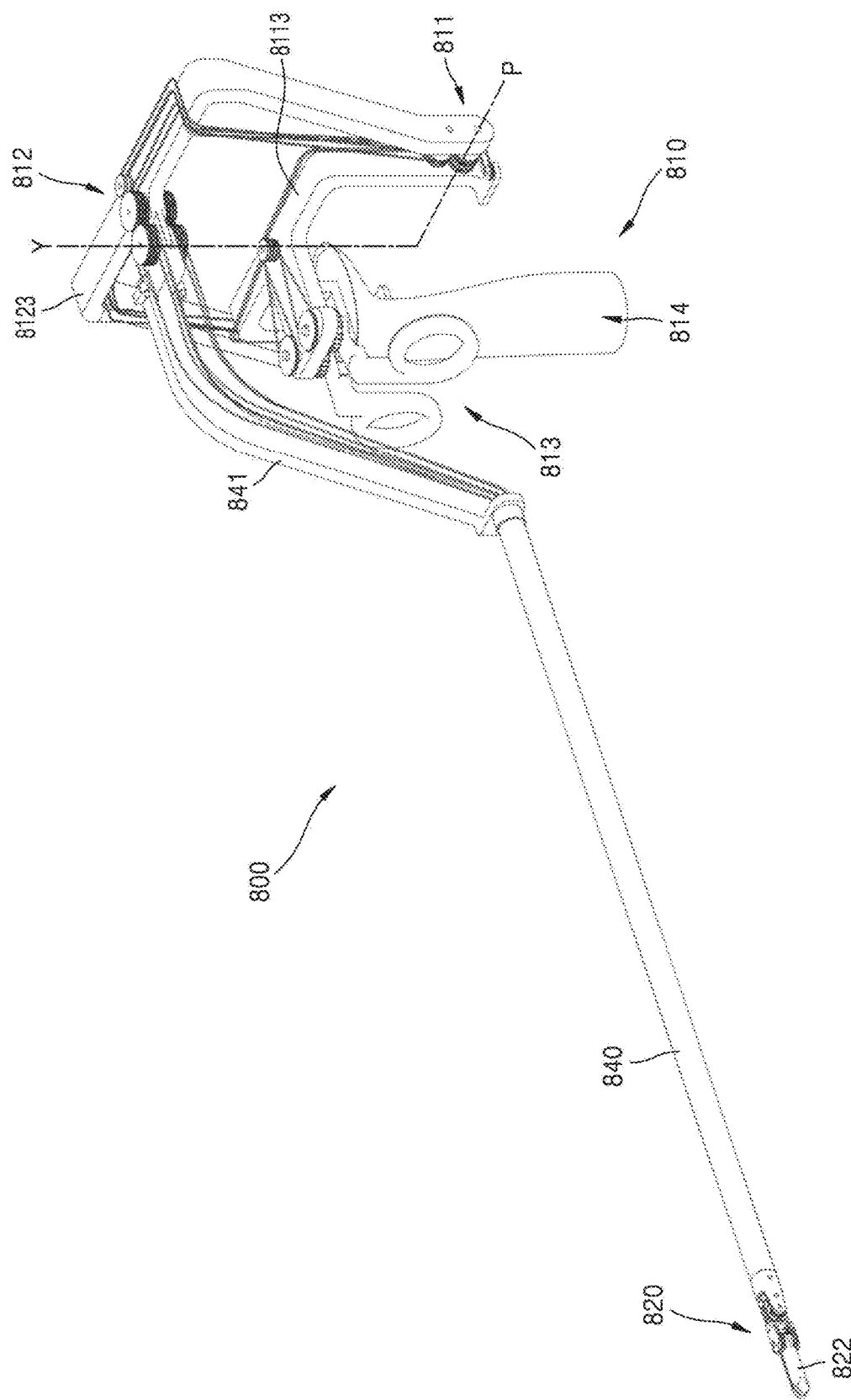
FIG. 70 is a perspective view illustrating an instrument for surgery according to an eighth embodiment of the present invention.
Figure 71:
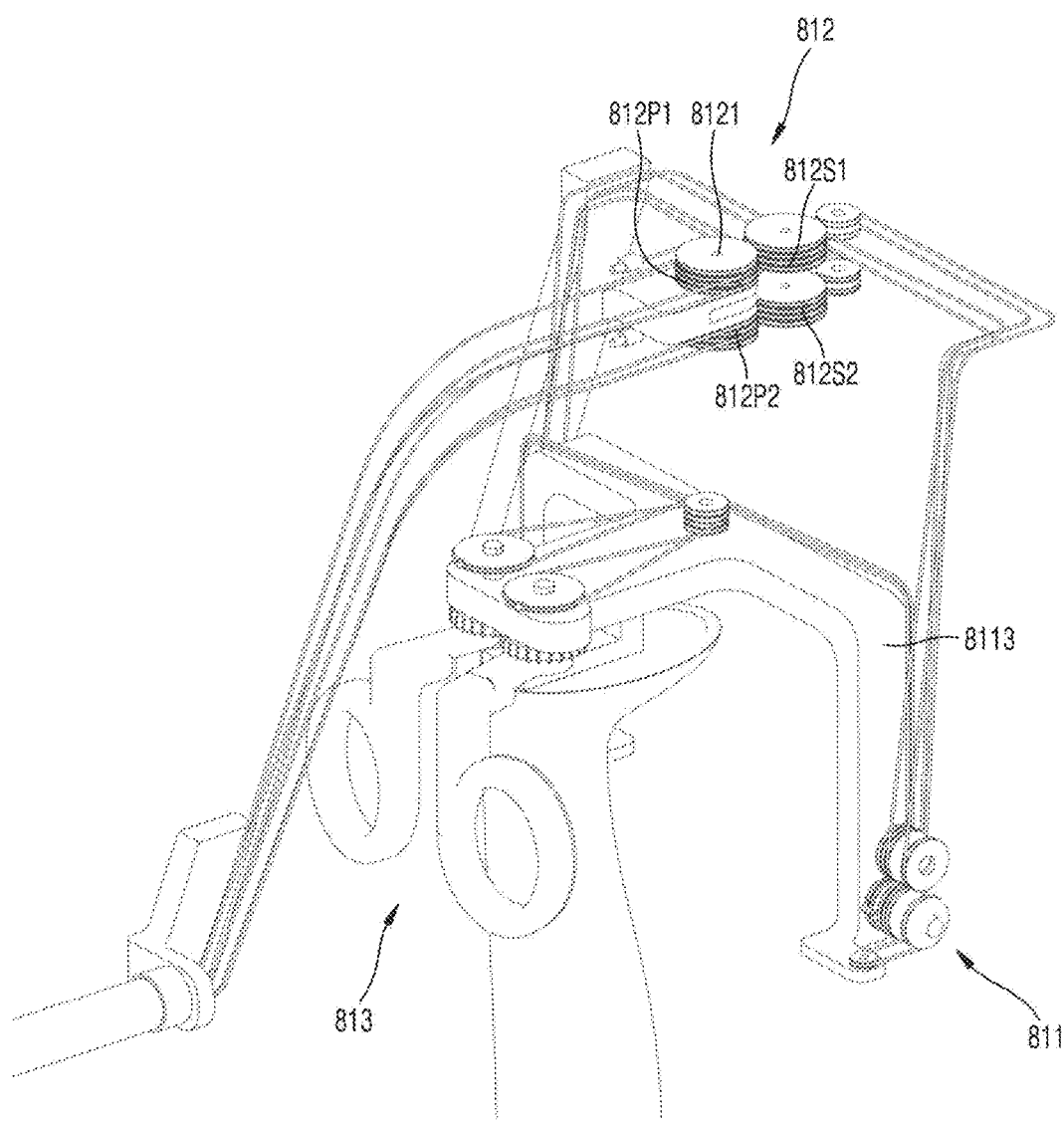
FIG. 71 is a perspective view illustrating a manipulation part of the instrument for surgery shown in FIG. 70.
Figure 72:
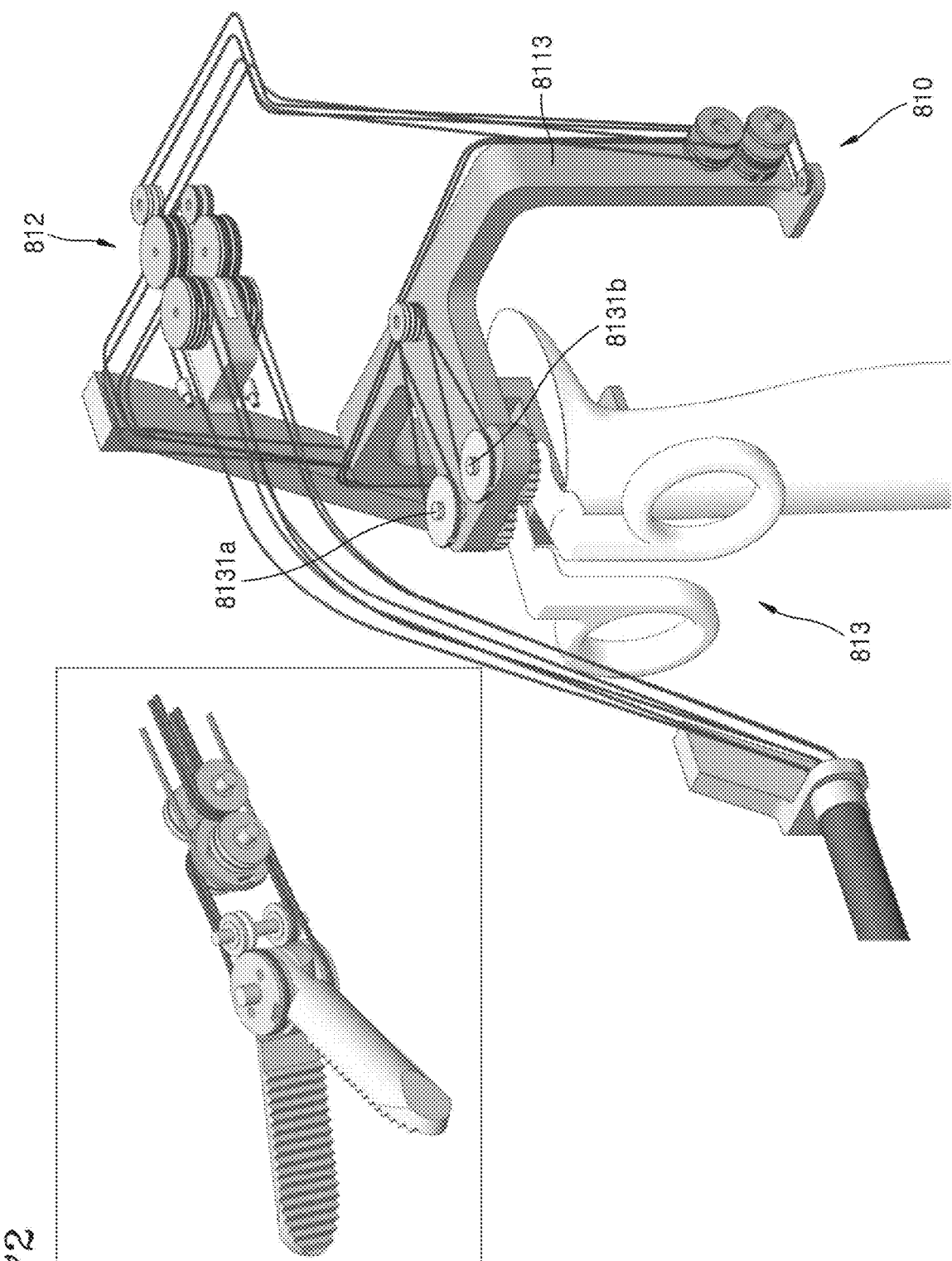
FIG. 72 is an inside perspective view illustrating a wiring structure of the instrument for surgery shown in FIG. 70.
Figure 73:
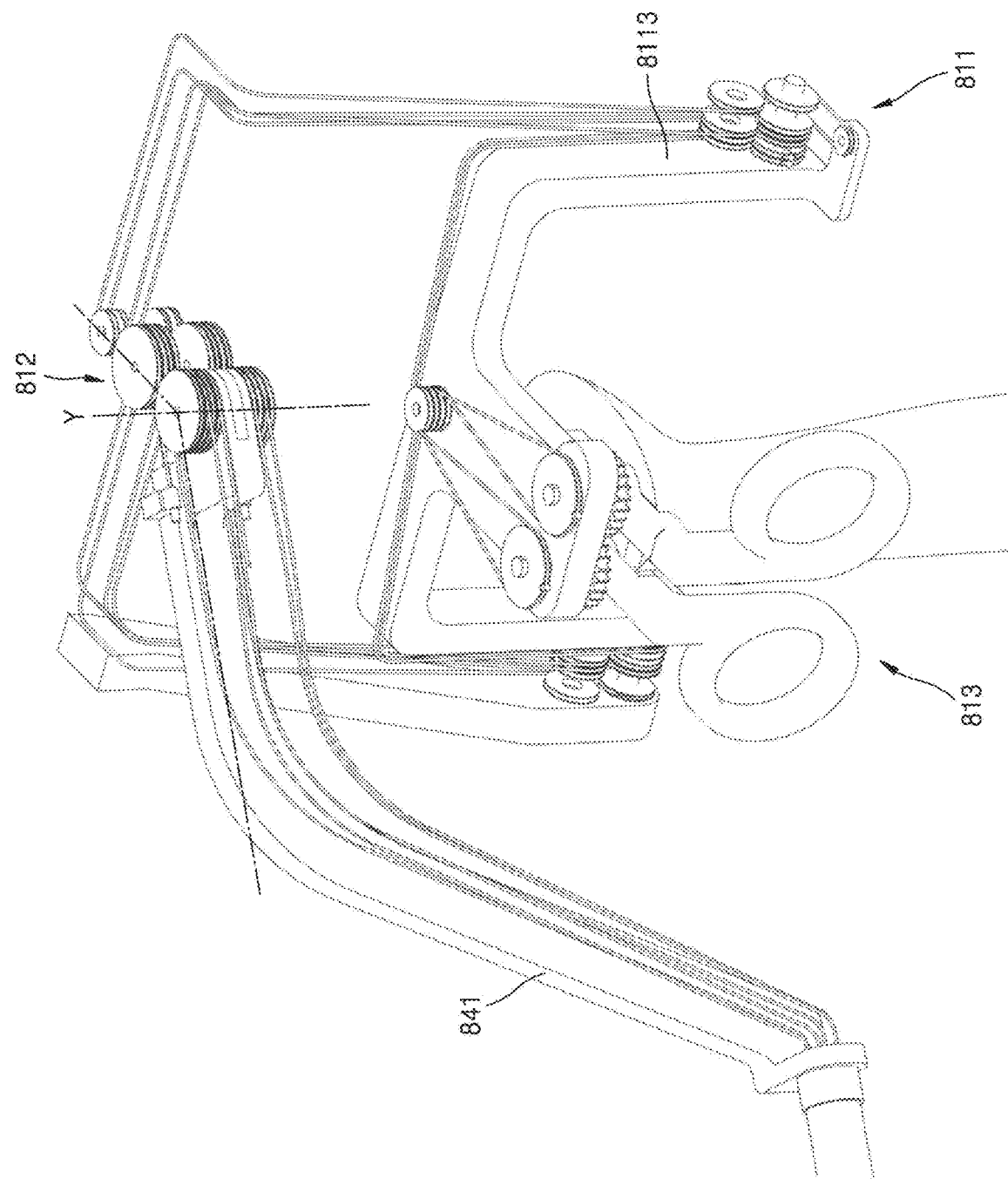
FIG. 73 is a perspective view illustrating a yaw motion of the instrument for surgery shown in FIG. 70.
Figure 74:
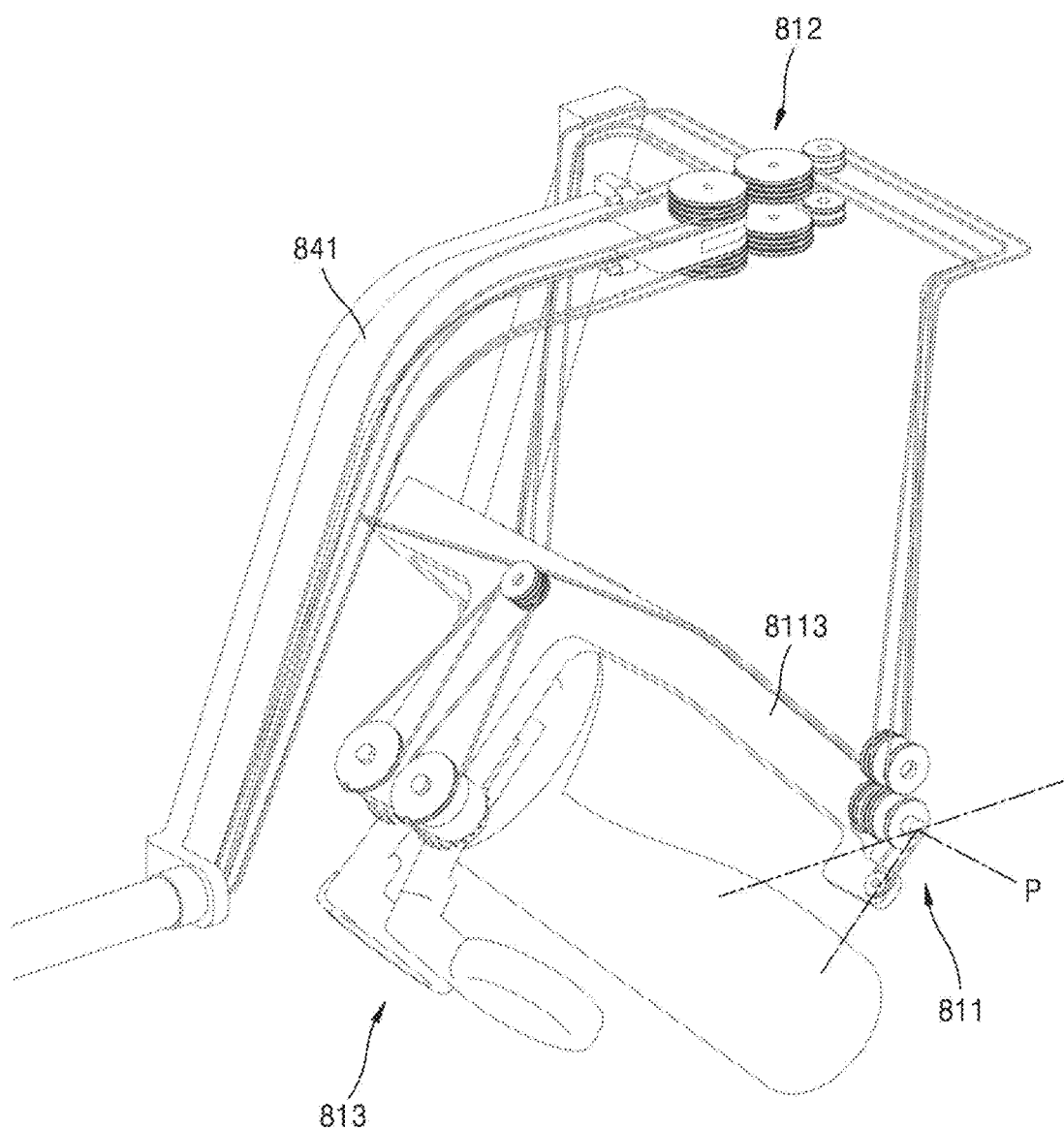
FIGS. 74, 75, and 76 are perspective views illustrating a pitch motion of the instrument for surgery shown in FIG. 70.
Figure 75:
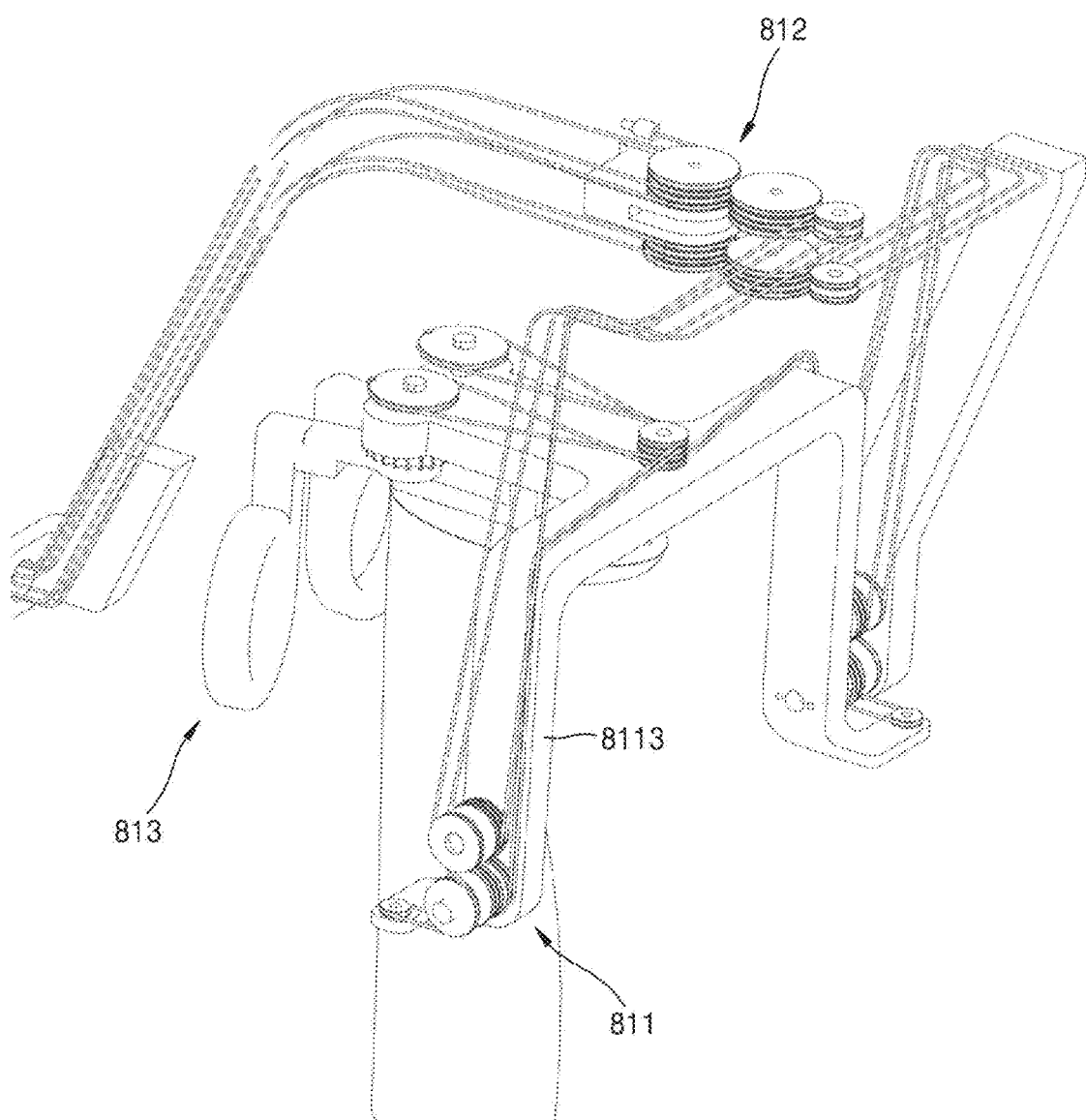
Figure 76:
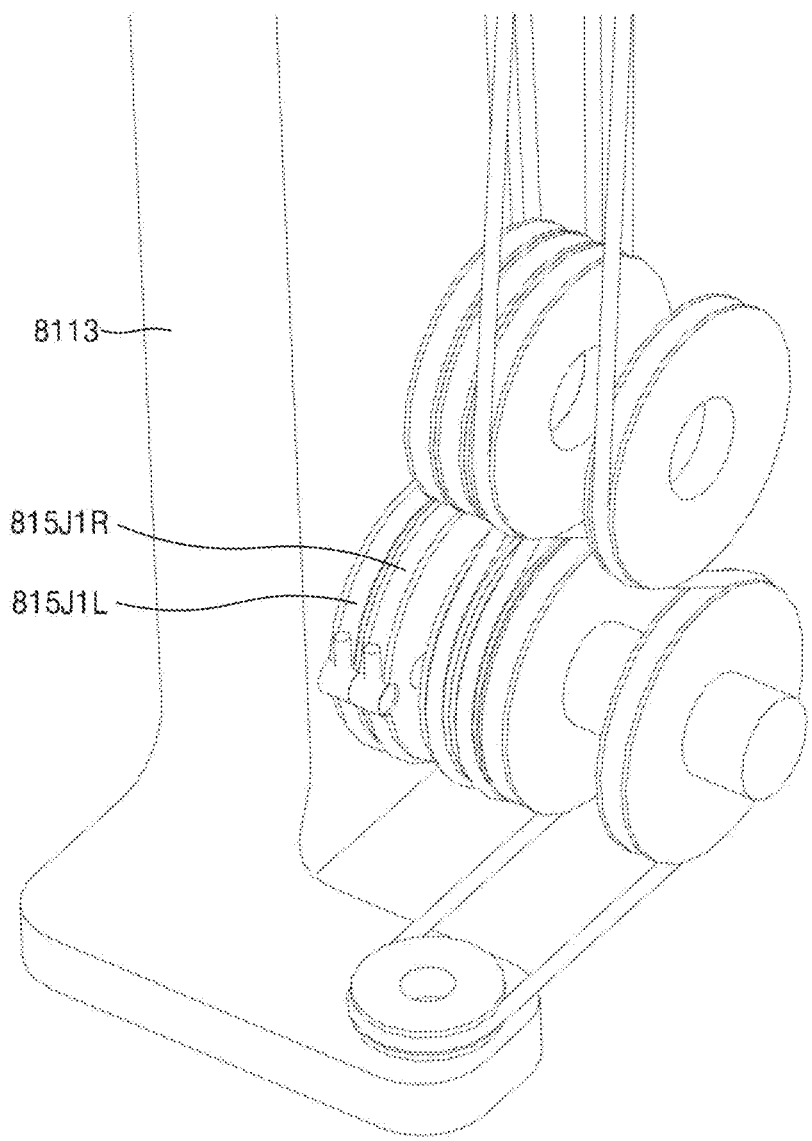

FIG. 70 is a perspective view illustrating the instrument for surgery according to the eighth embodiment of the present invention, FIG. 71 is an inside perspective view illustrating the instrument for surgery of FIG. 70, and FIG. 72 is an inside perspective view illustrating a wiring structure of the instrument for surgery of FIG. 70. FIG. 73 is a perspective view illustrating a yaw motion of the instrument for surgery of FIG. 70, and FIGS. 74, 75, and 76 are perspective views illustrating a pitch motion of the instrument for surgery of FIG. 70.

The configuration difference between the eighth embodiment and the sixth embodiment is the same as the configuration difference between the seventh embodiment and the first embodiment. That is, the seventh embodiment is different from the first embodiment in that the path of each jaw wire and pulleys for the wire are divided into two, and similarly, the eighth embodiment is different from the sixth embodiment in that the path of each jaw wire and pulleys for the wire are divided into two. Therefore, the configuration of the eighth embodiment may be sufficiently understood from the descriptions of the sixth embodiment and the seventh embodiment, and thus a detailed description thereof will be omitted.

One of main features of the present embodiment is that since the bent part 841 and the manipulation part 810 are divided into two parts, a rotation axis of a yaw joint and a rotation axis of a pitch joint of the manipulation part may be placed as close as possible, for example, in a crossed manner as shown in FIG. 64, and a space may be formed at or near a crossing point to receive a user's hand or wrist. To this end, in the present embodiment, elements of the manipulation part 810 (such as pulleys and wires) are divided into two groups and arranged at both division sides. However, the configuration for the above-mentioned feature may be variously modified. That is, elements of the manipulation part 810 (such as pulleys and wires) may be arranged only at one of both division sides. Furthermore, instead of dividing the bent part 841 and the manipulation part 810 into both sides, the bent part 841 and the manipulation part 810 may be bent only at one side to form a space for accommodating a user's hand or wrist. That is, in the two-part division structure of the present embodiment, one part may be omitted. Such modifications may be sufficiently deduced from the above-description of the present embodiment, and thus detailed descriptions thereof will be omitted.

<Ninth Embodiment of Instrument for Surgery>

Hereinafter, an instrument 900 for surgery will be described according to a ninth third embodiment of the present invention. The instrument 900 for surgery of the ninth embodiment of the present invention is characteristically different in the configuration of a manipulation part 910 of the instrument 900 from the instrument 100 for surgery (refer to FIG. 2) of the first embodiment of the present invention. This different configuration from the first embodiment will now be described in detail.

Figure 77:
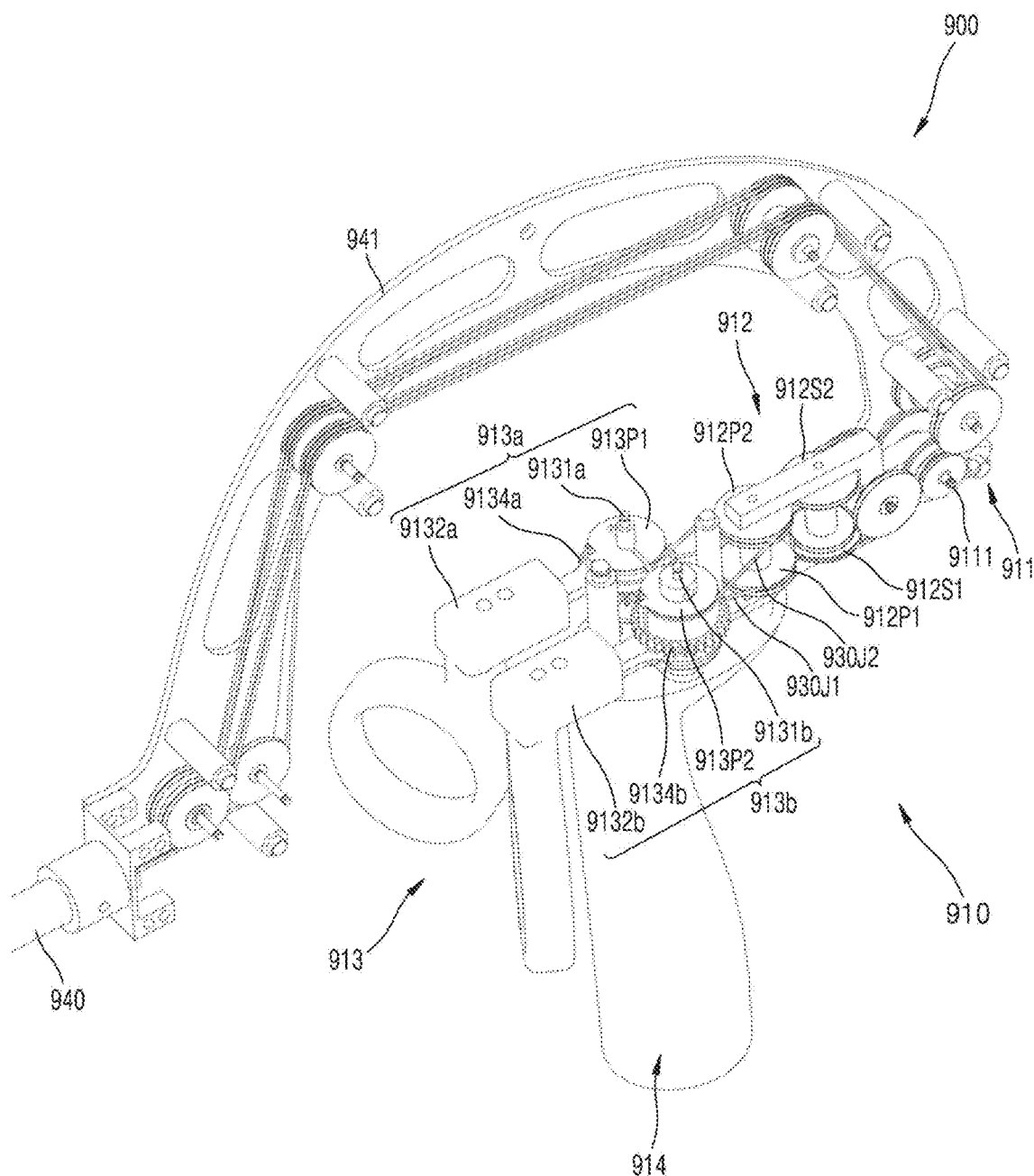
FIG. 77 is an inside perspective view illustrating an instrument for surgery according to a ninth embodiment of the present invention.
Figure 78:
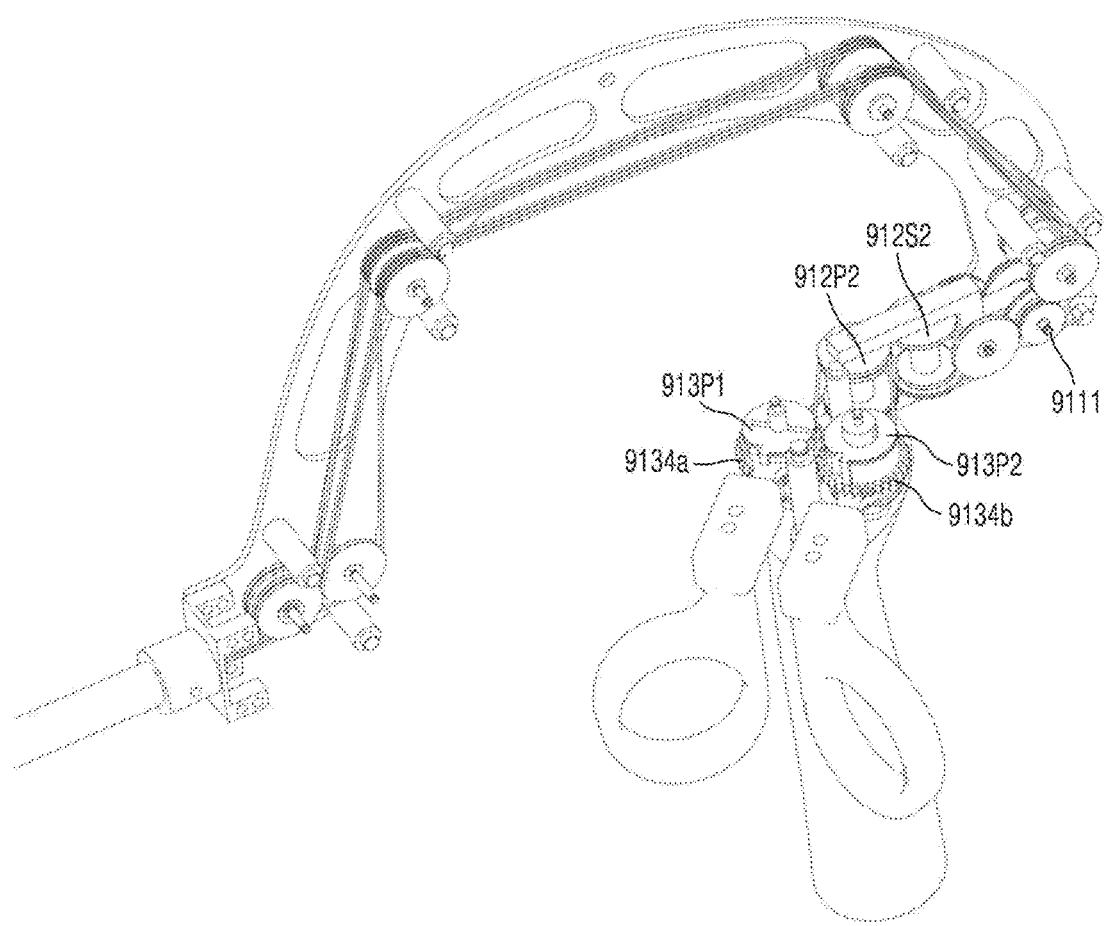
FIG. 78 is a perspective view illustrating a yaw motion of the instrument for surgery shown in FIG. 77.
Figure 79:
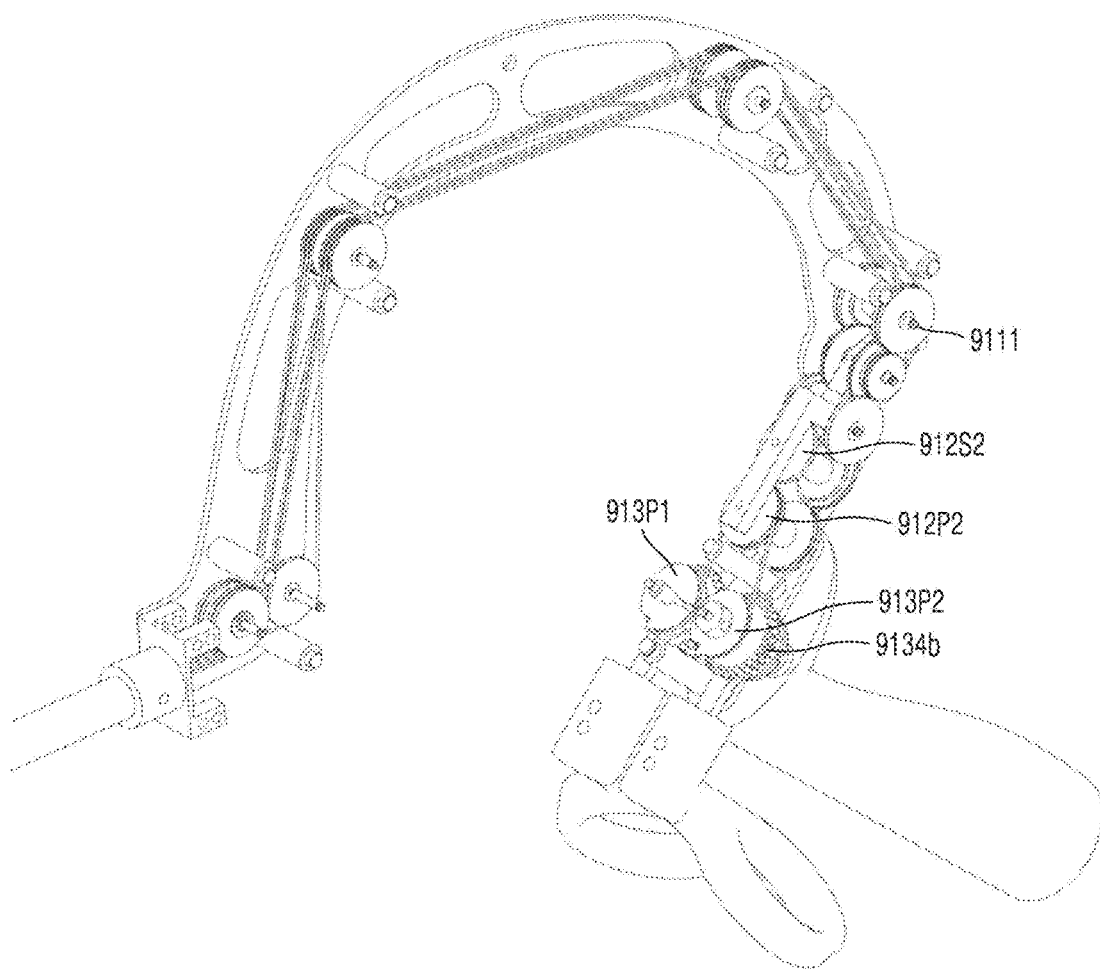
FIG. 79 is a perspective view illustrating a pitch motion of the instrument for surgery shown in FIG. 77.

FIG. 77 is an inside perspective view illustrating the instrument for surgery according to the ninth embodiment of the present invention, FIG. 78 is a perspective view illustrating a yaw motion of the instrument for surgery of FIG. 77, and FIG. 79 is a perspective view illustrating a pitch motion of the instrument for surgery of FIG. 77.

In the instrument 900 for surgery of the ninth embodiment of the present invention, the modification shown in FIG. 25A is specifically embodied. That is, the first jaw yaw auxiliary pulley 112S1 of FIG. 25A corresponds to a first jaw yaw auxiliary pulley 912S1 of FIG. 77, the first jaw yaw pulley 112P1 of FIG. 25A corresponds to a first jaw yaw pulley 912P1 of FIG. 77, and the first actuation pulley 113P1 and the second actuation pulley 113P2 of FIG. 25A correspond to a first actuation pulley 913P1 and a second actuation pulley 913P2 of FIG. 77.

Here, the present embodiment is different from the first embodiment in that ends of both strands of a jaw wire are not coupled to the same actuation pulley but are coupled to different actuation pulleys. That is, an end of a strand of the first jaw wire 930J1 is coupled to the first actuation pulley 913P1, and an end of the other strand of the first jaw wire 930J1 is coupled to the second actuation pulley 913P2.

In addition, the first actuation pulley 913P1 is fixedly coupled to a first actuation gear 9134a and rotatable together with the first actuation gear 9134a, the second actuation pulley 913P2 is fixedly coupled to a second actuation gear 9134b and rotatable together with the second actuation gear 9134b, and the first actuation gear 9134a and the second actuation gear 9134b are engaged with each other such that rotations of the two actuation pulleys may be synchronized. Therefore, if one of the actuation pulleys is rotated, the other actuation pulley may be accordingly rotated.

As described above, since rotations of the two actuation pulleys are synchronized with each other, although both strands of the first jaw wire 930J1 are not wound around one actuation pulley but are wound around different actuation pulleys, the same effect may be obtained. Therefore, as shown in FIG. 25B, it is possible to provide structures such as a structure in which both strands of the first jaw wire 930J1 are respectively wound around the actuation pulleys, and since these structures can be easily conceived of, detailed descriptions thereof will be omitted.

<Tenth Embodiment of Instrument for Surgery>

Hereinafter, an instrument 1000 for surgery will be described according to a tenth embodiment of the present invention. The instrument 1000 for surgery of the tenth embodiment of the present invention is characteristically different in the configuration of a manipulation part 1010 of the instrument 1000 from the instrument 100 for surgery (refer to FIG. 2) of the first embodiment of the present invention. This different configuration from the first embodiment will now be described in detail.

Figure 80:
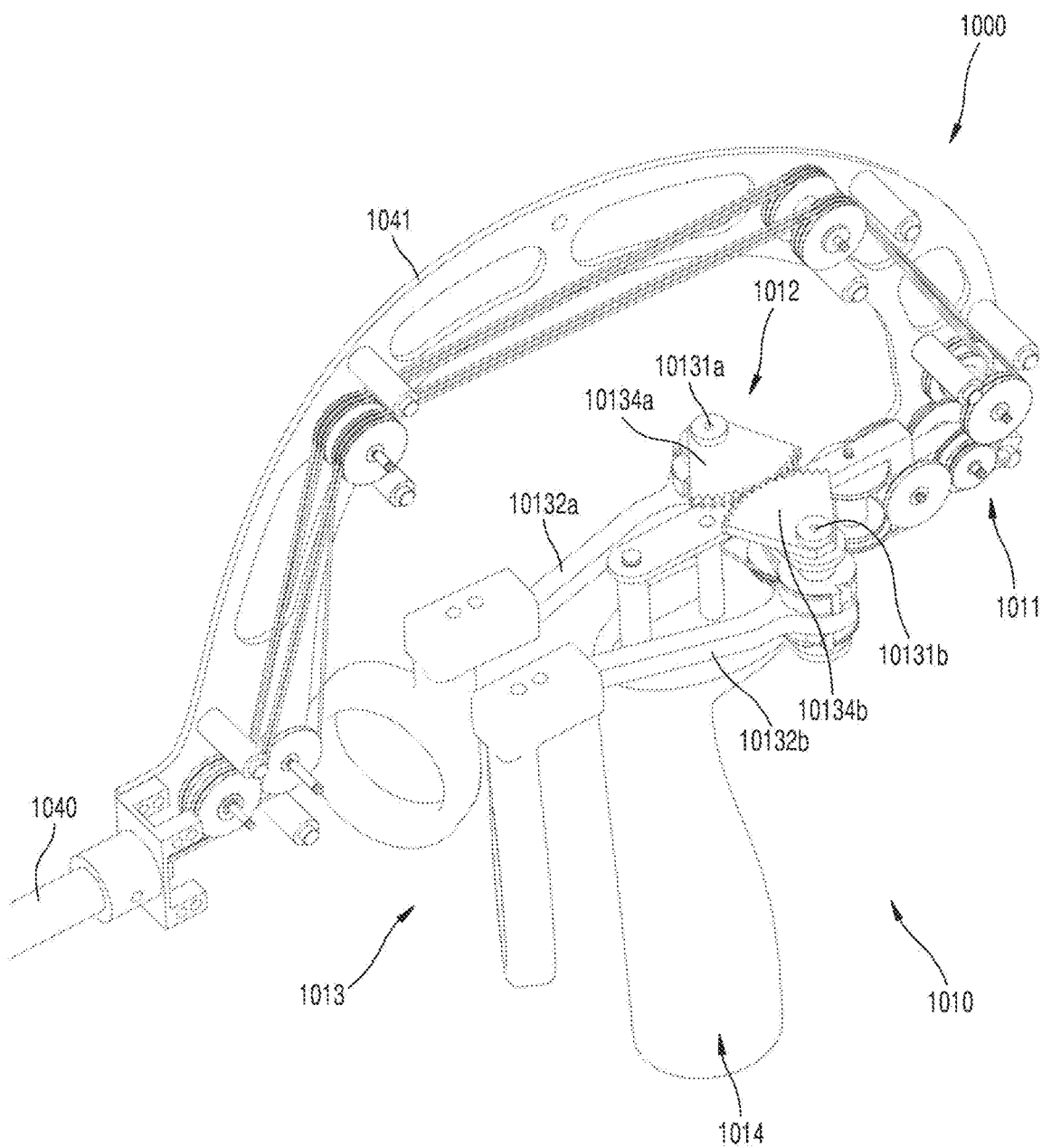
FIG. 80 is an inside perspective view illustrating an instrument for surgery according to a tenth embodiment of the present invention.
Figure 81:
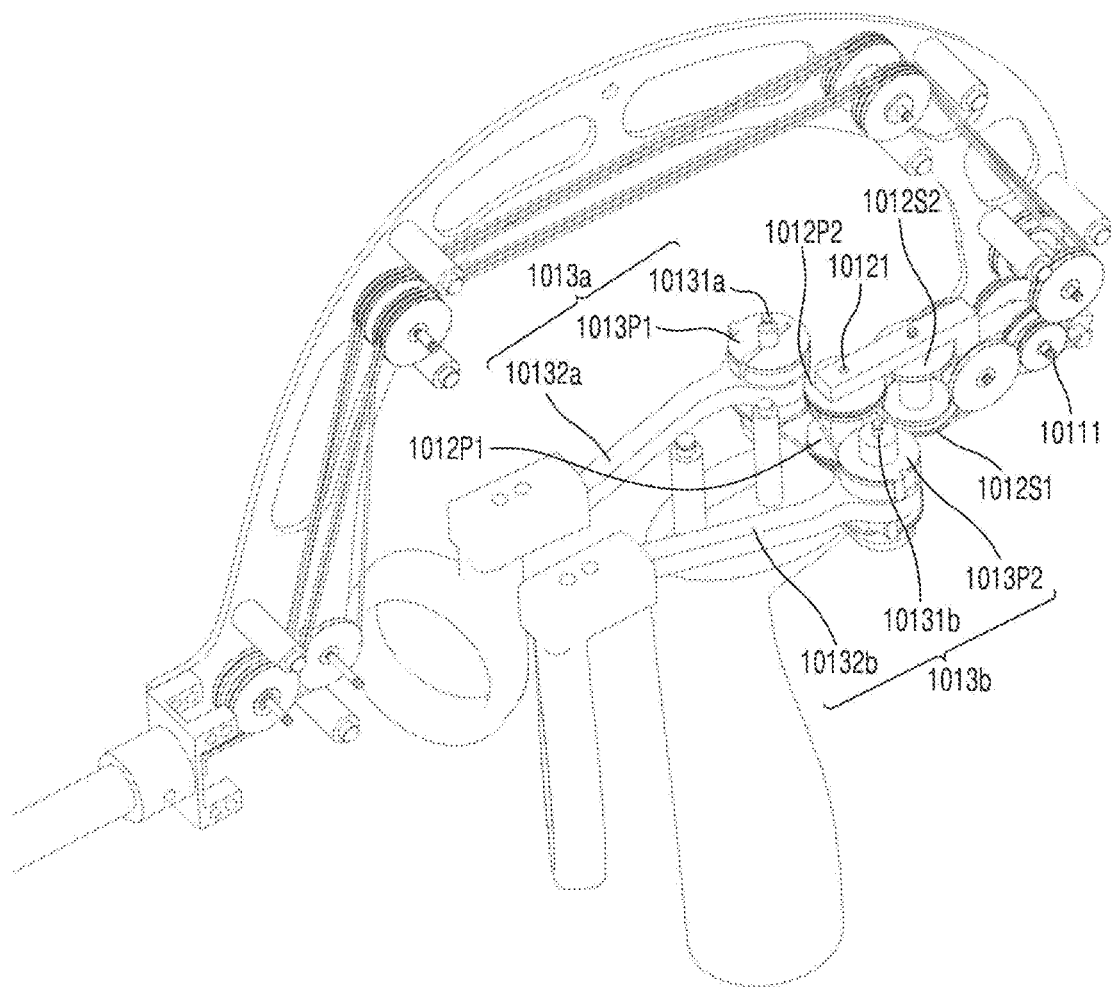
FIG. 81 is an inside perspective view illustrating the instrument for surgery of FIG. 80 with actuation gears.
Figure 82:
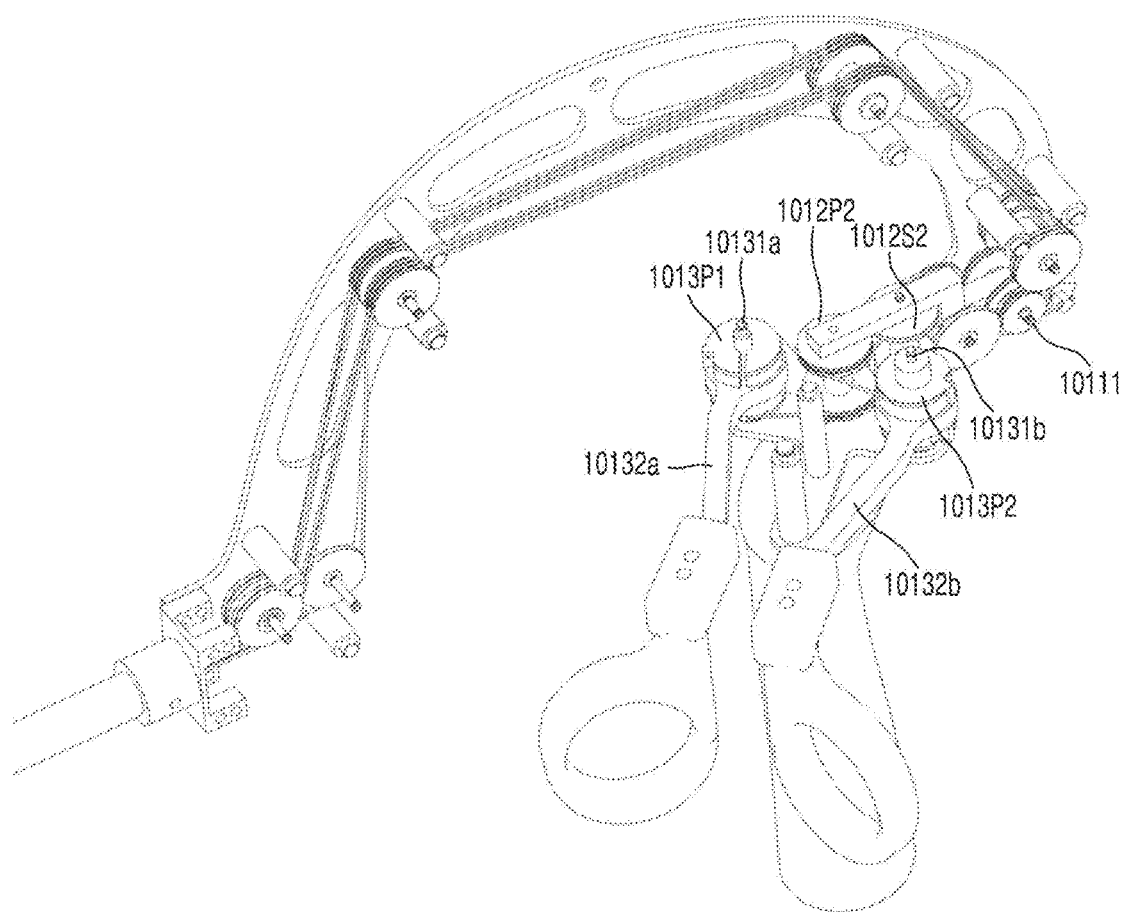
FIG. 82 is a perspective view illustrating a yaw motion of the instrument for surgery shown in FIG. 81.
Figure 83:
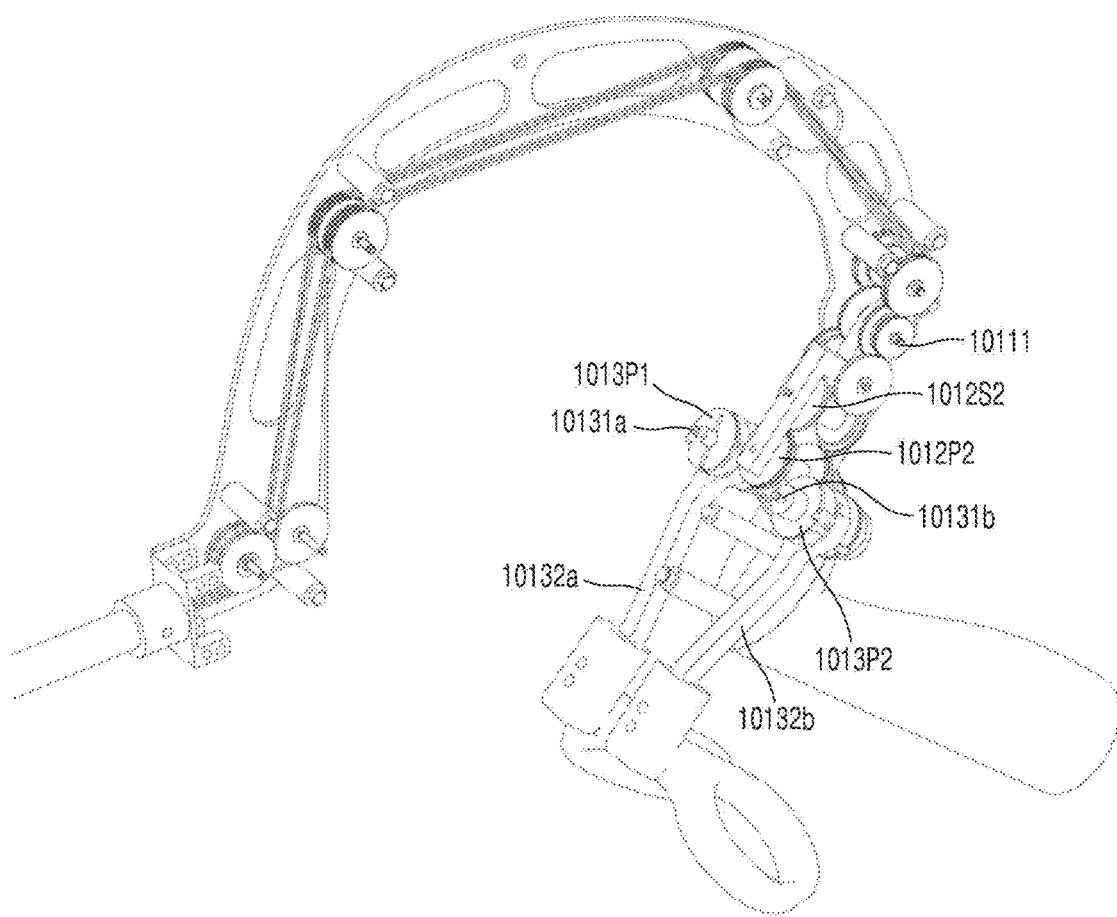
FIG. 83 is a perspective view illustrating a pitch motion of the instrument for surgery shown in FIG. 81.

FIG. 80 is an inside perspective view illustrating the instrument for surgery according to the tenth embodiment of the present invention, FIG. 81 is an inside perspective view illustrating the instrument for surgery of FIG. 80 except for actuation gears, FIG. 82 is a perspective view illustrating a yaw motion of the instrument for surgery of FIG. 81, and FIG. 83 is a perspective view illustrating a pitch motion of the instrument for surgery of FIG. 81.

In the instrument 1000 for surgery of the tenth embodiment of the present invention, the modification shown in FIG. 26 is specifically embodied. That is, the first jaw yaw auxiliary pulley 112S1 of FIG. 26 corresponds to a first jaw yaw auxiliary pulley 1012S1 of FIG. 81, the first jaw yaw pulley 112P1 of FIG. 26 corresponds to a first jaw yaw pulley 1012P1 of FIG. 81, and the first actuation pulley 113P1 and the second actuation pulley 113P2 of FIG. 26 correspond to a first actuation pulley 1013P1 and a second actuation pulley 1013P2 of FIG. 81.

Here, the present embodiment is different from the first embodiment in that ends of both strands of a jaw wire are not coupled to the same actuation pulley but are coupled to different actuation pulleys. That is, an end of a strand of a first jaw wire 1030J1 is coupled to the first actuation pulley 1013P1, and an end of the other strand of the first jaw wire 1030J1 is coupled to the second actuation pulley 1013P2.

In addition, the first actuation pulley 1013P1 is fixedly coupled to a first actuation gear 10134a and rotatable together with the first actuation gear 10134a, the second actuation pulley 1013P2 is fixedly coupled to a second actuation gear 10134b and rotatable together with the second actuation gear 10134b, and the first actuation gear 10134a and the second actuation gear 10134b are engaged with each other such that rotations of the two actuation pulleys may be synchronized. Therefore, if one of the actuation pulleys is rotated, the other actuation pulley may be accordingly rotated.

In addition, the present embodiment is different from the embodiment shown in FIG. 2 in that the two actuation pulleys are not adjacent to each other but are spaced apart from each other and are opposite each other with respect to the first jaw yaw pulley 112P1.

In addition, the first actuation gear 10134a and the second actuation gear 10134b may have relative large diameters compared to the previous embodiments such that the first actuation gear 10134a and the second actuation gear 10134b distant from each other may engage with each other and rotate together.

This configuration makes it possible to place the actuation pulleys at more rearward positions than in other embodiments. That is, a long actuation handle may be provided, and thus actuation motion may be more easily performed. The reason for this is that as the length of a handle increases, actuation manipulation is performed with less force owing to the principle of the lever.

<Eleventh Embodiment of Instrument for Surgery>

Hereinafter, an instrument 1100 for surgery will be described according to an eleventh embodiment of the present invention. The instrument 1100 for surgery of the tenth embodiment of the present invention is characteristically different in the configuration of a manipulation part 1110 of the instrument 1100 from the instrument 100 for surgery (refer to FIG. 2) of the first embodiment of the present invention. This different configuration from the first embodiment will now be described in detail.

Figure 84:
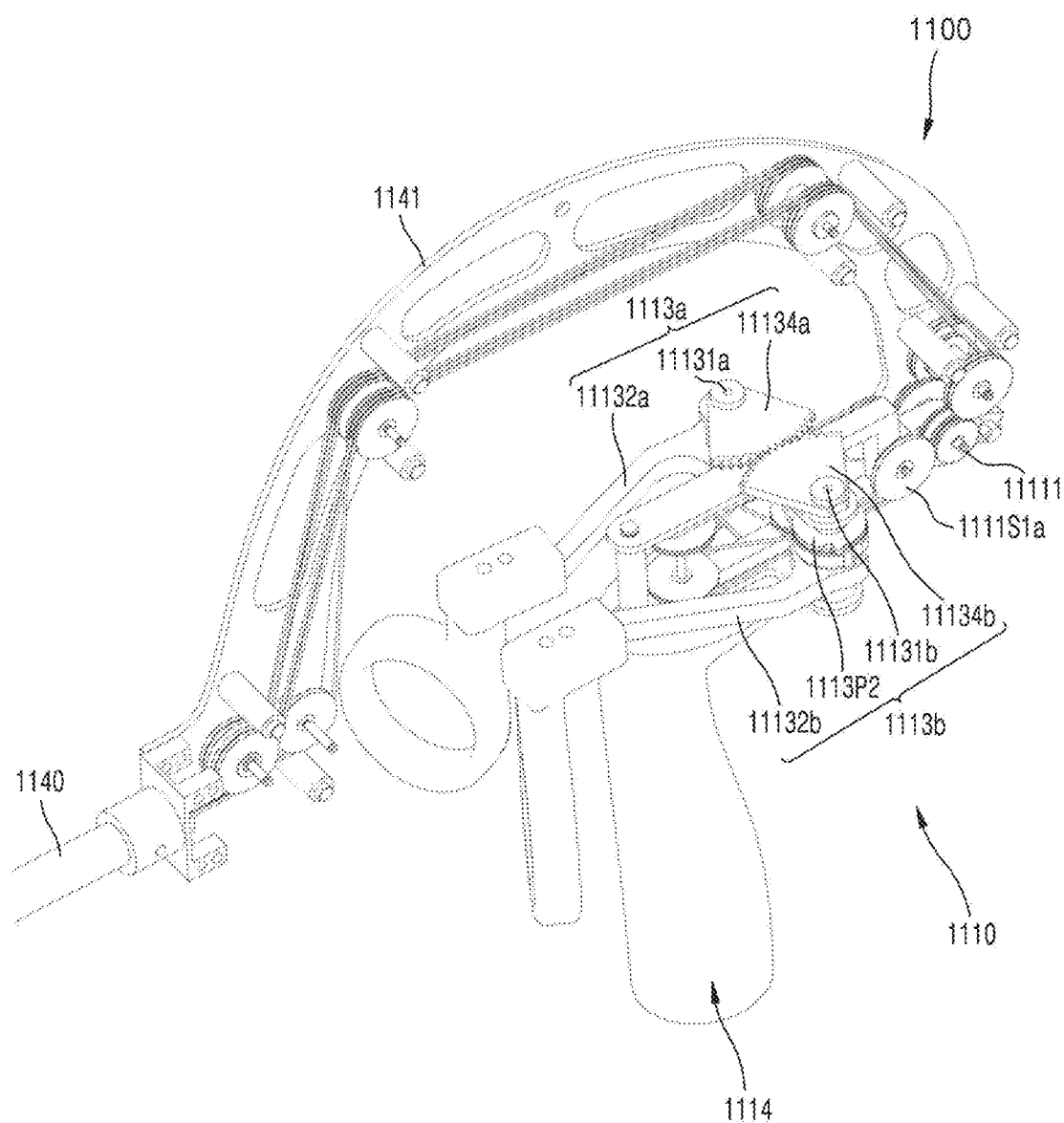
FIG. 84 is an inside perspective view illustrating an instrument for surgery according to an eleventh embodiment of the present invention.
Figure 85:
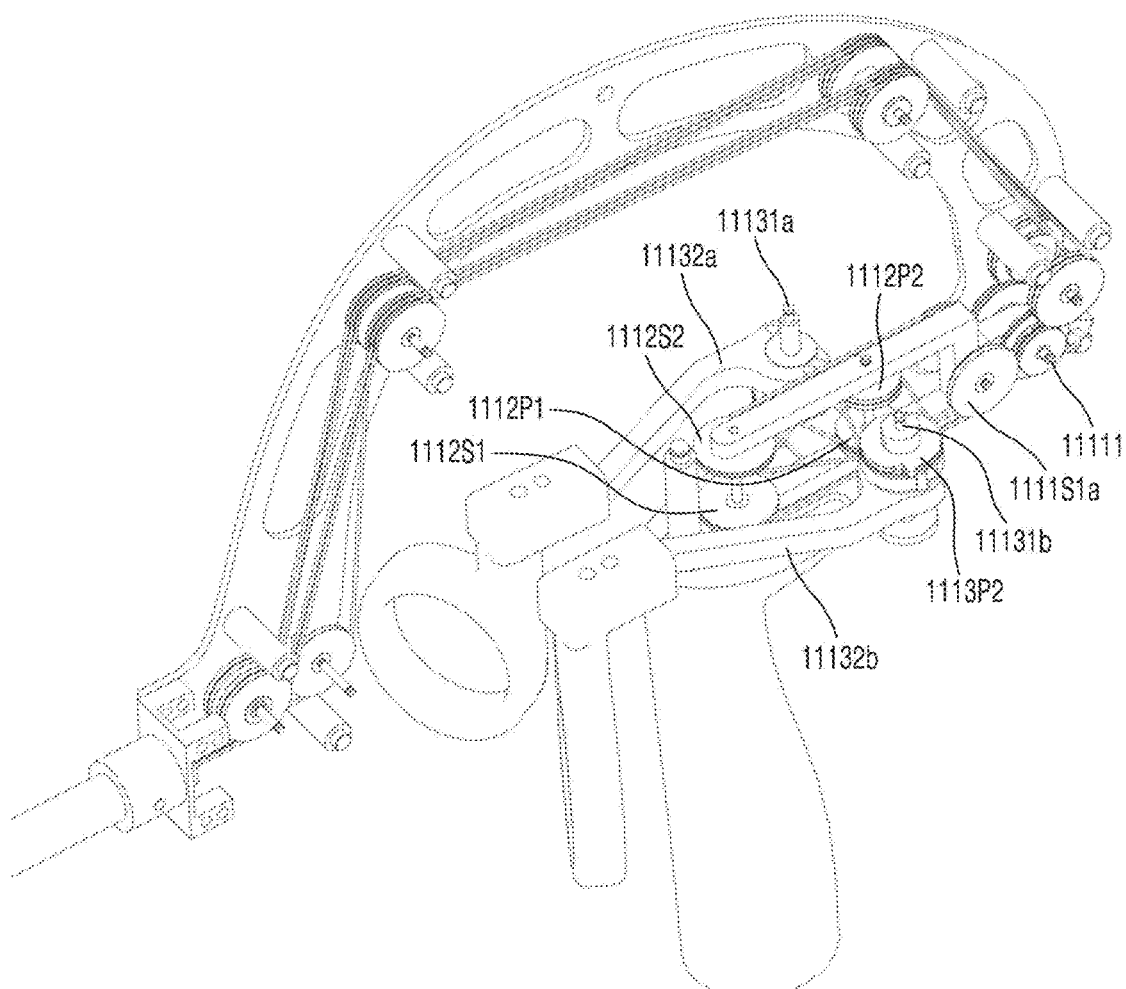
FIG. 85 is an inside perspective view illustrating the instrument for surgery of FIG. 84 with actuation gears.
Figure 86:
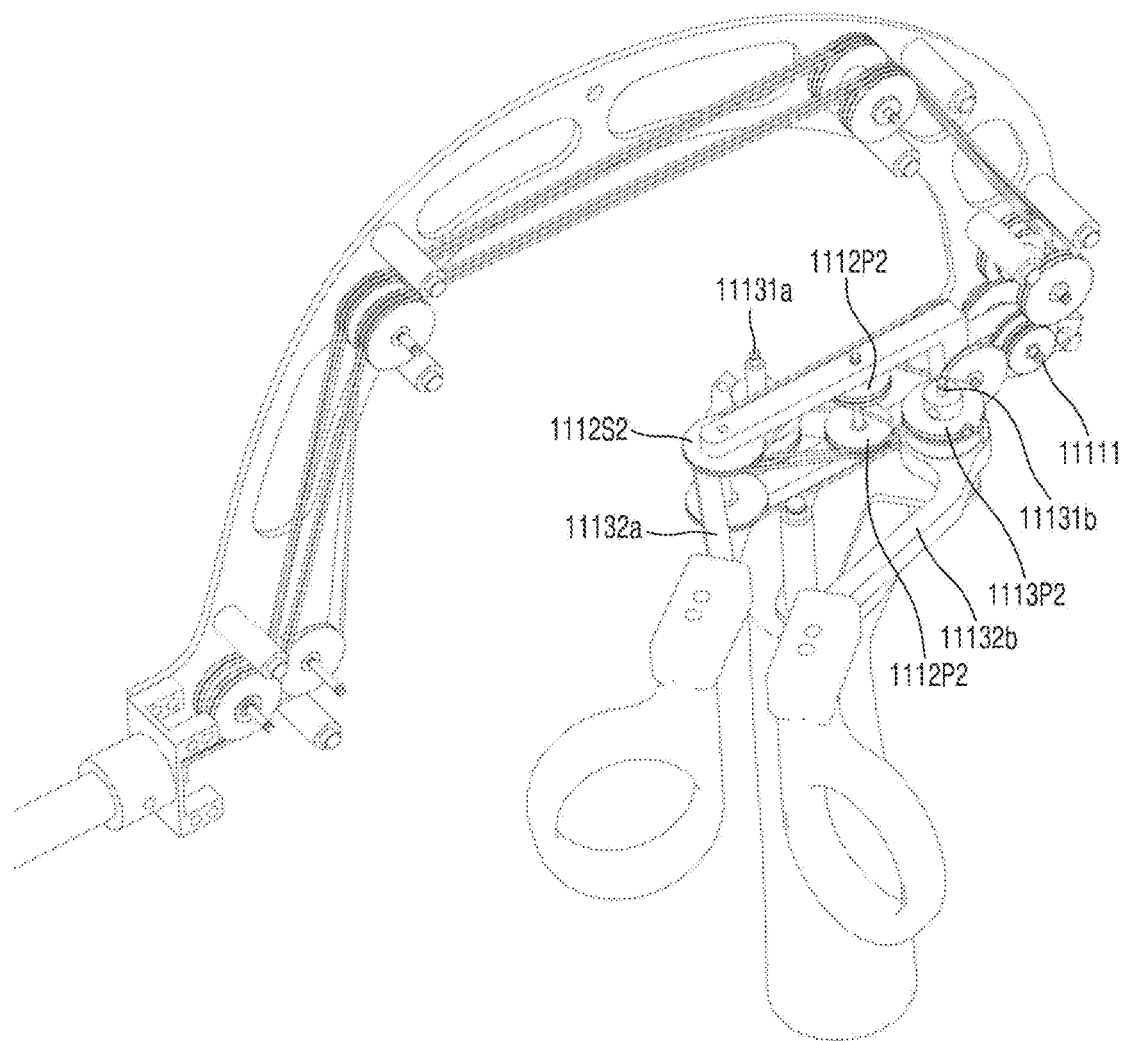
FIG. 86 is a perspective view illustrating a yaw motion of the instrument for surgery shown in FIG. 84.
Figure 87:
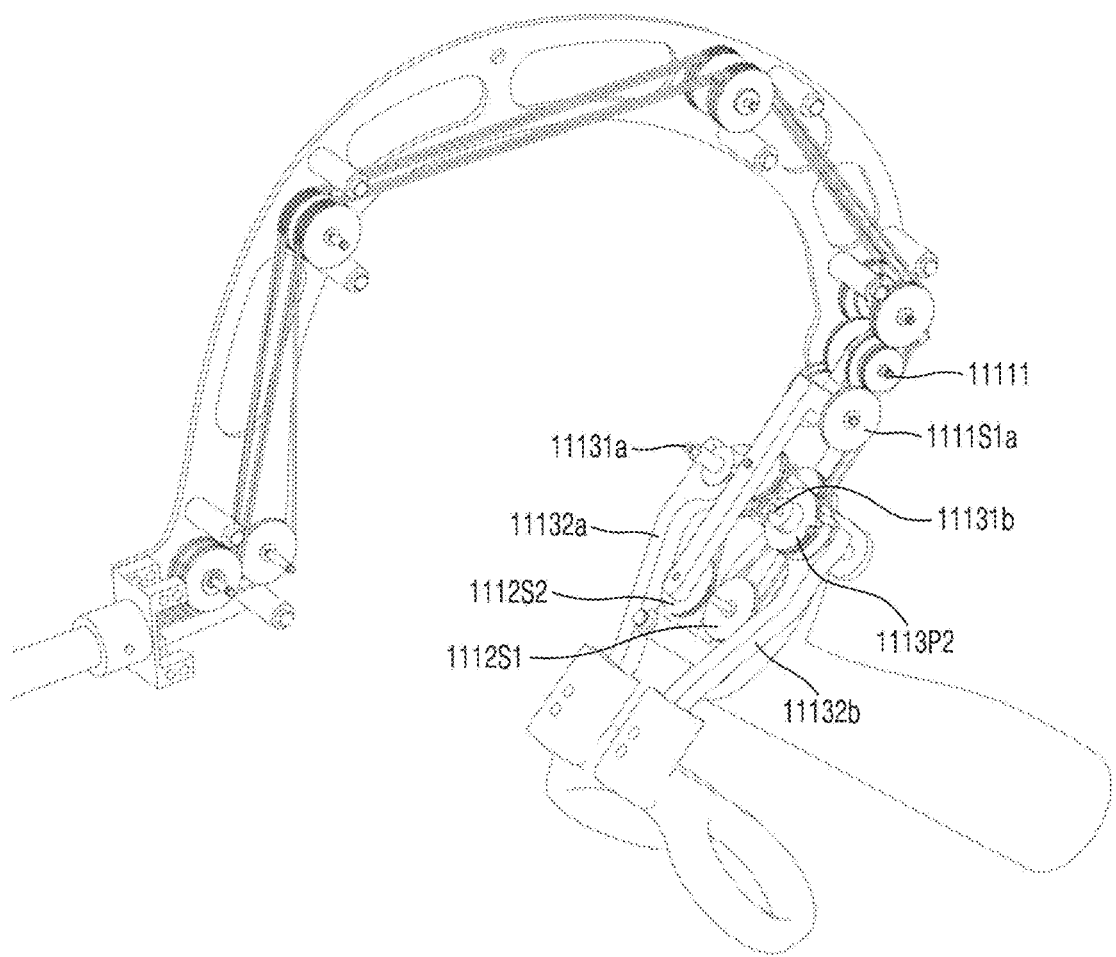
FIG. 87 is a perspective view illustrating a pitch motion of the instrument for surgery shown in FIG. 84.

FIG. 84 is an inside perspective view illustrating the instrument for surgery according to the eleventh embodiment of the present invention, FIG. 85 is an inside perspective view illustrating the instrument for surgery of FIG. 84 except for actuation gears, FIG. 86 is a perspective view illustrating a yaw motion of the instrument for surgery of FIG. 84, and FIG. 87 is a perspective view illustrating a pitch motion of the instrument for surgery of FIG. 84.

In the instrument 1100 for surgery of the eleventh embodiment of the present invention, the modification shown in FIG. 27 is specifically embodied. That is, the first jaw yaw auxiliary pulley 112S1 of FIG. 27 corresponds to a first jaw yaw auxiliary pulley 1112S1 of FIG. 84, the first jaw yaw pulley 112P1 of FIG. 27 corresponds to a first jaw yaw pulley 1112P1 of FIG. 84, and the first actuation pulley 113P1 and the second actuation pulley 113P2 of FIG. 27 correspond to a first actuation pulley 1113P1 and a second actuation pulley 1113P2 of FIG. 84.

Here, the present embodiment is different from the first embodiment in that two actuation pulleys are not adjacent to each other but are spaced apart from each other and are opposite each other with respect to a yaw pulley. In addition, to this end, the first actuation pulley 1113P1 is fixedly coupled to a first actuation gear 11134a and rotatable together with the first actuation gear 11134a, the second actuation pulley 1113P2 is fixedly coupled to a second actuation gear 11134b and rotatable together with the second actuation gear 11134b, and the first actuation gear 11134a and the second actuation gear 11134b are engaged with each other such that rotations of the two actuation pulleys may be synchronized. Therefore, if one of the actuation pulleys is rotated, the other actuation pulley may be accordingly rotated.

In addition, the first actuation gear 11134a and the second actuation gear 11134b may have relative large diameters compared to the previous embodiments such that the first actuation gear 11134a and the second actuation gear 11134b distant from each other may engage with each other and rotate together.

In addition, the present embodiment is different from the first embodiment in that the positional relationship (front-rear positional relationship) between a yaw pulley and a yaw auxiliary pulley is modified. That is, even in a direct-type joint, a pulley located at a right side in the drawings is the first jaw yaw pulley 1112P1, and a rotation shaft of the first jaw yaw pulley 1112P1 functions as a yaw rotation axis. In addition, to this end, a first jaw wire passing over a first jaw pitch auxiliary pulley-a 111S1a is wound around the first jaw yaw auxiliary pulley 1112S1, and is then fixedly coupled to the first actuation pulley 1113P1 after passing over the first jaw yaw auxiliary pulley 1112S1. In addition, the first jaw wire passing over the first jaw pitch auxiliary pulley-b (not shown) is passed over the first jaw yaw pulley 1112P1 and directly fixedly coupled to the first actuation pulley 1113P1 without passing over the first jaw yaw auxiliary pulley 1112S1.

In this configuration, a yaw rotation axis may be located closer to a pitch rotation axis than in other embodiments. As a result, a user may perform more natural, intuitive manipulation. In addition, this configuration makes it possible to place the actuation pulleys at more rearward positions than in other embodiments. That is, a long actuation handle may be provided, and thus actuation motion may be more easily performed. The reason for this is that as the length of a handle increases, actuation manipulation is performed with less force owing to the principle of the lever.

<Twelfth Embodiment of Instrument for Surgery>

Hereinafter, an instrument 1200 for surgery will be described according to a twelfth embodiment of the present invention. Here, the instrument 1200 for surgery of the twelfth embodiment of the present invention is characteristically different in the configuration of a manipulation part 1210 of the instrument 1200 from the instrument 100 for surgery (refer to FIG. 2) of the first embodiment of the present invention.

Figure 88:
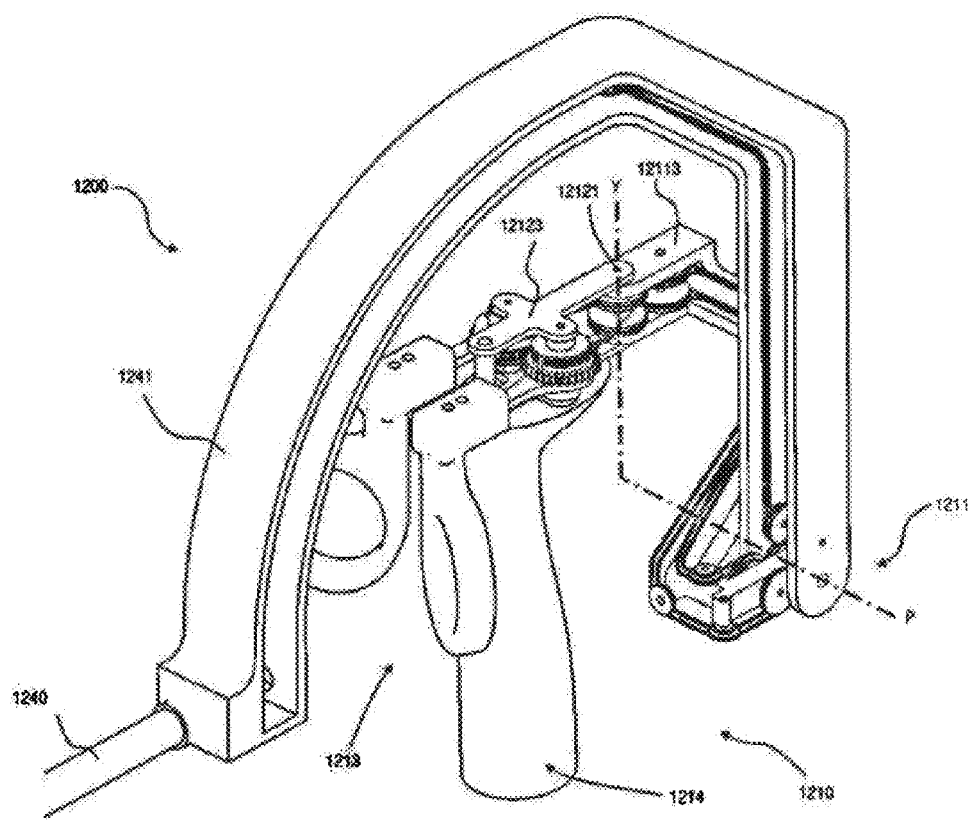
FIG. 88 is a perspective view illustrating an instrument for surgery according to a twelfth embodiment of the present invention.
Figure 89:
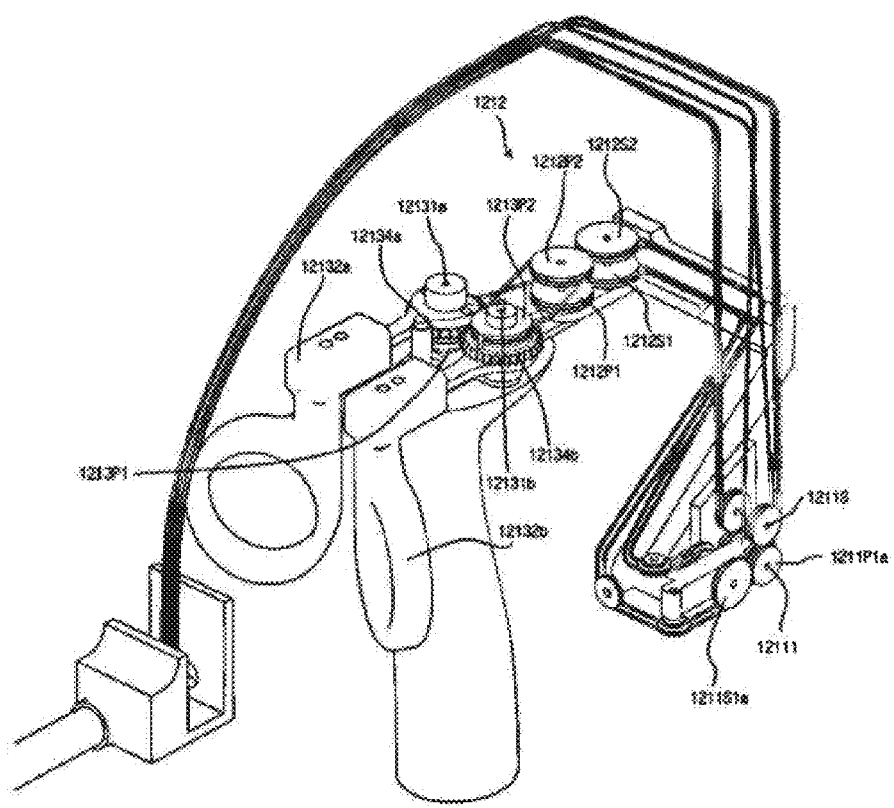
FIG. 89 is an inside perspective view illustrating structures such as a wiring structure of the instrument for surgery shown in FIG. 88.

FIG. 88 is a perspective view illustrating the instrument for surgery according to the twelfth embodiment of the present invention, and FIG. 89 is an inside perspective view illustrating structures such as a wiring structure of the instrument for surgery of FIG. 88.

As in the sixth embodiment, in the joint structure of the manipulation part 1210 for manipulating the operation of an end tool (not shown), a pitch yaw manipulation part 1211, a yaw manipulation part 1212, and an actuation manipulation part 1213 are sequentially arranged when viewed based on wires connected from the end tool to the manipulation part 1210.

The configuration of the twelfth embodiment is characteristically different the configuration of the first embodiment in that a pitch rotation shaft 12111 is significantly spaced apart from a yaw rotation shaft 12121 as in the seventh embodiment. Owing to this, as shown in FIG. 88, the yaw rotation shaft 12121 of a yaw joint and the pitch rotation shaft 12111 of a pitch joint may be placed close to each other, for example, in a crossed manner, and along with this, a space for accommodating a user's hand or wrist may be formed at or near a crossing point.

However, the configuration of the twelfth embodiment is characteristically different from the configuration of the seventh embodiment in the configuration of the manipulation part. In the seventh embodiment, the bent part 741 and the pitch frame 7113 are divided into left and right branch parts to form an approximate '∩' shape, and both left and right branch end portions of the pitch frame 7113 are connected to both left and right branch end portions of the bent part 741 through the pitch rotation shafts 7111. However, in the twelfth embodiment, as shown in FIG. 88, a bent part 1241 and the manipulation part 1210 are not divided into two parts but are bent only at one side.

Owing to this structure, although additional relay pulleys (such as the relay pulleys 715J1R and 715J1L) used in the seventh embodiment are not used, a first jaw wire (not shown) and a second jaw wire (not shown) may be connected from the end tool (not shown) to the manipulation part 1210.

Therefore, the yaw rotation shaft 12121 of the yaw joint and the pitch rotation shaft 12111 of the pitch joint of the manipulation part 1210 may be intuitively identical to a user's wrist joint performing yaw and pitch manipulations by holding a handle. Thus, users may perform more natural, intuitive manipulations.

Except for the bent part 1241 and a pitch frame 12113 having a bent structure, the configuration of the manipulation part 1210 of the twelfth embodiment is the same as the configuration of yaw and pitch pulleys of the instrument 100 for surgery of the first embodiment and the configuration of the instrument 700 for surgery of the seventh embodiment. Therefore, the configuration of the twelfth embodiment may be sufficiently understood from the descriptions of the first embodiment and the seventh embodiment, and thus a detailed description thereof will be omitted.

While the present invention has been described with reference to the accompanying drawings according to embodiments, these embodiments are for illustrative purposes only, and it will be understood by those of ordinary skill in the art that various changes and modifications may be made therefrom. Therefore, the scope and spirit of the present invention should be defined by the following claims.

INDUSTRIAL APPLICABILITY

The present invention relates to an instrument for surgery and, more specifically, to an instrument for surgery which may be manually operated in order to be used for laparoscopic surgery or various other types of surgery.

The invention claimed is:

1. An end tool of a surgical instrument, comprising:
   a first jaw and a second jaw configured to rotate independently;
   a J11 pulley coupled to the first jaw and configured to be rotate around a first axis formed at an end tool hub;
   a J16 pulley formed at one side of the J11 pulley and configured to rotate around a second axis formed at one side of the first axis;
   a J12 pulley and a J14 pulley formed at one side of the J16 pulley, and configured to rotate around a third axis formed at a predetermined angle with the first axis and formed at one side of the end tool hub;
   a J21 pulley coupled to the second jaw and configured to rotate around an axis that is substantially identical to or parallel to the first axis;
   a J26 pulley formed at one side of the J21 pulley and configured to rotate around an axis that is substantially identical to or parallel to the second axis; and
   a J22 pulley and a J24 pulley formed at one side of the J26 pulley and configured to rotate around an axis that is substantially identical to or parallel to the third axis,
   wherein, based on a first plane perpendicular to the first axis and passing between the J11 pulley and the J21 pulley, two strands of a first jaw wire coupled to the J11 pulley contact one side from among an upper side and a lower side of the J12 pulley and J14 pulley, and two strands of a second jaw wire coupled to the J21 pulley contact one side from among the upper side and the lower side of the J22 pulley and J24 pulley, which is different from the one side from among the upper side and the lower side of the J12 pulley and J14 pulley.

2. The end tool of claim 1, wherein the first jaw wire is configured to at least partially contact the J12 pulley, J11 pulley, J16 pulley, and J14 pulley; and the second jaw wire is configured to at least partially contact the J22 pulley, J21 pulley, J26 pulley, and J24 pulley.

3. The end tool of claim 1, wherein the two strands of the first jaw wire wound around the J11 pulley are arranged, by the J16 pulley, at one side based on a plane perpendicular to the third axis and passing through the first axis, and the two strands of the second jaw wire wound around the J21 pulley are arranged, by the J26 pulley, at the other side based on the plane perpendicular to the third axis and passing through the first axis.

4. The end tool of claim 1, wherein the J16 pulley is arranged at an opposite side of the first jaw and the second jaw based on the J11 pulley, and the J26 pulley is arranged at an opposite side of the first jaw and the second jaw based on the J21 pulley.

5. The end tool of claim 1, wherein the first jaw wire is fixedly coupled to the J11 pulley, and the second jaw wire is fixedly coupled to the J21 pulley.

6. The end tool of claim 1, wherein a diameter of the J16 pulley is smaller than a diameter of the J11 pulley, and a diameter of the J26 pulley is smaller than a diameter of the J21 pulley.

7. The end tool of claim 1, wherein a connector hub is configured to rotate around the third axis with respect to the end tool hub at one side of the end tool hub, and the J12 pulley, J14 pulley, J22 pulley, and J24 pulley are formed on a common axis of the end tool hub and the connector hub.

8. The end tool of claim 7, wherein at the connector hub, a J13 pulley and a J15 pulley are configured to rotate around an axis substantially parallel to the third axis, and a J23 pulley and a J25 pulley are configured to rotate around the axis substantially parallel to the third axis.

9. The end tool of claim 8, wherein the first jaw wire is configured to pass between the J12 pulley and the J13 pulley, and the second jaw wire is configured to pass between the J22 pulley and the J23 pulley.

10. The end tool of claim 7, wherein, based on the first plane, one strand of the first jaw wire from among the two strands of the first jaw wire coupled to the J11 pulley sequentially contacts a lower side of the J12 pulley and an upper side of the J13 pulley, and the other strand of the first jaw wire from among the two strands of the first jaw wire coupled to the J11 pulley sequentially contacts a lower side of the J14 pulley and an upper side of the J15 pulley.

11. The end tool of claim 7, wherein, based on the first plane, one strand of the second jaw wire from among the two strands of the second jaw wire coupled to the J21 pulley sequentially contacts an upper side of the J22 pulley and a lower side of the J23 pulley, and the other strand of the second jaw wire from among the two strands of the second jaw wire coupled to the J21 pulley sequentially contacts an upper side of the J24 pulley and a lower side of the J25 pulley.

12. The end tool of claim 1, wherein, with respect to the first jaw wire or the second jaw wire, a pitch motion of the end tool is performed when both sides of a wire wound around the end tool is pulled.

13. The end tool of claim 1, wherein, with respect to the first jaw wire or the second jaw wire, a yaw motion or an actuation motion of the end tool is performed when one side of a wire wound around the end tool is pulled and the other side is pushed.

14. The end tool of claim 1, wherein both strands of the first jaw wire wound around the J11 pulley are arranged at a same side with respect to the second axis, and both strands of the second jaw wire wound around the J21 pulley are arranged at a same side with respect to the second axis.

15. The end tool of claim 1, wherein any one side of the first jaw wire wound around the J11 pulley is configured to pass between the J11 pulley and the J16 pulley, and any one side of the second jaw wire wound around the J21 pulley is configured to pass between the J21 pulley and the J26 pulley.

16. The end tool of claim 1, wherein the first jaw wire is located on an internal tangent of the J11 pulley and the J16 pulley, and a rotation angle of the J11 pulley is increased by the J16 pulley, and the second jaw wire is located on an internal tangent of the J21 pulley and the J26 pulley, and a rotation angle of the J21 pulley is increased by the J26 pulley.

17. The end tool of claim 1, wherein the J12 pulley and the J14 pulley are arranged at one side based on a plane perpendicular to the third axis and passing through the first axis, and the J22 pulley and the J24 pulley are arranged at the other side based on the plane perpendicular to the third axis and passing through the first axis.

18. The end tool of claim 1, wherein the first jaw wire and the J11 pulley are fixedly coupled by a coupler, and the first jaw wire is configured to be located on an internal tangent of the J11 pulley and the J16 pulley such that a rotation angle of the coupler is increased.

19. The end tool of claim 18, wherein the coupler of the first jaw wire and the J11 pulley is rotatable until the coupler is located on an internal common tangent of the J11 pulley and the J16 pulley.

20. The end tool of claim 1, wherein, from a proximal portion to a distal portion of the end tool, the two strands of the first jaw wire coupled to the J11 pulley are wound around the J12 pulley and the J14 pulley in a first direction from among a clockwise direction and a counterclockwise direction, and the two strands of the second jaw wire coupled to the J21 pulley are wound around the J22 pulley and the J24 pulley in a direction different from the first direction.

* * * * *